United States Patent
Kubo et al.

(10) Patent No.: US 7,534,887 B2
(45) Date of Patent: May 19, 2009

(54) THIAZOLINE DERIVATIVE AND USE OF THE SAME

(75) Inventors: Keiji Kubo, Osaka (JP); Takanobu Kuroita, Osaka (JP); Masaki Kawamura, Osaka (JP); Hiroki Sakamoto, Osaka (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 0 days.

(21) Appl. No.: 10/574,048

(22) PCT Filed: Sep. 29, 2004

(86) PCT No.: PCT/JP2004/014685

§ 371 (c)(1),
(2), (4) Date: May 12, 2006

(87) PCT Pub. No.: WO2005/030740

PCT Pub. Date: Apr. 7, 2005

(65) Prior Publication Data

US 2007/0010528 A1    Jan. 11, 2007

(30) Foreign Application Priority Data

Sep. 30, 2003  (JP) .............................. 2003-341430

(51) Int. Cl.
  C07D 413/00  (2006.01)
  A61K 31/497  (2006.01)
(52) U.S. Cl. .................................. 544/369; 514/252.12
(58) Field of Classification Search .................. None
  See application file for complete search history.

(56) References Cited

U.S. PATENT DOCUMENTS 6,727,269 B1    4/2004    Moinet et al.
2003/0187023 A1  10/2003    Kubo et al.

FOREIGN PATENT DOCUMENTS

| JP | 11-236372 | 8/1999 |
|----|-----------|--------|
| JP | EP 1 048 652 | 11/2000 |
| JP | 2001-011071 | 1/2001 |
| JP | 1 564 213 | 8/2005 |
| WO | WO 98/54164 | 12/1998 |
| WO | WO 99/33805 | 7/1999 |
| WO | WO 01/07424 | 2/2001 |
| WO | WO 02/06234 | 1/2002 |
| WO | WO 02/055510 | 7/2002 |
| WO | WO 02/060894 | 8/2002 |
| WO | WO 2004/048363 | 10/2004 |

OTHER PUBLICATIONS von Walther, caplus an 1913:10137.*
Lifeblood, The Thrombosis Charity fact sheet for Venous Thrombosis.*
Orvim et al., http://atvb.ahajournals.org/cgi/content/full/atvbaha;15/12/2188, 17 pages.*
Fressinaud et al., Blood, vol. 80, 1992, 988-994.*
Lifeblood, The Thrombosis Charity fact sheet for Arterial Thrombosis.*
http://www.answers.com/topic/myocardial-infarction?cat=health (1 Page).*
http://www.webmd.com/heart-disease/tc/deep-vein-thrombosis-topic-overview?page=2.*
Lieberman et al., J. Bone Joint Surg Am, 2005, 87, 2097-2112.*
Paiement et al., J. Bone Joint Surg Am, 1993, 75, 893-898.*
Qiao et al., Bioorg. Med. Chem. Lett. 17 (2007) 4419-4427.*

* cited by examiner

Primary Examiner—Kamal A Saeed
Assistant Examiner—Sun Jae Y Loewe
(74) Attorney, Agent, or Firm—Hamre, Schumann, Mueller & Larson, P.C.

(57) ABSTRACT

A thiazoline derivative represented by Formula (I):

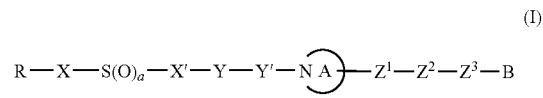

(I)

wherein R is a cyclic hydrocarbon group which may be substituted, or a heterocyclic group which may be substituted; X is a bond or a divalent chain hydrocarbon group which may be substituted; X' is a bond or —N(R$^5$)—; Y is a divalent hydrocarbon group which may be substituted; Y' is a bond or —C(=O)—; ring A is a nitrogen-containing heterocycle which may be substituted; Z$^1$ and Z$^3$ are each independently a bond or a divalent chain hydrocarbon group which may be substituted; Z$^2$ is a bond or —N(R$^6$)—; and B is a group represented by the formula:

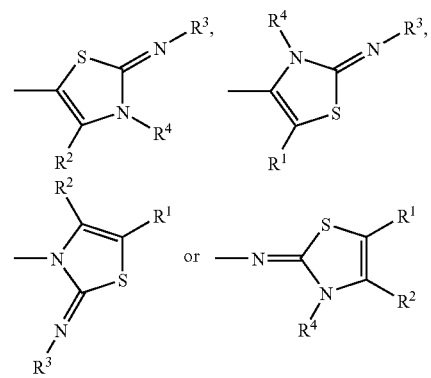

which is useful as a therapeutic drug for thrombosis, is provided.

11 Claims, No Drawings

THIAZOLINE DERIVATIVE AND USE OF THE SAME

This application is the National Phase filing of International Patent Application No. PCT/JP2004/014685, filed Sep. 29, 2004.

TECHNICAL FIELD

The present invention relates to a novel thiazoline derivative having an anti-coagulating effect and an anti-thrombotic effect by inhibiting activated blood coagulation factor X (FXa), which is useful for preventing and treating arterial and venous thrombotic obstructive diseases, inflammation, cancer and the like, and use of the same.

BACKGROUND ART

It is important to suppress the formation of thrombi for preventing and treating myocardial infarction, cerebral thrombosis and the like, and various antithrombin agents, platelet aggregation inhibitors and the like have been studied and developed as thrombosis inhibitors. However, since not only platelet aggregation inhibitors, but also anti-thrombin agents suppress the aggregation of platelets in addition to their anticoagulant activity, these medicaments tend to cause bleeding and the like as adverse side-effects. Therefore, there is a problem in their safety. On the other hand, it is considered that the FXa inhibitor is a safe anticoagulant agent for specifically inhibiting only coagulating factor. Hitherto, compounds having the FXa inhibiting activity have been disclosed, for example, in the following publications. JP 7-112970 A, JP 5-208946 A, WO 96/16940, WO 96/40679, WO 96/10022, WO 97/21437, WO 99/26919, WO 99/33805, WO 00/09480, WO 01/44172, WO 02/06234, US 2002/0045616 A, WO 2004/035579, WO 2004/048363, and Journal of Medicinal Chemistry, 1998, Vol. 41, page 3357.

OBJECT OF THE INVENTION

Development of a novel compound is desired, which has excellent efficacy, oral absorbability, sustained effect and the like, with fewer side effects, and which is more useful as a therapeutic agent for thrombosis, as compared with conventional FXa inhibitors.

DISCLOSURE OF THE INVENTION

The inventors of the present invention envisaged that a thiazoline derivative having high selectivity for and strong inhibiting action against FXa can exhibit a persistent and sufficient effect upon oral administration, and thus would be useful for prevention and treatment of thrombotic occlusive diseases in arteries and veins, inflammation, cancer and the like. Thus, they have devotedly continued their study.

As a result, the inventors have found that a novel thiazoline derivative represented by the following Formula (I), or a salt thereof (hereinafter, may be referred to as Compound (I)) has a selectively strong FXa inhibiting effect and excellent safety, and thus exhibits a sustained and sufficient effect upon oral administration, thus completing the invention.

Thus, the invention relates to:
(1) A compound represented by Formula (I):

(I)

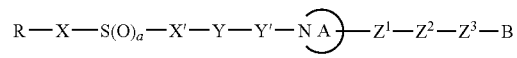

wherein R is a cyclic hydrocarbon group which may be substituted or a heterocyclic group which may be substituted; X is a bond or a divalent chain hydrocarbon group which may be substituted; X' is a bond or —N(R$^5$)— (wherein R$^5$ is a hydrogen atom, a hydrocarbon group which may be substituted, an esterified or amidated carboxyl group, or an acyl group); Y is a divalent hydrocarbon group which may be substituted; Y' is a bond or —C(=O)—; ring A is a nitrogen-containing heterocycle which may be substituted; Z$^1$ and Z$^3$ are each independently a bond or a divalent chain hydrocarbon group which may be substituted; Z$^2$ is a bond or —N(R$^6$)— (wherein R$^6$ is a hydrogen atom, a hydrocarbon group which may be substituted, or an acyl group); B is a group represented by the formula:

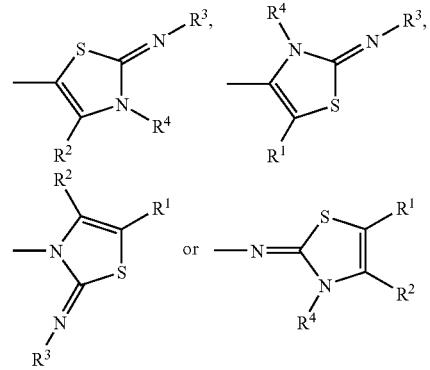

(wherein R$^1$ and R$^2$ are each independently a hydrogen atom, a halogen atom, a hydrocarbon group which may be substituted, an alkoxy group which may be substituted, a carboxyl group which may be esterified or amidated, an acyl group, or an amino group which may be substituted; R$^3$ is a hydrogen atom, a hydrocarbon group which may be substituted, a carboxyl group which may be esterified or amidated, or an acyl group; R$^4$ is a hydrocarbon group which may be substituted; and R$^2$ and R$^1$ or R$^4$, and R$^3$ and R$^4$ may be respectively bonded to each other to form a ring which may be substituted); R$^6$ and R$^1$, R$^2$, R$^3$ or R$^4$ may be bonded to each other to form a ring which may be substituted; and a is 0, 1 or 2, or a salt thereof;

(2) A prodrug of the compound according to the above-mentioned (1);

(3) The compound according to the above-mentioned (1), wherein R is an aryl group which may be substituted with a substituent selected from a halogen atom, $C_{1-6}$ alkyl, $C_{2-6}$ alkenyl, $C_{2-6}$ alkynyl, amino which may be substituted, nitro, cyano, amidino which may be substituted, and carboxyl which may be esterified or amidated;

(4) The compound according to the above-mentioned (1), wherein R is a heterocyclic group which may be substituted with a substituent selected from a halogen atom, $C_{1-6}$ alkyl, $C_{2-6}$ alkenyl, $C_{2-6}$ alkynyl, amino which may be substituted, nitro, cyano, amidino which may be substituted, and carboxyl which may be esterified or amidated;

(5) The compound according to the above-mentioned (1), wherein R is naphthyl which may be substituted with a halogen atom;

(6) The compound according to the above-mentioned (1), wherein X is a bond, X' is a bond, Y is $C_{1-3}$ alkylene which may be substituted, and Y' is —C(=O)—;

(7) The compound according to the above-mentioned (6), wherein Y is $C_{1-3}$ alkylene substituted with a hydroxyl group;

(8) The compound according to the above-mentioned (1), wherein $Z^1$ and $Z^2$ are each a bond, and $Z^3$ is $C_{1-3}$ alkylene which may be substituted;

(9) The compound according to the above-mentioned (1), wherein ring A is a piperazine ring which may be substituted or a piperidine ring which may be substituted;

(10) The compound according to the above-mentioned (1), wherein ring A is a ring represented by the formula:

wherein ring A' may be further substituted, or the formula:

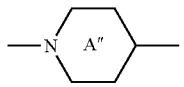

wherein ring A" may be further substituted;

(11) The compound according to the above-mentioned (1), wherein $R^5$ is a hydrogen atom;

(12) The compound according to the above-mentioned (1), wherein a is 2;

(13) A compound selected from the group consisting of N-(4-((4-(3-((6-chloro-2-naphthyl)sulfonyl)propanoyl)-1-piperazinyl)methyl)-3-methyl-1,3-thiazol-2(3H)-ylidene)-N-methylamine, 4-((4-(3-((6-chloro-2-naphthyl)sulfonyl) propanoyl) -1-piperazinyl)methyl)-3-Methyl -1,3-thiazol-2 (3H)-imine, N-(5-((1-(3-((6-chloro-2-naphthyl)sulfonyl) propanoyl)-4-piperidinyl)methyl)-3-methyl-1,3-thiazol-2 (3H)-ylidene)-N-methylamine, 5-(1-(3-((6-chloro-2-naphthyl)sulfonyl)propanoyl)-4-piperidinyl)-3-Methyl-1,3-thiazol-2(3H)-imine, and 2-(2-((1-(3-((6-chloro -2-naphthyl) sulfonyl)propanoyl)-4-piperidinyl)imino)-1,3-thiazol-3 (2H)-yl)ethanol, or a salt thereof or a prodrug thereof;

(14) A compound represented by Formula (II'):

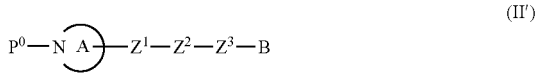

wherein $P^0$ is a hydrogen atom, or a protective group of an imino group; and the other symbols have the same meanings as defined in the above-mentioned (1), or a salt thereof;

(15) A pharmaceutical composition comprising the compound according to the above-mentioned (1) or (2);

(16) The pharmaceutical composition according to the above-mentioned (15), which is an anticoagulant;

(17) The pharmaceutical composition according to the above-mentioned (15), which is an activated blood coagulation factor X inhibitor;

(18) The pharmaceutical composition according to the above-mentioned (15), which is a medicament for preventing or treating myocardial infarction, cerebral infarction, deep vein thrombosis, pulmonary thromboembolism or atherosclerotic obliterans;

(19) The pharmaceutical composition according to the above-mentioned (15), which is a medicament for preventing or treating economy-class syndrome, thromboembolism during and post operation, or the secondary onset of deep vein thrombosis;

(20) A method for inhibiting blood coagulation in a mammal, which comprises administering an effective amount of the compound according to the above-mentioned (1) or a prodrug thereof to a mammal;

(21) A method for inhibiting an activated blood coagulation factor X in a mammal, which comprises administering an effective amount of the compound according to the above-mentioned (1) or a prodrug thereof to a mammal;

(22) A method for preventing or treating myocardial infarction, cerebral infarction, deep vein thrombosis, pulmonary thromboembolism or atherosclerotic obliterans in a mammal, which comprises administering an effective amount of the compound according to the above-mentioned (1) or a prodrug thereof to a mammal;

(23) Use of the compound according to the above-mentioned (1) or a prodrug thereof, for manufacturing a medicament for inhibiting blood coagulation;

(24) Use of the compound according to the above-mentioned (1) or a prodrug thereof, for manufacturing a medicament for inhibiting an activated blood coagulation factor X;

(25) Use of the compound according to the above-mentioned (1) or a prodrug thereof, for manufacturing a medicament for preventing or treating myocardial infarction, cerebral infarction, deep vein thrombosis, pulmonary thromboembolism or atherosclerotic obliterans; and the like.

In the above-described formulas, R is a cyclic hydrocarbon group which may be substituted, or a heterocyclic group which may be substituted (preferably, an aryl group which may be substituted, or an aromatic heterocyclic group which may be substituted).

The "cyclic hydrocarbon group" of the "cyclic hydrocarbon group which may be substituted" represented by R, may be exemplified by an alicyclic hydrocarbon group, an aryl group or the like. Among them, an aryl group or the like is preferred.

The "alicyclic hydrocarbon group" as an example of the cyclic hydrocarbon group may be exemplified by a saturated or unsaturated alicyclic hydrocarbon group such as a cycloalkyl group, a cycloalkenyl group, a cycloalkadienyl group or the like.

Here, the "cycloalkyl group" may be exemplified by a $C_{3-9}$ cycloalkyl group such as cyclopropyl, cyclobutyl, cyclopentyl, cyclohexyl, cycloheptyl, cyclooctyl or cyclononyl, or the like (preferably, a $C_{5-7}$ cycloalkyl group or the like).

The "cycloalkenyl group" may be exemplified by a $C_{3-9}$ cycloalkenyl group such as 2-cyclopenten-1-yl, 3-cyclopenten-1-yl, 2-cyclohexen-1-yl, 3-cyclohexen-1-yl, 1-cyclobuten-1-yl, 1-cyclopenten-1-yl, 1-cyclohexen-1-yl or 1-cyclohepten-1-yl, or the like (preferably, a $C_{5-7}$ cycloalkenyl group or the like).

The "cycloalkadienyl group" may be exemplified by a $C_{4-6}$ cycloalkadienyl group such as 2,4-cyclopentadien-1-yl, 2,4-cyclohexadien-1-yl or 2,5-cyclohexadien-1-yl, or the like.

The "aryl group" as an example of the cyclic hydrocarbon group may be exemplified by a monocyclic or fused polycyclic aromatic hydrocarbon group, and for example, a $C_{6-14}$ aryl group such as phenyl, naphthyl, anthryl, phenanthryl or acenaphthylenyl, and the like are preferred, with phenyl, 1-naphthyl, 2-naphthyl and the like among them being particularly preferred.

Examples of the cyclic hydrocarbon group further include a bicyclic or tricyclic hydrocarbon group derived from condensation of identical or different 2 to 3 rings (preferably, rings of two or more species) that are selected from the rings constituting the above-described alicyclic hydrocarbon groups and aromatic hydrocarbon groups, such as 1,2-dihydronaphthyl, 1,2,3,4-tetrahydronaphthyl, indenyl, dihydrobenzocycloheptenyl and fluorenyl, and the like.

The "heterocyclic group" of the "heterocyclic group which may be substituted" represented by R, may be exemplified by an aromatic heterocyclic group, a saturated or unsaturated non-aromatic heterocyclic group (aliphatic heterocyclic group) or the like, respectively containing at least one (preferably 1 to 3, more preferably 1 to 2) heteroatom of 1 to 3 species (preferably 1 to 2 species) selected from oxygen, sulfur and nitrogen atoms and the like, as the atom constituting the ring system (ring atom).

Examples of the "aromatic heterocyclic group" may be exemplified by a 5- to 6-membered aromatic monocyclic heterocyclic group such as furyl, thienyl, pyrrolyl, oxazolyl, isoxazolyl, thiazolyl, isothiazolyl, imidazolyl, pyrazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl, tetrazolyl, pyridyl, pyridazinyl, pyrimidinyl, pyrazinyl, triazinyl or the like; and a 8- to 16-membered (preferably, 10- to 12-membered) aromatic fused heterocyclic group (preferably, a heterocyclic group derived from a heterocycle resulting from condensation of 1 to 2 (preferably, one) heterocycles constituting the above-described 5- to 6-membered aromatic monocyclic heterocyclic group, with 1 to 2 benzene rings (preferably, one), or a heterocyclic group derived from a heterocycle resulting from condensation of 2 to 3 (preferably, two) identical or different heterocycles constituting the above-described 5- to 6-membered aromatic monocyclic heterocyclic group, more preferably a heterocyclic group derived from a heterocycle resulting from condensation of a heterocycle constituting the above-described 5- to 6-membered aromatic monocyclic heterocyclic group, with a benzene ring, and particularly preferably indolyl, benzofuranyl, benzo[b]thienyl, benzopyranyl or the like), such as benzofuranyl, isobenzofuranyl, benzo[b]thienyl, indolyl, isoindolyl, 1H-indazolyl, benzimidazolyl, benzoxazolyl, 1,2-benzoisoxazolyl, benzothiazolyl, benzopyranyl, 1,2-benzoisothiazolyl, 1H-benzotriazolyl, quinolyl, isoquinolyl, cinnolinyl, quinazolinyl, quinoxalinyl, phthalazinyl, naphthyridinyl, purinyl, pteridinyl, carbazolyl, α-carbolinyl, β-carbolinyl, γ-carbolinyl, acridinyl, phenoxazinyl, phenothiazinyl, phenazinyl, phenoxathiinyl, thianthrenyl, phenanthridinyl, phenanthrolinyl, indolizinyl, pyrrolo[1,2-b]pyridazinyl, pyrazolo[1,5-a]pyridyl, imidazo[1,2-a]pyridyl, imidazo[1,5-a]pyridyl, imidazo[1,2-b]pyridazinyl, imidazo[1,2-a]pyrimidinyl, 1,2,4-triazolo[4,3-a]pyridyl, or 1,2,4-triazolo[4,3-b]pyridazinyl; or the like.

Examples of the "non-aromatic heterocyclic group" include a 3- to 8-membered (preferably, 5- to 6-membered) saturated or unsaturated (preferably, saturated) non-aromatic monocyclic heterocyclic group (aliphatic monocyclic heterocyclic group) such as oxiranyl, azetidinyl, oxetanyl, thietanyl, pyrrolidinyl, tetrahydrofuryl, thiolanyl, piperidyl, tetrahydropyranyl, morpholinyl, thiomorpholinyl, piperazinyl or the like; a heterocyclic group derived from a heterocycle resulting from condensation of 1 to 2 (preferably, one) heterocycles which constitute the above-described non-aromatic monocyclic heterocyclic group such as 1,3-dihydroisoindolyl or the like, with 1 to 2 (preferably, one) benzene rings; a heterocyclic group derived from a heterocycle resulting from condensation of 1 to 2 (preferably, one) heterocycles which constitute the above-described non-aromatic monocyclic heterocyclic group, with 1 to 2 (preferably, one) heterocycles which constitute the above-described 5- to 6-membered aromatic monocyclic heterocyclic group; or a non-aromatic heterocyclic group resulting from saturation of part or all of the double bonds in the above-described aromatic monocyclic heterocyclic group or aromatic fused heterocyclic group, such as 1,2,3,4-tetrahydroquinolyl, 1,2,3,4-tetrahydroisoquinolyl or the like; and the like.

Examples of the substituent for the "cyclic hydrocarbon group which may be substituted" and the "heterocyclic group which may be substituted" represented by R, include alkyl which may be substituted, alkenyl which may be substituted, alkynyl which may be substituted, aryl which may be substituted, cycloalkyl which may be substituted, cycloalkenyl which may be substituted, heterocyclic group which may be substituted, amino which may be substituted, imidoyl which may be substituted [for example, a group represented by the formula: —C(U')=N—U, wherein U and U' are each a hydrogen atom or a substituent for imidoyl (U is preferably a hydrogen atom), etc.], amidino which may be substituted [for example, a group represented by the formula —C(NT'T")=N—T, wherein T, T' and T" are each a hydrogen atom or a substituent for amidino (T is preferably a hydrogen atom), etc.], hydroxyl which may be substituted, thiol which may be substituted, carboxyl which may be esterified or amidated, thiocarbamoyl which may be substituted, sulfamoyl which may be substituted, halogen atom (e.g., fluorine, chlorine, bromine, iodine, etc., preferably chlorine, bromine, etc.), cyano, nitro, acyl (carboxylic acid-derived acyl, sulfonic acid-derived acyl, sulfinic acid-derived acyl), and the like. Any of these substituents may be substituted at 1 to 5 (preferably, 1 to 3) substitutable positions. Also, the "cyclic hydrocarbon group which may be substituted" and the "heterocyclic group which may be substituted" represented by R may have an oxo group or a thioxo group, and for example, when R is benzopyranyl, R may form benzo-α-pyronyl, benzo-γ-pyronyl or the like.

The "aryl" of the "aryl which may be substituted" as a substituent for the "cyclic hydrocarbon group which may be substituted" and the "heterocyclic group which may be substituted" represented by R, may be exemplified by $C_{6-14}$ aryl such as phenyl, naphthyl, anthryl, phenanthryl or acenaphthylenyl, or the like. Here, the substituent which may be carried by the aryl may be exemplified by lower alkoxy (e.g., $C_{1-6}$ alkoxy such as methoxy, ethoxy or propoxy, etc.), a halogen atom (e.g., fluorine, chlorine, bromine, iodine, etc.), lower alkyl (e.g., $C_{1-6}$ alkyl such as methyl, ethyl or propyl, etc.), lower alkenyl (e.g., $C_{2-6}$ alkenyl such as vinyl or allyl, etc.), lower alkynyl (e.g., $C_{2-6}$ alkynyl such as ethynyl or propargyl, etc.), amino which may be substituted, hydroxyl which may be substituted, cyano, amidino which may be substituted, carboxyl, lower alkoxycarbonyl (e.g., $C_{1-6}$ alkoxycarbonyl such as methoxycarbonyl or ethoxycarbonyl, etc.), carbamoyl which may be substituted (e.g., carbamoyl which may be substituted with $C_{1-6}$ alkyl or acyl (e.g., formyl, $C_{2-6}$ alkanoyl, benzoyl, $C_{1-6}$ alkoxycarbonyl which may be halogenated, $C_{1-6}$ alkylsulfonyl which may be halogenated, benzenesulfonyl, etc.) which may be substituted with a 5- to 6-membered aromatic monocyclic heterocyclic group (e.g., pyridinyl, etc.), 1-azetidinylcarbonyl, 1-pyrrolidinylcarbonyl, piperidinocarbonyl, morpholinocarbonyl, thiomorpholinocarbonyl (the sulfur atom may be oxidized), 1-piperazinylcarbonyl, etc.), or the like. Any of these substituents may be substituted at 1 to 3 substitutable positions.

For the "amino which may be substituted", "hydroxyl which may be substituted" and "amidino which may be substituted" as the substituents for the "aryl which may be substituted" as a substituent for the "cyclic hydrocarbon group which may be substituted" and the "heterocyclic group which may be substituted" represented by R, mention may be made of groups such as the "amino which may be substituted", "hydroxyl which may be substituted" and "amidino which may be substituted" as the substituents for the "cyclic hydrocarbon group which may be substituted" and the "heterocyclic group which may be substituted" represented by R described below.

The "alkyl" of the "alkyl which may be substituted" as a substituent for the "cyclic hydrocarbon group which may be substituted" and the "heterocyclic group which may be substituted" represented by R, may be exemplified by $C_{1-6}$ alkyl such as methyl, ethyl, n-propyl, isopropyl, n-butyl, isobutyl, sec-butyl, tert-butyl, n-pentyl, isopentyl, neopentyl, 1-methylpropyl, n-hexyl, isohexyl, 1,1-dimethylbutyl, 2,2-dimethylbutyl, 3,3-dimethylbutyl or 3,3-dimethylpropyl or the like. Here, as the substituent for the alkyl, mention may be made of the same groups of the same number as the substituents which may be carried by the aryl of the above-described "aryl which may be substituted", and an oxo group, a thioxo group, and the like.

The "alkenyl" of the "alkenyl which may be substituted" as a substituent for the "cyclic hydrocarbon group which may be substituted" and the "heterocyclic group which may be substituted" represented by R, may be exemplified by $C_{2-6}$ alkenyl such as vinyl, allyl, isopropenyl, 2-methylallyl, 1-propenyl, 2-methyl-1-propenyl, 1-butenyl, 2-butenyl, 3-butenyl, 2-ethyl-1-butenyl, 2-methyl-2-butenyl, 3-methyl-2-butenyl, 1-pentenyl, 2-pentenyl, 3-pentenyl, 4-pentenyl, 4-methyl-3-pentenyl, 1-hexenyl, 2-hexenyl, 3-hexenyl, 4-hexenyl or 5-hexenyl, or the like. Here, as the substituent for the alkenyl, mention may be made of the same groups of the same number as the substituents which may be carried by the aryl of the above-described "aryl which may be substituted", and an oxo group, a thioxo group and the like.

The "alkynyl" of the "alkynyl which may be substituted" as a substituent for the "cyclic hydrocarbon group which may be substituted" and the "heterocyclic group which may be substituted" represented by R, may be exemplified by $C_{2-6}$ alkynyl such as ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl or 5-hexynyl, or the like. Here, as the substituent for the alkynyl, mention may be made of the same groups of the same number as the substituents which may be carried by the aryl of the above-described "aryl which may be substituted", and an oxo group, a thioxo group, and the like.

The "cycloalkyl" of the "cycloalkyl which may be substituted" as a substituent for the "cyclic hydrocarbon group which may be substituted" and the "heterocyclic group which may be substituted" represented by R, may be exemplified by $C_{3-7}$ cycloalkyl such as cyclopropyl, cyclobutyl, cyclopentyl, cyclohexyl or cycloheptyl, or the like. Here, as the substituent for the cycloalkyl, mention may be made of the same groups of the same number as the substituents which may be carried by the above-described "aryl which may be substituted", and an oxo group, a thioxo group and the like.

The "cycloalkenyl" of the "cycloalkenyl which may be substituted" as a substituent for the "cyclic hydrocarbon group which may be substituted" and the "heterocyclic group which may be substituted" represented by R, may be exemplified by $C_{3-6}$ cycloalkenyl such as cyclopropenyl, cyclobutenyl, cyclopentenyl or cyclohexenyl, or the like. Here, as the substituent for the cycloalkenyl which may be substituted, mention may be made of the same groups of the same number as the substituents which may be carried by the aryl of the above-described "aryl which may be substituted", and an oxo group, a thioxo group or the like.

The "heterocyclic group" of the "heterocyclic group which may be substituted" as a substituent" for the "cyclic hydrocarbon group which may be substituted" and the "heterocyclic group which may be substituted" represented by R, may be exemplified by the same groups as the heterocyclic groups for the "heterocyclic group which may be substituted" represented by R, or the like.

The substituent which may be carried by the heterocyclic group for the "heterocyclic group which may be substituted", may be exemplified by the same groups of the same number as the substituents which may be carried by the aryl of the above-described "aryl which may be substituted", and an oxo group, a thioxo group and the like.

As the substituent for the "amino which may be substituted", "imidoyl which may be substituted", "amidino which may be substituted", "hydroxyl which may be substituted" and "thiol which may be substituted" as substituents for the "cyclic hydrocarbon group which may be substituted" and the "heterocyclic group which may be substituted" represented by R, mention may be made of, for example, lower alkyl (e.g., $C_{1-6}$ alkyl such as methyl, ethyl, propyl, isopropyl, butyl, isobutyl, tert-butyl, pentyl or hexyl, etc.) which may be substituted with a substituent selected from a halogen atom (e.g., fluorine, chlorine, bromine, iodine, etc.) and $C_{1-6}$ alkoxy which may be halogenated (e.g., methoxy, ethoxy, trifluoromethoxy, 2,2,2-trifluoroethoxy, trichloromethoxy, 2,2,2-trichloroethoxy, etc.), acyl ($C_{1-6}$ alkanoyl (e.g., formyl, acetyl, propionyl, pivaloyl, etc.), benzoyl, $C_{1-6}$ alkylsulfonyl (e.g., methanesulfonyl, etc.), benzenesulfonyl, etc.), $C_{1-6}$ alkoxycarbonyl which may be halogenated (e.g., methoxycarbonyl, ethoxycarbonyl, trifluoromethoxycarbonyl, 2,2,2-trifluoroethoxycarbonyl, trichloromethoxycarbonyl, 2,2,2-trichloroethoxycarbonyl, etc.), $C_{1-6}$ alkoxycarbonyl which may be substituted with phenyl (e.g., benzyloxycarbonyl, etc.), a heterocyclic group (the same groups as the "heterocyclic groups" of the "heterocyclic group which may be substituted" represented by R, etc.), and the like. The "amino" of the "amino which may be substituted" as a substituent may be substituted with imidoyl which may be substituted (e.g., $C_{1-6}$ alkylimidoyl (formylimidoyl, acetylimidoyl, etc.), $C_{1-6}$ alkoxyimidoyl, $C_{1-6}$ alkylthioimidoyl, amidino, etc.), amino which may be substituted with one to two $C_{1-6}$ alkyl, or the like, and two substituents together with a nitrogen atom may form cyclic amino. In this case, the cyclic amino may be exemplified by 3- to 8-membered (preferably, 5- to 6-membered) cyclic amino such as 1-azetidinyl, 1-pyrrolidinyl, piperidino, thiomorpholino, morpholino, 1-piperazinyl, 1-piperazinyl which may have lower alkyl (e.g., $C_{1-6}$ alkyl such as methyl, ethyl, propyl, isopropyl, butyl, t-butyl, pentyl or hexyl, etc.), aralkyl (e.g., $C_{7-10}$ aralkyl such as benzyl or phenethyl, etc.), aryl (e.g., $C_{6-10}$ aryl such as phenyl, 1-naphthyl or 2-naphthyl, etc.) or the like on the 4-position, 1-pyrrolyl, 1-imidazolyl, or the like.

The "carboxyl which may be esterified or amidated" as a substituent for the "cyclic hydrocarbon group which may be substituted" and the "heterocyclic group which may be substituted" represented by R, may be exemplified by free carboxyl, esterified carboxyl, amidated carboxyl or the like.

Examples of the "esterified carboxyl" include lower alkoxycarbonyl, aryloxycarbonyl, aralkyloxycarbonyl, and the like.

Examples of the "lower alkoxycarbonyl" include $C_{1-6}$ alkoxycarbonyl such as methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl, isopentyloxycarbonyl and neopentyloxycarbonyl, and the like. Among them, $C_{1-3}$ alkoxycarbonyl such as methoxycarbonyl, ethoxycarbonyl or propoxycarbonyl is preferred.

The "aryloxycarbonyl" is preferably, for example, $C_{6-10}$ aryloxycarbonyl such as phenoxycarbonyl, 1-naphthoxycarbonyl or 2-naphthoxycarbonyl, or the like.

The "aralkyloxycarbonyl" is preferably, for example, $C_{7-10}$-aralkyloxycarbonyl such as benzyloxycarbonyl or phenethyloxycarbonyl (preferably, $C_{6-10}$ aryl-$C_{1-4}$ alkoxycarbonyl, etc.), or the like.

The "aryloxycarbonyl" and "aralkyloxycarbonyl" may be substituted, and as the substituent, the same groups of the same number as the groups exemplified as the substituents for the aryl and aralkyl as the exemplary substituents for the above-described N-monosubstituted carbamoyl are used.

The "amidated carboxyl" may be exemplified by N-monosubstituted carbamoyl and N,N-disubstituted carbamoyl, in addition to unsubstituted carbamoyl.

The substituent for the "N-monosubstituted carbamoyl" may be exemplified by lower alkyl (e.g., $C_{1-6}$ alkyl such as methyl, ethyl, propyl, isopropyl, butyl, isobutyl, tert-butyl, pentyl or hexyl, etc.), lower alkenyl (e.g., $C_{2-6}$ alkenyl such as vinyl, allyl, isopropenyl, propenyl, butenyl, pentenyl or hexenyl, etc.), cycloalkyl (e.g., $C_{3-6}$ cycloalkyl such as cyclopropyl, cyclobutyl, cyclopentyl or cyclohexyl, etc.), aryl (e.g., $C_{6-10}$ aryl such as phenyl, 1-naphthyl or 2-naphthyl, etc.), aralkyl (e.g., $C_{7-10}$ aralkyl such as benzyl or phenethyl, preferably phenyl-$C_{1-4}$ alkyl, etc.), arylalkenyl (e.g., $C_{8-10}$ arylalkenyl such as cinnamyl, preferably phenyl-$C_{2-4}$ alkenyl, etc.), a heterocyclic group (for example, the same group as the "heterocyclic group" of the above-described "heterocyclic group which may be substituted" represented by R, etc.), amino which may be substituted with one to two $C_{1-6}$ alkyl, or the like. The lower alkyl, lower alkenyl, cycloalkyl, aryl, aralkyl, arylalkenyl and heterocyclic group may be substituted, and as the substituent, mention may be made of, for example, hydroxyl, amino which may be substituted [this amino may be substituted with 1 or 2 substituents selected from, for example, lower alkyl (e.g., $C_{1-6}$ alkyl such as methyl, ethyl, propyl, isopropyl, butyl, isobutyl, tert-butyl, pentyl or hexyl, etc.), acyl (e.g., $C_{1-6}$ alkanoyl such as formyl, acetyl, propionyl or pivaloyl, benzoyl, etc.), carboxyl, $C_{1-6}$ alkoxycarbonyl and the like], halogen atom (for example, fluorine, chlorine, bromine, iodine, etc.), nitro, cyano, lower alkyl which may be substituted with 1 to 5 halogen atoms (for example, fluorine, chlorine, bromine, iodine, etc.), lower alkoxy which may be substituted with 1 to 5 halogen atoms (for example, fluorine, chlorine, bromine, iodine, etc.), and the like. The lower alkyl may be exemplified by $C_{1-6}$ alkyl such as methyl, ethyl, n-propyl, isopropyl, n-butyl, isobutyl, sec-butyl, tert-butyl, pentyl or hexyl, or the like, and particularly methyl, ethyl and the like are preferred. The lower alkoxy may be exemplified by $C_{1-6}$ alkoxy such as methoxy, ethoxy, n-propoxy, isopropoxy, n-butoxy, isobutoxy, sec-butoxy or tert-butoxy, or the like, and particularly methoxy, ethoxy and the like are preferred. It is preferable that 1, 2 or 3 (preferably, 1 or 2) of these substituents, whether identical or different, are used for the substitution.

The "N,N-disubstituted carbamoyl" refers to a carbamoyl group having two substituents on the nitrogen atom, and examples of the substituent include, on one side, the same groups as the substituents for the above-described "N-monosubstituted carbamoyl, and on the other side, for example, lower alkyl (e.g., $C_{1-6}$ alkyl such as methyl, ethyl, propyl, isopropyl, butyl, tert-butyl, pentyl or hexyl, etc.), $C_{3-6}$ cycloalkyl (e.g., cyclopropyl, cyclobutyl, cyclopentyl, cyclohexyl, etc.), $C_{7-10}$ aralkyl (e.g., benzyl, phenethyl, etc., preferably phenyl-$C_{1-4}$ alkyl, etc.), and the like. Further, two substituents together with the nitrogen atom may form cyclic amino, and in this case, the cyclic aminocarbamoyl may be exemplified by 3- to 8-membered (preferably, 5- to 6-membered) cyclic aminocarbonyl such as 1-azetidinylcarbonyl, 1-pyrrolidinylcarbonyl, piperidinocarbonyl, morpholinocarbonyl, thiomorpholinocarbonyl (the sulfur atom may be oxidized), 1-piperazinylcarbonyl, and 1-piperazinylcarbonyl which may have lower alkyl (e.g., $C_{1-6}$ alkyl such as methyl, ethyl, propyl, isopropyl, butyl, tert-butyl, pentyl or hexyl, etc.), aralkyl (e.g., $C_{7-10}$ aralkyl such as benzyl or phenethyl, etc.), aryl (e.g., $C_{6-10}$ aryl such as phenyl, 1-naphthyl or 2-naphthyl, etc.) or the like on the 4-position, or the like.

As the substituent for the "thiocarbamoyl which may be substituted" and "sulfamoyl which may be substituted" as the substituents for the "cyclic hydrocarbon group which may be substituted" and the "heterocyclic group which may be substituted" represented by R, mention may be made of the same groups as the substituents for the above-described "carbamoyl which may be substituted", or the like.

The acyl as a substituent for the "cyclic hydrocarbon group which may be substituted" and the "heterocyclic group which may be substituted" represented by R, may be exemplified by carboxylic acid-derived acyl, sulfonic acid-derived acyl, sulfinic acid-derived acyl or the like.

The "carboxylic acid-derived acyl" may be exemplified by the groups formed by the binding of carbonyl with a hydrogen atom, lower alkyl (e.g., $C_{1-6}$ alkyl such as methyl, ethyl, propyl, isopropyl, butyl, isobutyl, tert-butyl, pentyl or hexyl, etc.), lower alkenyl (e.g., $C_{2-6}$ alkenyl such as vinyl, allyl, isopropenyl, propenyl, butenyl, pentenyl or hexenyl, etc.), cycloalkyl (e.g., $C_{3-6}$ cycloalkyl such as cyclopropyl, cyclobutyl, cyclopentyl or cyclohexyl, etc.), aryl (e.g., $C_{6-10}$ aryl such as phenyl, 1-naphthly or 2-naphthyl, etc.), aralkyl (e.g., $C_{7-10}$ aralkyl such as benzyl or phenethyl, preferably phenyl-$C_{1-4}$ alkyl, etc.), arylalkenyl (e.g., $C_{8-10}$ arylalkenyl such as cinnamyl, preferably phenyl-$C_{2-4}$ alkenyl, etc.), or the like. Preferably, mention may be made of $C_{1-6}$ alkanoyl such as formyl, acetyl, propionyl or pivaloyl, benzoyl, or the like.

The "sulfonic acid-derived acyl" may be exemplified by the groups formed by the binding of sulfonyl with the groups forming the above-described "carboxylic acid-derived acyl" by binding with carbonyl, or the like. Preferably, mention may be made of $C_{1-6}$ alkylsulfonyl such as methanesulfonyl or ethanesulfonyl, benzenesulfonyl, toluenesulfonyl, or the like.

The "sulfinic acid-derived acyl" may be exemplified by the groups formed by the binding of sulfinyl with the groups forming the above-described "carboxylic acid-derived acyl" by binding with carbonyl, or the like. Preferably, mention may be made of $C_{1-6}$ alkylsulfonyl such as methanesulfinyl or ethanesulfinyl, or the like.

The substituent for the "cyclic hydrocarbon group which may be substituted" and the "heterocyclic group which may be substituted" represented by R, may be a phosphono group (for example, (mono- or di-$C_{1-4}$ alkyl)phosphono which may form a ring, such as dimethylphosphono, diethylphosphono, diisopropylphosphono, dibutylphosphono or 2-oxido-1,3,2-dioxaphosphinan-2-yl, etc.).

R is preferably an aryl group which may be substituted with a substituent selected from a halogen atom, $C_{1-6}$ alkyl, $C_{2-6}$ alkenyl, $C_{2-6}$ alkynyl, amino which may be substituted, nitro, cyano, amidino which may be substituted, and carboxyl which may be esterified or amidated; or a heterocyclic group which may be substituted with a substituent selected from a halogen atom, $C_{1-6}$ alkyl, $C_{2-6}$ alkenyl, $C_{2-6}$ alkynyl, amino which may be substituted, nitro, cyano, amidino which may be substituted, and carboxyl which may be esterified or amidated.

Among these, R is preferably aryl which may be substituted, and inter alia, aryl (preferably, $C_{6-14}$ aryl such as phenyl, 1-naphthyl or 2-naphthyl, etc.) which may be substituted with a halogen atom or $C_{2-4}$ alkenyl (preferably, a halogen atom) is preferred.

R is also preferably a heterocyclic group which may be substituted, and inter alia, a heterocyclic group (preferably, indolyl, benzofuranyl, benzothienyl, benzopyranyl, etc., more preferably indolyl) which may be substituted with a halogen atom is preferred.

In particular, R is preferably naphthyl which may be substituted with a halogen atom.

In the above-described formulas, X is a bond or a divalent chain hydrocarbon group which may be substituted.

The "divalent chain hydrocarbon group" of the "divalent chain hydrocarbon group which may be substituted" represented by X, may be exemplified by $C_{1-6}$ alkylene (for example, methylene, ethylene, trimethylene, tetramethylene, etc.), $C_{2-6}$ alkenylene (for example, vinylene, propylene, 1- or 2-butenylene, butadienylene, etc.), $C_{2-8}$ alkynylene (for example, ethynylene, 1- or 2-propynylene, 1- or 2-butynylene, etc.), or the like.

The substituent which may be carried by the "divalent chain hydrocarbon group" of the "divalent chain hydrocarbon group which may be substituted" represented by X, may be exemplified by the same groups as the substituents which may be carried by the above-described "cyclic hydrocarbon group" of the "cyclic hydrocarbon group which may be substituted" represented by R, and these substituents may substitute 1 to 3 of any substitutable positions.

X is, for example, preferably a bond, $C_{1-6}$ alkenylene or the like, and among them, a bond is more preferred.

In the above-described formulas, X' is a bond or —N($R^5$)—, and $R^5$ as used herein may be exemplified by a hydrogen atom, a hydrocarbon group which may be substituted, an esterified or amidated carboxyl group, an acyl group or the like.

The "hydrocarbon group" of the "hydrocarbon group which may be substituted" represented by $R^5$, may be exemplified by alkyl, alkenyl, alkynyl, aryl, cycloalkyl, cycloalkenyl, aralkyl or the like.

For the alkyl, alkenyl, alkynyl, aryl, cycloalkyl and cycloalkenyl, mention may be made of the same groups as the alkyl, alkenyl, alkynyl, aryl, cycloalkyl and cycloalkenyl of the "alkyl which may be substituted", "alkenyl which may be substituted", "alkynyl which may be substituted", "aryl which may be substituted", "cycloalkyl which may be substituted" and "cycloalkenyl which may be substituted", respectively, as the substituents for the above-described "cyclic hydrocarbon group which may be substituted" represented by R.

The aralkyl may be exemplified by a $C_{7-16}$ aralkyl group such as a phenyl-$C_{1-6}$ alkyl group, such as benzyl, phenethyl, 3-phenylpropyl or 4-phenylbutyl, a naphthyl-$C_{1-6}$ alkyl group such as (1-naphthyl)methyl, 2-(1-naphthyl)ethyl or 2-(2-naphthyl)ethyl, or the like.

The substituent for the "hydrocarbon group which may be substituted" represented by $R^5$, may be exemplified by the same groups as the substituents for the above-described "cyclic hydrocarbon group which may be substituted" represented by R, or the like. Among them, lower alkyl (e.g., $C_{1-6}$ alkyl such as methyl, ethyl or propyl, etc.), lower alkenyl (e.g., $C_{2-6}$ alkenyl such as vinyl or allyl, etc.), lower alkynyl (e.g., $C_{2-6}$ alkynyl such as ethynyl or propargyl, etc.), amino which may be substituted, hydroxyl which may be substituted, halogen atom, cyano, amidino which may be substituted, carboxyl, lower alkoxycarbonyl (e.g., $C_{1-6}$ alkoxycarbonyl such as methoxycarbonyl or ethoxycarbonyl, etc.), carbamoyl which may be substituted (e.g., carbamoyl which may be substituted with $C_{1-6}$ alkyl or acyl (e.g., formyl, $C_{2-6}$ alkanoyl, benzoyl, $C_{1-6}$ alkoxycarbonyl which may be halogenated, $C_{1-6}$ alkylsulfonyl which may be halogenated, benzenesulfonyl, etc.), etc.), oxo and the like are preferred, and these substituents may substitute 1 to 3 of any substitutable positions.

The "esterified or amidated carboxyl group" represented by $R^5$ may be exemplified by the same group as the "esterified or amidated carboxyl group" as a substituent for the "cyclic hydrocarbon group which may be substituted" represented by R, or the like.

The acyl group represented by $R^5$ may be exemplified by the same group as the acyl group as a substituent for the "cyclic hydrocarbon group which may be substituted" represented by R, or the like.

$R^5$ is preferably hydrogen atom, lower alkyl which may be substituted (for example, $C_{1-6}$ alkyl such as methyl, ethyl or propyl, which may be substituted with carbamoyl, amino, hydroxyl, halogen atom or the like, etc.), lower alkenyl which may be substituted (for example, $C_{2-6}$ alkenyl such as vinyl or allyl, which may be substituted with carbamoyl, amino, hydroxyl, halogen atom or the like, etc.), lower alkynyl which may be substituted (for example, $C_{2-6}$ alkynyl such as ethynyl or propargyl, which may be substituted with carbamoyl, amino, hydroxyl, halogen atom or the like, etc.), or the like. Among them, $C_{1-6}$ alkyl which may be substituted with a hydrogen atom or carbamoyl (particularly, hydrogen atom) is preferred.

$R^5$ may be also bonded to the substituent carried by the divalent chain hydrocarbon group for X, or the substituent for ring A, to form a ring. The ring may be exemplified by the same rings as the below-described "rings" formed by the binding of $R^2$ with $R^1$ or $R^4$, and $R^3$ with $R^4$, or the like.

X' is preferably a bond.

In the above-described formulas, Y is a divalent hydrocarbon group which may be substituted (preferably, a divalent chain hydrocarbon group which may be substituted).

The "divalent hydrocarbon group" of the "divalent hydrocarbon group which may be substituted" represented by Y, may be exemplified by the "divalent chain hydrocarbon group", "divalent cyclic hydrocarbon group", a divalent hydrocarbon group obtained by combination thereof, or the like.

The "divalent chain hydrocarbon group" may be exemplified by the same group as the "divalent chain hydrocarbon group" of the above-described "divalent chain hydrocarbon group which may be substituted" represented by X, or the like.

The "divalent cyclic hydrocarbon group" may be exemplified by the "divalent cyclic hydrocarbon group" formed by eliminating any one hydrogen atom from the "cyclic hydrocarbon group" of the above-described "cyclic hydrocarbon group which may be substituted" represented by R, or the like. Inter alia, mention may be made of a divalent aryl group, particularly a phenylene group or the like, is preferred, and the phenylene group may be exemplified by 1,2-phenylene, 1,3-phenylene, 1,4-phenylene or the like.

The substituent which may be carried by the divalent hydrocarbon group of the "divalent hydrocarbon group which may be substituted" represented by Y, may be exemplified by the same groups as the substituents for the above-described "cyclic hydrocarbon group which may be substituted" represented by R, or the like. Among these, lower alkyl (e.g., $C_{1-6}$ alkyl such as methyl, ethyl and propyl, etc.), lower alkenyl (e.g., $C_{2-6}$ alkenyl such as vinyl and allyl, etc.), lower alkynyl (e.g., $C_{2-6}$ alkynyl such as ethynyl and propargyl, etc;), amino which may be substituted, hydroxyl which may be substituted, cyano, amidino which may be substituted, carboxyl, lower alkoxycarbonyl (e.g., $C_{1-6}$ alkoxycarbonyl such as methoxycarbonyl and ethoxycarbonyl, etc.), carbamoyl which may be substituted (e.g., carbamoyl which may be substituted with $C_{1-6}$ alkyl or acyl (e.g., formyl, $C_{2-6}$ alkanoyl, benzoyl, $C_{1-6}$ alkoxycarbonyl which may be halogenated, $C_{1-6}$ alkylsulfonyl which may be halogenated, benzenesulfonyl, etc.), etc.), and oxo are preferred, and these substituents may substitute 1 to 3 of any substitutable positions.

Y is preferably a divalent chain hydrocarbon group which may be substituted, and inter alia, $C_{1-6}$ alkylene (particularly, ethylene, etc.) which may be substituted is preferred. Y is preferably $C_{1-3}$ alkylene substituted with hydroxyl.

In the above-described formulas, Y' is a bond or —(=O)— (carbonyl).

Y' is preferably —(=O)—.

The compound represented by Formula (I) is preferably a compound in which X is a bond, X' is a bond, Y is $C_{1-3}$ alkylene which may be substituted (preferably, Y is $C_{1-3}$ alkylene substituted with hydroxyl), and Y' is —C(=O)—.

In the above-described formulas, ring A is a nitrogen-containing heterocycle which may be substituted.

For the "nitrogen-containing heterocycle" of the "nitrogen-containing heterocycle which may be substituted" represented by ring A, among those exemplified as the "heterocycle" constituting the above-described "heterocyclic group which may be substituted" represented by R, those containing at least one nitrogen atom, and the like, mention may be made of, for example, nitrogen-containing aromatic heterocycle which contains at least one nitrogen atom as the atom (ring atom) constituting the ring system, and which may further contain 1 to 3 (preferably, 1 to 2) heteroatoms of 1 to 3 species (preferably, 1 to 2 species) selected from oxygen, sulfur and nitrogen atoms and the like; saturated or unsaturated nitrogen-containing non-aromatic heterocycle (nitrogen-containing aliphatic heterocycle); and the like. However, nitrogen-containing aliphatic heterocycle (nitrogen-containing non-aromatic heterocycle) and the like -are preferred.

The "nitrogen-containing heterocycle" of the "nitrogen-containing heterocycle which may be substituted" represented by ring A is preferably "monocyclic 5- to 12-membered nitrogen-containing heterocycle".

For the "nitrogen-containing aliphatic heterocycle", among those exemplified as the "aromatic heterocycle" constituting the above-described aromatic monocyclic heterocyclic groups and aromatic fused heterocyclic groups represented by R, mention may be made of, for example, nitrogen-containing aliphatic heterocycle in which part or all of the double bonds of the "nitrogen-containing aromatic heterocycle" containing at least one nitrogen atom are saturated, such as 3- to 8-membered (preferably, 5- to 6-membered) saturated or unsaturated (preferably, saturated) monocyclic nitrogen-containing aliphatic heterocycle such as azetidine, pyrrolidine, piperazine, morpholine, thiomorpholine, piperazine, homopiperazine or the like. Among them, piperazine, piperidine and the like are preferably used.

The substituent which may be carried by the "nitrogen-containing heterocycle" of the "nitrogen-containing heterocycle which may be substituted" represented by ring A, may be exemplified by the same groups as the substituents which may be carried by the "heterocyclic group" of the above-described "heterocyclic group which may be substituted" represented by R, and these substituents may substitute 1 to 5 (preferably, 1 to 3) of any substitutable positions.

Ring A is preferably a piperazine ring which may be substituted or a piperidine ring which may be substituted, and among these, the formula in Formula (I):

is preferably the formula:

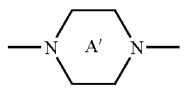

wherein ring A' may be further substituted, or the formula:

wherein ring A" may be further substituted.

In the above-described formulas, $Z^1$ and $Z^3$ are each independently a bond or a divalent chain hydrocarbon group which may be substituted.

The "divalent chain hydrocarbon group" of the "divalent chain hydrocarbon group which may be substituted" represented by $Z^1$ and $Z^3$, respectively, may be exemplified by the same group as the "divalent chain hydrocarbon group" of the "divalent chain hydrocarbon group which may be substituted" represented by X, or the like.

The substituents for the "divalent chain hydrocarbon group which may be substituted" represented by $Z^1$ and $Z^3$, respectively, may be exemplified by the same groups of the same number as the substituents for the "divalent chain hydrocarbon group which may be substituted" represented by X, or the like.

$Z^1$ and $Z^3$ are each preferably a bond, or $C_{1-6}$ alkylene such as methylene, ethylene, trimethylene or tetramethylene, or the like.

In the above-described formulas, $Z^2$ is a bond or —N($R^6$)—, wherein $R^6$ is a hydrogen atom, a hydrocarbon group which may be substituted, or an acyl group.

The "hydrocarbon group" of the "hydrocarbon group which may be substituted" represented by $R^6$, may be exemplified by the same group as the "hydrocarbon group" of the above-described "hydrocarbon group which may be substituted" represented by $R^5$, or the like.

The substituent for the "hydrocarbon group which may be substituted" represented by $R^6$, may be exemplified by the same groups of the same number as the substituents for the above-described "hydrocarbon group which may be substituted" represented by $R^5$, or the like.

The acyl group represented by $R^6$ may be exemplified by the same group as the acyl group represented by $R^5$, or the like.

$Z^2$ is preferably a bond or the like.

The compound represented by Formula (I) is preferably a compound in which $Z^1$ and $Z^2$ are each a bond, and $Z^3$ is $C_{1-3}$ alkylene which may be substituted.

In the above-described formulas, B is a group represented by the formula:

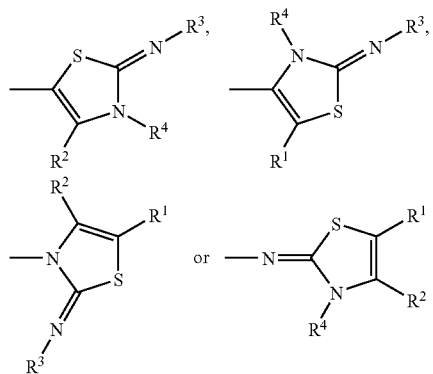

wherein $R^1$ and $R^2$ are each independently a hydrogen atom, a halogen atom, a hydrocarbon group which may be substituted, an alkoxy group which may be substituted, a carboxyl group which may be esterified or amidated, an acyl group, or an amino group which may be substituted; $R^3$ is a hydrogen atom, a hydrocarbon group which may be substituted, a carboxyl group which may be esterified or amidated, or an acyl group; $R^4$ is a hydrocarbon group which may be substituted; and $R^2$ and $R^1$ or $R^4$, and $R^3$ and $R^4$ may be respectively bonded to each other to form a ring which may be substituted.

The "hydrocarbon group" of the "hydrocarbon group which may be substituted" represented by $R^1$, $R^2$, $R^3$ and $R^4$, respectively, may be exemplified by the same group as the "hydrocarbon group" of the "hydrocarbon group which may be substituted" represented by $R^5$, or the like, and the substituents which may be carried by the "hydrocarbon group" may be exemplified by the same groups of the same number as the substituents for the above-described "hydrocarbon group which may be substituted" represented by $R^5$, or the like.

The alkoxy group of the "alkoxy group which may be substituted" represented by $R^1$ or $R^2$, may be exemplified by a $C_{1-6}$ lower alkoxy group (e.g., methoxy, ethoxy, propoxy, butoxy, pentyloxy, hexyloxy, isopropoxy, etc.).

The substituents which may be carried by the alkoxy group of the "alkoxy group which may be substituted" represented by $R^1$ or $R^2$, may be exemplified by the same groups of the same number as the substituents for the above-described "hydrocarbon group which may be substituted" represented by $R^5$, or the like.

The acyl group represented by $R^1$, $R^2$ or $R^3$ may be exemplified by the same group as the acyl group as a substituent for the "cyclic hydrocarbon group which may be substituted" represented by R, or the like.

The "carboxyl group which may be esterified or amidated" represented by $R^1$, $R^2$ or $R^3$, may be exemplified by the same group as the "carboxyl which may be esterified or amidated" as a substituent for the above-described "cyclic hydrocarbon group which may be substituted" represented by R, or the like.

The "ring" of the "ring which may be substituted" which may be formed by $R^2$ and $R^1$ or $R^4$, and $R^3$ and $R^4$, respectively, by binding to each other, may be either homocycle or heterocycle.

Examples of the "homocycle or heterocycle" include (i) aromatic heterocycle or non-aromatic heterocycle containing preferably 1 to 3 heteroatoms of 1 or 2 species selected from nitrogen, sulfur and oxygen atoms in addition to carbon atoms, and (2) cyclic hydrocarbon (homocycle) consisting of carbon atoms, and the like.

The "aromatic heterocycle" may be exemplified by a 5- to 6-membered aromatic heterocycle containing 1 to 3 heteroatoms selected from nitrogen, oxygen and sulfur atoms in addition to carbon atoms (for example, pyridine, pyrazine, pyrimidine, pyridazine, pyrrole, imidazole, pyrazole, triazole, thiophene, furan, thiazole, isothiazole, oxazole, isoxazole ring, etc.), or the like.

The "non-aromatic heterocycle" may be exemplified by a 5- to 9-membered (preferably, 5- or 6-membered) non-aromatic heterocycle containing 1 to 3 heteroatoms selected from nitrogen, oxygen and sulfur atoms in addition to carbon atoms (for example, tetrahydropyridine, dihydropyridine, tetrahydropyrazine, tetrahydropyrimidine, tetrahydropyridazine, dihydropyran, dihydropyrrole, dihydrothiophene, dihydrofuran, piperidine, piperazine, hexahydropyrimidine, hexahydropyridazine, tetrahydropyran, morpholine, pyrrolidine, pyrazoline, imidazolidine, thiazoline, isothiazoline, oxazoline, isoxazoline, pyrazolidine, tetrahydrothiophene, tetrahydrofuran, tetrahydrothiazole, tetrahydroisothiazole, tetrahydrooxazole, tetrahydroisoxazole ring, etc.), or the like.

The "cyclic hydrocarbon (homocycle)" may be exemplified by a 3- to 10-membered (preferably, 5- to 9-membered, more preferably 5- or 6-membered) cyclic hydrocarbon, or the like, for example, benzene, $C_{3-10}$ cycloalkene (for example, cyclobutene, cyclopentene, cyclohexene, cycloheptene, cyclooctene, etc.), $C_{3-10}$ cycloalkane (for example, cyclobutane, cyclopentane, cyclohexane, cycloheptane, cyclooctane, etc.), or the like. The cycloalkene is preferably $C_{5-6}$ cycloalkene (for example, cyclopentene, cyclohexene, etc.), or the like, while the cycloalkane is preferably $C_{5-6}$ cycloalkane (for example, cyclohexane, cyclopentane, etc.), or the like.

The "ring" which is formed by $R^2$ and $R^1$ or $R^4$, and $R^3$ and $R^4$ by binding to each other is preferably, for example, a 5- to 9-membered (preferably, 5- or 6-membered) non-aromatic heterocycle-containing 1 to 2 (preferably, two) nitrogen atoms in addition to carbon atoms, and inter alia, tetrahydropyridine, tetrahydropyrazine, tetrahydropyrrole, tetrahydroimidazole and the like may be mentioned as preferred examples.

The substituents for the "ring which may be substituted" which is formed by $R^2$ and $R^1$ or $R^4$, and $R^3$ and $R^4$ by binding to each other, may be exemplified by the same groups as the substituents for the above-described "heterocyclic group which may be substituted" represented by R, or the like, and these substituents may substitute 1 to 5 (preferably, 1 to 3) of any substitutable positions. The substituent for the "ring which may be substituted" is, inter alia, preferably a $C_{1-6}$ alkyl group, a hydroxyl group, an oxo group, or the like.

$R^6$ may be bonded to $R^1$, $R^2$, $R^3$ or $R^4$ to form a ring which may be substituted, and the ring may be exemplified by the same ring as the "ring" formed by $R^2$ and $R^1$ or $R^4$ by binding to each other, or the like. The substituents for the "ring which may be substituted" may be exemplified by the same groups as the substituents for the above-described "heterocyclic group which may be substituted" represented by R, and these substituents may substitute 1 to 5 (preferably, 1 to 3) of any substitutable positions.

In the above-described formulas, a is 0, 1 or 2 (preferably, 2).

For the compound represented by Formula (I), N-(4-((4-(3-((6-chloro-2-naphthyl)sulfonyl)propanoyl)-1-piperazinyl)methyl)-3-methyl-1,3-thiazol-2(3H)-ylidene)-N-methylamine, 4-((4-(3-((6-chloro-2-naphthyl)sulfonyl)propanoyl)-1-piperazinyl)methyl)-3-methyl-1,3-thiazol-2(3H)-imine, N-(5-((1-(3-((6-chloro-2-naphthyl)sulfonyl)propanoyl)-4-piperidinyl)methyl)-3-methyl-1,3-thiazol-2(3H)-ylidene)-N-methylamine, 5-(1-(3-((6-chloro-2-naphthyl)sulfonyl)propanoyl)-4-piperidinyl)-3-methyl-1,3-thiazol-2(3H)-imine, and 2-(2-((1-(3-((6-chloro-2-naphthyl)sulfonyl)propanoyl)-4-piperidinyl)imino)-1,3-thiazol-3(2H)-yl)ethanol and the like, and salts thereof are preferably used.

The salt of the compound represented by Formula (I) may be exemplified by a pharmaceutically acceptable salt or the like, for example, an acid addition salt with an acid such as trifluoroacetic acid, acetic acid, lactic acid, succinic acid, maleic acid, tartaric acid, citric acid, gluconic acid, ascorbic acid, benzoic acid, methanesulfonic acid, p-toluenesulfonic acid, cinnamic acid, fumaric acid, phosphonic acid, hydrochloric acid, nitric acid, hydrobromic acid, hydroiodic acid, sulfamic acid, sulfuric acid or the like; a salt with metal such as sodium, potassium, magnesium, calcium or the like; an organic salt such as tromethamine, t-butylamine, trimethylamine, triethylamine, pyridine, picoline, N-methylpyrrolidine, N-methylpiperidine, N-methylmorpholine or the like; or the like.

When an optically active form of Compound (I) is needed, for example, an optically active form can be obtained by using an optically active starting material, or by resolving a racemate of the compound using conventional methods.

A prodrug of Compound (I) refers to a compound which is converted to Compound (I) by an in vivo reaction caused by an enzyme, gastric acid or the like under physiological conditions, that is, a compound which is converted to Compound (I) upon occurrence of enzymatic oxidation, reduction, hydrolysis or the like, or a compound which is converted to Compound (I) upon occurrence of hydrolysis or the like by gastric acid or the like. The prodrug of Compound (I) may be exemplified by compounds resulting from acylation, alkylation or phosphorylation of the amino group of Compound (I) (for example, the compounds in which the amino group of Compound (I) is in the form of eicosanoyl, alanyl, pentylaminocarbonyl, (5-methyl-2-oxo-1,3-dioxolen-4-yl)methoxycarbonyl, tetrahydrofuranyl, pyrrolidylmethyl, pivaloyloxymethyl, tert-butyl or the like); compounds resulting from acylation, alkylation, phosphorylation or boration of the hydroxyl group of Compound (I) (for example, the compounds in which the hydroxyl group of Compound (I) is in the form of acetyl, palmitoyl, propanoyl, pivaloyl, succinyl, fumaryl, alanyl, dimethylaminomethylcarbonyl or the like); compounds resulting from esterification or amidation of the carboxyl group of Compound (I) (for example, the compounds in which the carboxyl group of Compound (I) is in the form of ethyl ester, phenyl ester, carboxymethyl ester, dimethylaminomethyl ester, pivaloyloxymethyl ester, ethoxycarbonyloxyethyl ester, phthalidyl ester, (5-methyl-2-oxo-1,3-dioxolen-4-yl)methyl ester, cyclohexyloxycarbonylethyl ester, methylamide or the like); or the like. These compounds can be prepared from Compound (I) by methods known per se in the art.

Furthermore, the prodrug of Compound (I) may be also a compound which is converted to Compound (I) under physiological conditions, as described in "Development of Pharmaceutical Products", Vol. 7, Design of Molecules, Hirokawa Publisher, pp. 163-198 (1990).

Also, Compound (I) may be labeled with isotopes (for example, $^3H$, $^{14}C$, $^{35}S$, $^{125}I$, etc.)

Compound (I) can be prepared by, for example, the following methods A to G. Each of the compounds described in the following reaction scheme may be in a salt form as long as the reaction is not adversely affected, and such salt may be exemplified by the same ones as the salts of the compound represented by Formula (I), or the like.

Method A

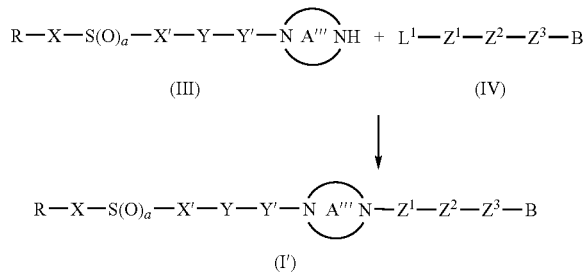

Method B

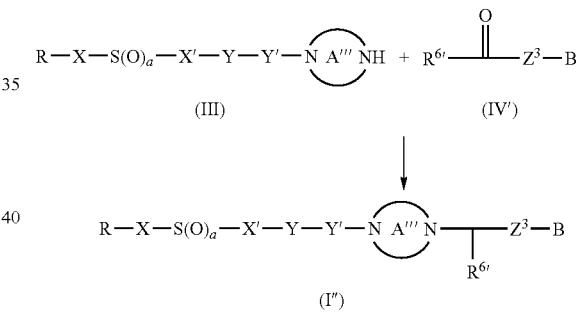

Method C

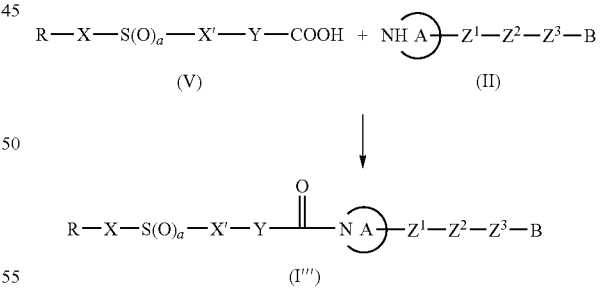

Method D

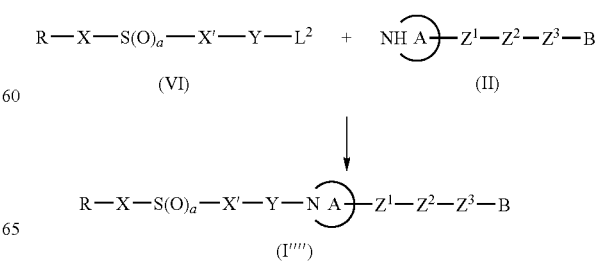

Method E

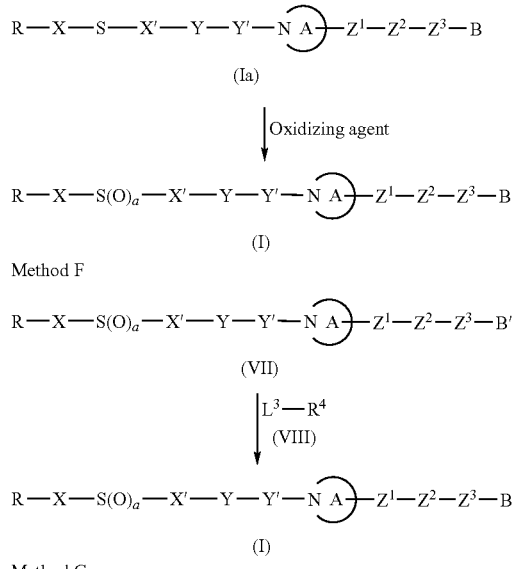

Method F

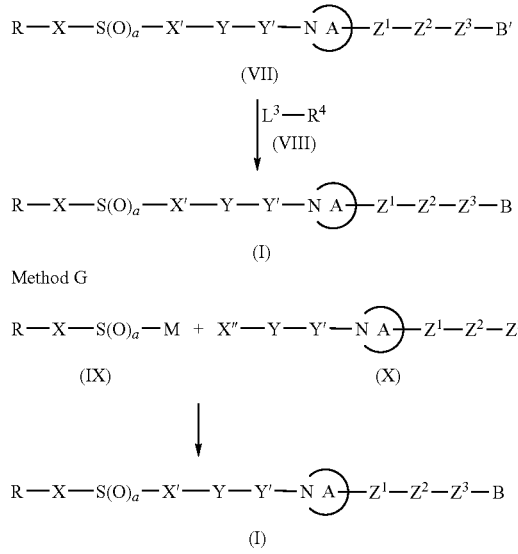

Method G

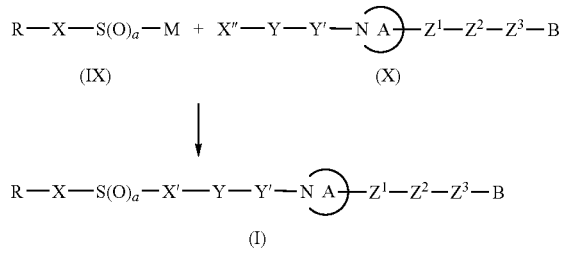

Method A

Compound (I') can be prepared by reacting Compound (IV) represented by Formula (IV):

$$L^1\text{-}Z^1\text{-}Z^{23}\text{-}B$$

wherein $L^1$ is a leaving group (for example, a halogen atom (e.g., fluorine, chlorine, bromine, iodine, etc.), or a group forming a reactive derivative of sulfonic acid (e.g., sulfonic acid ester, active sulfonic acid amide (e.g., 1,2,4-triazolide, imidazolide, etc.), quaternary aminesulfonyl product (e.g., N-methylpyrrolidinium salt, etc.), bis-sulfonylimide (e.g., N-phenylbis-sulfonylimide, etc.), etc.), or the-like)-, and the-other symbols have the meanings as defined above, or a salt thereof with Compound (III) represented by Formula (III):

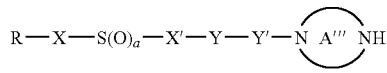

wherein ring A''' is a nitrogen-containing heterocycle which may be substituted, containing at least two nitrogen atoms as the ring atom, and the other symbols have the meanings as defined above, or a salt thereof. The salt of Compound (III) or Compound (IV) may be exemplified by the acid addition salts with the above-described acids that form acid addition salts with Compound (I).

The present reaction is in general carried out in a solvent, and a solvent which does not obstruct the reaction is appropriately selected. For such solvent, alcohols (e.g., methanol, ethanol, propanol, isopropanol, butanol, tert-butanol, etc.), ethers (e.g., dioxane, tetrahydrofuran, diethyl ether, tert-butyl methyl ether, diisopropyl ether, ethylene glycol-dimethyl ether, ethylene glycol-monomethyl ether, etc.), esters (e.g., ethyl formate, ethyl acetate, n-butyl acetate, etc.), carboxylic acids (e.g., formic acid, acetic acid, propionic acid, etc.), halogenated hydrocarbons (e.g., dichloromethane, chloroform, carbon tetrachloride, trichloroethylene, 1,2-dichloroethane, chlorobenzene, etc.), hydrocarbons (e.g., n-hexane, benzene, toluene, etc.), amides (e.g., formamide, N,N-dimethylformamide, N,N-dimethylacetamide, etc.), ketones (e.g., acetone, methyl ethyl ketone, methyl isobutyl ketone, etc.), nitrites (e.g., acetonitrile, propionitrile, etc.) and the like, as well as dimethyl sulfoxide, sulfolane, hexamethyl phosphoramide, water and the like are used individually or as mixed solvents.

The present reaction may be carried out in the presence of base, if necessary, and such base may be exemplified by inorganic bases such as lithium hydroxide, potassium hydroxide, sodium hydroxide, calcium hydroxide, sodium carbonate, potassium carbonate, sodium hydrogen carbonate, potassium hydrogen carbonate or the like; alkali metal salts of $C_{1-6}$ lower fatty acid such as sodium formate, sodium acetate, potassium acetate or the like; or tertiary amines such as triethylamine, tri(n-propyl)amine, tri(n-butyl)amine, diisopropylethylamine, cyclohexyldimethylamine, pyridine, lutidine, γ-collidine, N,N-dimethylaniline, N-methylpiperidine, N-methylpyrrolidine, N-methylmorpholine or the like.

The reaction is carried out by using 0.5 to 5 equivalents, preferably 0.8 to 2 equivalents, of Compound (IV) with respect to Compound (III).

The reaction temperature is −20 to 200° C., preferably 0 to 170° C.

The reaction time may vary depending on the type of Compound (III) or Compound (IV), type of solvent, reaction temperature or the like, but is usually about 1 minute to about 72 hours, preferably about 15 minutes to about 24 hours.

Method B

Compound (I'') can be prepared by reacting Compound (IV') represented by Formula (IV'):

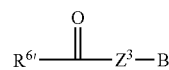

wherein $R^{6'}$ is a straight-chained hydrocarbon group which may be substituted, and the other symbols have the meanings as defined above, or a salt thereof with Compound (III) or a salt thereof. The salt of Compound (IV') or Compound (III) may be exemplified by the acid addition salts with the above-described acids forming acid addition salts with Compound (I).

In the present method, Compound (I'') can be prepared by forming an imine from Compound (IV') or a salt thereof and Compound (III) or a salt thereof, and then reducing the imine. Formation of the imine may be carried out in the presence of an acid catalyst, if necessary, and such acid catalyst may be exemplified by hydrochloric acid, sulfuric acid, carboxylic acids (e.g., formic acid, acetic acid, propionic acid, etc.), sulfonic acids (methanesulfonic acid, ethanesulfonic acid, benzenesulfonic acid, toluenesulfonic acid, camphorsulfonic acid, etc.), or the like, while the reducing agent may be exemplified by NaBH$_4$, LiBH$_4$, or the like. The present method is also applicable to the preparation of Compound (I'') by reacting Compound (IV') or a salt thereof and Compound (III) or a salt thereof (an inorganic salt, an organic salt, etc.), in the presence of the above-mentioned acid, using NaBH(OAc)$_3$ or NaCNBH$_3$.

The present reaction is in general carried out in a solvent, and a solvent which does not obstruct the reaction is appropriately selected. For such solvent, alcohols (e.g., methanol, ethanol, propanol, isopropanol, butanol, tert-butanol, etc.), ethers (e.g., dioxane, tetrahydrofuran, diethyl ether, tert-butyl methyl ether, diisopropyl ether, ethylene glycol-dimethyl ether, ethylene glycol-monomethyl ether, etc.), esters (e.g., ethyl formate, ethyl acetate, n-butyl acetate, etc.), halogenated hydrocarbons (e.g., dichloromethane, chloroform, carbon tetrachloride, trichloroethylene, 1,2-dichloroethane, chlorobenzene, etc.), hydrocarbons (e.g., n-hexane, benzene, toluene, etc.), amides (e.g., formamide, N,N-dimethylformamide, N,N-dimethylacetamide, etc.), nitriles (e.g., acetonitrile, propionitrile, etc.) and the like, as well as dimethyl sulfoxide, sulfolane, hexamethyl phosphoramide, water and the like are used individually or as mixed solvents.

The reaction is carried out by using 0.5 to 5 equivalents, preferably 0.8 to 2 equivalents, of Compound (IV') with respect to Compound (III).

The reaction temperature is −50 to 150° C., preferably −20 to 100° C.

The reaction time may vary depending on the type of Compound (III) or Compound (IV'), types of solvent and base, reaction temperature or the like, but is usually about 1 minute to about 100 hours, preferably about 15 minutes to about 48 hours.

Method C

Compound (I''') can be prepared by reacting Compound (V) represented by Formula (V):

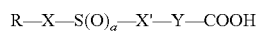

wherein the symbols have the same meanings as defined above,
or a salt thereof with Compound (II) represented by Formula (II):

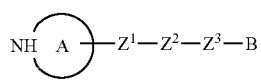

wherein the symbols have the same meanings as defined above.

The present method is carried out by reacting Compound (II) or a salt thereof with-free acid (V) or a salt thereof (an inorganic salt, an organic salt, etc.) or a reactive derivative thereof (for example, acid halide, ester, acid azide, acid anhydride, mixed acid anhydride, active amide, active ester, active thioester, etc.). The salt of Compound (II) may be exemplified by the acid addition salts with the above-described acids forming acid addition salts with Compound (I).

The inorganic salt used for Compound (V) may be exemplified by alkali metal salts (for example, sodium salts, potassium salts, etc.), alkaline earth metal salts (for example, calcium salts, etc.), while the organic salts may be exemplified by trimethylamine salts, triethylamine salts, tert-butyldimethylamine salts, dibenzylmethylamine salts, benzyldimethylamine salts, N,N-dimethylaniline salts, pyridine salts, quinoline salts or the like. The acid halide may be exemplified by acid chloride, acid bromide or the like, while the ester may be exemplified by lower alkyl esters such as methyl, ethyl or the like. The mixed acid anhydride may be exemplified by mono-$C_{1-4}$ alkyl carbonate mixed acid anhydrides (for example, mixed acid anhydrides such as free acid (V) with monomethyl carbonate, monoethyl carbonate, monoisopropyl carbonate, monoisobutyl carbonate, mono-tert-butyl carbonate, monobenzyl carbonate, mono(p-nitrobenzyl) carbonate, monoallyl carbonate or the like), $C_{1-6}$ aliphatic carboxylic acid mixed acid anhydrides (for example, mixed acid anhydrides such as free acid (V) with acetic acid, cyanoacetic acid, propionic acid, butyric acid, isobutyric acid, valeric acid, isovaleric acid, pivalic acid, trifluoroacetic acid, trichloroacetic acid, acetoacetic acid or the like), $C_{7-11}$ aromatic carboxylic acid mixed acid anhydrides (for example, free acid (V) with benzoic acid, p-toluyl acid, p-chlorobenzoic acid or the like), organic sulfonic acid mixed acid anhydrides (for example, methanesulfonic acid, ethanesulfonic acid, benzenesulfonic acid, p-toluenesulfonic acid or the like), or the like. The active amide may be exemplified by an amide with a nitrogen-containing heterocyclic compound (for example, acid amides such as free acid (V) with pyrazole, imidazole, benzotriazole, or the like and these nitrogen-containing heterocyclic compounds may be substituted with $C_{1-6}$ alkyl (for example, methyl, ethyl propyl, isopropyl, butyl, isobutyl, sec-butyl, tert-butyl, etc.), $C_{1-6}$ alkoxy (for example, methoxy, ethoxy, propoxy, isopropoxy, butoxy, tert-butoxy, etc.), halogen atom (for example, fluorine, chlorine, bromine, etc.), oxo, thioxo, $C_{1-6}$ alkylthio (for example, methylthio, ethylthio, propylthio, butylthio, etc.), etc.).

The active ester may be exemplified by organic phosphoric acid esters (for example, diethoxyphosphoric acid ester, diphenoxyphosphoric acid ester, etc.), as well as p-nitrophenyl ester, 2,4-dinitrophenyl ester, cyanomethyl ester, pentachlorophenyl ester, N-hydroxysuccinimide ester, N-hydroxyphthalimide ester, 1-hydroxybenzotriazole ester, 6-chloro-1-hydroxybenzotriazole ester, 1-hydroxy-1H-2-pyrridone ester, or the like. The active thioester may be exemplified by esters of aromatic heterocyclic thiol compounds [these heterocycles may be substituted with $C_{1-6}$ alkyl (for example, methyl, ethyl, propyl, isopropyl, butyl, isobutyl, sec-butyl, tert-butyl, etc.), $C_{1-6}$ alkoxy (for example, methoxy, ethoxy, propoxy, isopropoxy, butoxy, tert-butoxy, etc.), halogen atom (for example, fluorine, chlorine, bromine, etc.), $C_{1-6}$ alkylthio (for example, methylthio, ethylthio, propylthio, butylthio, etc.), or the like] [e.g., 2-pyridylthiol ester, 2-benzothiazolylthiol ester], or the like.

The present reaction is in general carried out in a solvent, and if necessary, is carried out in the presence of base or a condensing agent (e.g., carbodiimide (DCC, WSC, DIC, etc.), phosphoric acid derivative (e.g., diethyl cyanophosphate, DPPA, BOP-Cl, etc.), 4-(4,6-dimethoxy-1,3-5-triazin-2-yl)-4-methylmorpholinium chloride (DMTMM: Kunishima, et al., Tetrahedron, 1999, 55, 13159), etc.). For such solvent, ethers (e.g., dioxane, tetrahydrofuran, diethyl ether, tert-butyl methyl ether, diisopropyl ether, ethylene glycol-dimethyl ether, etc.), esters (e.g.-, ethyl formate, ethyl acetate, n-butyl acetate, etc.), halogenated hydrocarbons (e.g., dichloromethane, chloroform, carbon tetrachloride, trichloroethylene, 1,2-dichloroethane, chlorobenzene, etc.), hydrocarbons (e.g., n-hexane, benzene, toluene, etc.), amides (e.g., formamide, N,N-dimethylformamide, N,N-dimethylacetamide, etc.), nitriles (e.g., acetonitrile, propionitrile, etc.), as well as sulfolane, hexamethylphosphoramide, water and the like are used individually or as mixed solvents. For the base, the bases listed for the above-described Method A are used.

The reaction is carried out by using 0.5 to 5 equivalents, preferably 0.8 to 2 equivalents, of Compound (II) with respect to Compound (V).

The reaction temperature is −50 to 150° C., preferably −20 to 100° C.

The reaction time may vary depending on the type of Compound (V) or Compound (II), types of solvent and base, reaction temperature or the like, but is usually about 1 minute to about 100 hours, preferably about 15 minutes to about 48 hours.

Method D

Compound (I'''') can be prepared by reacting Compound (VI) represented by Formula (VI):

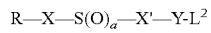

wherein $L^2$ is the same leaving group as $L^1$ of Formula (IV), and the other symbols have the same meanings as defined above, or a salt thereof with Compound (II) or a salt thereof.

The reaction of the present method is carried out in general in a solvent, and a solvent which does not obstruct the reaction is appropriately selected. For such solvent, the same solvents as those listed for the above-described Method A are used.

The present reaction may be carried out in the presence of base, and the base may be exemplified by alkali metal hydrides such as potassium hydride, sodium hydride, or the like; metal alkoxides having 1 to 6 carbon atoms such as lithium ethoxide, lithium tert-butoxide, sodium methoxide, sodium ethoxide, potassium tert-butoxide or the like; inorganic bases such as lithium hydroxide, potassium hydroxide, sodium hydroxide, sodium carbonate, potassium carbonate, sodium hydrogen carbonate or the like; or tertiary amines such as triethylamine, tri(n-propyl)amine, tri(n-butyl)amine, diisopropylethylamine, cyclohexyldimethylamine, pyridine, lutidine, γ-collidine, N,N-dimethylaniline, N-methylpiperidine, N-methylpyrrolidine, N-methylmorpholine or the like.

The reaction is carried out by using 0.5 to 10 equivalents, preferably 0.8 to 3-equivalents, of Compound (II) with respect to Compound (VI).

The reaction temperature is −30 to 250° C., preferably −10 to 150° C.

The reaction time may vary depending on the type of Compound (VI) or Compound (II), type of solvent, reaction temperature or the like, but is usually about 1 minute to 72 hours, preferably about 15 minutes to about 24 hours.

Method E

A compound in which a is 1 or 2 with respect to Formula (I) can be prepared by oxidizing Compound (Ia) represented by Formula (Ia):

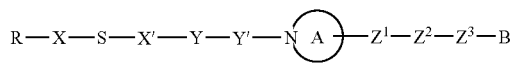

wherein the symbols have the meanings as defined above, or a salt thereof.

The oxidation reaction is carried out in the presence of an oxidizing agent. Here, the oxidizing agent may be exemplified by oxygen, hydrogen peroxide, an organic peracid such as perbenzoic acid, m-chloroperbenzoic acid, peracetic acid or the like; a perchlorate such as lithium perchlorate, silver perchlorate, tetrabutylammonium perchlorate or the like; a periodate such as odium periodate or the like; periodic acid; manganese dioxide; lead tetraacetate; a permanganate such as potassium permanganate or the like; halogen such as iodine, bromine, chlorine or the like; N-bromosuccinic acid imide, N-chlorosuccinic acid imide, sulfuryl chloride, chloramine T, or the like.

The present reaction is in general carried out in a solvent, and a solvent which does not obstruct the reaction is appropriately selected. For such solvent, alcohols (e.g., methanol, ethanol, propanol, isopropanol, butanol, tert-butanol, etc.), ethers (e.g., dioxane, tetrahydrofuran, diethyl ether, tert-butyl methyl ether, diisopropyl ether, ethylene glycol-dimethyl ether, etc.), esters (e.g., ethyl formate, ethyl acetate, n-butyl acetate, etc.), carboxylic acids (e.g., formic acid, acetic acid, propionic acid, etc.), halogenated hydrocarbons (e.g., dichloromethane, chloroform, carbon tetrachloride, trichloroethylene, 1,2-dichloroethane, chlorobenzene, etc.), hydrocarbons (e.g., n-hexane, benzene, toluene, etc.), amides (e.g., formamide, N,N-dimethylformamide, N,N-dimethylacetamide, etc.), ketones (e.g., acetone, methyl ethyl ketone, methyl isobutyl ketone, etc.), nitriles (e.g., acetonitrile, propionitrile, etc.) and the like, as well as sulfolane, hexamethyl phosphoramide, water and the like are used individually or as mixed solvents.

The present reaction can be carried out in the presence of base. For such base, inorganic bases such as, for example, alkali metal hydroxides such as lithium hydroxide, sodium hydroxide, potassium hydroxide and the like; alkali earth metal hydroxides such as magnesium hydroxide, calcium hydroxide and the like; alkali metal carbonates such as sodium carbonate, potassium carbonate and the like; alkali metal hydrogen carbonates such as sodium hydrogen carbonate, potassium hydrogen carbonate and the like are used.

The reaction is carried out by using 0.1 to 20 equivalents, preferably about 0.4 to 10 equivalents, of the oxidizing agent, and 0.1 to 20 equivalents, preferably 0.4 to 10 equivalents of the base, with respect to Compound (Ia).

The present reaction may be carried out in the presence of acid, if necessary, and for such acid, mineral acids such as hydrochloric acid, hydrobromic acid, sulfuric acid, phosphoric acid, perchloric acid and the like; sulfonic acids such as methanesulfonic acid, ethanesulfonic acid, benzenesulfonic acid, toluenesulfonic acid, camphorsulfonic acid and the like; and organic acids such as formic acid, acetic acid, propionic acid, trifluoroacetic acid and the like are used. The amount of use for these acids is 0.1 to 20 equivalents, preferably 0.5 to 10 equivalents, with respect to Compound (Ia).

The reaction temperature is about −10° C. to about 250° C., preferably about −5° C. to about 150° C.

The reaction time may vary depending on the type of Compound (Ia), types of solvent and base, reaction temperature or the like, but is usually about 1 minute to about 50 hours, preferably about 5 minutes to about 24 hours.

Method F

Compound (I) can be prepared by reacting Compound (VII) represented by Formula (VII):

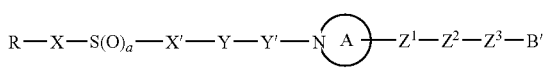

wherein B' is a group represented by the formula:

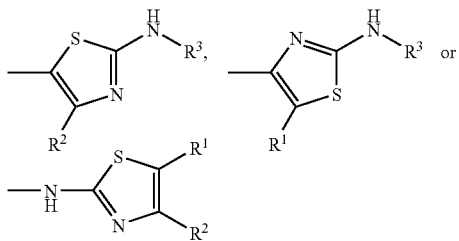

(wherein the symbols have the meanings as defined above), and the other symbols have the meanings as defined above, with Compound (VIII) represented by Formula (VIII):

$L^3\text{-}R^4$ wherein $L^3$ is a leaving group (for example, a halogen atom (e.g., fluorine, chlorine, bromine, iodine, etc.), a $C_{1-6}$ alkylsulfonyloxy group which may be substituted with 1 to 3 halogen atoms (e.g., methanesulfonyloxy, ethanesulfonyloxy, trifluoromethanesulfonyloxy, etc.), an arylsulfonyloxy group which may be substituted (e.g., benzenesulfonyloxy, p-toluenesulfonyloxy, p-bromobenzenesulfonyloxy, etc.), or the like; and the other symbols have the meanings as defined above.

The present method is carried out by reacting Compound (VII) with Compound (VIII).

The present reaction is in general carried out in a solvent, and a solvent which does not obstruct the reaction is appropriately selected. For such solvent, the same ones as the solvents listed for the above-described method D, and the like are used.

The reaction is carried out by using 0.5 to 5 equivalents, preferably 0.8 to 2 equivalents, of Compound (VIII) with respect to Compound (VII).

The reaction temperature is −50 to 150° C., preferably −20 to 100° C.

The reaction time may vary depending on the type of Compound (VII) or Compound (VIII), types of solvent and base, reaction temperature, or the like, but is usually about 1 minute to about 100 hours, preferably about 15 minutes to about 48 hours.

Method G

Compound (I) can be prepared by reacting Compound (IX) represented by Formula (IX):

$R\text{—}X\text{—}S(O)_a\text{—}M$ wherein M is a hydrogen atom, an alkali metal, an alkaline earth metal or a leaving group (for example, a halogen atom (e.g., fluorine, chlorine, bromine, iodine, etc.), and the other symbols have the meanings as defined above, or a salt thereof with a compound represented by Formula (X):

wherein X″ is alkenyl or alkynyl (preferably, $C_{2-8}$ alkenyl or $C_{2-8}$ alkynyl) in which the carbon atom at the remotest position from the carbon atom bound to Y has an unsaturated bonds, or alkyl (preferably, $C_{1-8}$ alkyl) in which the carbon atom at the remotest position from the carbon atom bound to Y has a leaving group (e.g., a halogen atom (e.g., fluorine, chlorine, bromine, iodine, etc.), a $C_{1-6}$ alkylsulfonyloxy group which may be substituted with 1 to 3 halogen atoms (e.g., methanesulfonyloxy, ethanesulfonyloxy, trifluoromethanesulfonyloxy, etc.), an arylsulfonyloxy group which may be substituted (e.g., benzenesulfonyloxy, p-toluenesulfonyloxy, p-bromobenzenesulfonyloxy, etc.), a hydroxyl group, etc.); and the other symbols have the meanings as defined above.

The present method is in general carried out in a solvent, and if necessary, is carried out in the presence of base. For such solvent and base, the same ones as the solvents and bases mentioned for the above-described Method A are used.

The reaction is carried out by using 0.5 to 3 equivalents, preferably 0.8 to 2 equivalents, of Compound (IX) with respect to Compound (X).

The reaction temperature is −50 to 150° C., preferably −20 to 120° C.

The reaction time may vary depending on the type of Compound (IX) or Compound (X), types of solvent and base, reaction temperature or the like, but is usually about 1 minute to about 100 hours, preferably about 15 minutes to about 24 hours.

The starting material compounds used in each of the above reactions can be synthesized by, for example, the following methods.

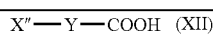
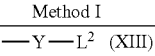
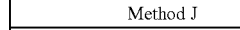
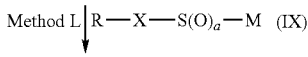
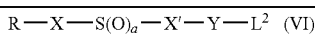

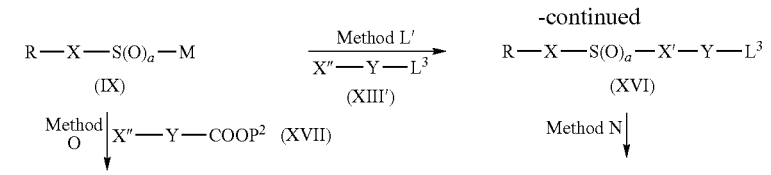
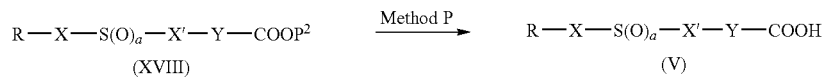
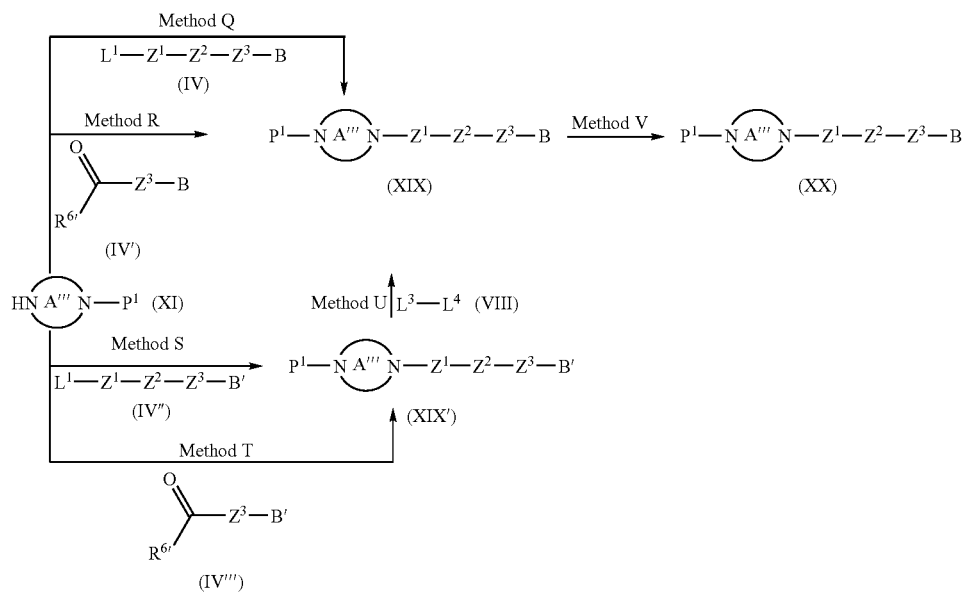
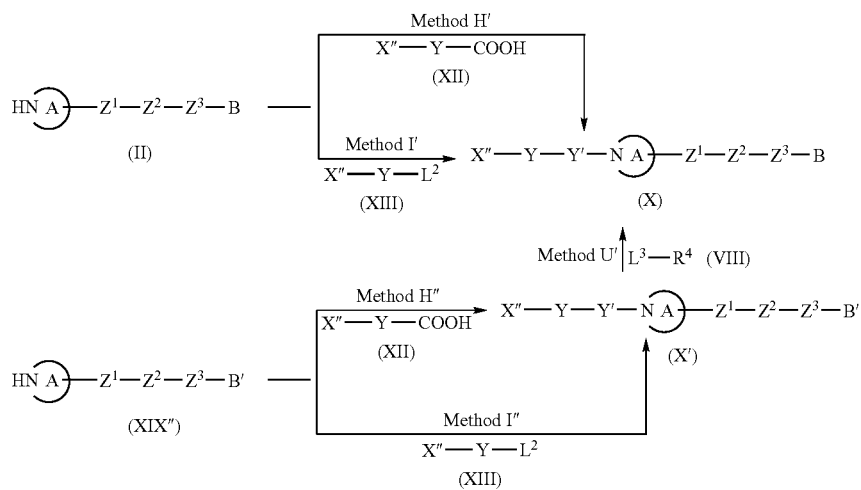

Method H

A compound in which Y' is —(C=O)— with respect to Formula (XIV):

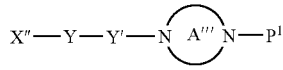

wherein the symbols have the meanings as defined above, is prepared by reacting Compound (XI) represented by Formula (XI):

wherein $P^1$ is a protective group for imino group, and the other symbols have the meanings as defined above, or a salt thereof with Compound (XII) represented by Formula (XII):

$$X''—Y—COOH$$

wherein the symbols have the meanings as defined above, or a salt thereof.

For the protective group for imino group represented by $P^1$, formyl, $C_{1-6}$ alkylcarbonyl (for example, acetyl, propionyl, etc.), benzoyl, $C_{1-6}$ alkoxycarbonyl (for example, methoxycarbonyl, ethoxycarbonyl, tert-butoxycarbonyl (Boc), etc.), allyloxycarbonyl (Aloc), phenoxycarbonyl, fluorenylmethyloxycarbonyl (Fmoc), $C_{7-10}$ aralkylcarbonyl (for example, benzylcarbonyl, etc.), $C_{7-10}$ aralkyloxycarbonyl (for example, benzyloxycarbonyl (Z), etc.), $C_{7-10}$ aralkyl (for example, benzyl, etc.), trityl, phthaloyl, N,N-dimethylaminomethylene and the like, which may be respectively substituted, are used. For their substituents, a phenyl group, a halogen atom (for example, fluorine, chlorine, bromine, iodine, etc.), a $C_{1-6}$ alkylcarbonyl (for example, methylcarbonyl, ethylcarbonyl, butylcarbonyl, etc.), a nitro group and the like are used, and the number of substituents is from about 1 to 3.

The present method can be carried out by the same method as the above-described Method C.

The reaction is carried out by using 0.5 to 5 equivalents, preferably 0.8 to 2 equivalents, of Compound (XII) with respect to Compound (XI).

The reaction temperature is −50 to 150° C., preferably −20 to 100° C.

The reaction time may vary depending on the type of Compound (XI) or Compound (XII), types of solvent and base, reaction temperature or the like, but is usually about 1 minute to about 100 hours, preferably about 15 minutes to about 48 hours.

Method I

A compound in which Y' is a bond with respect to Formula (XIV):

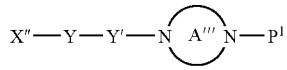

wherein the symbols have the meanings as defined above, is prepared by reacting Compound (XI) or a salt thereof with Compound (XIII) represented by Formula (XIII):

$$X''—Y-L^2$$

wherein the symbols have the meanings as defined above, or a salt thereof.

The present method can be carried out by the same method as the above-described Method D.

The reaction is carried out by using 0.5 to 5 equivalents, preferably 0.8 to 2 equivalents, of Compound (XIII) with respect to Compound (XI).

The reaction temperature is −50 to 150° C., preferably −20 to 100° C.

The reaction time may vary depending on the type of Compound (XI) or Compound (XIII), types of solvent and base, reaction temperature or the like, but is usually about 1 minute to about 100 hours, preferably about 15 minutes to about 48 hours.

Method J

A compound in which Y' is —(C=O)— with respect to Formula (XV):

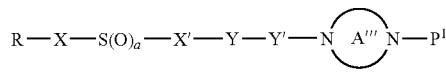

wherein the symbols have the meanings as defined above, is prepared by reacting Compound (XI) or a salt thereof with Compound (V) represented by Formula (V):

$$R—X—S(O)_a—X'—Y—COOH$$

wherein the symbols have the meanings as defined above, or a salt thereof.

The present method can be carried out by the same method as the above-described Method C.

The reaction is carried out by using 0.5 to 5 equivalents, preferably 0.8 to 2 equivalents, of Compound (V) with respect to Compound (XI).

The reaction temperature is −50 to 150° C., preferably −20 to 100° C.

The reaction time may vary depending on the type of Compound (XI) or Compound (V), types of solvent and base, reaction temperature or the like, but is usually about 1 minute to about 100 hours, preferably about 15 minutes to about 48 hours.

Method K

A compound in which Y' is a bond with respect to Formula (XV):

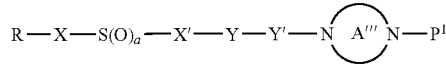

wherein the symbols have the meanings as defined above, is prepared by reacting Compound (XI) or a salt thereof with Compound (VI) represented by Formula (VI):

$$R—X—S(O)_a—X—Y-L^2$$

wherein the symbols have the meanings as defined above, or a salt thereof.

The present method can be carried out by the same method as the above-described Method D.

The reaction is carried out by using 0.5 to 5 equivalents, preferably 0.8 to 2 equivalents, of Compound (VI) with respect to Compound (XI).

The reaction temperature is −50 to 150° C., preferably −20 to 100° C.

The reaction time may vary depending on the type of Compound (XI) or Compound (VI), types of solvent and base, reaction temperature or the like, but is usually about 1 minute to about 100 hours, preferably about 15 minutes to about 48 hours.

Method L

Compound (XV) represented by Formula (XV):

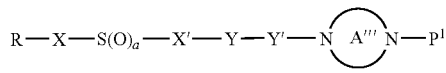

wherein the symbols have the meanings as defined above, is prepared by reacting Compound (XIV) or a salt thereof with Compound (IX) represented by Formula (IX):

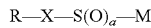

wherein the symbols have the meanings as defined above, or a salt thereof.

The present method can be carried out by the same method as the above-described Method G.

The reaction is carried out by using 0.5 to 5 equivalents, preferably 0.8 to 2 equivalents, of Compound (IX) with respect to Compound (XIV).

The reaction temperature is −50 to 150° C., preferably −20 to 100° C.

The reaction time may vary depending on the type of Compound (XIV) or Compound (IX), types of solvent and base, reaction temperature or the like, but is usually about 1 minute to about 100 hours, preferably about 15 minutes to about 48 hours.

Method M

Compound (III) represented by Formula (III):

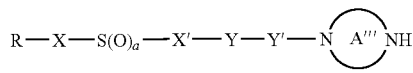

wherein the symbols have the meanings as defined above, or a salt thereof can be prepared by eliminating the protective group ($P^1$) for imino group from Compound (XV) or a salt thereof.

The method of eliminating the protective group for imino group can be carried out according to, for example, the method described in T. W. Green et al., "Protective Groups in Organic Synthesis", John Wiley & Sons, Inc., New York, or a method equivalent thereto. For example, methods of using acid, base, reduction, ultraviolet ray, palladium acetate and the like are used.

The reaction temperature is −50 to 150° C., preferably −20 to 100° C.

The reaction time may vary depending on the type of Compound (XV), types of solvent and base, reaction temperature or the like, but is usually about 1 minute to about 100 hours, preferably about 15 minutes to about 48 hours.

Method L'

Compound (XVI) represented by Formula (XVI):

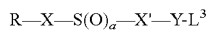

wherein the symbols have the meanings as defined above, is prepared by reacting Compound (IX) represented by Formula (IX):

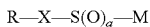

wherein the symbols have the meanings as defined above, or a salt thereof with Compound (XIII') represented by Formula (XIII'):

wherein $L^3$ is a functional group which can be derived into a carboxyl group (for example, alkoxycarbonyl, cyano, carbamoyl which may be substituted, etc.), and the other symbols have the meanings as defined above, or a salt thereof.

The present method can be carried out by the same method as the above-described Method G.

The reaction is carried out by using 0.5 to 5 equivalents, preferably 0.8 to 2 equivalents, of Compound (XIII') with respect to Compound (IX).

The reaction temperature is −50 to 150° C., preferably −20 to 100° C.

The reaction time may vary depending on the type of Compound (IX) or Compound (XIII'), types of solvent and base, reaction temperature or the like, but is usually about 1 minute to about 100 hours, preferably about 15 minutes to about 48 hours.

Method N

Compound (V) represented by Formula (V):

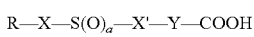

wherein the symbols have the meanings as defined above, is prepared from Compound (XVI) represented by Formula (XVI):

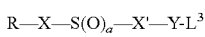

wherein the symbols have the meanings as defined above, or a salt thereof.

In the present method, $L^3$ (a functional group which can be derived into a carboxyl group) is subjected to a reaction such as acid hydrolysis (e.g., hydrochloric acid, hydrobromic acid, sulfuric acid or the like is used), alkali hydrolysis (e.g., sodium hydroxide, potassium hydroxide, lithium hydroxide, sodium carbonate, potassium carbonate, sodium hydrogen carbonate or the like is used), or the like. In addition, the reaction solvent, reaction time, reaction temperature and reaction time are set according to the reaction solvent, reaction time, reaction temperature and reaction time described in Method A, or a method equivalent thereto.

The reaction temperature is −50 to 150° C., preferably −20 to 100° C.

The reaction time may vary depending on the type of Compound (XVI), types of solvent and base, reaction temperature or the like, but is usually about 1 minute to about 100 hours, preferably about 15 minutes to about 48 hours.

Method O

Compound (XVIII) represented by Formula (XVIII):

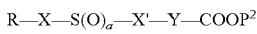

wherein the symbols have the meanings as defined above, is prepared by reacting Compound (IX) or a salt thereof with Compound (XVII) represented by Formula (XVII):

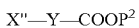

wherein P² is $C_{1-6}$ alkyl (for example, methyl, ethyl, propyl, tert-butyl, allyl, etc.) or aralkyl (benzyl, phenethyl, etc.) or the like, and the other symbols have the meanings as defined above, or a salt thereof.

The present method can be carried out by the same method as the above-described Method G.

The reaction is carried out by using 0.5 to 5 equivalents, preferably 0.8 to 2 equivalents, of Compound (XVII) with respect to Compound (IX).

The reaction temperature is −50 to 150° C., preferably −20 to 100° C.

The reaction time may vary depending on the type of Compound (IX) or Compound (XVII), types of solvent and base, reaction temperature or the like, but is usually about 1 minute to about 100 hours, preferably about 15 minutes to about 48 hours.

Method P

Compound (V) or a salt thereof can be prepared by hydrolyzing Compound (XVIII) or a salt thereof, or the like.

In the present method, the hydrolysis of ester COOP² is carried out by a reaction such as acid hydrolysis (e.g., hydrochloric acid, hydrobromic acid, sulfuric acid or the like is used), alkali hydrolysis (e.g., sodium hydroxide, potassium hydroxide, lithium hydroxide, sodium carbonate, potassium carbonate, sodium hydrogen carbonate or the like is used), or the like. In addition, the reaction solvent, reaction time, reaction temperature and reaction time are set according to the reaction solvent, reaction time, reaction temperature and reaction time described in Method A, or a method equivalent thereto.

The reaction temperature is −50 to 150° C., preferably −20 to 100° C.

The reaction time may vary depending on the type of Compound (XVIII), types of solvent and base, reaction temperature or the like, but is usually about 1 minute to about 100 hours, preferably about 15 minutes to about 48 hours.

Method Q

Compound (XIX) represented by Formula (XIX):

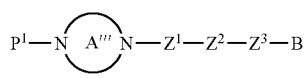

wherein the symbols have the meanings as defined above, is prepared by reacting Compound (XI) or a salt thereof with Compound (IV) or a salt thereof.

The present method can be carried out by the same method as the above-described Method A.

The reaction is carried out by using 0.5 to 5 equivalents, preferably 0.8 to 2 equivalents, of Compound (IV) with respect to Compound (XI).

The reaction temperature is −50 to 150° C., preferably −20 to 100° C.

The reaction time may vary depending on the type of Compound (XI) or Compound (IV), types of solvent and base, reaction temperature or the like, but is usually about 1 minute to about 100 hours, preferably about 15 minutes to about 48 hours.

Method R

A compound in which $Z^1$ is —CH($R^{6'}$)— and $Z^2$ is a bond with respect to Formula (XIX), is prepared by reacting Compound (XI) or a salt thereof with Compound (IV') or a salt thereof.

The present method can be carried out by the same method as the above-described Method B.

The reaction is carried out by using 0.5 to 5 equivalents, preferably 0.8 to 2 equivalents, of Compound (IV') with respect to Compound (XI).

The reaction temperature is −50 to 150° C., preferably −20 to 100° C.

The reaction time may vary depending on the type of Compound (XI) or Compound (IV'), types of solvent and base, reaction temperature or the like, but is usually about 1 minute to about 100 hours, preferably about 15 minutes to about 48 hours.

Method S

Compound (XIX') represented by Formula (XIX'):

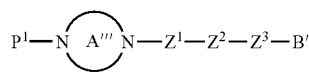

wherein the symbols have the meanings as defined above, is prepared by reacting Compound (XI) or a salt thereof with Compound (IV") represented by Formula (IV"):

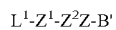

wherein the symbols have the meanings as defined above, or a salt thereof.

The present method can be carried out by the same method as the above-described Method A.

The reaction is carried out by using 0.5 to 5 equivalents, preferably 0.8 to 2 equivalents, of Compound (IV") with respect to Compound (XI).

The reaction temperature is −50 to 150° C., preferably −20 to 100° C.

The reaction time may vary depending on the type of Compound (XI) or Compound (IV"), types of solvent and base, reaction temperature or the like, but is usually about 1 minute to about 100 hours, preferably about 15 minutes to about 48 hours.

Method T

A compound in which $Z^1$ is —CH($R^{6'}$)— and $Z^2$ is a bond with respect to Formula (XIX'), is prepared by reacting Compound (XI) or a salt thereof with Compound (IV''') represented by Formula (IV'''):

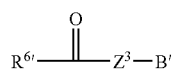

wherein the symbols have the meanings as defined above, or a salt thereof.

The present method can be carried out by the same method as the above-described Method B.

The reaction is carried out by using 0.5 to 5 equivalents, preferably 0.8 to 2 equivalents, of Compound (IV''') with respect to Compound (XI).

The reaction temperature is −50 to 150° C., preferably −20 to 100° C.

The reaction time may vary depending on the type of Compound (XI) or Compound (IV'''), types of solvent and base, reaction temperature or the like, but is usually about 1 minute to about 100 hours, preferably about 15 minutes to about 48 hours.

Method U

Compound (XIX) or a salt thereof can be prepared by reacting Compound (XIX') or a salt thereof with Compound (VIII).

The reaction conditions, reaction solvent, reaction time and the like for the present reaction are set according to the reaction conditions and the like described for the reaction between Compound (VII) and Compound (VIII) according to Method F, or a method equivalent thereto.

Method V

Compound (XX) represented by Formula (XX):

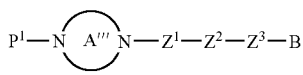

wherein the symbols have the meanings as defined above, or a salt thereof can be prepared by eliminating the protective group ($P^1$) on the nitrogen atom constituting ring A of Compound (XIX) or a salt thereof.

The reaction conditions, reaction solvent, reaction time and the like for the present reaction are set according to the reaction conditions and the like described for the deprotection reaction for Compound (XV) according to Method M, or a method equivalent thereto.

Method H'

A compound in which Y' is —(C=O)— with respect to Formula (X) is prepared by reacting Compound (II) or a salt thereof with Compound (XII) or a salt thereof.

The present method can be carried out by the same method as the above-described Method C.

The reaction is carried out by using 0.5 to 5 equivalents, preferably 0.8 to 2 equivalents, of Compound (XII) with respect to Compound (II).

The reaction temperature is −50 to 150° C., preferably −20 to 100° C.

The reaction time may vary depending on the type of Compound (II) or Compound (XII), types of solvent and base, reaction temperature or the like, but is usually about 1 minute to about 100 hours, preferably about 15 minutes to about 48 hours.

Method I'

A compound in which Y' is a bond with respect to Formula (X) is prepared by reacting Compound (II) or a salt thereof with Compound (XIII) or a salt thereof.

The present method can be carried out by the same method as the above-described Method D.

The reaction is carried out by using 0.5 to 5 equivalents, preferably 0.8 to 2 equivalents, of Compound (XIII) with respect to Compound (II).

The reaction temperature is −50 to 150° C., preferably −20 to 100° C.

The reaction time may vary depending on the type of Compound (II) or Compound (XIII), types of solvent and base, reaction temperature or the like, but is usually about 1 minute to about 100 hours, preferably about 15 minutes to about 48 hours.

Method H"

A compound in which Y' is —(C=O)— with respect to Formula (X'):

is prepared by reacting Compound (XIX") represented by Formula (XIX"):

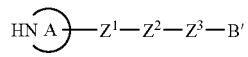

wherein the symbols have the meanings as defined above, or a salt thereof with Compound (XII) or a salt thereof.

The present method can be carried out by the same method as the above-described Method C.

The reaction is carried out by using 0.5 to 5 equivalents, preferably 0.8 to 2 equivalents, of Compound (XII) with respect to Compound (XIX").

The reaction temperature is −50 to 150° C., preferably −20 to 100° C.

The reaction time may vary depending on the type of Compound (XIX") or Compound (XII), types of solvent and base, reaction temperature or the like, but is usually about 1 minute to about 100 hours, preferably about 15 minutes to about 48 hours.

Method I"

A compound in which Y' is a bond with respect to Formula (X') is prepared by reacting Compound (XIX") or a salt thereof with Compound (XIII) or a salt thereof.

The present method can be carried out by the same method as the above-described Method D.

The reaction is carried out by using 0.5 to 5 equivalents, preferably 0.8 to 2 equivalents, of Compound (XIII) with respect to Compound (XIX").

The reaction temperature is −50 to 150° C., preferably −20 to 100° C.

The reaction time may vary depending on the type of Compound (XIX") or Compound (XIII), types of solvent and base, reaction temperature or the like, but is usually about 1 minute to about 100 hours, preferably about 15 minutes to about 48 hours.

Method U'

Compound (X) or a salt thereof can be prepared by reacting Compound (X') or a salt thereof with Compound (VIII).

The reaction conditions, reaction solvent, reaction time and the like for the present reaction are set according to the reaction conditions and the like described for the reaction between Compound (VII) and Compound (VIII) according to Method F, or a method equivalent thereto.

Other starting material Compounds (IV), (IV'), (VI), (VIII) and (IX) can be prepared according to methods known per se, or methods equivalent thereto.

When the compounds are obtained in their free forms by the above-described reactions, the compounds may be converted to salt forms according to conventional methods, and when the compounds are obtained in salt forms, the compounds may be converted to free products or other salts according to conventional methods.

Here, the salt may be any salt as long as it does not adversely affect the reaction, but for example, the same ones as the salts used as Compound (I) may be mentioned.

In the respective reactions for the syntheses of the above-described Compound (I) and starting material compounds, when a starting material compound has an amino group, a carboxyl group, a hydroxyl group or the like as the substituent, those in which the protective groups that are in general likely to be used in peptide chemistry or the like have been introduced, may be used as such groups, and after the reaction, the desired compounds can be obtained by eliminating the protective groups, if necessary.

For the protective group for amino group, for example, the same groups as the above-described protective groups for imino group, and phthaloyl and the like are used.

For the protective group for carboxyl group, for example, $C_{1-6}$ alkyl (for example, methyl, ethyl, n-propyl, isopropyl, n-butyl, tert-butyl, etc.) which may be substituted, allyl, benzyl, phenyl, trityl, trialkylsilyl and the like are used. For their substituent, halogen atom (for example, fluorine, chlorine, bromine, iodine, etc.), formyl, $C_{1-6}$ alkylcarbonyl (for example, acetyl, propionyl, valeryl, etc.), nitro and the like are used, and the number of substituents is about 1 to 3.

For the protective group for hydroxyl group, for example, $C_{1-6}$ alkyl (for example, methyl, ethyl, n-propyl, isopropyl, n-butyl, tert-butyl, etc.) which may be substituted, $C_{7-10}$ aralkyl (for example, benzyl, etc.), formyl, $C_{1-6}$ alkylcarbonyl (for example, acetyl, propionyl, etc.), benzoyl, $C_{7-10}$ aralkylcarbonyl (for example, benzylcarbonyl, etc.), tetrahydropyranyl, furanyl, silyl and the like are used. For their substituent, halogen atom (for example, fluorine, chlorine, bromine, iodine, etc.), $C_{1-6}$ alkyl (for example, methyl, ethyl, n-propyl, etc.), phenyl, $C_{7-10}$ aralkyl (for example, benzyl, etc.), $C_{1-6}$ alkoxy (for example, methoxy, ethoxy, n-propoxy, etc.), nitro and the like are used, and the number of substituents is about 1 to 4.

For the method of eliminating protective groups, methods known per se, or methods equivalent thereto are used, and for example, methods of treating with acid, base, reduction, ultraviolet ray, hydrazine, phenylhydrazine, sodium N-methyldithiocarbamate, tetrabutylammonium fluoride, palladium acetate and the like are used.

The Compound (I) thus obtained can be isolated and purified from the reaction mixture by means that are known per se, for example, by using means such as extraction, concentration, neutralization, filtration, recrystallization, column chromatography, thin layer chromatography and the like.

The salt of the compound represented by Formula (I) can be prepared by means that are known per se, for example, by adding an inorganic acid or an organic acid to the compound represented by Formula (I).

When Compound (I) is obtained as optical isomers, these individual optical isomers and mixtures thereof are of course included in the scope of the invention, and if desired, these isomers can be optically resolved according to methods known per se, or can be prepared individually.

Compound (I) may be also a hydrate, and hydrates and anhydrates are all included in the scope of the invention.

The compound represented by Formula (II'):

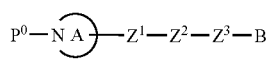

(II')

wherein $P^0$ is a hydrogen atom or a protective group for imino group, and the other symbols have the meanings as defined above, or a salt thereof is useful as a synthetic intermediate of pharmaceutical compound for Compound (I), or the like.

For the protective group for imino group represented by $P^0$, the same ones as the above-described protective groups for imino group represented by $P^1$, and the like are used.

The compound (I) or its salt of the present invention is safe with low toxicity (for example, it is superior as medicaments from the viewpoints such as acute toxicity, chronic toxicity, genetic toxicity, reproductive toxicity, cardiac toxicity, drug interactions, carcinogenicity, and the like), inhibits FXa, and has anticoagulation effect; therefore it is useful for preventing and treating various arterial and venous thrombosis of animals, in particular mammals (for example, human being, monkey, cat, pig, horse, cattle, mouse, rat, guinea pig, dog, rabbit, and the like), for example, myocardial infarction, cerebral infarction, deep vein thrombosis, pulmonary thromboembolism or atherosclerotic obliterans, economy-class syndrome, thromboembolism during and post operation, and the following disorders.

Among these, it is preferably used for preventing and treating ischemic cerebral infarction (in particular, thromboembolic stroke due to atrial fibrillation, and the like; and ischemic cerebral infarction caused by progression of atherosclerosis or activation of blood coagulation system), deep vein thrombosis or pulmonary thromboembolism.

Brain:

Prevention or treatment of cerebral infarction, ischemic cerebrovascular disorder, thromboembolic stroke caused by atrial fibrillation, heart failure or valvular disease, acute ischemic cerebral apoplexy, acute stage cerebral thrombosis, cerebrovascular contraction after subarachnoid hemorrhage, Alzheimer's disease, transient ischemic attack (TIA), mixed dementia, cerebrovascular dementia, asymptomatic/multiple cerebral infarction, lacunar infarction and the like, prognosis improvement or secondary onset prevention of cerebral infarction, prevention or treatment of thrombus after an extracranial and intracranial arterial bypass operation, combination use or supplemental use with a thrombolytic agent against cerebral infarction (among them, ischemic cerebrovascular disorder), combination therapy with an anti-platelet drug such as aspirin in preventing onset of cerebral infarction.

Heart:

Prevention or treatment of acute coronary disease such as acute myocardial infarction, myocardial infarction, ischemic coronary disease, unstable angina, myocardiopathy, acute heart failure, congestive chronic heart failure, valvular disease and the like, prognosis improvement or secondary onset prevention of acute coronary disease such as angina, prevention or treatment of thrombus formation after artificial valve or artificial heart replacement, prevention or treatment of vascular reocclusion and restenosis after coronary intervention such as stent indwelling or PTCA (percutaneous transluminal coronary angioplasty) or atherectomy, prevention or treatment of vascular reocclusion and restenosis after coronary bypass operation, combination use or supplemental use with a thrombolytic agent against acute coronary disease, combination therapy with an anti-platelet drug such as aspirin in preventing onset of myocardial infarction.

Periphery:

Prevention or treatment of deep vein thrombosis, chronic arterial obliterans, atherosclerotic obliterans, peripheral circulation failure such as Buerger's disease, peripheral circulation failure after frostbite, aneurysm, varix, adult respiratory distress syndrome, acute renal failure, chronic renal disease (e.g. diabetic nephropathy, chronic glumerular nephritis, IgA nephropathy etc.), diabetic circulation disorder, pain, nerve disorder, diabetic complication such as diabetic retinopathy and the like, prognosis improvement or secondary onset prevention of deep vein thrombosis, prevention or treatment of deep vein thrombosis or pulmonary thromboembolism after a joint operation including total hip arthroplasty (THA) or total knee arthroplasty (TKA), prevention or treatment of deep vein thrombosis or pulmonary thromboembolism after an orthopedic, plastic surgical or general surgical operation including a spine operation, prevention or treatment of thrombus after a peripheral vascular bypass operation or artificial vessel or vena cava filter indwelling, prevention or treatment of reocclusion and restenosis after stent indwelling or PTA (percutaneous transluminal angioplasty) or peripheral vascular intervention such as atherectomy, prevention or treatment of deep vein thrombosis or pulmonary thromboembolism accompanied with acute internal disease, combination use or supplemental therapy with a thrombolytic agent against deep vein thrombosis and pulmonary thromboembolism, combination therapy with an anti-platelet drug such as aspirin in therapy of peripheral circulation failure such as arteriosclerotic obliterans.

Others:

Prevention or treatment of pulmonary embolism, acute pulmonary embolism, economy class syndrome, thrombocytopenia or activation of blood coagulation system or complement activation caused by dialysis, thrombocytopenia on a major operation, thrombocytopenic purpura, disseminated intravascular coagulation syndrome (DIC) developed in a patient suffering from progression of arteriosclerosis or cancer metastasis or systemic inflammatory reaction syndrome (SIRS) or pancreatitis or cancer or leukemia or a major operation or sepsis or the like, various organ disorders such as liver function disorder caused by oligemia or ischemia or retention of blood, various organ failures caused by progression of shock or DIC (e.g. lung failure, liver failure, kidney failure, heart failure etc.), systemic lupus erythematosus, diffuse collagen disease, hyperthyroidism, puerperal palsy and the like, inhibition of rejective response on transplantation, organ protection or function improvement on transplantation, prevention of perfusion blood coagulation during blood extracorporeal circulation, substitute therapeutic use against development of thrombocytopenia caused by heparin administration, promotion of bedsore or wound healing, inhibition of activation of blood excessive coagulation reaction on various hormone supplement therapy, substitute therapeutic use for a patient resistant or contraindicative to a coumarin drug including warfarin, inhibition of activation of excessive coagulation reaction on administration of a blood preparation or a blood coagulation factor-containing preparation, and the like.

Compound (I) of the invention can be administered orally or parenterally, as received or as a mixture with a pharmaceutically acceptable carrier.

The preparation of the invention containing Compound (I) of the invention may be exemplified, as a formulation for oral administration, by tablet (including sugar-coated tablet and film-coated tablet), pill, granule, powder, capsule (including soft capsule and microcapsule), syrup, emulsion, suspension or the like; and as a formulation for parenteral administration, by injectable preparation, infusion, drip infusion, suppository or the like. It is also effective for the preparation to be provided as combination sustained release preparations with suitable bases (e.g., polymers of butyric acid, polymers of glycolic acid, copolymers of butyric acid-glycolic acid, mixture of polymers of butyric acid and polymers of glycolic acid, polyglycerol fatty acid esters, etc.).

The content of Compound (I) in the preparation of the invention may vary depending on the form of preparation, but is usually 2 to 85% by weight, preferably 5 to 70% by weight, with respect to the total preparation.

For the method of preparing Compound (I) in the above-described formulations, it is possible to apply known preparation methods that are generally used in the related art. When the above-described formulations are prepared, it is possible, if necessary, to prepare the formulations by suitably adding appropriate amounts of excipient, binding agent, disintegrant, gliding agent, sweetener, surfactant, suspending agent, emulsifying agent and the like that are conventionally used in the art of pharmaceutical preparation.

For example, when Compound (I) is prepared into a tablet, preparation can be carried out by adding excipient, binding agent, disintegrant, gliding agent and the like; while when prepared into a pill or a granule, preparation can be carried out by adding excipient, binding agent, disintegrant and the like. When Compound (I) is prepared into a powder or a capsule, preparation can be carried out by adding excipient and the like; when prepared into a syrup, by adding sweetener and the like; and while when prepared into an emulsion or a suspension, by adding suspending agent, surfactant, emulsifying agent and the like.

Examples of the excipient include lactose, white sugar, glucose, starch, sucrose, microcrystalline cellulose, powdered licorice, mannitol, sodium hydrogen carbonate, calcium phosphate, calcium sulfate and the like.

Examples of the binding agent include a 5 to 10 wt % starch liquid paste, a 10 to 20 wt % gum arabic solution or gelatin solution, a 1 to 5 wt % tragacanth solution, a carboxymethylcellulose solution, a sodium alginate solution, glycerin and the like.

Examples of the disintegrant include starch, calcium carbonate and the like.

Examples of the gliding agent include magnesium stearate, stearic acid, calcium stearate, purified talc and the like.

Examples of the sweetener include glucose, fructose, invert sugar, sorbitol, xylitol, glycerin, simple syrup and the like.

Examples of the surfactant include sodium lauryl sulfate, Polysorbate 80, sorbitan monofatty acid ester, Polyoxyl 40 stearate and the like.

Examples of the suspending agent include gum arabic, sodium alginate, carboxymethylcellulose sodium, methylcellulose, bentonite and the like.

Examples of the emulsifying agent include gum arabic, tragacanth, gelatin, Polysorbate 80 and the like.

In addition, when Compound (I) is prepared into the above-described formulations, if desired, appropriate amounts of colorant, preservative, fragrance, flavoring agent, stabilizer, thickening agent and the like that are conventionally used in the art of purification can be suitably added.

The preparation of the invention containing Compound (I) can be used safely with stability and low toxicity. Daily dose of the preparation may vary depending on the condition or body weight of the patient, type of compound, administration route and the like; however, for example, when the preparation is to be orally administered to a patient having thrombosis, the daily dose for adult (body weight about 60 kg) is about 1 to 1000 mg, preferably about 3 to 500 mg, and more preferably about 5 to 300 mg, in terms of the effective ingredient (the compound represented by Formula (I) or a salt thereof), which can be administered all at once, or in 2 to 3 portions.

When Compound (I) of the invention is to be parenterally administered, it is usually administered in the form of liquid formulation (for example, injectable preparation). Daily dose thereof may vary depending on the subject of administration, subject organ, symptoms, administration method and the like; however, the preparation is favorably administered, for example, in the form of injectable preparation in an amount of usually about 0.01 mg to about 100 mg, preferably about 0.01 to about 50 mg, and more preferably about 0.01 to about 20 mg, per 1 kg of body weight, through intravenous injection. The injectable preparation includes, in addition to intravenous injectable preparation, subcutaneous injectable preparation, intradermal injectable preparation, muscular injectable preparation, drip infusion preparation and the like, while the sustained preparation includes iontophoretic transdermal preparation and the like. Such injectable preparations are prepared by methods known per se, that is, by dissolving, suspending or emulsifying Compound (I) of the invention in sterile aqueous liquid or oily liquid. Examples of the aqueous liquid for injection include physiological saline, isotonic solutions containing glucose or other pharmaceutical adjuvants (for example, D-sorbitol, D-mannitol, sodium chloride, etc.) and the like, and these may be used in combination with appropriate dissolution aids, for example, alcohol (for example, ethanol), polyalcohol (for example, propylene glycol, polyethylene glycol), nonionic surfactant (for example, Polysorbate 80, HCO-50) and the like. Examples of the oily liquid include sesame oil, soybean oil and the like, and these may be used in combination with dissolution aids such as benzyl benzoate, benzyl alcohol and the like. Furthermore, buffering agent (for example, phosphate buffer solution, sodium acetate buffer solution), soothing agent (for example, benzalkonium chloride, procaine chloride, etc.), stabilizer (for example, human serum albumin, polyethylene glycol, etc.), preservative (for example, benzyl alcohol, phenol, etc.) and the like may be mixed therewith. Prepared injection liquids are usually filled in ampoules.

The preparation of the invention can be used in combination with suitable drugs (hereinafter, abbreviated to combination drugs) such as thrombolytic agent (e.g., TPA, heparin, urokinase, etc.), Alzheimer's drug (for example, Avan, Calan, etc.), anti-cholesterol drug (e.g., HMG-CoA reductase inhibitor such as simvastatin or pravastatin, etc.), TG lower drug (e.g., Clofibrat, etc.), AII antagonistic drug (e.g., candesartan cilexetil, losartan, etc.), antiplatelet drug (e.g., clopidogrel, abciximab, aspirin, etc.), Ca antagonistic drug (e.g., calslot, amlodipine, etc.), ACE inhibitor (e.g., enalapril, captopril, etc.), β-blocking drug (e.g., metoprolol, carvedilol, etc.), anti-arrhythmic drug (e.g., procaine amide, etc.), and the like. These combination drugs may be low molecular weight compounds, or may be proteins of high molecular weight, polypeptides, antibodies, vaccines or the like. Here, the administration form of the compound of the invention and the combination drugs is not particularly limited, and it is favorable that the compound of the invention and the combination drugs are in a combined state upon administration. For such administration form, for example, mention may be made of (1) administration of a single preparation obtained by simultaneously formulating the compound of the invention and the combination drug, (2) simultaneous administration through the same administration route of two preparations obtained by separately formulating the compound of the invention and the combination drug, (3) administration with a time interval through the same administration route of two preparations obtained by separately formulating the compound of the invention and the combination drug, (4) simultaneous administration through different administration routes of two preparations obtained by separately formulating the compound of the invention and the combination drug, (5) administration with a time interval through different administration routes of two preparations obtained by separately formulating the compound of the invention and the combination drug (for example, administration in order of the compound of the invention→combination drug, or administration in the reverse order), or the like. The amount of the combination drug to be administered can be appropriately selected with reference to the clinically used dosage. The mixing ratio of the compound of the invention and the combination drug can be appropriately selected in accordance with the subject of administration, administration route, disease to be treated, symptoms, combination, and the like. For example, when the subject of administration is human, the combination drug may be used in an amount of 0.01 to 100 parts by weight relative to 1 part by weight of the compound of the invention.

Compound (I) of the invention has excellent FXa inhibiting effect, and is useful as an anti-coagulant capable of oral uptake and having less side effect of hemorrhage. Compound (I) of the invention is advantageously used for the prevention and/or treatment of various diseases caused by thrombus and infarction.

The present invention is further described in detail in reference to Examples, Preparation Examples and Experimental Examples, but they are not intended to limit the invention and may be modified in the range not to be construed to limit the scope thereof.

The elution in column chromatography of Examples was carried out under observation by means of TLC (Thin Layer Chromatography). In the TLC observation, 60F254 (manufactured by Merck & Co., Inc.) or NH (manufactured by Fuji Silysia Chemical, Ltd.) were adopted as a TLC plate, the solvent used for the elution in column chromatography was adopted as an eluent, a UV detector was adopted as the means for detection. As the silica gel for column, Kieselgel 60 (70 to 230 meshes) or Kieselgel 60 (230 to 400 meshes) was used. As the basic silica gel for column, NH-DM 1020 (manufactured by Fuji Silysia Chemical, Ltd.; 100 to 200 mesh) was used. NMR spectra were measured with a Varian Gemini 200 spectrometer by using tetramethylsilane as internal or external standard. The chemical shift was indicated by δ, and a coupling constant was indicated by Hz. IR spectra were measured with a Shimadzu FTZR-8200 spectrometer. The numeric value in parenthesis with regard to a mixed solvent is a volumetric mixing ratio of each solvent. Moreover, "%" in the solution represents the number of grams in 100 mL of a solution. Abbreviations employed in Examples are described below.

s: singlet
d: doublet
t: triplet
q: quartet
dd: double doublet
m: multiplet
br: broad
brs: broad singlet
brd: broad doublet
J: coupling constant
WSC: water soluble carbodiimide
THF: tetrahydrofuran
DMF: dimethylformamide
DMSO: dimethyl sulfoxide
HOBt: 1-hydroxybenzotriazole
AIBN: 2,2'-azobis(isobutyronitrile)

NBS: N-bromosuccinimide
Me: methyl
Et: ethyl
Pr: propyl
Bu: butyl
Ac: acetyl

EXAMPLE 1

3-((1-(3-((6-Chloro-2-naphthyl)sulfonyl)propanoyl)-1-piperidinyl)methyl)-5,6-dihydroimidazo[2,1-b][1,3]thiazole hydrochloride

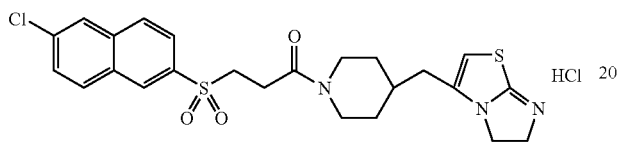

1a) tert-Butyl 4-((5,6-dihydroimidazo[2,1-b][1,3]thiazol-3-yl)methyl)piperidine-1-carboxylate hydrobromide tert-Butyl 4-(2-oxopropyl)piperidine-1-carboxylate (1.0 g) and 5,5-dibromobarbituric acid (1.2 g) were dissolved in ether (30 mL) and mixed overnight. The precipitated crystals were filtered off, and the filtrate was concentrated. To the residue were added ethylenethiourea (0.46 g) and ethanol (30 mL), and the mixture was refluxed overnight. The precipitated crystals were collected by filtration to give the title compound (0.55 g) as pale yellow crystals.

NMR (CDCl$_3$) δ: 1.02-1.21 (2H, m), 1.45 (9H, s), 1.66-1.91 (3H, m), 2.20 (1H, d, J=6.9), 2.61-2.80 (2H, m), 3.73 (2H, t, J=9.3), 4.07-4.13 (2H, m), 4.22 (2H, t, J=9.3), 5.23 (1H, s).

1b) 3-((1-(3-((6-Chloro-2-naphthyl)sulfonyl)propanoyl)-1-piperidinyl)methyl)-5,6-dihydroimidazo[2,1-b][1,3]thiazole The compound (0.55 g) obtained in Example 1a) was dissolved in trifluoroacetic acid (10 mL) and mixed at room temperature for 1 hour. The solvent was concentrated, and then to the residue were added dichloromethane (20 mL) and triethylamine (0.38 mL). With ice cooling, 3-((6-chloro-2-naphthyl)sulfonyl)propionic acid (0.4 g), HOBt (0.23 g) and WSC (0.29 g) were added thereto and mixed at room temperature for 16 hours. The reaction solution was basified with an aqueous potassium carbonate solution, then extracted with chloroform, and the extract was dried over anhydrous magnesium sulfate. The solvent was distilled off, and the residue was purified with a basic silica gel column to give the title compound (0.13 g) as a white powder.

NMR (CDCl$_3$) δ: 1.08-1.22 (1H, m), 1.78-1.93 (3H, m), 2.25-2.31 (2H, m), 2.53-2.69 (1H, m), 2.90-3.15 (4H, m), 3.59-3.85 (2H, m), 3.80-3.95 (3H, m), 4.32 (2H, t, J=9.2), 4.55-4.62 (1H, m), 5.40 (1H, s), 7.66 (1H, dd, J=2.2, 8.8), 7.95-8.05 (4H, m), 8.55 (1H, s).

1c) 3-((1-(3-((6-Chloro-2-naphthyl)sulfonyl)propanoyl)-1-piperidinyl)methyl)-5,6-dihydroimidazo[2,1-b][1,3]thiazole hydrochloride The compound (0.23 g) obtained in Example 1b) was treated with a solution of hydrogen chloride in ether to give the title compound (0.16 g) as white crystals.

NMR (DMSO-d$_6$) δ: 0.65-0.91 (1H, m), 0.96-1.22 (2H, m), 1.43-4.79 (3H, m), 2.30-2.47 (2H, m), 2.60-2.79 (2H, m), 2.84-3.12 (1H, m), 3.52-3.68 (2H, m), 3.69-3.89 (1H, m), 4.07-4.40 (5H, m), 6.49 (1H, s), 7.96-7.73 (1H, m), 7.93-7.97 (1H, m), 8.17-8.28 (3H, m), 8.61 (1H, s), 9.78 (1H, s).

EXAMPLE 2

3-(1-(3-((6-Chloro-2-naphthyl)sulfonyl)propanoyl)-1-piperidinyl)-5,6-dihydroimidazo[2,1-b][1,3]thiazole

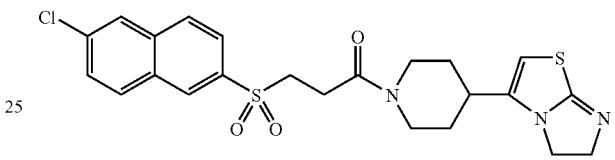

2a) tert-Butyl 4-(5,6-dihydroimidazo[2,1-b][1,3]thiazol-3-yl)piperidine-1-carboxylate hydrobromide tert-Butyl 4-acetylpiperidine-1-carboxylate (1.0 g) and 5,5-dibromobarbituric acid (1.2 g) were dissolved in ether (30 mL) and mixed overnight. The precipitated crystals were filtered off, and the filtrate was concentrated. To the residue were added ethylenethiourea (0.46 g) and ethanol (30 mL), and the mixture was refluxed overnight. The precipitated crystals were collected by filtration to give the title compound (0.55 g) as pale yellow crystals.

NMR (CDCl$_3$) δ: 1.12-1.58 (2H, m), 1.45 (9H, s), 1.68-2.05 (3H, m), 2.60-2.88 (2H, m), 3.76 (2H, t, J=9.2), 4.05-4.15 (2H, m), 4.22 (2H, t, J=9.2), 5.23 (1H, s).

2b) 3-(1-(3-((6-Chloro-2-naphthyl)sulfonyl)propanoyl)-1-piperidinyl)–5,6-dihydroimidazo[2,1-b][1,3]thiazole The compound (0.50 g) obtained in Example 2a) was dissolved in trifluoroacetic acid (10 mL) and mixed at room temperature for 1 hour. The solvent was distilled off, and to the residue were added dichloromethane (20 mL) and triethylamine (0.38 mL). With ice cooling, 3-((6-chloro-2-naphthyl)sulfonyl)propionic acid (0.4 g), HOBt (0.23 g) and WSC (0.29 g) were added thereto, and the mixture was mixed at room temperature for 16 hours. The reaction solution was basified with an aqueous potassium carbonate solution, then extracted with chloroform, and the extract was dried over anhydrous magnesium sulfate. The solvent was distilled off, and the residue was purified with a basic silica gel column to give the title compound (0.16 g) as a white powder.

NMR (CDCl$_3$) δ: 1.21-1.61 (2H, m), 1.85-1.99 (2H, m), 2.33-2.50 (1H, m), 2.55-2.62 (2H, m), 2.83-2.91 (2H, m), 3.01-3.13 (1H, m), 3.51-3.59 (1H, m), 3.77 (2H, t, J=9.2), 3.88-3.95 (1H, m), 4.22 (2H, t, J=9.2), 4.55-4.62 (1H, m), 5.23 (1H, s), 7.58 (1H, dd, J=1.8, 8.8), 7.86-7.95 (4H, m), 8.46 (1H, s).

EXAMPLE 3

3-((4-(3-((6-Chloro-2-naphthyl)sulfonyl)propanoyl)-1-piperazinyl)methyl)-5,6-dihydroimidazo[2,1-b][1,3]thiazole hydrochloride

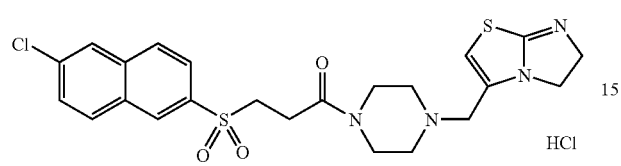

3a) 1-(3-((6-Chloro-2-naphthyl)sulfonyl)propionyl)piperazine tert-Butyl 1-piperazine carboxylate (5.0 g) was dissolved in dichloromethane (20 mL), and triethylamine (3.8 mL) was added thereto. With ice cooling, 3-((6-chloro-2-naphthyl)sulfonyl)propionic acid (8.0 g), HOBt (4.5 g) and WSC (5.7 g) were added thereto, and the mixture was mixed at room temperature for 16 hours. The reaction solution was basified with an aqueous potassium carbonate solution, then extracted with chloroform, and the extract was dried over anhydrous magnesium sulfate. The solvent was distilled off, and the residue was dissolved in trifluoroacetic acid (25 mL) and mixed at room temperature for 1 hour. After concentrating the reaction solution, the residue was basified with an aqueous potassium carbonate solution and extracted with chloroform. The extract was dried over anhydrous magnesium sulfate, and then the solvent was concentrated to give the title compound (8.7 g) as a pale brown oily matter.

NMR (CDCl$_3$) δ: 2.77 (2H, t, J=5.1), 2.83-2.88 (4H, m), 3.42 (2H, t, J=9.2), 3.48-3.58 (4H, m), 7.57 (1H, dd, J=2.1, 9.0), 7.90-7.94 (4H, m), 8.46 (1H, s).

3b) 3-((4-(3-((6-Chloro-2-naphthyl)sulfonyl)propanoyl)-1-piperazinyl)methyl)-5,6-dihydroimidazo[2,1-b][1,3]thiazole The compound (1.0 g) obtained in Example 3a) was dissolved in DMF (30 mL). Potassium carbonate (0.75 g) and 3-chloromethyl-5,6-dihydroimidazo[2,1-b][1,3]thiazole hydrochloride (0.58 g) were added thereto, and the mixture was mixed at 70° C. for 4 hours. After distilling off the solvent, the residue was poured into water, extracted with a mixture of chloroform-methanol, and the extract was dried over anhydrous magnesium sulfate. The solvent was distilled off, and the residue was purified with a basic silica gel column to give a colorless oily matter. The oily matter was dissolved in ethyl acetate, and a 4 N solution of hydrogen chloride in ethyl acetate (0.4 mL) was added thereto. The precipitated solid was collected by filtration to give the title compound (0.80 g) as a colorless powder.

NMR (DMSO-d$_6$) δ: 2.75-2.89 (4H, m), 3.46-3.67 (6H, m), 4.26-4.31 (6H, m), 4.56-4.68 (2H, m), 7.02-7.23 (1H, s), 7.73-7.79 (1H, m), 7.98-8.04 (1H, m), 8.18-8.34 (3H, m), 8.67 (1H, s).

EXAMPLE 4

1-(3-((6-Chloro-2-naphthyl)sulfonyl)propyl)-4-(5,6-dihydroimidazo[2,1-b][1,3]thiazol-3-yl)methyl-2-piperazinone hydrochloride

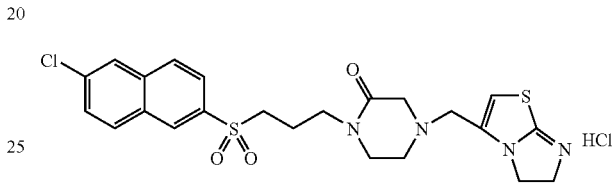

4a) tert-Butyl 4-(3-((6-chloro-2-naphthyl)thio)propyl)-3-oxopiperazine-1-carboxylate tert-Butyl 3-oxopiperazine-1-carboxylate (2.0 g) was dissolved in DMF (30 mL), and sodium hydride (0.5 g) was added thereto. With ice cooling, 2-chloro-6-((3-chloropropyl)thio)naphthalene (2.7 g) was added thereto, and the mixture was mixed at 60° C. for 3 hours. The reaction solution was poured into water, then extracted with chloroform, and the extract was dried over anhydrous magnesium sulfate. The solvent was distilled off, and the residue was purified with a silica gel column to give the title compound (4.0 g) as a pale brown oily matter.

NMR (CDCl$_3$) δ: 1.48 (9H, s), 1.92-1.99 (2H, m), 3.05 (2H, t, J=6.8), 3.34 (2H, t, J=5.8), 3.57 (2H, t, J=6.8), 3.64 (2H, t, J=5.8), 4.09 (2H, s), 7.40-7.46 (2H, m), 7.68-7.79 (4H, m).

4b) tert-Butyl 4-(3-((6-chloro-2-naphthyl)sulfonyl)propyl)-3-oxopiperazine-1-carboxylate The compound (4.0 g) obtained in Example 4a) was dissolved in ethyl acetate (50 mL). 3-Chloroperbenzoic acid (7.4 g) was added thereto at 5° C. or lower, and the mixture was mixed for 1 hour. The reaction solution was poured into an aqueous potassium carbonate solution, then extracted with chloroform, and the extract was dried over anhydrous magnesium sulfate. The solvent was distilled off to give the title compound (2.6 g) as white crystals.

NMR (CDCl$_3$) δ: 1.48 (9H, s), 2.04-2.12 (2H, m), 3.18-3.23 (2H, m), 3.36 (2H, t, J=8.0), 3.54 (2H, t, J=10.5), 3.66 (2H, t, J=8.0), 4.06 (2H, s), 7.61 (1H, dd, J=2.7, 13.8), 7.92-7.99 (4H, m), 8.48 (1H, s).

4c) 1-(3-((6-Chloro-2-naphthyl)sulfonyl)propyl)-2-piperazinone

The compound (2.6 g) obtained in Example 4b) was dissolved in trifluoroacetic acid (15 mL) and mixed at room temperature for 1 hour. The solvent was distilled off, and the residue was poured into an aqueous potassium carbonate solution. Then, the mixture solution was extracted with chloroform, and the extract was dried over anhydrous magnesium sulfate. The solvent was distilled off to give the title compound (2.4 g) as a brown oily matter.

NMR (CDCl$_3$) δ: 2.01-2.08 (2H, m), 3.07 (2H, t, J=4.6), 3.18-3.23 (2H, m), 3.31 (2H, t, J=4.6), 4.48-4.52 (4H, m), 7.58-7.60 (1H, m), 7.90-7.97 (4H, m), 8.46 (1H, s).

4d) 1-(3-((6-Chloro-2-naphthyl)sulfonyl)propyl)-4-(5,6-dihydroimidazo[2,1-b][1,3]thiazol-3-yl)methyl-2-piperazinone The compound (1.0 g) obtained in Example 4c) was dissolved in DMF (30 mL). Potassium carbonate (0.75 g) and 3-chloromethyl-5,6-dihydroimidazo[2,1-b][1,3]thiazole hydrochloride (0.58 g) were added thereto, and the mixture was mixed at 70° C. for 4 hours. After distilling off the solvent, the residue was poured into water, extracted with a mixture of chloroform-methanol, and the extract was dried over anhydrous magnesium sulfate. The solvent was distilled off, and the residue was purified with a basic silica gel column to give an oily matter. The oily matter was dissolved in acetone, a 4 N solution of hydrogen chloride in diethyl ether was added thereto, and the precipitated solid was collected by filtration to give the title compound (0.33 g) as a pale yellow powder.

NMR (DMSO-d$_6$) δ: 1.81-1.98 (2H, m), 3.42-3.98 (12H, m), 4.33-4.38 (2H, m), 4.51-4.55 (2H, m), 7.05 (1H, s), 7.82-7.87 (1H, m), 8.07-8.11 (1H, m), 8.26-8.42 (3H, m), 8.74 (1H, s), 9.84 (1H, brs).

EXAMPLE 5

N-((2Z)-4-((4-(3-((6-Chloro-2-naphthyl)sulfonyl)propanoyl)-1-piperazinyl)methyl)-3-methyl-1,3-thiazol-2(3H)-ylidene)-N-methylamine dihydrochloride

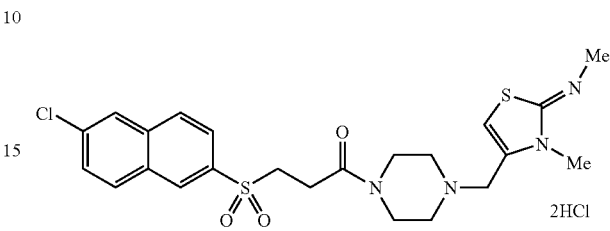

A suspension of 1-(3-((6-chloro-2-naphthyl)sulfonyl)propionyl)piperazine (2.5 g) obtained in Example 3a), N-((2Z)-4-chloromethyl-3-methyl-1,3-thiazol-2(3H)-ylidene)-N-methylamine hydrochloride (2.2 g) and potassium carbonate (2.4 g) in DMF (50 mL) was mixed at 65° C. for 3 hours. The solvent was distilled off under reduced pressure, the residue was diluted with an aqueous potassium carbonate solution, and extracted with chloroform. The extract was dried over anhydrous magnesium sulfate, and then concentrated under reduced pressure. The product, which was obtained by the purification of the residue with a basic silica gel column, was dissolved in ethyl acetate. A solution of hydrogen chloride in ether was added thereto, and the mixture was concentrated and dried to give the title compound (2.4 g) as a colorless powder.

NMR (CDCl$_3$) δ: 1.70-1.82 (2H, m), 2.44-2.55 (4H, m), 2.93-3.01 (2H, m), 3.11 (3H, s), 3.34 (2H, s), 3.46 (3H, s), 3.53-3.70 (4H, m), 5.84 (1H, s), 7.68-7.73 (1H, m), 8.04-8.08 (4H, m), 8.58 (1H, s).

EXAMPLE 6

N-((2Z)-4-((4-(3-((6-Chloro-2-naphthyl)sulfonyl)propanoyl)-1-piperazinyl)methyl)-3-propyl-1,3-thiazol-2(3H)-ylidene)-N-propylamine

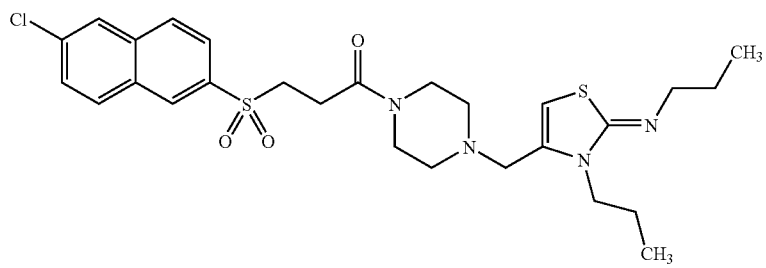

In the same manner as in Example 3b), the title compound (1.5 g) as pale yellow crystals was obtained from 1-(3-((6-chloro-2-naphthyl)sulfonyl)propionyl)piperazine (2.0 g) obtained in Example 3a) and N-(4-chloromethyl-3-propyl-1,3-thiazol-2(3H)-ylidene)-N-propylamine hydrochloride (1.6 g).

NMR (CDCl$_3$) δ: 1.01-1.11 (6H, m), 1.72-1.83 (4H, m), 2.43-2.55 (4H, m), 2.97 (2H, t, J=7.6), 3.14 (2H, t, J=7.0), 3.37 (2H, s), 3.53-3.70 (6H, m), 3.86 (2H, t, J=7.8), 5.76 (1H, s), 7.61 (1H, dd, J=1.4, 8.8), 8.04-8.08 (4H, m), 8.58 (1H, s).

EXAMPLE 7

N-((2Z)-3-Butyl-4-((4-(3-((6-chloro-2-naphthyl)sulfonyl)propanoyl)-1-piperazinyl)methyl)-1,3-thiazol-2(3H)-ylidene)-1-butylamine The oily matter, which was obtained from 1-(3-((6-chloro-2-naphthyl)sulfonyl)propionyl)piperazine (1.5 g) obtained in Example 3a) and N-(4-chloromethyl-3-ethyl-1,3-thiazol-2(3H)-ylidene)-N-ethylamine hydrochloride (1.0 g) in the same manner as in Example 3b), was dissolved in acetone (2 mL). A solution of hydrogen chloride in ethanol was added thereto, and the precipitated solid was collected by filtration to give the title compound (0.51 g) as white crystals.

NMR (DMSO-d$_6$) δ: 1.19 (3H, t, J=6.8), 1.29 (3H, t, J=7.3), 2.80 (3H, t, J=7.1), 3.39 (3H, dt, J=12.4, 6.2), 3.57-3.68 (3H, m), 3.95 (6H, s), 4.33 (3H, s), 7.75 (1H, dd, J=8.7, 2.1), 8.00 (1H, dd, J=8.8, 1.8), 8.20 (1H, d, J=8.9), 8.26-8.33 (2H, m), 8.66 (1, s).

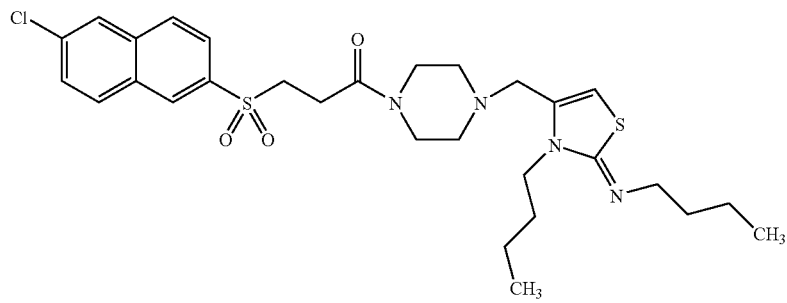

In the same manner as in Example 3b), the title compound (1.7 g) as pale yellow crystals was obtained from 1-(3-((6-chloro-2-naphthyl)sulfonyl)propionyl)piperazine (2.5 g) obtained in Example 3a) and N-(3-butyl-4-chloromethyl-1,3-thiazol-2(3H)-ylidene)-N-butylamine hydrochloride (2.3 g).

NMR (CDCl$_3$) δ: 0.99-1.09 (6H, m), 1.37-1.76 (8H, m), 2.44-2.53 (4H, m), 2.97 (2H, t, J=7.4), 3.17 (2H, t, J=7.0), 3.31 (2H, s), 3.53-3.70 (6H, m), 3.90 (2H, t, J=8.2), 5.76 (1H, s), 7.61 (1H, dd, J=1.4, 8.8), 8.04-8.08 (4H, m), 8.59 (1H, s).

EXAMPLE 8

N-((2Z)-4-((4-(3-((6-Chloro-2-naphthyl)sulfonyl)propanoyl)-1-piperazinyl)methyl)-3-ethyl-1,3-thiazol-2(3H)-ylidene)-N-ethylamine hydrochloride

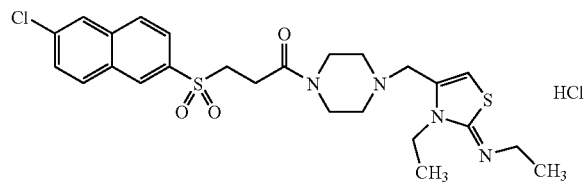

EXAMPLE 9

N-((2Z)-4-((4-(3-((6-Chloro-2-naphthyl)sulfonyl)propanoyl)-1-piperazinyl)methyl)-3-isopropyl-1,3-thiazol-2(3H)-ylidene)-N-isopropylamine hydrochloride

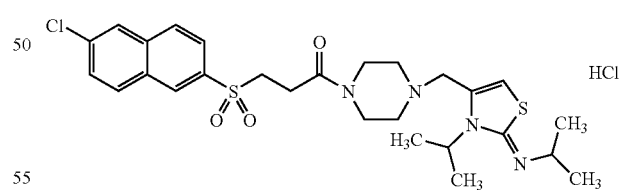

In the same manner as in Example 3b), the title compound (1.0 g) as white crystals was obtained from 1-(3-((6-chloro-2-naphthyl)sulfonyl)propionyl)piperazine (1.4 g) obtained in Example 3a) and N-(4-chloromethyl-3-isopropyl-1,3-thiazol-2(3H)-ylidene)-N-isopropylamine hydrochloride (1.0 g).

NMR (CDCl$_3$) δ: 1.23-1.27 (12H, m), 1.36-1.49 (2H, m), 2.45-2.54 (4H, m), 2.93-2.96 (2H, m), 3.25 (2H, s), 3.55-3.70 (6H, m), 4.41-4.58 (1H, m), 5.67 (1H, s), 7.68-7.73 (1H, m), 8.04-8.13 (4H, m), 8.58 (1H, s).

EXAMPLE 10

N-((2Z)-4-((1-(3-((6-Chloro-2-naphthyl)sulfonyl)propanoyl)-1-piperidinyl)methyl)-3-methyl-1,3-thiazol-2(3H)-ylidene)-N-methylamine hydrochloride

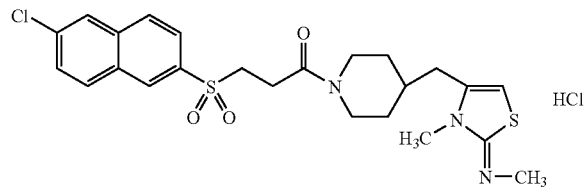

10a) tert-Butyl 4-(((2Z)-3-methyl-2-(methylimino)-2,3-dihydro-1,3-thiazol-4-yl)methyl)piperidine-1-carboxylate hydrobromide tert-Butyl 4-(2-oxopropyl)piperidine-1-carboxylate (1.0 g) and 5,5-dibromobarbituric acid (1.2 g) were dissolved in ether (30 mL) and mixed overnight. The precipitated crystals were filtered off, and the filtrate was concentrated. To the residue were added N,N'-dimethylthiourea (0.46 g) and ethanol (30 mL), and the mixture was refluxed overnight. The precipitated crystals were collected by filtration to give the title compound (0.60 g) as a pale yellow oily matter.

NMR (CDCl$_3$) δ: 1.01-1.15 (2H, m), 1.28 (9H, s), 1.62-1.72 (3H, m), 2.31-2.34 (2H, m), 2.62-2.78 (3H, m), 2.98 (3H, s), 3.02 (2H, d, J=4.5), 3.23 (3H, s), 5.52 (1H, s).

10b) N-((2Z)-4-((1-(3-((6-Chloro-2-naphthyl)sulfonyl)propanoyl)-1-piperidinyl)methyl)-3-methyl-1,3-thiazol-2(3H)-ylidene)-N-methylamine The compound (1.2 g) obtained in Example 10a) was dissolved in concentrated hydrochloric acid (5 mL) and mixed at room temperature for 1 hour. The solvent was distilled off, and to the residue were added dichloromethane (50 mL) and triethylamine (0.87 mL). With ice cooling, 3-((6-chloro-2-naphthyl)sulfonyl)propionic acid (0.92 g), HOBt (0.52 g) and WSC (0.65 g) were added to the solution, and mixed at room temperature for 16 hours. The reaction solution was basified with an aqueous potassium carbonate solution, then extracted with chloroform, and the extract was dried over anhydrous magnesium sulfate. The reaction solution was distilled off, and the residue was purified with a basic silica gel column to give the title compound (0.31 g) as a colorless powder.

NMR (CDCl$_3$) δ: 0.94-1.16 (3H, m), 1.61-1.77 (3H, m), 2.26 (2H, d, J=6.6), 2.39-2.48 (1H, m), 2.77-2.84 (4H, m), 3.17 (3H, s), 3.47-3.61 (2H, m), 3.75-3.80 (1H, m), 4.12-4.46 (1H, m), 5.46 (1H, s), 7.51 (1H, dd, J=1.8, 8.8), 7.83-7.90 (4H, m), 8.41 (1H, s).

EXAMPLE 11

N-((2Z)-4-((4-(3-((5-Chloro-1H-indol-2-yl)sulfonyl)propanoyl)-1-piperazinyl)methyl)-3-methyl-1,3-thiazol-2(3H)-ylidene)-N-methylamine

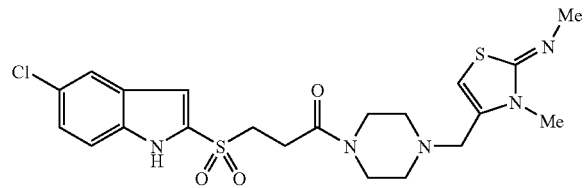

11a) tert-Butyl 4-(((2Z)-3-methyl-2-methylimino-2,3-dihydro-1,3-thiazol-4-yl)methyl)piperazine-1-carboxylate tert-Butyl piperazine-1-carboxylate (2.5 g) was dissolved in acetonitrile (50 mL). Potassium carbonate (3.7 g) and N-(4-chloromethyl-3-methyl-1,3-thiazol-2(3H)-ylidene)-N-methylamine hydrochloride (3.2 g) were added thereto, and the mixture was mixed under reflux for 4 hours. The solvent was distilled off, and to the residue was added an aqueous potassium bicarbonate solution. The mixture was then extracted with chloroform, and the extract was dried over anhydrous magnesium sulfate. The solvent was distilled off, and the residue was purified with a basic silica gel column to give the title compound (4.3 g) as a brown oily matter.

NMR (CDCl$_3$) δ: 1.43 (9H, s), 2.35-3.36 (3H, m), 2.97 (3H, s), 2.31 (2H, s), 3.33 (3H, s), 3.36-3.40 (4H, m), 5.69 (1H, s).

11b) N-((2Z)-4-((4-(3-((5-Chloro-1H-indol-2-yl)sulfonyl)propanoyl)-1-piperazinyl)methyl)-3-methyl-1,3-thiazol-2(3H)-ylidene)-N-methylamine The compound (1.5 g) obtained in Example 11a) was dissolved in concentrated hydrochloric acid (5 mL) and mixed at room temperature for 1 hour. The reaction solution was concentrated, and then to the residue were added dichloromethane (50 mL) and triethylamine (1.3 mL). With ice cooling, (3-((1-tert-butoxycarbonyl-5-chloro-1H-indol-2-yl)sulfonyl)propionic acid (1.8 g), HOBt (0.77 g) and WSC (0.96 g) were added thereto, and the mixture was mixed at room temperature for 16 hours. The reaction solution was basified with an aqueous potassium carbonate solution, then extracted with chloroform, and the extract was dried over anhydrous magnesium sulfate. The solvent was distilled off, and the residue was purified with a basic silica gel column to give the title compound (0.31 g) as white crystals.

NMR (CDCl$_3$) δ: 2.36-2.47 (4H, m), 2.93 (2H, t, J=7.6), 3.09 (3H, s), 3.29 (2H, s), 3.43 (3H, s), 3.48-3.58 (4H, m), 3.76 (2H, t, J=7.6), 5.84 (1H, s), 7.20 (1H, s), 7.33-7.49 (3H, m), 7.75 (1H, d, J=1.4).

EXAMPLE 12

4-((4-(3-((6-Chloro-2-naphthyl)sulfonyl)propanoyl)-1-piperazinyl)methyl)-3-methyl-1,3-thiazol-2(3H)-imine dihydrochloride

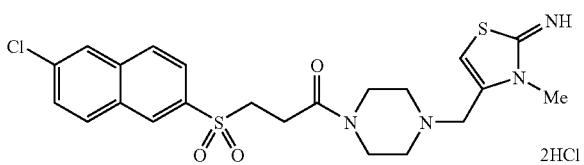

12a) 4-((4-(3-((6-Chloro-2-naphthyl)sulfonyl)propanoyl)-1-piperazinyl)methyl)-1,3-thiazol-2-amine A suspension of 1-(3-((6-chloro-2-naphthyl)sulfonyl)propionyl)piperazine (1.5 g) obtained in Example 3a), 4-chloromethyl-1,3-thiazol-2-amine hydrochloride (0.76 g) and potassium carbonate (1.12 g) in acetonitrile (50 mL) was refluxed for 4 hours, and then the solvent was distilled off under reduced pressure. The residue was diluted with potassium carbonate, and extracted with chloroform. The extract was dried over anhydrous magnesium sulfate, and then the solvent was distilled off under reduced pressure. The residue was purified with a basic silica gel column to give the title compound (1.4 g) as white crystals.

NMR (CDCl$_3$) δ: 2.37 (2H, t, J=5.1), 2.44 (2H, t, J=5.1), 2.84 (2H, t, J=7.8), 3.38 (2H, s), 3.45-3.57 (6H, m), 4.92 (2H, brs), 6.31 (1H, s), 7.58 (1H, dd, J=2.1, 9.0), 7.90-7.95 (4H, m), 8.45 (1H, s).

12b) 4-((4-(3-((6-Chloro-2-naphthyl)sulfonyl)propanoyl)-1-piperazinyl)methyl)-3-methyl-1,3-thiazol-2(3H)-imine dihydrochloride The compound (0.5 g) obtained in Example 12a) was dissolved in DMF (1.0 mL), methyl iodide (0.13 mL) was added thereto at room temperature, and the mixture was mixed at 80° C. overnight. The reaction solution was poured into water and extracted with a mixed solution of chloroform and methanol, and the extract was dried over anhydrous magnesium sulfate. The solvent was distilled off, and the residue was purified with a basic silica gel column. The product was treated with a solution of hydrogen chloride in ether (5 mL) to give the title compound (0.23 g) as white crystals.

NMR (CDCl$_3$) δ: 2.28-2.41 (4H, m), 2.78-2.86 (2H, m), 3.15 (2H, s), 3.30 (3H, s), 3.34-3.55 (6H, m), 5.57 (1H, s), 7.55 (1H, dd, J=1.8, 8.8), 7.87-7.92 (4H, m), 8.43 (1H, s).

EXAMPLE 13

Ethyl (2Z)-4-((4-(3-((6-chloro-2-naphthyl)sulfonyl) propanoyl)-1-piperazinyl)methyl)-3-methyl-2-(methylimino)-2,3-dihydro-1,3-thiazole-5-carboxylate

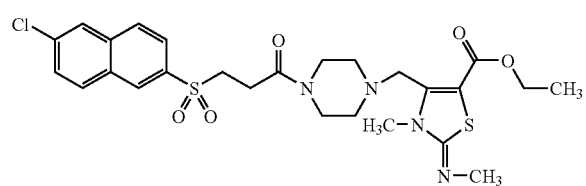

Ethyl (2Z)-3,4-dimethyl-2-methylimino-2,3-dihydro-1,3-thiazole-5-carboxylate (2.8 g) was dissolved in 1,2-dichloroethane (30 mL). AIBN (0.1 g) and NBS (2.3 g) were added thereto, and the mixture was refluxed for 1 hour. The reaction solution was basified with an aqueous potassium carbonate solution, and then extracted with chloroform. The extract was dried over anhydrous magnesium sulfate, and the solvent was distilled off. In the same manner as in Example 3b), the title compound (0.14 g) as a white powder was obtained from the resulting ethyl (2Z)-4-bromomethyl-3-methyl-2-methylimino-2,3-dihydro-1,3-thiazole-5-carboxylate (1.5 g) and 1-(3-((6-chloro-2-naphthyl)sulfonyl)propionyl)piperazine (1.5 g) obtained in Example 3a).

NMR (CDCl$_3$) δ: 1.28 (3H, t, J=7.2), 2.39-2.48 (4H, m), 2.79 (2H, t, J=7.8), 2.96 (3H, s), 3.37 (3H, s), 3.32-3.53 (6H, m), 3.81 (2H, s), 4.19 (2H, q, J=7.2), 7.52 (1H, dd, J=1.8, 8.8), 7.86-7.91 (4H, m), 8.41 (1H, s).

EXAMPLE 14

N-((2Z)-4-(1-(3-((6-Chloro-2-naphthyl)sulfonyl) propanoyl)-1-piperidinyl)-3-methyl-1,3-thiazol-2 (3H)-ylidene)-N-methylamine

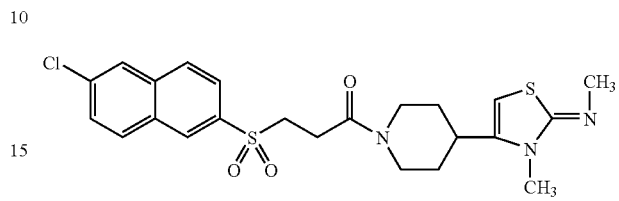

14a) tert-Butyl 4-((2Z)-3-methyl-2-methylimino-2,3-dihydro-1,3-thiazol-4-yl)piperidine-1-carboxylate hydrobromide tert-Butyl 4-acetylpiperidine-1-carboxylate (2.0 g) and 5,5-dibromobarbituric acid (2.4 g) were dissolved in ether (30 mL) and mixed overnight. The precipitated crystals were filtered off, and the filtrate was concentrated. To the residue were added N,N'-dimethylthiourea (0.95 g) and ethanol (30 mL), and the mixture was refluxed overnight. The precipitated crystals were collected by filtration to give the title compound (0.16 g) as pale yellow crystals.

NMR (CDCl$_3$) δ: 1.11-1.15 (2H, m), 1.45 (9H, s), 1.68-1.67 (3H, m), 2.31-2.34 (2H, m), 2.62-2.68 (2H, m), 2.98 (3H, s), 3.02 (2H, d, J=4.5), 3.23 (3H, s), 5.52 (1H, s).

14b) N-((2Z)-4-(1-(3-((6-Chloro-2-naphthyl)sulfonyl)propanoyl)-1-piperidinyl)-3-methyl-1,3-thiazol-2 (3H)-ylidene)-N-methylamine The compound (1.2 g) obtained in Example 14a) was dissolved in 1 N hydrochloric acid and mixed for 1 hour. The reaction solution was basified with an aqueous potassium carbonate solution, then extracted with chloroform, and the extract was dried over anhydrous magnesium sulfate. The solvent was distilled off, and to the residue were added dichloromethane (50 mL) and triethylamine (1.6 mL). With ice cooling, 3-((6-chloro-2-naphthyl)sulfonyl)propionic acid (1.7 g), HOBt (0.97 g) and WSC (1.2 g) were added thereto, and the mixture was mixed at room temperature for 16 hours. The reaction solution was basified with an aqueous potassium carbonate solution, then extracted with chloroform, and the extract was dried over anhydrous magnesium sulfate. The solvent was distilled off, and the residue was purified with a basic silica gel column to give the title compound (0.16 g) as a white powder.

NMR (CDCl$_3$) δ: 1.36-1.51 (2H, m), 1.94-2.11 (2H, m), 2.60-2.72 (2H, m), 2.93-3.02 (2H, m), 3.04 (3H, s), 3.12-3.25 (1H, m), 3.33 (3H, s), 3.61-3.69 (2H, m), 3.98-4.05 (1H, m), 4.66-4.72 (1H, m), 5.54 (1H, s), 7.64 (1H, dd, J=1.8, 8.8), 8.00-8.04 (4H, m), 8.55 (1H, m).

EXAMPLE 15

N-((2Z)-5-((4-(3-((6-Chloro-2-naphthyl)sulfonyl)propanoyl)-1-piperazinyl)carbonyl)-3,4-dimethyl-1,3-thiazol-2(3H)-ylidene)-N-methylamine

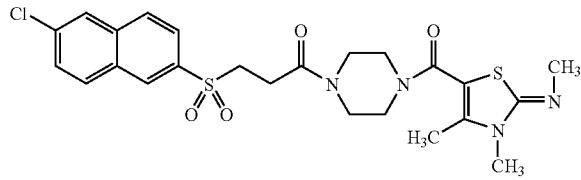

(2Z)-3,4-Dimethyl-2-methylimino-2,3-dihydro-1,3-thiazole-5-carboxylic acid (0.6 g) was dissolved in dichloromethane (30 mL), and triethylamine (0.14 mL) was added thereto. With ice cooling, 1-(3-((6-chloro-2-naphthyl)sulfonyl)propionyl)piperazine (1.0 g), HOBt (0.42 g) and WSC (0.57 g) were added thereto, and the mixture was mixed at room temperature for 16 hours. The reaction solution was basified with an aqueous potassium carbonate solution, then extracted with chloroform, and the extract was dried over anhydrous magnesium sulfate. The solvent was distilled off, and the residue was purified with a basic silica gel column to give the title compound (0.13 g) as a white powder.

NMR (CDCl$_3$) δ: 2.21-2.38 (2H, m), 2.24 (3H, s), 2.86-2.93. (2H, m), 2.99 (3H, s), 3.27 (3H, s), 3.27-3.30 (2H, m), 3.50-3.64 (6H, m), 7.58 (1H, dd, J=1.8, 8.4), 7.91-7.97 (4H, m), 8.47 (1H, s).

EXAMPLE 16

N-((2Z)-4-((4-(3-((6-Chloro-2-naphthyl)sulfonyl)propanoyl)-1-piperazinyl)methyl)-3-ethyl-1,3-thiazol-2(3H)-ylidene)-N-methylamine

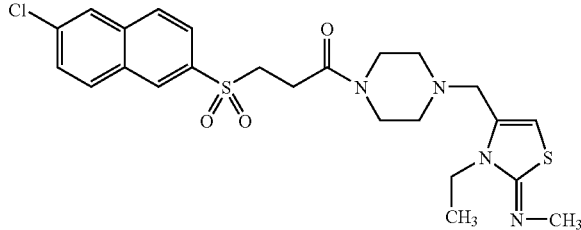

16a) 4-((4-(3-((6-Chloro-2-naphthyl)sulfonyl)propanoyl)-1-piperazinyl)methyl)-N-methyl-1,3-thiazol-2-amine In the same manner as in Example 3b), the title compound (1.2 g) as white crystals was obtained from 1-(3-((6-chloro-2-naphthyl)sulfonyl)propionyl)piperazine (1.5 g) obtained in Example 3a) and 4-chloromethyl-N-methyl-1,3-thiazol-2-amine hydrochloride (0.81 g).

NMR (CDCl$_3$) δ: 2.37 (2H, t, J=5.1), 2.46 (2H, t, J=5.1), 2.82-2.87 (2H, m), 2.95 (3H, t, J=5.1), 3.40 (2H, s), 3.45-3.57 (6H, m), 5.15-5.16 (1H, m), 6.30 (1H, s), 7.58 (1H, dd, J=1.5, 8.7), 7.90-7.95 (4H, m), 8.45 (1H, s).

16b) N-((2Z)-4-((4-(3-((6-Chloro-2-naphthyl)sulfonyl)propanoyl)-1-piperazinyl)methyl)-3-ethyl-1,3-thiazol-2(3H)-ylidene)-N-methylamine The compound (0.5 g) obtained in Example 11a) was dissolved in DMF (1.0 mL), ethyl iodide (0.21 mL) was added thereto at room temperature, and the mixture was mixed at 80° C. overnight. The reaction solution was poured into water, extracted with a mixed solution of chloroform and methanol, and the extract was dried over anhydrous magnesium sulfate. The solvent was distilled off, and the residue was purified with a basic silica gel column to give the title compound (0.04 g) as a colorless powder.

NMR (CDCl$_3$) δ: 1.22 (3H, t, J=6.9), 2.31-2.41 (4H, m), 2.81-2.86 (2H, m), 2.96 (3H, s), 3.20 (2H, s), 3.40-3.56 (6H, m), 3.85 (2H, q, J=6.9), 5.68 (1H, s), 7.55 (1H, dd, J=1.8, 8.8), 7.86-7.93 (4H, m), 8.44 (1H, s).

EXAMPLE 17

Methyl 1-(3-((6-chloro-2-naphthyl)sulfonyl)propanoyl)-4-(((2Z)-3-methyl-2-(methylimino)-2,3-dihydro-1,3-thiazol-4-yl)methyl)piperazine-2-carboxylate

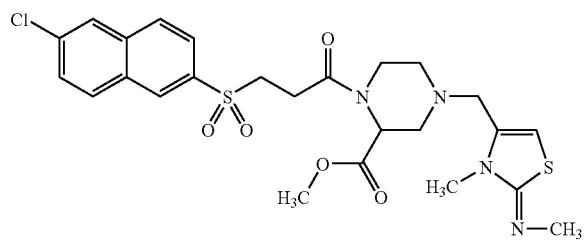

17a) 1-tert-Butyl 3-methyl 4-(3-((6-chloro-2-naphthyl)sulfonyl)propionyl)piperazine-1,3-dicarboxylate 1-tert-Butyl 3-methyl piperazine-1,3-dicarboxylate (JP-W No. 3-232864: 5.0 g) was dissolved in dichloromethane (20 mL), and triethylamine (3.8 mL) was added thereto. With ice cooling, 3-((6-chloro-2-naphthyl)sulfonyl)propionic acid (8.0 g), HOBt (4.5 g) and WSC (5.7 g) were added thereto, and the mixture was mixed at room temperature for 16 hours. The reaction solution was basified with an aqueous potassium carbonate solution, then extracted with chloroform, and the extract was dried over anhydrous magnesium sulfate. The solvent was distilled off to give the title compound (8.7 g) as a pale brown oily matter.

NMR (CDCl$_3$) δ: 1.38 (9H, s), 2.85-3.01 (4H, m), 3.65 (3H, m), 3.50-3.61 (4H, m), 3.97-4.15 (1.3H, m), 4.25-4.34 (0.7H, m), 4.48-4.70 (0.7H, m), 4.92-4.96 (1.3H, m), 7.59 (1H, dd, J=2.1, 9.0), 7.90-7.94 (4H, m), 8.46 (1H, s).

17b) Methyl 1-(3-((6-chloro-2-naphthyl)sulfonyl)propanoyl)-4-(((2Z)-3-methyl-2-(methylimino)-2,3-dihydro-1,3-thiazol-4-yl)methyl)piperazine-2-carboxylate The compound (2.4 g) obtained in Example 17a) was dissolved in concentrated hydrochloric acid (15 mL) and mixed at room temperature for 1 hour. The reaction solution was basified with an aqueous potassium carbonate solution, then extracted with chloroform, and the extract was dried over anhydrous magnesium sulfate. The solvent was distilled off, and the residue was dissolved in DMF (30 mL). Potassium carbonate (0.84 g) and N-(4-chloromethyl-3-methyl-1,3-thiazol-2(3H)-ylidene)-N-methylamine hydrochloride (0.65 g) were added thereto, and the mixture was mixed at 70° C. for 4 hours. The solvent was distilled off, and the residue was poured into water. The mixture was extracted with a mixed solution of chloroform-methanol, and the extract was dried over anhydrous magnesium sulfate. The solvent was distilled off, and the residue was purified with a basic silica gel column to give the title compound (0.98 g) as a white powder.

NMR (CDCl$_3$) δ: 1.91-2.32 (2H, m), 2.64-3.10 (2H, m), 2.99 (3H, s), 3.18-3.35 (1H, m), 3.24 (3H, s), 3.31-3.63 (5.6H, m), 3.65 (3H, s), 3.70 (0.6H, s), 4.22-4.30 (0.4H, m), 4.32-4.48 (0.4H, m), 5.13 (1H, s), 5.74 (1H, s), 7.57 (1H, dd, J=2.1, 8.0), 7.91-7.95 (4H, m), 8.46 (1H, s).

EXAMPLE 18

3-(2-(1-(3-((6-Chloro-2-naphthyl)sulfonyl)propanoyl)-1-piperidinyl)ethyl)-1,3-thiazol-2(3H)-imine

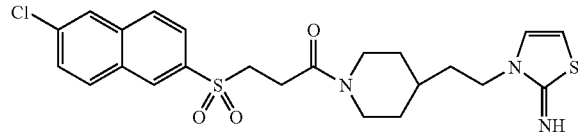

18a) 3-((6-Chloro-2-naphthyl)sulfonyl)propionyl chloride 3-((6-Chloro-2-naphthyl)sulfonyl)propionic acid (14.9 g), thionyl chloride (4.4 mL) and DMF (2 drops) were added to toluene (100 mL), and the mixture was refluxed for 1.5 hours. The solvent was distilled off under reduced pressure, and the residue was washed with ether and hexane to give the title compound (15.5 g) as a brown solid.

NMR (CDCl$_3$) δ: 3.35-3.44 (2H, m), 3.49-3.57 (2H, m), 7.62 (1H, dd, J=2.0, 8.0), 7.87-8.00 (4H, m), 8.48 (1H, s).

18b) 2-(1-(3-((6-chloro-2-naphthyl)sulfonyl)propionyl)-1-piperidinyl)ethanol

To a solution of ice-cooled 2-(4-piperidyl)ethanol (3.70 g) and sodium hydrogen carbonate (2.03 g) in water (50 mL)-THF (50 mL) was portionwise added the compound (7.57 g) obtained in Example 18a). The reaction mixture was mixed at 0° C. for 1 hour, and then THF was distilled off under reduced pressure and extracted with ethyl acetate. The extract was washed with water, and then dried over anhydrous magnesium sulfate. The solvent was distilled off, and the residue was purified with a silica gel column to give the title compound (6.18 g) as a brown oily matter.

NMR (CDCl$_3$) δ: 1.01-1.13 (2H, m), 1.45-1.56 (2H, m), 1.67-1.81 (2H, m), 2.45-2.57 (1H, m), 2.80-2.90 (2H, m), 2.93-3.06 (1H, m), 3.52-3.60 (2H, m), 3.66-3.83 (3H, m), 4.44-4.50 (1H, m), 7.59 (1H, dd, J=1.8, 8.8), 7.93-7.97 (4H, m), 8.47 (1H, s).

18c) 1-(3-((6-Chloro-2-naphthyl)sulfonyl)propanoyl)-4-(2-iodoethyl)piperidine

To a solution of the compound (6.18 g) obtained in Example 18b) in ethyl acetate (100 mL), methane sulfonyl chloride (1.4 mL) was added with ice cooling, and the mixture was mixed at 0° C. for 1.5 hours. The reaction solution was washed with water and dried over anhydrous magnesium sulfate, and the solvent was distilled off. The residue was dissolved in acetonitrile (100 mL), sodium iodide (11.3 g) was added thereto, and the mixture was mixed at room temperature for 24 hours. The solvent was distilled off under reduced pressure, water was added thereto, and the mixture was extracted with ethyl acetate. The extract was washed with water, and then dried over anhydrous magnesium sulfate. The solvent was distilled off, and then the residue was purified with a silica gel column to give the title compound (5.58 g).

NMR (CDCl$_3$) δ: 0.90-1.23 (2H, m), 1.60-1.84 (5H, m), 2.46-2.58 (1H, m), 2.82-2.90 (2H, m), 2.95-3.08 (1H, m), 3.20 (2H, t, J=6.7), 3.51-3.60 (2H, m), 3.79 -3.86 (1H, m), 4.46-4.53 (1H, m), 7.60 (1H, dd, J=1.8, 8.8), 7.92-7.97 (4H, m), 8.48 (1H, s).

18d) 3-(2-(1-(3-((6-Chloro-2-naphthyl)sulfonyl)propanoyl)-1-piperidinyl)ethyl)-1,3-thiazol-2(3H)-imine 1,3-Thiazol-2-amine (0.12 g) was dissolved in DMF (0.5 mL), and the compound (0.6 g) obtained in Example 18c) was added thereto at room temperature, and the mixture was mixed at 80° C. overnight. The reaction solution was poured into water, extracted with a mixed solution of chloroform and methanol, and the extract was dried over anhydrous magnesium sulfate. The solvent was distilled off, and the residue was purified with a basic silica gel column to give the title compound (0.11 g) as a white powder.

NMR (CDCl$_3$) δ: 0.82-1.13 (2H, m), 1.38-1.84 (6H, m), 2.36-2.48 (1H, m), 2.74-2.98 (3H, m), 3.45-3.54 (2H, m), 3.61-3.76 (3H, m), 4.35-4.42 (1H, m), 5.68 (1H, d, J=5.2), 6.29 (1H, d, J=5.2), 7.52 (1H, dd, J=1.8, 8.8), 7.86-7.90 (4H, m), 8.40 (1H, s).

EXAMPLE 19

4-(3-((6-Chloro-2-naphthyl)sulfonyl)propanoyl)-1-(((2Z)-3-methyl-2-(methylimino)-2,3-dihydro-1,3-thiazol-4-yl)methyl)-2-piperazinone

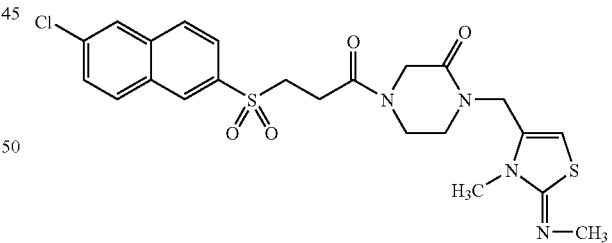

tert-Butyl 3-oxopiperazine-1-carboxylate (1.5 g) was dissolved in DMF (50 mL), and sodium hydride (0.3 g) was added thereto. With ice cooling, N-(4-chloromethyl-3-methyl-1,3-thiazol-2(3H)-ylidene)-N-methylamine hydrochloride (1.6 g) was added thereto, and the mixture was mixed at 80° C. for 3 hours. The solvent was distilled off, and the residue was poured into water, then extracted with chloroform, and the extract was dried over anhydrous magnesium sulfate. The solvent was distilled off to give 1-(((2Z)-3-methyl-2-(methylimino)-2,3-dihydro-1,3-thiazol-4-yl)methyl)-2-piperazinone (1.7 g) as a pale brown oily matter (a crude product). The resulting oily matter was dissolved in concentrated hydrochloric acid (5 mL) and mixed at room temperature for 1 hour. After concentrating the reaction solution, the residue was dissolved in dichloromethane (30 mL), and triethylamine (1.4 mL) was added thereto. With ice cooling, 3-((6-chloro-2-naphthyl)sulfonyl)propionic acid (1.5 g), HOBt (0.84 g) and WSC (1.0 g) were added thereto, and the mixture was mixed at room temperature for 16 hours. The reaction solution was basified with an aqueous potassium carbonate solution, then extracted with chloroform, and the extract was dried over anhydrous magnesium sulfate. The solvent was distilled off, and the residue was purified with a basic silica gel column to give the title compound (0.25 g) as a colorless powder.

NMR (CDCl$_3$) δ: 2.51-2.84 (2H, m), 2.90 (3H, s), 3.12 (3H, s), 3.16-3.26 (2H, m), 3.46-3.50 (2H, m), 3.52-3.74 (2H, m), 4.12-4.15 (2H, m), 4.34-4.39 (2H, m), 5.76 (1H, s), 7.51 (1H, dd, J=2.2, 8.8), 7.83-7.91 (4H, m), 8.40 (1H, s).

EXAMPLE 20

Methyl 4-(3-((6-chloro-2-naphthyl)sulfonyl)propanoyl)-1-(((2Z)-3-methyl-2-(methylimino)-2,3-dihydro-1,3-thiazol-4-yl)methyl)piperazine-2-carboxylate

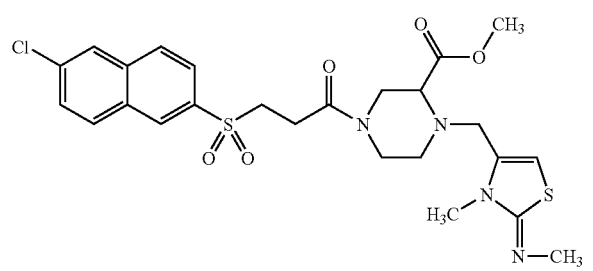

1-tert-Butyl 3-methyl piperazine-1,3-dicarboxylate (1.5 g) was dissolved in DMF (50 mL). Potassium carbonate (1.7 g) and N-(4-chloromethyl-3-methyl-1,3-thiazol-2(3H)-ylidene)-N-methylamine hydrochloride (1.4 g) were added thereto, and the mixture was mixed at 80° C. overnight. The solvent was distilled off, the residue was poured into water, extracted with a mixed solution of chloroform-methanol, and the extract was dried over anhydrous magnesium sulfate. The solvent was distilled off to give tert-butyl 4-(((2Z)-3-methyl-2-(methylimino)-2,3-dihydro-1,3-thiazol-4-yl)methyl)-3-oxopiperazine-1-carboxylate (1.2 g) as a pale brown oily matter. The resulting oily matter was dissolved in trifluoroacetic acid (10 mL) and mixed at room temperature for 1 hour. The mixture was dissolved in dichloromethane (50 mL), and triethylamine (0.87 mL) was added thereto. With ice cooling, 3-((6-chloro-2-naphthyl)sulfonyl)propionic acid (0.97 g), HOBt (0.53 g) and WSC (0.65 g) were added thereto, and the mixture was mixed at room temperature for 16 hours. The reaction solution was basified with an aqueous potassium carbonate solution, then extracted with chloroform, and the extract was dried over anhydrous magnesium sulfate. The solvent was distilled off, and the residue was purified with a basic silica gel column to give the title compound (1.8 g) as a white powder.

NMR (CDCl$_3$) δ: 2.38-2.52 (1H, m), 2.83-2.91 (3.7H, m), 2.94 (3H, s), 3.23-3.40 (3.7H, m), 3.29 (3H, s), 3.48-3.66 (6.3H, m), 4.06-4.29 (1H, m), 4.77-4.96 (0.3H, m), 5.71 (0.3H, s), 7.73 (0.7H, s), 7.49-7.55 (1H, m), 7.88-7.94 (4H, m), 8.43 (1H, m).

EXAMPLE 21

(2Z)-4-((4-(3-(((6-Chloro-2-naphthyl)sulfonyl)propanoyl)-1-piperazinyl)methyl)-N,3-dimethyl-2-(methylimino)-2,3-dihydro-1,3-thiazole-5-carboxamide

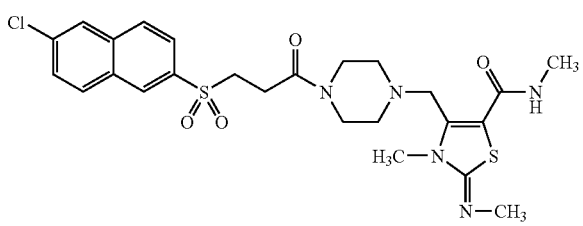

In the same manner as in Example 13, the title compound (0.54 g) as a white powder was obtained from (2Z)-N,3,4-trimethyl-2-(methylimino)-2,3-dihydro-1,3-thiazole-5-carboxamide (2.0 g).

NMR (CDCl$_3$) δ: 2.39-2.51 (4H, m), 2.72-2.87 (5H, m), 2.94 (3H, s), 3.32 (3H, s), 3.40-3.53 (6H, m), 5.24 (2H, s), 6.44-6.69 (1H, m), 7.52 (1H, dd, J=2.2, 8.8), 7.80-7.91 (4H, m), 8.40 (1H, s).

EXAMPLE 22

(2Z)-4-((4-(3-(((6-Chloro-2-naphthyl)sulfonyl)propanoyl)-1-piperazinyl)methyl)-N,N,3-trimethyl-2-(methylimino)-2,3-dihydro-1,3-thiazole-5-carboxamide

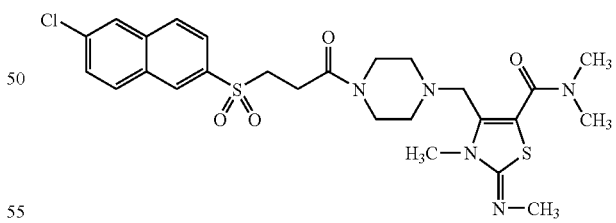

In the same manner as in Example 13, the title compound (0.27 g) as a white powder was obtained from (2Z)-N,N,3,4-tetramethyl-2-(methylimino)-2,3-dihydro-1,3-thiazole-5-carboxamide (2.0 g).

NMR (CDCl$_3$) δ: 2.31-2.42 (4H, m), 2.70-2.78 (2H, m), 2.93 (3H, s), 2.97 (6H, s), 3.32 (3H, s), 3.35-3.51 (8H, m), 7.52 (1H, dd, J=2.2, 8.8), 7.84-7.90 (4H, m), 8.39 (1H, s).

EXAMPLE 23 tert-Butyl 1-(3-((6-chloro-2-naphthyl)sulfonyl)propanoyl)-4-(((2Z)-3-methyl-2-(methylimino)-2,3-dihydro-1,3-thiazol-4-yl)methyl)piperazine-2-carboxylate

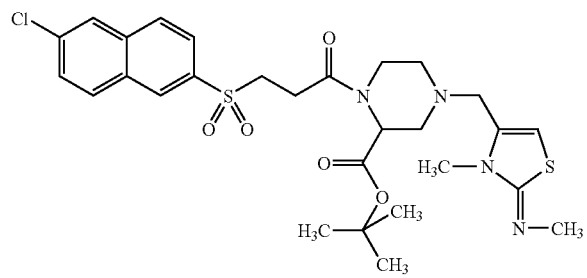

23a) Di-tert-butyl 4-(3-((6-chloro-2-naphthyl)sulfonyl)propanoyl)piperazine-1,3-dicarboxylate Di-tert-butyl piperazine-1,3-dicarboxylate (Wu, Guosheng, et al., Enantiomer 6, pp. 343-345, (2001): 4.1 g) was dissolved in dichloromethane (50 mL), and triethylamine (4.0 mL) was added thereto. With ice cooling, 3-((6-chloro-2-naphthyl)sulfonyl)propionic acid (4.3 g), HOBt (2.4 g) and WSC (3.0 g) were added thereto, and the mixture was mixed at room temperature for 16 hours. The reaction solution was basified with an aqueous potassium carbonate solution, then extracted with chloroform, and the extract was dried over anhydrous magnesium sulfate. The solvent was distilled off, and the residue was purified with a silica gel column to give the title compound (5.0 g).

NMR (CDCl$_3$) δ: 1.43 (9H, s), 1.46 (9H, s), 2.84-3.11 (4H, m), 3.51-3.61 (4H, m), 3.92-4.17 (1.3H, m), 4.25-4.35 (0.7H, m), 4.47-4.72 (0.7H, m), 4.93-4.96 (0.7H, m), 7.58 (1H, dd, J=2.1, 9.0), 7.93-7.97 (4H, m), 8.48 (1H, s).

23b) tert-Butyl 1-(3-((6-chloro-2-naphthyl)sulfonyl)propanoyl)-4-(((2Z)-3-methyl-2-(methylimino)-2,3-dihydro-1,3-thiazol-4-yl)methyl)piperazine-2-carboxylate The compound (5.0 g) obtained in Example 23a) was dissolved in dichloromethane (50 mL). With ice cooling, tetramethylsilyl triflate (1.9 g) was added thereto, and the mixture was mixed for 30 minutes. The reaction solution was basified with an aqueous potassium carbonate solution, then extracted with chloroform, and the extract was dried over anhydrous magnesium sulfate. The solvent was distilled off, and the residue was dissolved in DMF (50 mL). Potassium carbonate (2.4 g) and N-(4-chloromethyl-3-methyl-1,3-thiazol-2(3H)-ylidene)-N-methylamine hydrochloride (1.9 g) were added thereto, and the mixture was mixed at 80° C. overnight. After distilling off the solvent, the residue was poured into water, extracted with chloroform, and the extract was dried over anhydrous magnesium sulfate. The solvent was distilled off, and the residue was purified with a silica gel column to give the title compound (4.2 g) as a white powder.

NMR (CDCl$_3$) δ: 1.34 (9H, s), 2.04-2.17 (2H, m), 2.79-2.88 (3H, m), 2.98 (3H, s), 3.23 (2H, s), 3.27 (3H, s), 3.38-3.64 (4.2H, m), 4.20-4.32 (0.8H, m), 4.95 (1H, s), 5.74 (1H, s), 7.58 (1H, dd, J=2.2, 8.0), 7.87-8.00 (4H, m), 8.45 (1H, s).

EXAMPLE 24

1-(3-((6-Chloro-2-naphthyl)sulfonyl)propanoyl)-4-(((2Z)-3-methyl-2-(methylimino)-2,3-dihydro-1,3-thiazol-4-yl)methyl)piperazine-2-carboxylic acid dihydrochloride

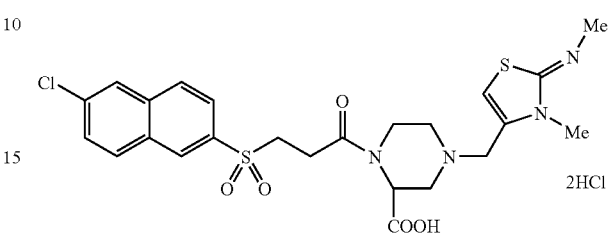

tert-Butyl 1-(3-((6-chloro-2-naphthyl)sulfonyl)propanoyl)-4-(((2Z)-3-methyl-2-(methylimino)-2,3-dihydro-1,3-thiazol-4-yl)methyl)piperazine-2-carboxylate (4.1 g) obtained in Example 23b) was dissolved in concentrated hydrochloric acid (15 mL) and mixed at room temperature for 1 hour. The reaction solution was concentrated, and then water was removed from the residue by azeotropy with toluene (30 mL), to give the title compound (4.2 g) as a white powder.

NMR (CDCl$_3$) δ: 2.03-2.42 (2H, m), 2.57-2.78 (2H, m), 2.80-2.97 (2H, m), 3.00 (3H, s), 3.11-3.43 (2H, m), 3.61 (3H, s), 3.63-3.86 (2H, m), 3.95-4.09 (1H, m), 4.86 (2H, s), 7.11 (1H, s), 7.74 (1H, dd, J=1.8, 8.6), 7.96-8.03 (1H, m), 8.15-8.31 (3H, m), 8.64-8.66 (1H, m).

EXAMPLE 25

1-(3-((6-Chloro-2-naphthyl)sulfonyl)propanoyl)-N-(2-hydroxyethyl)-4-(((2Z)-3-methyl-2-(methylimino)-2,3-dihydro-1,3-thiazol-4-yl)methyl)piperazine-2-carboxamide

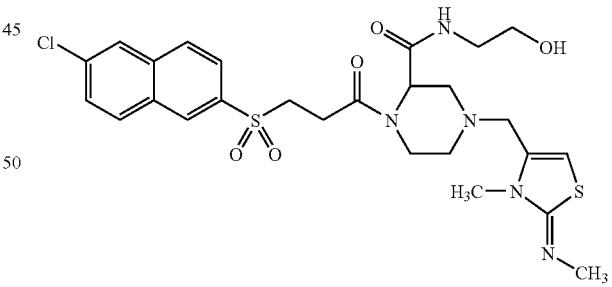

1-(3-((6-Chloro-2-naphthyl)sulfonyl)propanoyl)-4-(((2Z)-3-methyl-2-(methylimino)-2,3-dihydro-1,3-thiazol-4-yl)methyl)piperazine-2-carboxylic acid dihydrochloride (0.4 g) obtained in Example 24 was dissolved in DMF (20 mL), and triethylamine (0.2 mL) was added thereto. With ice cooling, 2-ethanolamine (0.04 g), HOBt (0.12 g) and WSC (0.16 g) were added thereto, and the mixture was mixed at room temperature for 16 hours. The reaction solution was basified with an aqueous potassium carbonate solution, then extracted with chloroform, and the extract was dried over anhydrous magnesium sulfate. The solvent was distilled off, and the residue was purified with a basic silica gel column to give the title compound (0.21 g) as a white powder.

NMR (CDCl$_3$) δ: 1.82-2.20 (2H, m), 2.77-2.86 (2H, m), 2.95 (3H, s), 3.05-3.45 (4H, m), 3.29 (3H, s), 3.49-3.80 (4.8H, m), 4.42-4.44 (0.6H, m), 5.12-5.15 (0.6H, m), 5.52-5.55 (2H, m), 5.78 (1H, s), 7.05-7.08 (0.6H, m), 7.29-7.32 (0.4H, m), 7.59 (1H, dd, J=1.8, 8.7), 7.86-7.98 (4H, m), 8.47 (1H, s).

EXAMPLE 26

N-(2-Amino-2-oxoethyl)-1-(3-((6-chloro-2-naphthyl)sulfonyl)propanoyl)-4-(((2Z)-3-methyl-2-(methylimino)-2,3-dihydro-1,3-thiazol-4-yl)methyl)piperazine-2-carboxamide

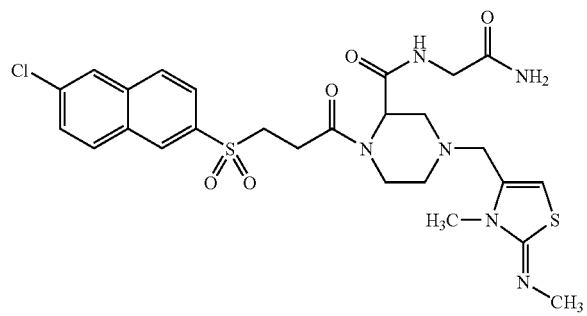

In the same manner as in Example 25, the title compound (0.19 g) as white crystals was obtained from aminoacetylamide (0.08 g).

NMR (CDCl$_3$) δ: 1.26-1.28 (2H, m), 2.04-2.22 (2H, m), 2.70-2.99 (2H, m), 2.94 (3H, s), 3.10-3.26 (2H, m), 3.27 (3H, s), 3.36-3.93 (6.6H, m), 4.01-4.18 (0.4H, m), 4.42 (0.4H, br), 5.14 (0.6H, br), 5.75 (1H, s), 6.00-6.08 (0.4H, m), 6.18-6.30 (0.6H, m), 7.57-7.60 (1H, m), 7.88-7.98 (4H, m), 8.46 (1H, s).

EXAMPLE 27

N-(2-(Acetylamino)ethyl)-1-(3-((6-chloro-2-naphthyl)sulfonyl)propanoyl)-4-(((2Z)-3-methyl-2-(methylimino)-2,3-dihydro-1,3-thiazol-4-yl)methyl)piperazine-2-carboxamide

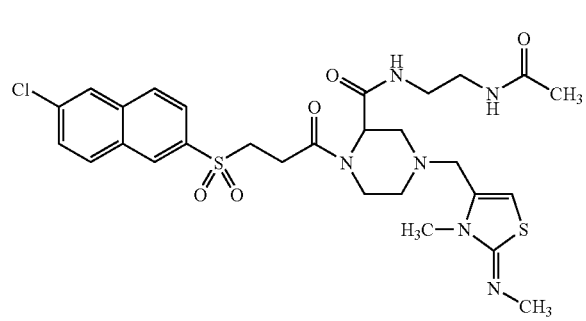

In the same manner as in Example 25, the title compound (0.15 g) as white crystals was obtained from N-acetylethylenediamine (0.08 g).

NMR (CDCl$_3$) δ: 1.84 (3H, s), 1.93-2.20 (2H, m), 2.78-2.93 (2H, m), 2.95 (3H, s), 3.10-3.33 (7H, m), 3.25 (3H, s), 3.59-3.70 (3.4H, m), 4.38 (0.4H, br), 5.04 (0.6H, br), 5.45- 5.68 (1.6H, m), 5.78 (1H, s), 7.22 (1H, br), 7.53 (1H, br), 7.57 (1H, dd, J=1.8, 8.7), 7.91-7.98 (4H, m), 8.48 (1H, s).

EXAMPLE 28

1-(3-((6-Chloro-2-naphthyl)sulfonyl)propanoyl)-N-methyl-4-(((2Z)-3-methyl-2-(methylimino)-2,3-dihydro-1,3-thiazol-4-yl)methyl)piperazine-2-carboxamide

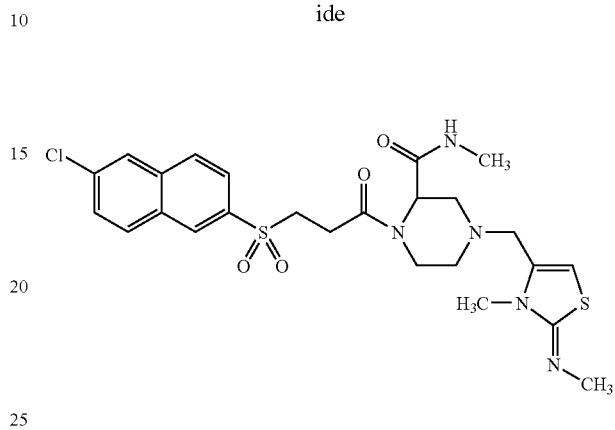

In the same manner as in Example 25, the title compound (0.23 g) as white crystals was obtained from methylamine hydrochloride (0.05 g).

NMR (CDCl$_3$) δ: 1.96-2.22 (2H, m), 2.71-2.89 (5H, m), 2.99 (3H, s), 3.11-3.28 (3H, m), 3.31 (3H, s), 3.37-3.85 (4.4H, m), 4.02-4.13 (0.4H, m), 4.36-4.53 (0.6H, m), 5.15 (0.6H, s), 5.78 (1H, s), 6.41 (0.6H, br), 6.71 (0.4H, br), 7.58-7.61 (1H, m), 7.87-7.97 (4H, m), 8.45 (1H, s).

EXAMPLE 29

N-((2Z)-4-((4-(3-((6-Chloro-2-naphthyl)sulfonyl)propanoyl)-3-(4-morpholinylcarbonyl)-1-piperazinyl)methyl)-3-methyl-1,3-thiazol-2(3H)-ylidene)-N-methylamine

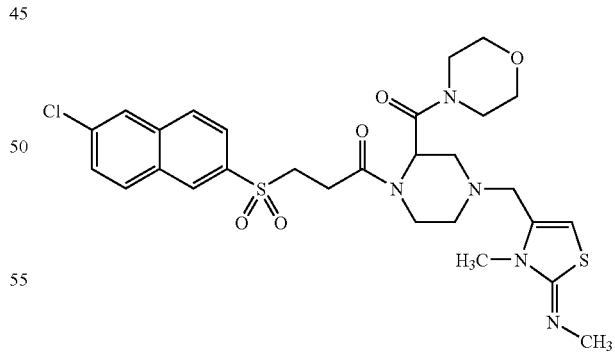

In the same manner as in Example 25, the title compound (0.09 g) as white crystals was obtained from morpholine (0.07 g).

NMR (CDCl$_3$) δ: 217-2.45 (2H, m), 2.62-3.19 (4H, m), 3.06 (3H, s), 3.33 (3H, s), 3.34-3.74 (12.2H, m), 4.00-4.22 (1.4H, m), 4.72-4.79 (0.4H, m), 5.23-5.24 (1H, m), 5.84 (1H, s), 7.66 (1H, dd, J=1.8, 8.8), 7.98-8.05 (4H, m), 8.54 (1H, s).

EXAMPLE 30 tert-Butyl ((2Z)-5-bromo-4-((4-(3-((6-chloro-2-naphthyl)sulfonyl)propanoyl)-1-piperazinyl)methyl)-3-methyl-1,3-thiazol-2(3H)-ylidene)carbamate

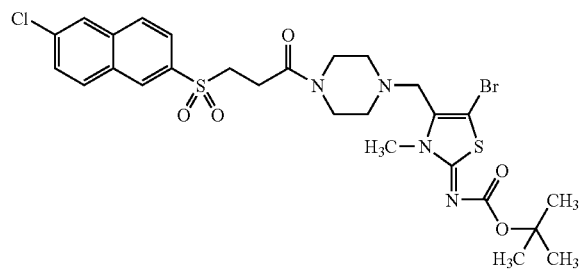

30a) tert-Butyl 3,4-dimethyl-1,3-thiazol-2(3H)-ylidenecarbamate

4-Methyl-1,3-thiazol-2-amine (10 g) was dissolved in DMF (20 mL), methyl iodide (6.5 mL) was added thereto at room temperature, and the mixture was mixed at 80° C. for 2 hours. The reaction solution was concentrated, and the resulting yellow crystals were dissolved in dichloromethane (100 mL). To the solution was added triethylamine (12 mL), was added di-tert-butyl dicarbonate (20 mL) at room temperature, and then the mixture was mixed at room temperature for 16 hours. The reaction solution was poured into water, extracted with chloroform, and the extract was dried over anhydrous magnesium sulfate. The solvent was distilled off to give the title compound (8.0 g) as white crystals.

NMR (CDCl$_3$) δ: 1.67 (9H, s), 2.36 (3H, d, J=1.4), 3.70 (3H, s), 6.29 (1H, d, J=1.4).

30b) tert-Butyl (5-bromo-3,4-dimethyl-1,3-thiazol-2(3H)-ylidene)carbamate

The compound (3.0 g) obtained in Example 30a) was dissolved in carbon tetrachloride (50 mL). AIBN (0.1 g) and NBS (2.3 g) were added thereto at room temperature, and the mixture was mixed at 80° C. for 1 hour. The reaction solution was poured into an aqueous potassium carbonate solution. The mixture was extracted with chloroform, and the extract was dried over anhydrous magnesium sulfate. The solvent was distilled off to give the title compound (2.9 g) as white crystals.

NMR (CDCl$_3$) δ: 1.55 (9H, s), 2.26 (3H, s), 3.62 (3H, s).

30c) tert-Butyl ((2Z)-5-bromo-4-((4-(3-((6-chloro-2-naphthyl)sulfonyl)propanoyl)-1-piperazinyl)methyl)-3-methyl-1,3-thiazol-2(3H)-ylidene)carbamate tert-Butyl (5-bromo-3,4-dimethyl-1,3-thiazol-2(3H)-ylidene)carbamate (2.9 g) obtained in Example 30b) was dissolved in 1,2-dichloroethane (50 mL). AIBN (0.1 g) and NBS (1.7 g) were added thereto at room temperature, and the mixture was mixed at 80° C. for 3 hours. The reaction solution was poured into an aqueous potassium carbonate solution. The mixture was extracted with chloroform, and the extract was dried over anhydrous magnesium sulfate. The solvent was distilled off to give tert-butyl (5-bromo-3-bromomethyl-4-methyl-1,3-thiazol-2(3H)-ylidene)carbamate (3.1 g) as a brown oily matter. The resulting compound and 1-(3-((6-chloro-2-naphthyl)sulfonyl)propionyl)piperazine (1.0 g) obtained in Example 3a) were dissolved in DMF (30 mL). Potassium carbonate (0.75 g) was added thereto and the mixture was mixed at 70° C. for 4 hours. The solvent was distilled off, and the residue was poured into water. The mixture was extracted with a mixed solution of chloroform-methanol, and the extract was dried over anhydrous magnesium sulfate. The solvent was distilled off, and the residue was purified with a basic silica gel column to give the title compound (1.2 g) as a white powder.

NMR (CDCl$_3$) δ: 1.56 (9H, s) 2.38-2.49 (4H, m), 2.83-2.91 (2H, m), 3.41-3.60 (8H, m), 3.73 (3H, s), 7.50 (1H, dd, J=2.2, 8.8), 7.92-7.97 (4H, m), 8.47 (1H, s).

EXAMPLE 31

5-Bromo-4-((4-(3-((6-chloro-2-naphthyl)sulfonyl)propanoyl)-1-piperazinyl)methyl)-3-methyl-1,3-thiazol-2(3H)-imine

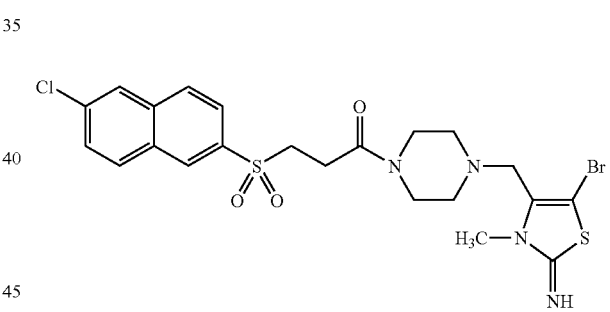

tert-Butyl ((2Z)-5-bromo-4-((4-(3-((6-chloro-2-naphthyl)sulfonyl)propanoyl)-1-piperazinyl)methyl)-3-methyl-1,3-thiazol-2(3H)-ylidene)carbamate (1.2 g) obtained in Example 30c) was dissolved in trifluoroacetic acid (10 mL), and the mixture was mixed at room temperature for 1 hour. The solvent was distilled off, and the residue was poured into an aqueous potassium carbonate solution. The mixture was extracted with a mixed solution of chloroform-methanol, and the extract was dried over anhydrous magnesium sulfate. The solvent was distilled off, and the residue was purified with a basic silica gel column to give the title compound (0.07 g) as a pale brown powder.

NMR (CDCl$_3$) δ: 2.39 (2H, t, J=5.1), 2.47 (2H, t, J=5.1), 2.86 (2H, t, J=7.8), 3.28 (2H, s), 3.36 (3H, s), 3.43-3.59 (6H, m), 7.58 (1H, dd, J=1.8, 8.4), 7.91-7.95 (4H, m), 8.46 (1H, s).

EXAMPLE 32

N-((2Z)-4-((4-(3-(((6-Chloro-2-naphthyl)sulfonyl)propanoyl)-1-piperazinyl)methyl)-3,5-dimethyl-1,3-thiazol-2(3H)-ylidene)-N-methylamine

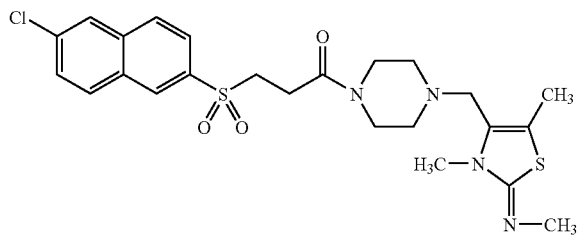

In the same manner as in Example 3, the title compound (0.39 g) as a white powder was obtained from 1-(3-((6-chloro-2-naphthyl)sulfonyl)propionyl)piperazine (1.0 g) obtained in Example 3a) and N-(4-chloromethyl-3,5-dimethyl-1,3-thiazol-2(3H)-ylidene)-N-methylamine hydrochloride (0.8 g).

NMR (CDCl$_3$) δ: 2.11 (3H, s), 2.35 (2H, t, J=5.4), 2.42 (2H, t, J=5.4), 2.86 (2H, t, J=7.8), 3.00 (3H, s), 3.21 (2H, s), 3.36 (3H, s), 3.42-3.58 (6H, m), 7.59 (1H, dd, J=1.8, 8.7), 7.88-7.95 (4H, m), 8.47 (1H, s).

EXAMPLE 33

Ethyl (1-(3-((6-chloro-2-naphthyl)sulfonyl)propanoyl)-4-(((2Z)-3-methyl-2-(methylimino)-2,3-dihydro-1,3-thiazol-4-yl)methyl)piperazin-2-yl)acetate

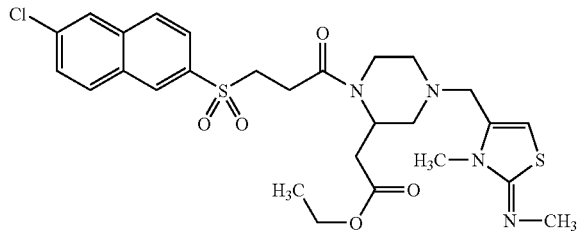

33a) tert-Butyl 4-(3-((6-chloro-2-naphthyl)sulfonyl)propanoyl)-3-(2-ethoxy-2-oxoethyl)piperazine-1-carboxylate tert-Butyl 3-(2-ethoxy-2-oxoethyl)piperazine-1-carboxylate (0.9 g) was dissolved in dichloromethane (20 mL), and triethylamine (0.92 mL) was added thereto. With ice cooling, 3-((6-chloro-2-naphthyl)sulfonyl)propionic acid (1.0 g), HOBt (0.55 g) and WSC (0.65 g) were added thereto, and the mixture was mixed at room temperature for 16 hours. The reaction solution was basified with an aqueous potassium carbonate solution, then extracted with chloroform, and the extract was dried over anhydrous magnesium sulfate. The solvent was distilled off to give the title compound (1.1 g) as a pale brown oily matter.

NMR (CDCl$_3$) δ: 1.15 (3H, t, J=7.2), 1.39 (9H, s), 2.42-2.98 (6H, m), 3.18-3.34 (0.3H, m), 3.41-3.58 (2.7H, m), 3.92-4.13 (5H, m), 4.25-4.31 (0.7H, m), 4.80-4.93 (0.3H, m), 7.48-7.56 (1H, m), 7.81-7.94 (4H, m), 8.31-8.43 (1H, m).

33b) Ethyl (1-(3-((6-chloro-2-naphthyl)sulfonyl)propanoyl)-4-(((2Z)-3-methyl-2-(methylimino)-2,3-dihydro-1,3-thiazol-4-yl)methyl)-2-piperazinyl)acetate The compound (1.1 g) obtained in Example 33a) was dissolved in trifluoroacetic acid (10 mL) and mixed at room temperature for 1 hour. The solvent was distilled off, and the residue was basified with an aqueous potassium carbonate solution. Then, the mixture was extracted with chloroform, and the extract was dried over anhydrous magnesium sulfate. The solvent was distilled off, and the residue was dissolved in DMF (20 mL). Potassium carbonate (0.55 g) and N-(4-chloromethyl-3-methyl-1,3-thiazol-2(3H)-ylidene)-N-methylamine hydrochloride (0.42 g) were added thereto and the mixture was mixed at 70° C. for 4 hours. The solvent was distilled off, and then the residue was poured into water. The mixture was extracted with a mixed solution of chloroform-methanol, and the extract was dried over anhydrous magnesium sulfate. The solvent was distilled off, and the residue was purified with a basic silica gel column to give the title compound (0.32 g) as a white powder.

NMR (CDCl$_3$) δ: 1.18 (3H, t, J=7.2), 1.83-2.13 (3H, m), 2.41-2.48 (0.5H, m), 2.62-2.91 (5H, m), 2.99 (3H, s), 3.02-3.27 (3H, m), 3.34 (3H, s), 3.47-3.62 (2H, m), 3.96-4.06 (2H, m), 4.34-4.38 (1H, m), 4.90-4.94 (0.5H, m), 5.73 (1H, s), 7.55-7.60 (1H, m), 7.82-7.96 (4H, m), 8.46-8.48 (1H, m).

EXAMPLE 34

N-((2Z)-4-((4-(3-((6-Chloro-2-naphthyl)sulfonyl)propanoyl)-3-((3-(4-morpholinyl)-1,2,4-oxadiazol-5-yl)methyl)-1-piperazinyl)methyl)-3-methyl-1,3-thiazol-2(3H)-ylidene)-N-methylamine

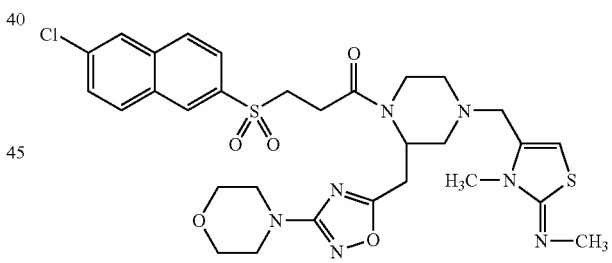

34a) 1-Aryl 4-tert-butyl 2-(2-ethoxy-2-oxoethyl)piperazine-1,4-dicarboxylate tert-Butyl 3-(2-ethoxy-2-oxoethyl)piperazine-1-carboxylate (5.5 g) was -dissolved in dichloromethane (50 mL), and triethylamine (6.3 mL) was added thereto. With ice cooling, aryl chloroformate (2.4 g) with ice cooling was added thereto, and the mixture was mixed at room temperature for 1 hour. The reaction solution was basified with an aqueous potassium carbonate solution, then extracted with chloroform, and the extract was dried over anhydrous magnesium sulfate. The solvent was distilled off to give the title compound (6.1 g) as a pale brown oily matter.

NMR (CDCl$_3$) δ: 1.25 (3H, t), 1.39 (9H, s), 2.63-3.10 (2H, m), 3.21-3.38 (2H, m), 3.69 (3H, s), 3.81-4.10 (2H, m), 4.50-4.71 (4H, m), 5.16-5.31 (2H, m), 5.77-6.02 (1H, m).

34b) 1-Aryl 4-tert-butyl 2-((3-morpholin-4-yl)-1,2,4-oxadiazol-5-yl)piperazine-1,4-dicarboxylate Morpholine-4-carboxamide oxime (2.1 g) was dissolved in anhydrous THF (50 mL), 4A molecular sieves powder (4.0 g) was added thereto, and the mixture was mixed at room temperature 3 hours. Then, sodium hydride (0.57 g) was added thereto, and the mixture was mixed at 60° C. for 20 minutes. To the reaction solution was added the compound (4.26 g) obtained in Example 34a), and refluxed for 1 hour. The reaction solution was concentrated, and the residue was purified with a silica gel column to give the title compound (1.3 g) as a pale brown oily matter.

NMR (CDCl₃) δ: 1.38 (9H, s), 2.57 (4H, t, J=4.5), 2.81-3.03 (1H, m), 3.24-3.47 (2H, m), 3.67 (2H, s), 3.72 (4H, t, J=4.5), 3.98-4.18 (2H, m), 4.58-4.74 (3H, m), 5.19-5.40 (2H, m), 5.53-5.63 (1H, m), 5.80-5.99 (1H, m).

34c) N-((2Z)-4-((4-(3-((6-Chloro-2-naphthyl)sulfonyl)propanoyl)-3-((3-(4-morpholinyl)-1,2,4-oxadiazol-5-yl)methyl)-1-piperazinyl)methyl)-3-methyl-1,3-thiazol-2(3H)-ylidene)-N-methylamine The compound (1.3 g) obtained in Example 34b) was dissolved in THF (20 mL). 1,3-Dimethylbarbituric acid (1.9 g) and tetrakis(triphenylphosphine)palladium (0.3 g) were added thereto, and the mixture was mixed at room temperature overnight having the reactor substituted with nitrogen. The reaction solution was basified with an aqueous potassium carbonate solution, then extracted with chloroform, and the extract was dried over anhydrous magnesium sulfate. The solvent was distilled off, the residue was dissolved in dichloromethane (20 mL), and triethylamine (0.92 mL) was added thereto. With ice cooling, 3-((6-chloro-2-naphthyl)sulfonyl)propionic acid (1.0 g), HOBt (0.55 g) and WSC (0.65 g) were added thereto, and the mixture was mixed at room temperature for 16 hours. The reaction solution was basified with an aqueous potassium carbonate solution, then extracted with chloroform, and the extract was dried over anhydrous magnesium sulfate. The solvent was distilled off to give tert-butyl 4-(3-((6-chloro-2-naphthyl)sulfonyl)propanoyl)-3-((3-(4-morpholinyl)-1,2,4-oxadiazol-5-yl)methyl)piperazine-1-carboxylate (2.3 g) as a pale brown oily matter. The resulting oily matter was dissolved in trifluoroacetic acid (15 mL), and mixed at room temperature for 1 hour. The reaction solution was concentrated, and then the residue was basified with an aqueous potassium carbonate solution. The mixture was then extracted with chloroform, and the extract was dried over anhydrous magnesium sulfate. The solvent was distilled off, and the residue was dissolved in DMF (30 mL). Potassium carbonate (1.0 g) and N-(4-chloromethyl-3-methyl-1,3-thiazol-2(3H)-ylidene)-N-methylamine hydrochloride (0.77 g) were added thereto and the mixture was mixed at 70° C. for 4 hours. The solvent was distilled off, and then the residue was poured into water. The mixture was extracted with a mixed solution of chloroform-methanol, and the extract was dried over anhydrous magnesium sulfate. The solvent was distilled off, and the residue was purified with a basic silica gel column to give the title compound (0.19 g) as a white powder.

NMR (CDCl₃) δ: 2.09-2.19 (1H, m), 2.39-2.61 (5H, m), 2.84-2.89 (1H, m), 2.96 (3H, s), 3.01 (3H, s), 3.06-3.30 (3H, m), 3.49-3.61 (6H, m), 3.64-3.78 (6H, m), 5.73 (1H, s), 5.86 (1H, s), 7.58 (1H, dd, J=2.4, 9.0), 7.88-7.96 (4H, m), 8.48 (1H, s).

EXAMPLE 35

((2Z)-4-((4-(3-((6-Chloro-2-naphthyl)sulfonyl)propanoyl)-1-piperazinyl)methyl)-3-methyl-2-(methylimino)-2,3-dihydro-1,3-thiazol-5-yl)methanol

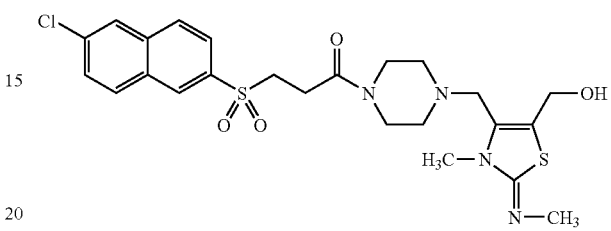

35a) tert-Butyl 4-(((2Z)-5-formyl-3-methyl-2-(methylimino)-2,3-dihydro-1,3-thiazol-4-yl)methyl)piperazine-1-carboxylate tert-Butyl 4-(((2Z)-3-methyl-2-methylimino-2,3-dihydro-1,3-thiazol-4-yl)methyl)piperazine-1-carboxylate (1.0 g) obtained in Example 11a) was dissolved in THF (20 mL), n-butyllithium (4.6 mL; a 1.6 M hexane solution) was added thereto at −70° C., and the mixture was mixed for 30 minutes. To the reaction solution was added DMF (1.0 mL), mixed at −70° C. for 1 hour, and then an aqueous ammonium chloride solution was added thereto at 0° C. The mixture was extracted with ethyl acetate, and the extract was dried over anhydrous magnesium sulfate. The solvent was distilled off to give the title compound (1.1 g) as a pale brown oily matter.

NMR (CDCl₃) δ: 1.46 (9H, s), 2.40-2.52 (4H, m), 3.06 (3H, s), 3.42-3.45 (4H, m), 3.49 (3H, s), 3.67 (2H, s), 9.75 (1H, s).

35b) tert-Butyl 4-(((2Z)-5-hydroxymethyl-3-methyl-2-(methylimino)-2,3-dihydro-1,3-thiazol-4-yl)methyl)piperazine-1-carboxylate The compound (1.1 g) obtained in Example 35a) was dissolved in a mixed solution of methanol (15 mL) and chloroform (15 mL). Sodium borohydride (0.18 g) was added thereto at 0° C., and the mixture was mixed at room temperature for 1 hour. The reaction solution was basified with an aqueous potassium carbonate solution, then extracted with chloroform, and the extract was dried over anhydrous magnesium sulfate. The solvent was distilled off to give the title compound (1.1 g) as pale brown crystals.

NMR (CDCl₃) δ: 1.45 (9H, s), 2.39-2.44 (4H, m), 2.99 (3H, s), 3.34 (3H, s), 3.34-3.43 (6H, m), 4.49 (2H, s).

35c) ((2Z)-4-((4-(3-((6-Chloro-2-naphthyl)sulfonyl)propanoyl)-1-piperazinyl)methyl)-3-methyl-2-(methylimino)-2,3-dihydro-1,3-thiazol-5-yl)methanol The compound (1.1 g) obtained in Example 35b) was dissolved in concentrated hydrochloric acid (10 mL) and mixed at room temperature for 1 hour. The reaction solution was concentrated, and then the residue was dissolved in a mixed solution of a saturated aqueous sodium bicarbonate solution (15 mL) and chloroform (15 mL). 3-((6-Chloro-2-naphthyl) sulfonyl)propionyl chloride (1.1 g) was added thereto at 0° C., and the mixture was mixed at room temperature for 2 hours. The reaction solution was poured into water, extracted with a mixed solution of chloroform-methanol, and the extract was dried over anhydrous magnesium sulfate. The solvent was distilled off, and the residue was purified with a basic silica gel column to give the title compound (0.50 g) as a white powder.

NMR (CDCl$_3$) δ: 2.38 (2H, t, J=5.1), 2.46 (2H, t, J=5.1), 2.86 (2H, t, J=8.1), 2.99 (3H, s), 3.32 (2H, s), 3.33 (3H, s), 3.44 (2H, t, J=5.1), 3.50-3.57 (4H, m), 4.48 (2H, s), 7.58 (1H, dd, J=2.1, 9.0), 7.90-7.96 (4H, m), 8.45 (1H, s).

EXAMPLE 36

N-((2Z)-4-((4-(3-((6-chloro-2-naphthyl)sulfonyl) propanoyl)-1-piperazinyl)methyl)-5-((dimethylamino)methyl)-3-methyl-1,3-thiazol-2(3H)-ylidene)-N-methylamine

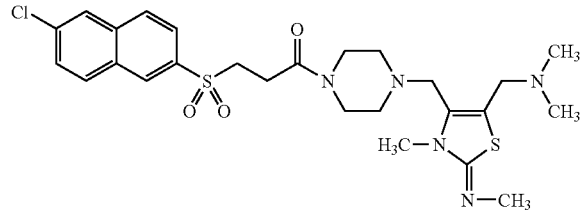

36a) tert-Butyl 4-(((2Z)-5-((dimethylamino)methyl)-3-methyl-2-(methylimino)-2,3-dihydro-1,3-thiazol-4-yl)methyl)piperazine-1-carboxylate tert-Butyl 4-(((2Z)-5-formyl-3-methyl-2-(methylimino)-2,3-dihydro-1,3-thiazol-4-yl)methyl)piperazine-1-carboxylate (1.0 g) obtained in Example 35a) and a 1 M solution of dimethylamine in THF (2.6 mL) were dissolved in a mixed solution of 1,2-dichloroethane (50 mL) and acetic acid (0.18 mL). Triacetoxy sodium borohydride (0.84 g) was added thereto at 0° C., and the mixture was mixed at room temperature overnight. The reaction solution was basified with an aqueous potassium carbonate solution, then extracted with chloroform, and the extract was dried over anhydrous magnesium sulfate. The solvent was distilled off to give the title compound (1.1 g) as pale brown crystals.

NMR (CDCl$_3$) δ: 1.46 (9H, s), 2.25 (6H, s), 2.35-2.40 (4H, m), 3.01 (3H, s), 3.27 (2H, s), 3.36 (3H, s), 3.40-3.50 (4H, m), 3.74 (2H, s).

36b) N-((2Z)-4-((4-(3-((6-Chloro-2-naphthyl)sulfonyl)propanoyl)-1-piperazinyl)methyl)-5-((dimethylamino)methyl)-3-methyl-1,3-thiazol-2(3H)-ylidene)-N-methylamine The compound (1.1 g) obtained in Example 36a) was dissolved in concentrated hydrochloric acid (10 mL) and mixed at room temperature for 1 hour. The reaction solution was concentrated, and then the residue was dissolved in a mixed solution of a saturated aqueous sodium bicarbonate solution (15 mL) and chloroform (15 mL). 3-((6-Chloro-2-naphthyl)sulfonyl)propionyl chloride (0.89 g) was added thereto at 0° C., and the mixture was mixed at room temperature for 2 hours. The reaction solution was poured into water, then extracted with a mixed solution of chloroform-methanol, and the extract was dried over anhydrous magnesium sulfate. The solvent was distilled off, and the residue was purified with a basic silica gel column to give the title compound (0.22 g) as a white powder.

NMR (CDCl$_3$) δ: 2.25 (6H, s), 2.34-2.43 (4H, m), 2.83-2.91 (2H, m), 3.00 (3H, d, J=1.8), 3.24-3.27 (2H, m), 3.28 (2H, s), 3.34 (3H, d, J=1.8), 3.44-3.59 (6H, m), 7.60 (1H, dd, J=1.4, 8.8), 7.92-7.97 (4H, m), 8.47 (1H, s).

EXAMPLE 37

N-((2Z)-4-((4-(3-((6-Chloro-2-naphthyl)sulfonyl) propanoyl)-1-piperazinyl)methyl)-3-methyl-5-(4-morpholinylmethyl)-1,3-thiazol-2(3H)-ylidene)-N-methylamine

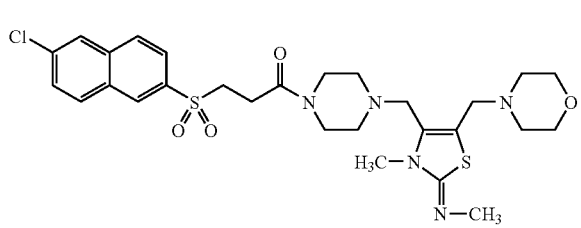

37a) tert-Butyl 4-(((2Z)-3-methyl-2-(methylimino)-5-(4-morpholinyl)methyl-2,3-dihydro-1,3-thiazol-4-yl)methyl)piperazine-1-carboxylate tert-Butyl 4-(((2Z)-5-formyl-3-methyl-2-(methylimino)-2,3-dihydro-1,3-thiazol-4-yl)methyl)piperazine-1-carboxylate (1.0 g) obtained in Example 35a) and morpholine (0.36 mL) were dissolved in a mixed solution of 1,2-dichloroethane (50 mL) and acetic acid (0.18 mL). Triacetoxy sodium borohydride (0.84 g) was added thereto at 0° C., and the mixture was mixed at room temperature overnight. The reaction solution was basified with an aqueous potassium carbonate solution, then extracted with chloroform, and the extract was dried over anhydrous magnesium sulfate. The solvent was distilled off to give the title compound (1.2 g) as pale brown crystals.

NMR (CDCl$_3$) δ: 1.46 (9H, s), 2.35-2.40 (4H, m), 2.43-2.47 (4H, m), 3.01 (3H, s), 3.27 (2H, s), 3.35 (3H, s), 3.37-3.42 (4H, m), 3.69-3.71 (4H, m), 3.74 (2H, s).

37b) N-((2Z)-4-((4-(3-((6-Chloro-2-naphthyl)sulfonyl)propanoyl)-1-piperazinyl)methyl)-3-methyl-5-(4-morpholinylmethyl)-1,3-thiazol-2-(3H)-ylidene)-N-methylamine The compound (1.2 g) obtained in Example 37a) was dissolved in concentrated hydrochloric acid (10 mL) and mixed at room temperature for 1 hour. The reaction solution was concentrated, and then the residue was dissolved in a mixed solution of a saturated aqueous sodium bicarbonate solution (15 mL) and chloroform (15 mL). 3-((6-Chloro-2-naphthyl) sulfonyl)propionyl chloride (0.89 g) was added thereto at 0° C., and the mixture was mixed at room temperature for 2 hours. The reaction solution was poured into water, then extracted with a mixed solution of chloroform-methanol, and the extract was dried over anhydrous magnesium sulfate. The solvent was distilled off, and the residue was purified with a basic silica gel column to give the title compound (0.22 g) as a white powder.

NMR (CDCl₃) δ: 2.18-2.44 (8H, m), 2.84-2.92 (2H, m), 3.01 (3H, s), 3.28 (2H, s), 3.35 (3H, s), 3.35-3.40 (2H, m), 3.43-3.55 (6H, m), 3.68-3.73 (4H, m), 7.60 (1H, dd, J=1.4, 8.8), 7.92-7.97 (4H, m), 8.48 (1H, s).

EXAMPLE 38

((2Z)-5-(1-(3-((6-Chloro-2-naphthyl)sulfonyl)propanoyl)-1-piperidinyl)-3-methyl-2-(methylimino)-2,3-dihydro-1,3-thiazol-4-yl)methanol

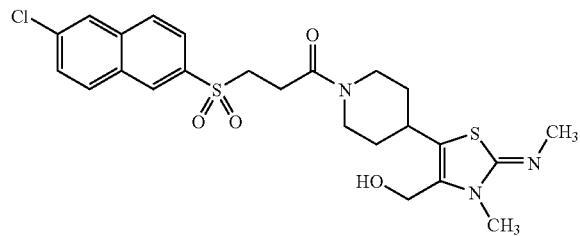

38a) tert-Butyl 4-(((2E)-4-formyl-3-methyl-2-(methylimino)-2,3-dihydro-1,3-thiazol-5-yl)methyl)piperidine-1-carboxylate In the same manner as in Example 35a), the title compound (2.7 g) was obtained from tert-butyl 4-(((2E)-3-methyl-2-(methylimino)-2,3-dihydro-1,3-thiazol-5-yl)methyl)piperidine-1-carboxylate (2.2 g).

NMR (CDCl₃) δ: 1.48 (9H, s), 1.63-1.87 (4H, m), 2.70-2.86 (2H, m), 3.04 (3H, s), 3.38-3.48 (1H, m), 3.56 (3H, s), 4.22-4.49 (2H, m), 9.77 (1H, s).

38b) tert-Butyl 4-(((2E)-4-hydroxymethyl-3-methyl-2-(methylimino)-2,3-dihydro-1,3-thiazol-5-yl)methyl)piperidine-1-carboxylate In the same manner as in Example 35b), the title compound (1.6 g) was obtained from the compound (2.7 g) obtained in Example 38a).

NMR (CDCl₃) δ: 1.47 (9H, s), 1.52-1.72 (4H, m), 2.68-2.82 (2H, m), 2.96 (3H, s), 3.18-3.29 (1H, m), 3.33 (3H, s), 4.15-4.21 (2H, m), 4.43 (2H, s).

38c) ((2Z)-5-(1-(3-((6-Chloro-2-naphthyl)sulfonyl)propanoyl)-1-piperidinyl)-3-methyl-2-(methylimino)-2,3-dihydro-1,3-thiazol-4-yl)methanol In the same manner as in Example 35c), the title compound (0.06 g) as a colorless powder was obtained from the compound (1.6 g) obtained in Example 38b).

NMR (CDCl₃) δ: 1.47-1.84 (5H, m), 2.48-2.60 (1H, m), 2.85-3.25 (3H, m), 2.93 (3H, s), 3.30 (3H, s), 3.52-3.60 (2H, m), 3.87-3.93 (1H, m), 4.41 (2H, s), 4.53-4.60 (1H, m), 7.59 (1H, dd, J=2.0, 8.8), 7.88-7.98 (4H, m), 8.48 (1H, s).

EXAMPLE 39

N-((2Z)-5-(1-(3-((6-Chloro-2-naphthyl)sulfonyl)propanoyl)-1-piperidinyl)-4-((dimethylamino)methyl)-3-methyl-1,3-thiazol-2(3H)-ylidene)-N-methylamine

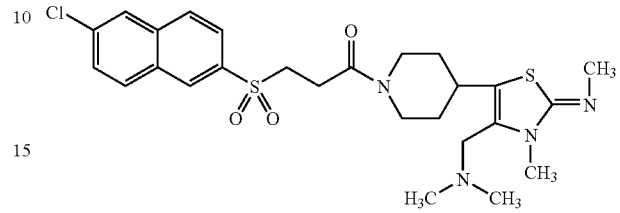

39a) tert-Butyl 4-(((2E)-4-((dimethylamino)methyl)-3-methyl-2-(methylimino)-2,3-dihydro-1,3-thiazol-5-yl)methyl)piperidine-1-carboxylate In the same manner as in Example 36a), the title compound (1.1 g) a-s a-white powder was obtained from; tert-butyl 4-(((2E)-4-formyl-3-methyl-2-(methylimino)-2,3-dihydro-1,3-thiazol-5-yl)methyl)piperidine-1-carboxylate (0.9 g) obtained in Example 38a) and a 1 M solution of dimethylamine in THF (2.6 mL).

NMR (CDCl₃) δ: 1.47 (9H, s), 1.53-1.95 (4H, m), 2.22 (6H, s), 2.69-2.89 (3H, m), 2.98 (3H, s), 3.15 (2H, s), 3.33 (3H, s), 4.17-4.23 (2H, m).

39b) N-((2Z)-5-(1-(3-((6-Chloro-2-naphthyl)sulfonyl)propanoyl)-1-piperidinyl)-4-((dimethylamino)methyl)-3-methyl-1,3-thiazol-2(3H)-ylidene)-N-methylamine In the same manner as in Example 36b), the title compound (0.43 g) as a white powder was obtained from the compound (1.1 g) obtained in Example 39a) and 3-((6-chloro-2-naphthyl)sulfonyl)propionyl chloride (0.89 g).

NMR (CDCl₃) δ: 1.47-1.70 (5H, m), 2.22 (6H, s), 2.49-2.61 (1H, m), 2.86-2.94 (2H, m), 2.98 (3H, s), 3.01-3.09 (1H, m), 3.14 (2H, s), 3.34 (3H, s), 3.53-3.61 (2H, m), 3.88-3.95 (1H, m), 4.58-4.64 (1H, m), 7.59 (1H, dd, J=1.8, 8.8), 7.88-7.98 (4H, m), 8.48 (1H, s).

EXAMPLE 40

N-((2Z)-4-(1-(3-((6-Chloro-2-naphthyl)sulfonyl)propanoyl)-1-piperidinyl)-5-((dimethylamino)methyl)-3-methyl-1,3-thiazol-2(-3H)-ylidene)-N-methylamine

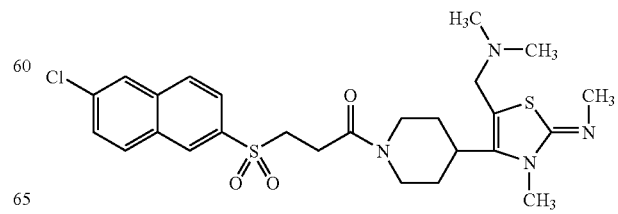

40a) tert-Butyl 4-((2Z)-5-formyl-3-methyl-2-(methylimino)-2,3-dihydro-1,3-thiazol-4-yl)piperidine-1-carboxylate In the same manner as in Example 35a), the title compound (2.4 g) was obtained from tert-butyl 4-((2Z)-3-methyl-2-methylimino-2,3-dihydro-1,3-thiazol-4-yl)piperidine-1-carboxylate hydrobromide (2.2 g) obtained in Example 14a).

NMR (CDCl$_3$) δ: 1.49 (9H, s), 1.90-2.00 (4H, m), 2.73-2.79 (2H, m), 3.05 (3H, s), 3.14-3.25 (1H, m), 3.47 (3H, s), 4.31-4.37 (2H, m), 9.88 (1H, s).

40b) tert-Butyl 4-((2Z)-5-((dimethylamino)methyl)-3-methyl-2-(methylimino)-2,3-dihydro-1,3-thiazol-4-yl)piperidine-1-carboxylate In the same manner as in Example 39a), the title compound (0.5 g) was obtained from the compound (0.75 g) obtained in Example 40a) and a 1 M solution of dimethylamine in THF (2.2 mL).

NMR (CDCl$_3$) δ: 1.49 (9H, s), 1.64-2.09 (4H, m), 2.26 (6H, s), 2.72-2.81 (3H, m), 2.99 (3H, s), 3.31 (3H, s), 3.32 (2H, s), 4.22-4.28 (2H, m).

40c) N-((2Z)-4-(1-(3-((6-Chloro-2-naphthyl)sulfonyl)propanoyl)-1-piperidinyl)-5-((dimethylamino)methyl)-3-methyl-1,3-thiazol-2(3H)-ylidene)-N-methylamine In the same manner as in Example 36b), the title compound (0.11 g) as a white powder was obtained from the compound (0.5 g) obtained in Example 40b) and 3-((6-chloro-2-naphthyl)sulfonyl)propionyl chloride (0.43 g).

NMR (CDCl$_3$) δ: 1.76-1.94 (4H, m), 2.05-2.20 (1H, m), 2.24 (6H, s), 2.50-2.59 (1H, m), 2.83-3.13 (3H, m), 2.98 (3H, s), 3.29 (2H, s), 3.30 (3H, s), 3.48-3.60 (2H, m), 3.97-4.01 (1H, m), 4.69-4.73 (1H, m), 7.58 (1H, dd, J=1.4, 8.8), 7.89-7.96 (4H, m), 8.47 (1H, s).

EXAMPLE 41

N-(((2Z)-4-(1-(3-((6-Chloro-2-naphthyl)sulfonyl)propanoyl)-1-piperidinyl)-3-methyl-2-(methylimino)-2,3-dihydro-1,3-thiazol-5-yl)methyl)-2-methoxy-N-methylethylamine

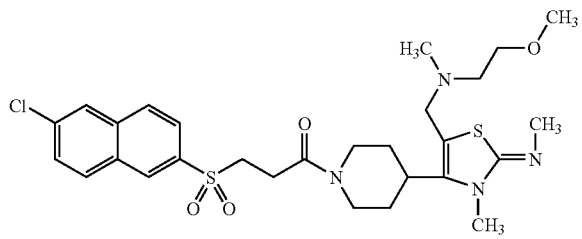

41a) tert-Butyl 4-((2Z)-5-(((2-methoxyethyl)(methyl)amino)methyl)-3-methyl-2-(methylimino)-2,3-dihydro-1,3-thiazol-4-yl)piperidine-1-carboxylate In the same manner as in Example 39a), the title compound (0.5 g) was obtained from tert-butyl 4-((2Z)-5-formyl-3-methyl-2-(methylimino)-2,3-dihydro-1,3-thiazol-4-yl)piperidine-1-carboxylate (0.75 g) obtained in Example 40a) and 2-methoxy-N-methylethylamine (0.23 g).

NMR (CDCl$_3$) δ: 1.48 (9H, s), 1.64-1.95 (4H, m), 2.30 (3H, s), 2.61 (2H, t, J=5.8), 2.71-2.82 (3H, m), 2.98 (3H, s), 3.31 (3H, s), 3.36 (3H, s), 3.46 (2H, s), 3.52 (2H, t, J=5.8), 4.17-4.32 (2H, m).

41b) N-(((2Z)-4-(1-(3-((6-Chloro-2-naphthyl)sulfonyl)propanoyl)-1-piperidinyl)-3-methyl-2-(methylimino)-2,3-dihydro-1,3-thiazol-5-yl)methyl)-2-methoxy-N-methylethylamine In the same manner as in Example 36b), the title compound (0.17 g) as a white powder was obtained from the compound (0.5 g) obtained in Example 41a) and 3-((6-chloro-2-naphthyl)sulfonyl)propionyl chloride (0.43 g).

NMR (CDCl$_3$) δ: 1.72-2.12 (5H, m), 2.28 (3H, s), 2.49-2.61 (3H, m), 2.86-3.13 (3H, m), 2.98 (3H, s), 3.29 (3H, s), 3.34 (3H, s), 3.43 (2H, s), 3.48-3.59 (4H, m), 3.96-4.00 (1H, m), 4.68-4.73 (1H, m), 7.59 (1H, dd, J=1.4, 8.8), 7.89-7.96 (4H, m), 8.48 (1H, s).

EXAMPLE 42

(2Z)-5-(1-(3-((6-Chloro-2-naphthyl)sulfonyl)propanoyl)-1-piperidinyl)-3-methyl-2-(methylimino)-2,3,4,5-tetrahydro-6H-pyrrolo[3,4-d][1,3]thiazol-6-one

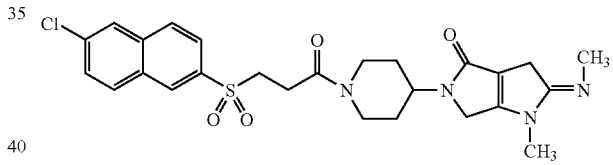

42a) Benzyl 4-((((2Z)-5-(ethoxycarbonyl)-3-methyl-2-(methylimino)-2,3-dihydro-1,3-thiazol-4-yl)methyl)amino)piperidine-1-carboxylate Ethyl (2Z)-4-bromomethyl-3-methyl-2-methylimino-2,3-dihydro-1,3-thiazole-5-carboxylate (3.0 g) obtained in Example 13) as a synthetic intermediate and benzyl 4-aminopiperidine-1-carboxylate (3.3 g) were dissolved in DMF (50 mL). Potassium carbonate (3.8 g) was added thereto, and the mixture was mixed at 70° C. for 4 hours. The solvent was distilled off, and the residue was poured into water. The mixture was then extracted with a mixed solution of chloroform-methanol, and the extract was dried over anhydrous magnesium sulfate. The solvent-was distilled off, and the residue was purified with a silica gel column to give the title compound (3.1 g) as pale yellow crystals.

NMR (CDCl$_3$) δ: 1.22-1.46 (2H, m), 1.33 (3H, t, J=7.4), 1.62-1.99 (3H, m), 2.61-2.82 (1H, m), 2.86-3.00 (1H, m), 3.01 (3H, s), 3.42 (3H, s), 4.05 (2H, s), 4.05-4.14 (2H, m), 4.25 (2H, q, J=7.4), 5.12 (2H, s), 7.34-7.37 (5H, m).

42b) Benzyl 4-((2Z)-3-methyl-2-(methylimino)-6-oxo-2,3,4,6-tetrahydro-5H-pyrrolo[3,4-d][1,3]thiazol-5-yl)piperidine-1-carboxylate The compound (3.1 g) obtained in Example 42a) and sodium hydroxide (0.59 g) were dissolved in methanol (30 mL)-water (10 mL) and mixed at 80° C. for 30 minutes. The reaction solution was acidified with 1 N hydrochloric acid, and the solvent was distilled off. The residue was dissolved in DMF (50 mL), and triethylamine (0.87 mL) was added thereto. With ice cooling, HOBt (1.0 g) and WSC (1.4 g) were added thereto, and the mixture was mixed at room temperature for 16 hours. The reaction solution was basified with an aqueous potassium carbonate solution, then extracted with chloroform, and the extract was dried over anhydrous magnesium sulfate. The solvent was distilled off, and the residue was purified with a basic silica gel column to give the title compound (1.4 g) as a brown oily matter.

NMR (CDCl$_3$) δ: 1.52-1.71 (2H, m), 1.79-1.85 (2H, m), 2.00-2.28 (1H, m), 2.81-3.04 (2H, m), 3.03 (3H, s), 3.29 (3H, s), 4.07 (2H, s), 4.29-4.35 (2H, m), 5.13 (2H, s), 7.36-7.38 (5H, m).

42c) (2Z)-5-(1-(3-((6-Chloro-2-naphthyl)sulfonyl)propanoyl)-1-piperidinyl)-3-methyl-2-(methylimino)-2,3,4,5-tetrahydro-6H-pyrrolo[3,4-d][1,3]thiazol-6-one The compound (1.4 g) obtained in Example 42b) was dissolved in a solution of hydrogen bromide in acetic acid (10 mL) and mixed at room temperature for 1 hour. The precipitated crystals were collected by filtration, and then dissolved in a mixed solution of a saturated aqueous sodium bicarbonate solution (15 mL) and chloroform (15 mL). 3-((6-Chloro-2-naphthyl)sulfonyl)propionyl chloride (1.1 g) was added thereto at 0° C., and the mixture was mixed at room temperature for 2 hours. The reaction solution was poured into water, then extracted with a mixed solution of chloroform-methanol, and the extract was dried over anhydrous magnesium sulfate. The solvent was distilled off, and the residue was purified with a basic silica gel column to give the title compound (1.2 g) as white crystals.

NMR (CDCl$_3$) δ: 1.51-1.61 (2H, m), 1.81-2.05 (2H, m), 2.58-2.70 (1H, m), 2.84-2.98 (2H, m), 3.03 (3H, s), 3.12-3.18 (1H, m), 3.28 (3H, s), 3.50-3.67 (2H, m), 3.93-3.99 (1H, m), 4.07 (2H, s), 4.14-4.41 (1H, m), 4.66-4.74 (H, m), 7.61 (1H, dd, J=1.4, 8.8), 7.89-7.98 (4H, m), 8.49 (1H, s).

EXAMPLE 43

1-(3-((6-Chloro-2-naphthyl)sulfonyl)propanoyl)-4-(((2Z)-3-methyl-2-(methylimino)-2,3-dihydro-1,3-thiazol-4-yl)methyl)piperazine-2-carboxamide

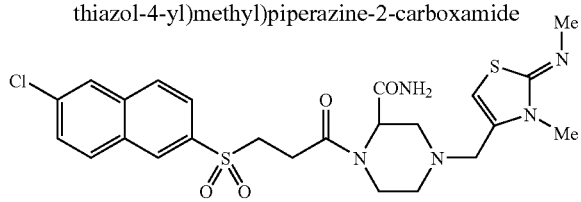

43a) Di-tert-butyl 4-(3-((6-chloro-2-naphthyl)sulfonyl)propanoyl)piperazine-1,3-dicarboxylate 3-((6-Chloro-2-naphthyl)sulfonyl)propanoic acid (0.33 g), HOBt (2.30 g) and WSC (2.88 g) were added to acetonitrile (50 mL) and mixed for 15 minutes. Then, di-tert-butyl piperazine-1,3-dicarboxylate (2.99 g) and triethylamine (3.03 g) were added thereto, and the mixture was mixed at room temperature for 15 hours. The reaction solution was concentrated under reduced pressure, and the residue was diluted with ethyl acetate and an aqueous potassium carbonate solution. The organic layer was collected by separation, and dried over anhydrous sodium sulfate. The solvent was distilled off, and the residue was purified with a silica gel column to give the title compound (2.40 g) as a colorless powder.

NMR (CDCl$_3$) δ: 1.42-1.47 (18H, m), 2.80-4.94 (11H, m), 7.60 (1H, dd, J=2.0, 8.8), 7.89-7.97 (4H, m), 8.47 (1H, s).

43b) tert-Butyl 1-(3-((6-chloro-2-naphthyl)sulfonyl)propanoyl)piperazine-2-carboxylate The compound (0.57 g) obtained in Example 43a) was dissolved in dichloromethane (10 mL). While cooling the mixture to 0° C., trimethylsilyl trifluoromethanesulfonate (0.27 g) was added thereto, and the mixture was mixed at 0° C. for 1 hour. To the reaction solution was basified by adding a saturated aqueous sodium bicarbonate solution, and then the organic layer was collected by separation. The organic layer was dried over anhydrous sodium sulfate, and the solvent was distilled off under reduced pressure to give the title compound (0.42 g) as a colorless powder.

NMR (CDCl$_3$) δ: 1.43 (9H, m), 2.60-4.89 (l1H, m), 7.59 (1H, dd, J=1.8, 2.0), 7.89-7.96 (4H, m), 8.48 (1H, s).

43c) tert-Butyl 1-(3-((6-chloro-2-naphthyl)sulfonyl)propanoyl)-4-(((2Z)-3-methyl-2-(methylimino)-2,3-dihydro-1,3-thiazol-4-yl)methyl)piperazine-2-carboxylate The compound (0.42 g) obtained in Example 32b), N-((2Z)-4-(chloromethyl)-3-methyl-1,3-thiazol-2(3H)-ylidene)-N-methylamine hydrochloride (0.19 g) and potassium carbonate (0.37 g) were suspended in DMF (5 mL) and mixed at 100° C. for 3 hours. The reaction solution was concentrated under reduced pressure, and the residue was diluted with a saturated aqueous sodium bicarbonate solution and ethyl acetate. The organic layer was collected by separation, and dried over anhydrous sodium sulfate. The solvent was distilled off under reduced pressure, and the residue was purified with a silica gel column to give the title compound (0.14 g) as a colorless powder.

NMR (CDCl$_3$) δ: 1.35 (9H, m), 1.90-6.36 (20H, m), 7.59 (1H, dd, J=9.0, 2.0), 7.92-7.97 (4H,- m), 8.47 (1H, s).

43d) 1-(3-((6-Chloro-2-naphthyl)sulfonyl)propanoyl)-4-(((2Z)-3-methyl-2-(methylimino)-2,3-dihydro-1,3-thiazol-4-yl)methyl)piperazine-2-carboxamide The compound (0.14 g) obtained in Example 43c) was dissolved in concentrated hydrochloric acid (3 mL) and mixed at room temperature for 1 hour. The reaction solution was concentrated under reduced pressure, and then water was removed from the residue by azeotropy with toluene. The resulting residue was dissolved in DMF (10 mL). HOBt-NH$_3$ complex (53 mg), WSC (66 mg) and triethylamine (0.14 g) were added thereto, and the mixture was mixed at room temperature for 15 hours. The reaction solution was concentrated under reduced pressure, and the residue was diluted with a saturated aqueous sodium bicarbonate solution and ethyl acetate. The organic layer was collected by separation, and dried over anhydrous sodium sulfate. The solvent was distilled off under reduced pressure, and the residue was purified with a basic silica gel column to give the title compound (50 mg) as a colorless powder.

NMR (CDCl$_3$) δ: 1.96-6.36 (22H, m), 7.61 (1H, dd, J=8.9, 1.9), 7.88-7.98 (4H, m), 8.47 (1H, s).

EXAMPLE 44

Methyl 1-(3-((6-chloro-2-naphthyl)sulfonyl)propanoyl)-4-(5,6-dihydroimidazo[2,1-b][1,3]thiazol-3-ylmethyl)piperazine-2-carboxylate

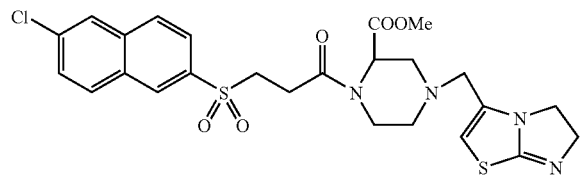

44a) 3-Methyl 1-tert-butyl 4-(3-((6-chloro-2-naphthyl)sulfonyl)propanoyl)piperazine-1,3-dicarboxylate In the same manner as in Example 43a), the title compound (1.00 g) as a colorless powder was obtained from 3-methyl 1-tert-butyl piperazine-1,3-dicarboxylate (2.80 g).

NMR (CDCl$_3$) δ: 1.44-1.45 (9H, m), 2.70-5.03 (14H, m), 7.57-7.61 (1H, m), 7.88-7.96 (4H, m), 8.46 (1H, s).

44b) Methyl 1-(3-((6-chloro-2-naphthyl)sulfonyl)-propanoyl)-4-(5,6-dihydroimidazo[2,1-b][1,3]thiazol-3-ylmethyl)piperazine-2-carboxylate The compound (0.50 g) obtained in Example 44a) was dissolved in concentrated hydrochloric acid (3 mL) and mixed at room temperature for 3 hours. The reaction solution was concentrated under reduced pressure, and then water was removed from the residue by azeotropy with toluene. The resulting residue was dissolved in DMF (5 mL). 3-(chloromethyl)-5,6-dihydroimidazo[2,1-b][1,3]thiazole hydrochloride (0.24 g) and potassium carbonate (0.32 g) were added thereto, and the mixture was mixed at 100° C. for 24 hours. The reaction solution was concentrated under reduced pressure, and the residue was diluted with a saturated aqueous sodium bicarbonate solution and ethyl acetate. The organic layer was collected by separation, and dried over anhydrous sodium sulfate. The solvent was distilled off under reduced pressure, and the residue was purified with a basic silica gel column to give the title compound (40 mg) as a colorless powder.

NMR (CDCl$_3$) δ: 2.63-5.13 (21H, m), 7.59 (1H, dd, J=8.8, 1.8), 7.91-7.96 (4H, m), 8.47 (1H, s).

EXAMPLE 45

N-((2Z)-4-((4-(3-((4-Bromophenyl)sulfonyl)propanoyl)-1-piperazinyl)methyl)-3-methyl-1,3-thiazol-2(3H)-ylidene)-N-methylamine

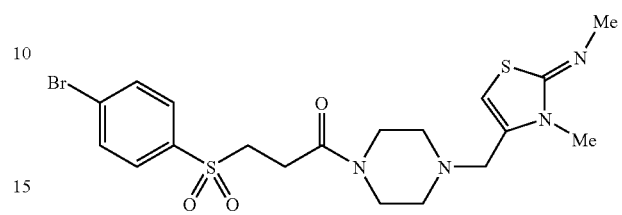

In the same manner as in Example 11b), the title compound (0.72 g) as white crystals was obtained from the compound (1.5 g) obtained in Example 11a) and 3-((4-bromophenyl)sulfonyl)propanoic acid (WO 09805635; 1.0 g).

NMR (CDCl$_3$) δ: 2.40-2.44 (4H, m), 2.82 (2H, t, J=7.8), 3.00 (3H, s), 3.26 (2H, s), 3.35 (3H, s), 3.42-3.49 (4H, m), 3.56 (2H, t, J=5.1), 5.74 (1H, s), 7.70-7.79 (4H, m).

EXAMPLE 46

N-((2Z)-5-(1-(3-((6-Chloro-2-naphthyl)sulfonyl)propanoyl)-1-piperidinyl)-3-methyl-1,3-thiazol-2(3H)-ylidene)-N-methylamine

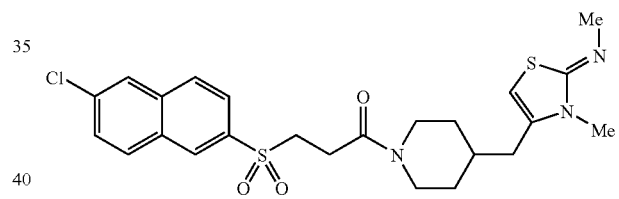

46a) tert-Butyl 4-((2Z)-3-methyl-2-(methylimino)-2,3-dihydro-1,3-thiazol-5-yl)piperidine-1-carboxylate tert-Butyl 4-(1-bromo-2-oxoethyl)piperidine-1-carboxylate (WO 0059502: 21.0 g) and a solution of N,N'-dimethylthiourea (6.0 g) in ethanol (300 mL) were heated under reflux. The reaction solution was concentrated, and the residue was dissolved in ethyl acetate and water. The aqueous layer was collected by separation. The aqueous layer was basified with an aqueous potassium carbonate solution, and extracted with chloroform. The extract was dried over anhydrous sodium sulfate, and then the solvent was distilled off to give the title compound (12.2 g) as a pale yellow solid.

NMR (CDCl$_3$) δ: 1.47 (9H, s), 1.46-1.55 (2H, m), 1.83-1.87 (2H, m), 2.55 (1H, m), 2.78 (2H, m), 2.98 (3H, s), 3.23 (3H, s), 4.14 (2H, br), 6.17 (1H, s).

46b) N-((2Z)-5-(1-(3-((6-Chloro-2-naphthyl)sulfonyl)propanoyl)-1-piperidinyl)-3-methyl-1,3-thiazol-2(3H)-ylidene)-N-methylamine To the compound (0.55 g) obtained in Example 46a) was added concentrated hydrochloric acid (4 mL), and the mixture was mixed. After completion of expansion, the mixture was diluted with ethanol and concentrated. To the residue were added triethylamine (0.49 mL) and DBU (0.54 mL), and the mixture was dissolved in acetonitrile (10 mL). The resulting solution was added to a suspension of 3-((6-chloro-2-naphthyl)sulfonyl)propanoic acid (0.53 g), WSC (0.50 g) and HOBt (0.40 g) in acetonitrile (10 mL) and mixed for 12 hours. The reaction solution was concentrated, and the residue was dissolved in chloroform and a saturated aqueous sodium bicarbonate solution to separate and collect the organic layer. The solvent was distilled off, and the residue was purified with silica gel chromatography to give the title compound (0.61 g) as a colorless solid.

NMR (CDCl$_3$) δ: 1.36-1.54 (2H, m), 1.86-1.94 (2H, m), 2.57-2.68 (2H, m), 2.86-2.92 (2H, m), 2.98 (3H, s), 3.11 (1H, m), 3.25 (3H, s), 3.53-3.60 (2H, m), 3.88 (1H, d, J=14.4), 4.53 (1H, d, J=14.4), 6.18 (1H, s), 7.59 (1H, dd, J=7.8, 8.7), 7.90-8.00 (4H, m), 8.48 (1H, s).

EXAMPLE 47

2-(1-(3-((6-Chloro-2-naphthyl)sulfonyl)propanoyl)-1-piperidinyl)-5,6-dihydroimidazo[2,1-b][1,3]thiazole

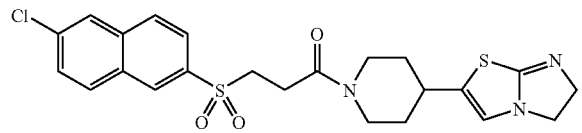

47a) tert-Butyl 4-(5,6-dihydroimidazo[2,1-b][1,3]thiazol-2-yl)piperidine-1-carboxylate In the same manner as in Example 46a), the title compound (1.46 g) was obtained from tert-butyl 4-(1-bromo-2-oxoethyl)piperidine-1-carboxylate (2.0 g) and ethylenethiourea (0.79 g) by using DMF as a solvent.

NMR (CDCl$_3$) δ: 1.36-1.56 (2H, m), 1.46 (9H, s), 1.78-1.94 (2H, m), 2.47 (1H, m), 2.71-2.85 (2H, m), 3.42-3.55 (2H, m), 3.62 (2H, m), 4.14 (2H, br), 5.91 (1H, s).

47b) 2-(1-(3-((6-Chloro-2-naphthyl)sulfonyl)propanoyl)-1-piperidinyl)-5,6-dihydroimidazo[2,1-b][1,3]thiazole In the same manner as in Example 46b), the title compound (0.18 g) as a white solid was obtained from the compound (0.50 g) obtained in Example 47a) and 3-((6-chloro-2-naphthyl)sulfonyl)propanoic acid (0.53 g).

NMR (CDCl$_3$) δ: 1.40-1.46 (2H, m), 1.76-2.20 (2H, m), 2.60 (1H, m), 2.71 (1H, m), 2.81-2.90 (2H, m), 3.11 (1H, m), 3.49-3.65 (2H, m), 3.89 (1H, br), 4.10 (2H, t, J=9.4), 4.29 (2H, t, J=9.4), 4.59 (1H, br), 6.46 (1H, s), 7.59 (1H, dd, J=2.0, 8.8), 7.87-7.99 (4H, m), 8.48 (1H, s).

EXAMPLE 48

2-(1-(3-((6-Chloro-2-naphthyl)sulfonyl)propanoyl)-1-piperidinyl)-6,7-dihydro-5H-[1,3]thiazolo[3,2-a]pyrimidine

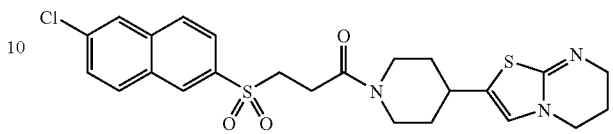

48a) tert-Butyl 4-(6,7-dihydro-5H-[1,3]thiazolo[3,2-a]pyrimidin-2-yl)piperidine-1-carboxylate In the same manner as in Example 46a), the title compound (1.28 g) was obtained by using DMF as a solvent from tert-butyl 4-(1-bromo-2-oxoethyl)piperidine-1-carboxylate (3.0 g) and propylenethiourea (0.90 g).

NMR (CDCl$_3$) δ: 1.36-1.56 (2H, m), 1.46 (9H, s), 1.78-1.94 (4H, m), 2.47 (1H, m), 2.75 (2H, t, J=12.0), 3.44 (2H, t, J=5.4), 3.62 (2H, t, J=5.4), 4.14 (2H, br), 5.91 (1H, s).

48b) 2-(1-(3-((6-Chloro-2-naphthyl)sulfonyl)propanoyl)-1-piperidinyl)-6,7-dihydro-5H-[1,3]thiazolo[3,2-a]pyrimidine In the same manner as in Example 46b), the title compound (0.18 g) as a white solid was obtained from the compound (0.50 g) obtained in Example 48a) and 3-((6-chloro-2-naphthyl)sulfonyl)propanoic acid (0.50 g).

NMR (CDCl$_3$) δ: 1.25-1.52 (2H, m), 1.82-1.98 (4H, m), 2.52-2.65 (2H, m), 2.87 (2H, dd, J=6.3, 9.7), 3.08 (1H, m), 3.42-3.50 (2H, m), 3.50-3.61 (2H, m), 3.63-3.71 (2H, m), 3.84 (1H, d, J=13.6), 4.52 (1H, d, J=13.6), 5.94 (1H, s), 7.59 (1H, dd, J=1.9, 8.6), 7.88-7.98 (4H, m), 8.47 (1H, s).

EXAMPLE 49

N-((2Z)-5-((1-(3-((6-Chloro-2-naphthyl)sulfonyl)propanoyl)-1-piperidinyl)methyl)-3-methyl-1,3-thiazol-2(3H)-ylidene)-N-methylamine

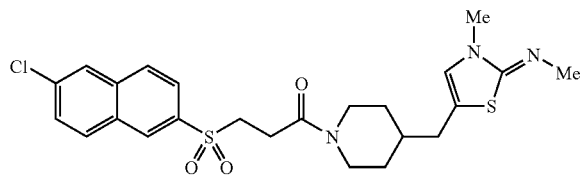

49a) tert-Butyl 4-(2-bromo-3-oxopropyl)piperidine-1-carboxylate

To a solution of tert-butyl 4-(3-oxopropyl)piperidine-1-carboxylate (Wityak J., et al., J. Med. Chem., 40, p. 50 (1997): 27.6 g) in diethyl ether was added dibromobarbituric acid (17.0 g), and the mixture was mixed for 12 hours. The insolubles were filtered off, and the filtrate was diluted with diethyl ether, sequentially washed with a saturated aqueous sodium bicarbonate solution and saturated brine, and then dried over anhydrous sodium sulfate. The solvent was distilled off to give the title compound (31.8 g) as a pale yellow viscous oily matter.

NMR (CDCl$_3$) δ: 1.07-1.27 (2H, m), 1.46 (9H, s), 1.64-1.94 (5H, m), 2.65-2.78 (2H, m), 4.05 (2H, br), 4.25 (1H, m), 9.45 (1H, s).

49b) tert-Butyl 4-(((2Z)-3-methyl-2-(methylimino)-2,3-dihydro-1,3-thiazol-5-yl)methyl)piperidine-1-carboxylate A solution of the compound (2.0 g) obtained in Example 49a) and N,N'-dimethylthiourea (0.55 g) in ethanol (20 mL) was heated under reflux. The reaction solution was concentrated under reduced pressure, and the residue was dissolved in water and washed with ethyl acetate. The aqueous phase was basified with an aqueous potassium carbonate solution, and then extracted with chloroform. The extract was dried over anhydrous sodium sulfate and concentrated under reduced pressure to give the title compound (0.56 g)

NMR (CDCl$_3$) δ: 1.06-1.16 (2H, m), 1.45 (9H, s), 1.60 (1H, m), 1.68 (2H, d, J=15.0), 2.36 (2H, d, J=6.9), 2.68 (2H, t, J=12.6), 2.98 (3H, s), 3.21 (3H, s), 4.10 (2H, br), 6.17 (1H, s).

49c) N-((2Z)-5-((1-(3-((6-Chloro-2-naphthyl)sulfonyl)propanoyl)-1-piperidinyl)methyl)-3-methyl-1,3-thiazol-2(3H)-ylidene)-N-methylamine To the compound (0.44 g) obtained in Example 49b) was added concentrated hydrochloric acid (4 mL). After completion of expansion, the mixture was diluted with ethanol and concentrated under reduced pressure. To the residue were added triethylamine (0.37 mL) and DBU (0.41 mL), and the mixture was dissolved in acetonitrile (10 mL). The resulting solution was added to a suspension of 3-((6-chloro-2-naphthyl)sulfonyl)propanoic acid (0.40 g), WSC (0.39 g) and HOBt (0.31 g) in acetonitrile (10 mL) and mixed for 12 hours. The reaction solution was concentrated under reduced pressure, and to the residue was added a saturated aqueous sodium hydrogen carbonate solution, and extracted with chloroform. The solvent was distilled off under reduced pressure, and the residue was purified with silica gel chromatography to give the title compound (0.46 g) as a pale yellow solid.

NMR (CDCl$_3$) δ: 0.95-1.10 (2H, m), 1.62-1.82 (3H, m), 2.35 (2H, d, J=6.9), 2.49 (1H, t, J=10.5), 2.83-2.89 (2H, m), 2.98 (3H, s), 2.99 (1H, t, J=10.5), 3.22 (3H, s), 3.50-3.61 (2H, m), 3.81 (1H, d, J=13.2), 4.48 (1H, d, J=13.2), 6.17 (1H, s), 7.58 (1H, dd, J=1.8, 8.7), 7.88-7.95 (4H, m), 8.47 (1H, s).

EXAMPLE 50

2-((1-(3-((6-Chloro-2-naphthyl)sulfonyl)propanoyl)-1-piperidinyl)methyl)-6,7-dihydro-5H-[1,3]thiazolo[3,2-a]pyrimidine

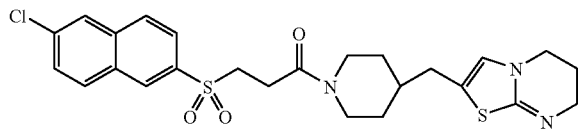

50a) tert-Butyl 4-(6,7-dihydro-5H-[1,3]thiazolo[3,2-a]pyrimidin-2-ylmethyl)piperidine-1-carboxylate In the same manner as in Example 46a), the title compound (0.46 g) was obtained from tert-butyl 4-(2-bromo-3-oxopropyl)piperidine-1-carboxylate (2.0 g) obtained in Example 49a) and propylenethiourea (0.61 g) by using DMF as a solvent.

NMR (CDCl$_3$) δ: 1.01-1.15 (2H, m), 1.45 (9H, s), 1.52 (1H, m), 1.66-1.87 (4H, m), 2.31 (2H, d, J=7.2), 2.67 (2H, m), 3.73 (2H, t, J=9.3), 4.11 (2H, m), 4.16 (2H, t, J=9.3), 6.17 (1H, s).

50b) 2-((1-(3-((6-Chloro-2-naphthyl)sulfonyl)propanoyl)-1-piperidinyl)methyl)-6,7-dihydro-5H-[1,3]thiazolo[3,2-a]pyrimidine In the same manner as in Example 46b), the title compound (0.08 g) as a pale yellow solid was obtained from the compound (0.45 g) obtained in Example 50a) and 3-((6-chloro-2-naphthyl)sulfonyl)propanoic acid (0.40 g).

NMR (CDCl$_3$) δ: 0.89-1.15 (2H, m), 1.66-1.87 (5H, m), 2.34 (2H, d, J=6.8), 2.47 (1H, m), 2.98 (1H, s), 3.47-3.67 (4H, m), 3.71-3.87 (3H, m), 4.47 (1H, d, J=13.5), 6.09 (1H, s), 7.60 (1H, dd, J=1.9, 8.6), 7.88-7.98 (4H, m), 8.47 (1H, s).

EXAMPLE 51

2-((1-(3-((6-Chloro-2-naphthyl)sulfonyl)propanoyl)-1-piperidinyl)methyl)-5,6-dihydroimidazo[2,1-b][1,3]thiazole

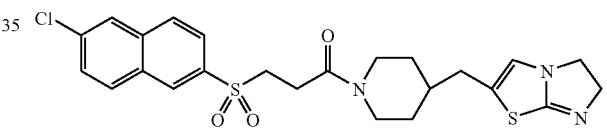

51a) tert-Butyl 4-(5,6-dihydroimidazo[2,1-b][1,3]thiazol-2-ylmethyl)piperidine-1-carboxylate In the same manner as in Example 46a), the title compound (0.41 g) was obtained from tert-butyl 4-(2-bromo-3-oxopropyl)piperidine-1-carboxylate (2.0 g) obtained in Example 49a) and ethylenethiourea (0.54 g) by using DMF as a solvent.

NMR (CDCl$_3$) δ: 1.01-1.15 (2H, m), 1.45 (9H, s), 1.52 (1H, m), 1.69 (2H, d, J=12.6), 2.31 (2H, d, J=7.2), 2.67 (2H, m), 3.73 (2H, t, J=9.3), 4.11 (2H, m), 4.16 (2H, t, J=9.3), 6.17 (1H, s).

51b) 2-((1-(3-((6-Chloro-2-naphthyl)sulfonyl)propanoyl)-1-piperidinyl)methyl)-5,6-dihydroimidazo[2,1-b][1,3]thiazole In the same manner as in Example 46b), the title compound (0.09 g) as a pale yellow solid was obtained from the compound (0.43 g) obtained in Example 51a) and 3-((6-chloro-2-naphthyl)sulfonyl)propanoic acid (0.40 g).

NMR (CDCl$_3$) δ: 0.93-1.17 (2H, m), 1.57-1.83 (3H, m), 3.30 (2H, d, J=6.6), 2.48 (1H, t, J=12.8), 2.81-2.89 (2H, m), 2.99 (1H, t, J=12.8), 3.51-3.60 (2H, m), 3.69-3.86 (3H, m), 4.10-4.20 (2H, m), 4.49 (1H, d, J=12.8), 6.19 (1H, s), 7.59 (1H, dd, J=1.8, 10.8), 7.88-7.97 (4H, s), 8.47 (1H, s).

EXAMPLE 52

N-((2Z)-5-(1-(3-((5-Chloro-1H-indol-2-yl)sulfonyl)propanoyl)-1-piperidinyl)-3-methyl-1,3-thiazol-2(3H)-ylidene)-N-methylamine dihydrochloride

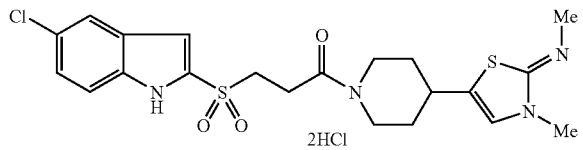

52a) tert-Butyl 5-chloro-2-((3-(4-((2Z)-3-methyl-2-(methylimino)-2,3-dihydro-1,3-thiazol-5-yl)-1-piperidinyl)-3-oxopropyl)sulfonyl)-1H-indole-1-carboxylate In the same manner as in Example 46b), the title compound (0.72 g) as a white solid was obtained from tert-butyl 4-((2Z)-3-methyl-2-(methylimino)-2,3-dihydro-1,3-thiazol-5-yl)piperidine-1-carboxylate (0.86 g) obtained in Example 46a) and 3-((1-tert-butoxycarbonyl)-5-chloro-1H-indol-2-yl)sulfonylpropanoic acid (1.07 g).

NMR (DMSO-$d_6$) δ: 1.12-1.34 (2H, m), 1.64 (9H, s), 1.75-1.92 (2H, m), 2.61 (1H, m), 2.69-2.82 (2H, m), 2.90-3.02 (5H, m), 3.58 (1H, s), 3.62-3.81 (2H, m), 3.84 (1H, br), 4.23 (1H, br), 7.15 (1H, d, J=1.3), 7.33 (1H, dd, J=2.1, 8.9), 7.52 (1H, d, J=8.9), 7.77 (1H, d, J=2.1).

52b) N-((2Z)-5-(1-(3-((5-Chloro-1H-indol-2-yl)sulfonyl)propanoyl)-1-piperidinyl)-3-methyl-1,3-thiazol-2(3H)-ylidene)-N-methylamine dihydrochloride To the compound (0.72 g) obtained in Example 52a) was added concentrated hydrochloric acid (5 mL), and the mixture was mixed. After completion of expansion, the mixture was concentrated by adding ethanol. The residue was washed with diethyl ether and dried to give the title compound (0.68 g) as a white solid.

NMR (DMSO-$d_6$) δ: 1.09 (1H, m), 1.43 (1H, m), 1.77-1.93 (2H, m), 2.59 (1H, m), 2.69-2.82 (2H, m), 2.90-3.02 (5H, m), 3.60 (3H, s), 3.62-3.74 (2H, m), 3.84 (1H, br), 4.23 (1H, br), 7.15 (1H, d, J=1.3), 7.33 (1H, dd, J=2.1, 8.9), 7.52 (1H, d, J=8.9), 7.77 (1H, d, J=2.1), 10.10 (1H, d, J=4.3), 12.62 (1H, d, J=1.3).

EXAMPLE 53

6-Chloro-N-(2-(4-((2Z)-3-methyl-2-(methylimino)-2,3-dihydro-1,3-thiazol-5-yl)-1-piperidinyl)-2-oxoethyl)-2-naphthalenesulfonamide

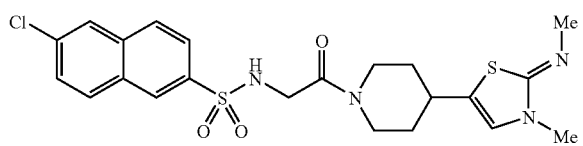

In the same manner as in Example 46b), the title compound (0.17 g) as a colorless solid was obtained from N-((6-chloro-2-naphthyl)sulfonyl)glycine (0.30 g) and tert-butyl 4-((2Z)-3-methyl-2-(methylimino)-2,3-dihydro-1,3-thiazol-5-yl)piperidine-1-carboxylate (0.30 g) obtained in Example 46a).

NMR (DMSO-$d_6$) δ: 1.04(1H, m), 1.31 (1H, m), 1.64-1.80 (2H, m), 2.52-2.67 (2H, m), 2.82 (3H, s), 2.97 (1H, m), 3.12 (3H, s), 3.69-3.84 (3H, m), 4.13 (1H, d), 6.58 (1H, s), 7.64 (1H, dd, J=2.1, 8.6), 7.89 (1H, s), 8.09 (1H, d, J=8.6), 8.13-8.23 (2H, m), 8.48 (1H, s).

EXAMPLE 54

2-(((6-Chloro-2-naphthyl)sulfonyl)(2-(4-((2Z)-3-methyl-2-(methylimino)-2,3-dihydro-1,3-thiazol-5-yl)-1-piperidinyl)-2-oxoethyl)amino)acetamide

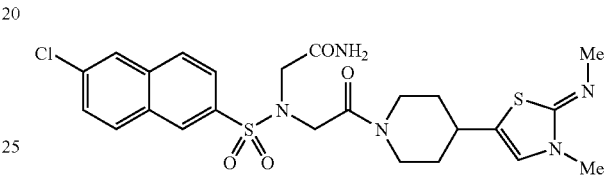

In the same manner as in Example 46b), the title compound (0.30 g) as a colorless solid was obtained from N-(2-amino-2-oxoethyl)-N-((6-chloro-2-naphthyl)sulfonyl)glycine (0.34 g) and tert-butyl 4-((2Z)-3-methyl-2-(methylimino)-2,3-dihydro-1,3-thiazol-5-yl)piperidine-1-carboxylate (0.30 g) obtained in Example 46a).

NMR (DMSO-$d_6$) δ: 1.18 (1H, m), 1.47 (1H, m), 1.72-1.86 (2H, m), 2.59-2.74 (2H, m), 2.82 (3H, s), 3.08 (1H, m), 3.13 (3H, s), 3.77-3.91 (3H, m), 4.24-4.37 (3H, m), 6.65 (1H, s), 7.14 (1H, s), 7.68 (1H, dd, J=1.8, 8.8), 7.88-8.01 (2H, m), 8.11 (1H, m), 8.17-8.25 (2H, m), 8.56 (1H, d, J=1.3).

EXAMPLE 55

N-((2Z)-5-(1-(3-(((E)-2-(4-Chlorophenyl)vinyl)sulfonyl)propanoyl)-1-piperidinyl)-3-methyl-1,3-thiazol-2(3H)-ylidene)-N-methylamine

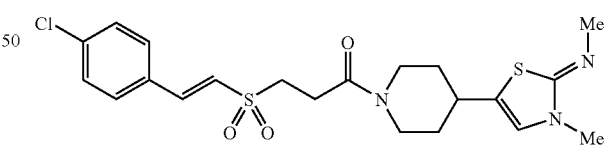

In the same manner as in Example 46b), the title compound (0.33 g) as a colorless solid was obtained from 3-(((E)-2-(4-chlorophenyl)vinyl)sulfonyl)propanoic acid (0.27 g) and tert-butyl 4-((2Z)-3-methyl-2-(methylimino)-2,3-dihydro-1,3-thiazol-5-yl)piperidine-1-carboxylate (0.3 g) obtained in Example 46a).

NMR (CDCl$_3$) δ: 1.30-1.57 (2H, m), 1.83-1.99 (2H, m), 2.57-2.70 (2H, m), 2.81-2.94 (2H, m), 2.98 (3H, s), 3.11 (1H, m), 3.24 (3H, s), 3.41-3.56 (2H, m), 3.88 (1H, d, J=13.0), 4.58 (1H, d, J=13.0), 6.14 (1H, s), 6.85 (1H, d, J=15.5), 7.38-7.48 (4H, m), 7.53 (1H, d).

EXAMPLE 56

N-((2Z)-5-(1-(3-((7-Chloro-2H-chromen-3-yl)sulfonyl)propanoyl)-1-piperidinyl)-3-methyl-1,3-thiazol-2(3H)-ylidene)-N-methylamine

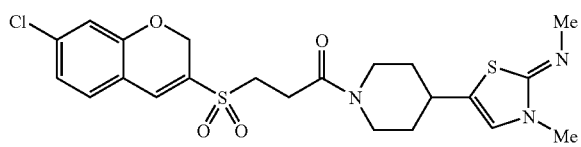

In the same manner as in Example 46b), the title compound (0.30 g) as a colorless solid was obtained from 3-((7-chloro-2H-chromen-3-yl)sulfonyl)propanoic acid (0.30 g) and tert-butyl 4-((2Z)-3-methyl-2-(methylimino)-2,3-dihydro-1,3-thiazol-5-yl)piperidine-1-carboxylate (0.30 g) obtained in Example 46a).

NMR (CDCl$_3$) δ: 1.41-1.50 (2H, m), 1.84-1.99 (2H, m), 2.58-2.70 (2H, m), 2.80-2.91 (2H, m), 2.98 (3H, s), 3.12 (1H, m), 3.25 (3H, s), 3.41-3.55 (2H, m), 3.87 (1H, d, J=13.6), 4.58 (1H, d, J=13.6), 5.03 (2H, s), 6.16 (1H, s), 6.90-6.98 (2H, m), 7.10 (1H, d, J=8.1), 7.32 (1H, s)

EXAMPLE 57

Allyl (2Z)-5-(1-(3-((6-chloro-2-naphthyl)sulfonyl)propanoyl)-4-piperidinyl)-3-methyl-1,3-thiazol-2(3H)-ylidenecarbamate

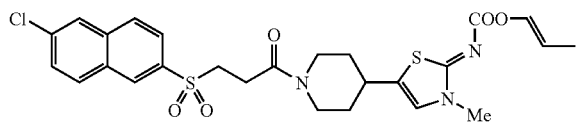

57a) tert-Butyl 4-(2-amino-1,3-thiazol-5-yl)piperidine-1-carboxylate

In the same manner as in Example 46a), the title compound (3.9 g) as a pale yellow solid was obtained from tert-butyl 4-(1-bromo-2-oxoethyl)piperidine-1-carboxylate (8.0 g) and thiourea (2.4 g).

NMR (CDCl$_3$) δ: 1.45 (9H, s), 1.46-1.66 (2H, m), 1.91 (2H, d, J=11.8), 2.80 (3H, m), 4.15 (2H, d, J=14.2), 4.81 (2H, s), 6.76 (1H, s).

57b) tert-Butyl 4-(2-imino-3-methyl-2,3-dihydro-1,3-thiazol-5-yl)piperidine-1-carboxylate To a solution of the compound (1.0 g) obtained in Example 57a) in DMF (5.0 mL), methyl iodide (0.44 mL) was added, and the mixture was mixed at 80° C. for 2 hours. The reaction solution was concentrated, and the residue was dissolved in chloroform and a saturated aqueous sodium bicarbonate solution and mixed for 15 minutes. The organic layer was collected by separation, and dried over anhydrous sodium sulfate. The solvent was distilled off, and the residue was purified with a silica gel chromatography to give the title compound (0.52 g) as a pale yellow solid.

NMR (CDCl$_3$) δ: 1.33-1.53 (2H, m), 1.46 (9H, s), 1.80 (2H, d, J=12.0), 2.49 (1H, m), 2.75 (2H, t, J=11.4), 3.23 (3H, s), 4.14 (2H, d, J=12.8), 6.05 (1H, s).

57c) tert-Butyl 4-((2Z)-2-(((allyloxy)carbonyl)imino)-3-methyl-2,3-dihydro-1,3-thiazol-5-yl)piperidine-1-carboxylate To a solution of the compound (0.47 g) obtained in Example 57b) in dichloromethane (10 mL), triethylamine (0.23 mL) and allyl chloroformate (0.18 mL) were added with ice cooling, and mixed for 1 hour. After adding the ice chips to the reaction solution and mixing for 15 minutes, the reaction solution was diluted with chloroform and a saturated aqueous sodium bicarbonate solution. The organic layer was collected by separation, and dried over anhydrous sodium sulfate. The solvent was distilled off to give the title compound (0.60 g) as a white solid.

NMR (CDCl$_3$) δ: 1.46 (9H, s), 1.48-1.89 (2H, m), 1.91 (2H, bd, J=9.0), 2.67-2.88 (3H, m), 3.60 (3H, s), 4.15 (2H, br), 4.69 (2 h, m), 5.21 (1H, m), 5.35 (1H, m), 6.03 (1H, m), 6.52 (1H, s).

57d) Allyl (2Z)-5-(1-(3-((6-chloro-2-naphthyl)sulfonyl)propanoyl)-4-piperidinyl)-3-methyl-1,3-thiazol-2(3H)-ylidenecarbamate The compound (0.68 g) obtained in Example 57c) was dissolved in a 4 N solution of hydrochloride in dioxane (10 mL), and mixed for 6 hours. The reaction solution was neutralized with a saturated aqueous sodium bicarbonate solution and extracted with chloroform. After distilling off the solvent, triethylamine (0.50 mL) was added to the residue, and the mixture was dissolved in acetonitrile (10 mL). This solution was added to a suspension of 3-((6-chloro-2-naphthyl)sulfonyl)propanoic acid (0.53 g), WSC (0.51 g) and HOBt (0.41 g) in acetonitrile (10 mL), and mixed for 12 hours. The reaction solution was concentrated, and the residue was dissolved in chloroform and a saturated aqueous sodium bicarbonate solution. The organic layer was collected by separation, and dried over anhydrous sodium sulfate. The solvent was distilled off, and the residue was purified with a silica gel column to give the title compound (0.88 g) as a colorless solid.

NMR (CDCl$_3$) δ: 1.41-1.53 (2H, m), 1.91-2.06 (2H, m), 2.64 (1H, m), 2.75 (1H, m), 2.88 (2H, t, J=8.6), 3.14 (1H, m), 3.56 (2H, t, J=8.6), 3.61 (3H, s), 3.92 (1H, d, J=13.4), 4.56 (1H, d, J=13.4), 4.70 (2H, m), 5.23 (1H, m), 5.36 (1H, m), 6.02 (1H, m), 6.52 (1H, s).

EXAMPLE 58

5-(1-(3-((6-Chloro-2-naphthyl)sulfonyl)propanoyl)-4-piperidinyl)-3-methyl-1,3-thiazol-2(3H)-imine

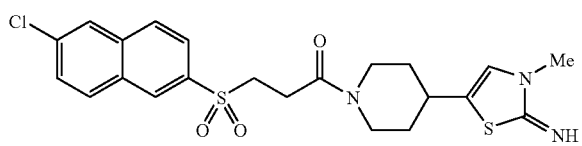

To a solution of allyl (2Z)-5-(1-(3-((6-chloro-2-naphthyl)sulfonyl)propanoyl)-4-piperidinyl)-3-methyl-1,3-thiazol-2(3H)-ylidenecarbamate (0.60 g) obtained in Example 57d) in THF, 1,3-dimethylbarbituric acid (0.25 g) and tetrakis(triphenylphosphine)palladium (0.06 g) were added thereto and mixed for 12 hours under argon atmosphere. The insolubles were filtered off, and the filtrate was concentrated. The residue was purified with a silica gel column to give the title compound (0.32 g) as a pale yellow solid.

NMR (CDCl$_3$) δ: 1.28-1.50 (2H, m), 1.82-1.94 (2H, m), 2.55-2.64 (2H, m), 2.85-2.90 (2H, m), 3.08 (1H, t, J=12.6), 3.23 (3H, s), 3.52-3.58 (2H, m), 3.87 (1H, d, J=13.5), 4.51 (1H, d, J=13.5), 6.03 (1H, s), 7.58 (1H, dd, J=1.8, 8.8), 7.88-7.95 (4H, m), 8.47 (1H, s).

EXAMPLE 59

Allyl (2Z)-5-(1-(3-((6-chloro-2-naphthyl)sulfonyl)propanoyl)-1-piperidinyl)-3-ethyl-1,3-thiazol-2(3H)-ylidenecarbamate

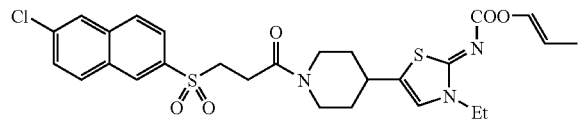

59a) tert-Butyl 4-(3-ethyl-2-imino-2,3-dihydro-1,3-thiazol-5-yl)piperidine-1-carboxylate In the same manner as in Example 57b), the title compound (0.48 g) was obtained from tert-butyl 4-(2-amino-1,3-thiazol-5-yl)piperidine-1-carboxylate (1.0 g) obtained in Example 57a) and ethyl iodide (0.73 mL).

NMR (CDCl$_3$) δ: 1.24 (3H, t, J=7.4), 1.33-1.54 (2H, m), 1.46 (9H, s), 1.80 (2H, d, J=12.0), 2.49 (1H, m), 2.75 (2H, t, J=11.4), 4.14 (2H, d, J=12.8), 4.11 (2H, q, J=7.4), 6.05 (1H, s).

59b) tert-butyl 4-((2Z)-2-(((allyloxy)carbonyl)imino)-3-ethyl-2,3-dihydro-1,3-thiazol-5-yl)piperidine-1-carboxylate In the same manner as in Example 57c), the title compound (0.60 g) was obtained from the compound (0.48 g) obtained in Example 59a).

NMR (CDCl$_3$) δ: 1.26 (3H, t, J=7.4), 1.47 (9H, s), 1.47-1.63 (2H, m), 1.92 (2H, d, J=11.2), 2.67-2.87 (3H, m), 4.11 (2H, q, J=7.4), 4.17 (2H, br), 4.69 (2H, m), 5.21 (1H, d, J=12.0), 5.35 (1H, d, J=17.2), 6.03 (1H, m), 6.56 (1H, s).

59c) Allyl (2Z)-5-(1-(3-((6-chloro-2-naphthyl)sulfonyl)propanoyl)-1-piperidinyl)-3-ethyl-1,3-thiazol-2(3H)-ylidenecarbamate In the same manner as in Example 57d), the title compound (0.69 g) was obtained from the compound (0.54 mg) obtained in Example 59b) and 3-((6-chloro-2-naphthyl)sulfonyl)propanoic acid (0.40 g).

NMR (CDCl$_3$) δ: 1.36 (3H, s, J=7.2), 1.39-1.55 (2H, m), 1.92-2.05 (2H, m), 2.64 (1H, m), 2.76 (1H, m), 2.89 (2H, t, J=8.0), 3.14 (1H, t, J=12.8), 3.57 (2H, t, J=8.0), 3.82 (1H, d, J=13.2), 4.10 (2H, q, J=7.2), 4.70 (2H, m), 5.22 (1H, m), 5.35 (1H, m), 6.03 (1H, m), 6.55 (1H, s), 7.60 (2H, dd, J=2.2, 8.8), 7.89-7.94 (4H, m), 8.49 (1H, s).

EXAMPLE 60

5-(1-(3-((6-Chloro-2-naphthyl)sulfonyl)propanoyl)-1-piperidinyl)-3-ethyl-1,3-thiazol-2(3H)-imine

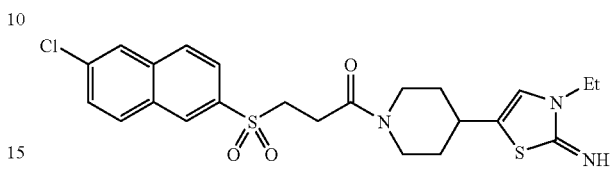

In the same manner as in Example 58), the title compound (0.33 g) was obtained from allyl (2Z)-5-(1-(3-((6-chloro-2-naphthyl)sulfonyl)propanoyl)-1-piperazinyl)-3-ethyl-1,3-thiazol-2(3H)-ylidenecarbamate (0.50 g) obtained in Example 59c).

NMR (CDCl$_3$) δ: 1.29 (3H, t, J=7.2), 1.24-1.44 (2H, m), 1.80-1.96 (4H, m), 2.50-2.65 (2H, m), 2.78-2.93 (2H, m), 3.08 (1H, m), 3.48-3.62 (2H, m), 3.71 (2H, q, J=7.2), 3.85 (1H, d, J=13.6), 4.53 (1H, d, J =13.6), 6.10 (1H, s), 7.59 (1H, dd, J=1.9, 8.6), 7.88-7.97 (4H, m), 8.47 (1H, s).

EXAMPLE 61

N-((2Z)-5-(1-(3-((6-Chloro-2-naphthyl)sulfonyl)propanoyl)-1-piperidinyl)-3-methyl-1,3-thiazol-2(3H)-ylidene)acetamide

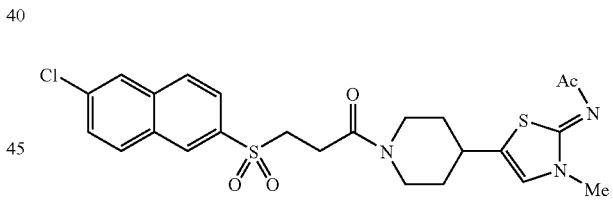

To a solution of 5-(1-(3-((6-chloro-2-naphthyl)sulfonyl)propanoyl)-1-piperazinyl)-3-methyl-1,3-thiazol-2(3H)-imine (0.20 g) obtained in Example 58) in dichloromethane (5 mL), triethylamine (0.5 mL) and acetic anhydride (0.5 mL) were added and mixed for 2 hours. After adding ice chips to the reaction solution and mixing for 15 minutes, the reaction solution was diluted with chloroform and a saturated aqueous sodium bicarbonate solution. The organic layer was collected by separation, and dried over anhydrous sodium sulfate. The solvent was distilled off, and the residue was purified with a silica gel column to give the title compound (0.22 g) as a white solid.

NMR (CDCl$_3$) δ: 1.40-1.59 (2H, m), 1.93-2.06 (2H, m), 2.29 (3H, s), 2.64 (1H, t, J=12.9), 2.81 (1H, m), 2.89 (2H, m), 3.13 (1H, t, J=12.9), 3.56 (2H, m), 3.67 (3H, s), 3.90 (1H, d, J=12.3), 4.56 (1H, d, J=12.3), 6.55 (1H, s), 7.58 (1H, dd, J=1.8, 8.7), 7.88-7.95 (4H, m), 8.47 (1H, s).

EXAMPLE 62

N-((2Z)-5-(1-(3-((6-Chloro-2-naphthyl)sulfonyl)propanoyl)-1-piperidinyl)-3-methyl-1,3-thiazol-2(3H)-ylidene)-N-propylamine

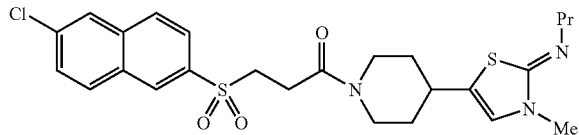

62a) tert-Butyl 4-(2-(propylamino)-1,3-thiazol-5-yl)piperidine-1-carboxylate In same manner as in Example 46a), the title compound (1.24 g) as a pale yellow solid was obtained from tert-butyl 4-(1-bromo-2-oxoethyl)piperidine-1-carboxylate (6.45 g) and N-propylthiourea (2.0 g).

NMR (CDCl$_3$) δ: 0.98 (3H, t, J=7.2), 1.47 (9H, s), 1.50-1.72 (4H, m), 1.92 (2H, m), 2.80 (3H, m), 3.20 (2H, t, J=7.2), 4.15 (2H, d, J=14.2), 5.23 (1H, s), 6.78 (1H, s)

62b) 5-(1-(3-((6-Chloro-2-naphthyl)sulfonyl)propanoyl)-1-piperidinyl)-N-propyl-1,3-thiazol-2-amine In the same manner as in Example 46b), the title compound (1.74 g) was obtained from the compound (1.27 g) obtained in Example 62a) and 3-((6-chloro-2-naphthyl)sulfonyl)propanoic acid (1.12 g).

NMR (CDCl$_3$) δ: 1.37-1.60 (2H, m), 1.91-2.04 (2H, m), 2.63 (1H, t, J=12.9), 2.83-2.91 (3H, m), 3.11 (1H, t, J=12.9), 3.53-3.60 (2H, m), 3.87 (1H, d, J=14.1), 4.51 (1H, d, J=14.1), 4.80 (2H, s), 6.74 (1H, s), 7.57 (1H, dd, J=1.8, 8.2), 7.88-7.95 (4H, m), 8.47 (1H, s).

62c) N-((2Z)-5-(1-(3-((6-Chloro-2-naphthyl)sulfonyl)propanoyl)-1-piperidinyl)-3-methyl-1,3-thiazol-2(3H))-ylidene)-N-propylamine In the same manner as in Example 57b), the title compound (0.28 g) was obtained from the compound (0.50 g) obtained in Example 62b) and methyl iodide (0.61 mL).

NMR (CDCl$_3$) δ: 0.97 (3H, t, J=7.2), 1.35-1.50 (2H, m), 1.63-1.73 (2H, m), 1.84-1.96 (2H, m), 2.57-2.65 (2H, m), 2.88 (2H, dd, J=6.6, 9.9), 3.01 (2H, t, J=7.2), 3.09 (1H, t, J=12.3), 3.22 (3H, s), 3.53-3.59 (1H, m), 3.86 (1H, d, J=12.9), 4.51 (1H, d, J=12.9), 6.11 (1H, s), 7.58 (1H, dd, J=1.8, 8.1), 7.88-7.95 (4H, m), 8.46 (1H, s).

EXAMPLE 63

N-((2Z)-5-(1-(3-((6-Chloro-2-naphthyl)sulfonyl)propanoyl)-1-piperidinyl)-3-ethyl-1,3-thiazol-2(3H)-ylidene)-N-methylamine

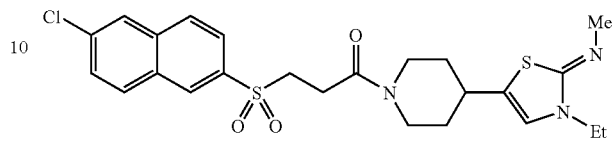

63a) tert-Butyl 4-(2-(methylamino)-1,3-thiazol-5-yl)piperidine-1-carboxylate In the same manner as in Example 46a), the title compound (1.74 g) as a pale yellow solid was obtained from tert-butyl 4-(1-bromo-2-oxoethyl)piperidine-1-carboxylate (6.45 g) and N-methylthiourea (1.53 g).

NMR (CDCl$_3$) δ: 1.47 (9H, s), 1.57 (2H, m), 1.92 (2H, dd, J=14.9), 2.80 (3H, m), 2.95 (3H, s), 4.15 (2H, d, J=13.6), 5.23 (1H, s), 6.80 (1H, s).

63b) 5-(1-(3-((6-Chloro-2-naphthyl)sulfonyl)propanoyl)-1-piperidinyl)-N-methyl-1,3-thiazol-2-amine In the same manner as in Example 46b), the title compound (2.36 g) as a pale yellow solid was obtained from the compound (1.74 g) obtained in Example 63a) and 3-((6-chloro-2-naphthyl)sulfonyl)propanoic acid (1.66 g).

NMR (CDCl$_3$) δ: 1.37-1.61 (2H, m), 1.91-2.04 (2H, m), 2.63 (1H, t, J=13.2), 2.83-2.92 (3H, m), 2.95 (3H, s), 3.12 (1H, t, J=13.2), 3.52-3.60 (2H, m), 3.85 (1H, d, J=13.5), 4.53 (1H, d, J=13.5), 4.94 (1H, s), 6.78 (1H, s), 7.58 (1H, dd, J=1.8, 7.8), 7.88-7.95 (4H, m), 8.47 (1H, s).

63c) N-((2Z)-5-(1-(3-((6-Chloro-2-naphthyl)sulfonyl)propanoyl)-1-piperidinyl)-3-ethyl-1,3-thiazol-2(3H)-ylidene)-N-methylamine In the same manner as in Example 57b), the title compound (0.29 g) as a pale yellow solid was obtained from the compound (0.50 g) obtained in Example 63b) and ethyl iodide (0.21 mL).

NMR (CDCl$_3$) δ: 1.25 (3H, t, J=7.2), 1.35-1.53 (2H, m), 1.84-1.99 (2H, m), 2.56-2.67 (2H, m), 2.88 (2H, t, J=7.0), 2.97 (3H, s), 3.10 (1H, m), 3.48 (2H, t, J=7.0), 3.68 (2H, q, J=7.2), 3.88 (1H, d, J=13.2), 4.52 (1H, d, J=13.2), 6.20 (1H, s), 7.59 (1H, dd, J=2.2, 9.2), 7.88-7.97 (4H, m), 8.48 (1H, s).

EXAMPLE 64

2-((2Z)-5-(1-(3-((6-Chloro-2-naphthyl)sulfonyl)propanoyl)-1-piperidinyl)-2-(methylimino)-1,3-thiazol-3(2H)-yl)ethanol

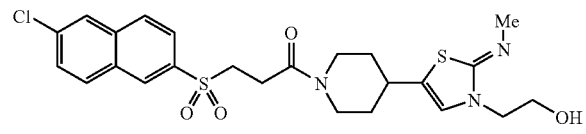

In the same manner as in Example 57b), the title compound (0.36 g) as a pale yellow solid was obtained from 5-(1-(3-((6-chloro-2-naphthyl)sulfonyl)propanoyl)-1-piperidinyl)-N-methyl-1,3-thiazol-2-amine (0.60 g) obtained in Example 63b) and 2-iodoethanol (0.20 mL).

NMR (CDCl$_3$) δ: 1.36-1.51 (2H, m), 1.85-1.98 (2H, m), 2.56-2.68 (2H, m), 2.86-2.89 (2H, m), 2.92 (3H, s), 3.10 (1H, m), 3.53-3.59 (2H, m), 3.81-3.91 (5H, m), 4.54 (1H, d, J=14.8), 6.16 (1H, s), 7.58 (1H, dd, J=1.8, 7.8), 7.88-7.95 (4H, m), 8.47 (1H, s).

EXAMPLE 65

2-(5-(1-(3-((6-Chloro-2-naphthyl)sulfonyl)pro-panoyl)-1-piperidinyl)-2-imino-1,3-thiazol-3(2H)-yl)-acetamide

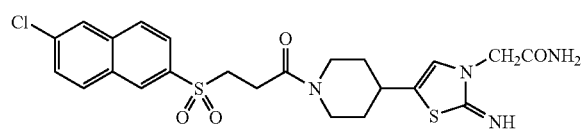

65a) 5-(1-(3-((6-Chloro-2-naphthyl)sulfonyl)pro-panoyl)-1-piperidinyl)-1,3-thiazol-2-amine In the same manner as in Example 46b), the title compound (0.86 g) as a pale yellow solid was obtained from tert-butyl 4-(2-amino-1,3-thiazol-5-yl)piperidine-1-carboxylate (1.83 g) obtained in Example 57a) and 3-((6-chloro-2-naphthyl)sulfonyl)propanoic acid (1.93 g).

NMR (CDCl$_3$) δ: 1.37-1.60 (2H, m), 1.91-2.04 (2H, m), 2.63 (1H, t, J=12.9), 2.83-2.91 (3H, m), 3.11 (1H, t, J=12.9), 3.53-3.60 (2H, m), 3.87 (1H, d, J=14.1), 4.51 (1H, d, J=14.1), 4.80 (2H, s), 6.74 (1H, s), 7.57 (1H, dd, J=1.8, 8.2), 7.88-7.95 (4H, m), 8.47 (1H, s).

65b) 2-(5-(1-(3-((6-Chloro-2-naphthyl)sulfonyl)pro-panoyl)-1-piperidinyl)-2-imino-1,3-thiazol-3(2H)-yl) acetamide In the same manner as in Example 57b), the title compound (0.24 g) as a pale yellow solid was obtained from the compound (0.50 g) obtained in Example 65a) and iodoacetamide (0.24 g).

NMR (CDCl$_3$) δ: 1.32-1.51 (2H, m), 1.82-1.95 (2H, m), 2.54-2.63 (2H, m), 2.85-2.90 (2H, m), 3.08 (1H, t, J=11.7), 3.52-3.58 (2H, m), 3.87 (1H, d, J=13.8), 4.27 (2H, s), 4.53 (1H, d, J=13.8), 5.35 (1H, s), 6.18 (1H, s), 7.25 (1H, s), 7.58 (1H, dd, J=1.8, 8.8), 7.88-7.95 (4H, m), 8.47 (1H, s).

EXAMPLE 66

2-(((2Z)-5-(1-(3-((6-Chloro-2-naphthyl)sulfonyl) propanoyl)-1-piperidinyl)-3-methyl-1,3-thiazol-2 (3H)-ylidene)amino)ethanol

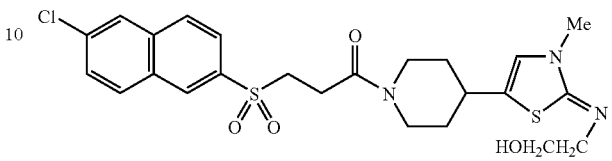

66a) N-(2-((tert-Butyldimethylsilyl)oxy)ethyl)thiourea

To a solution of 2-((tert-butyldimethylsilyl)oxy)etha-namine (WO 0007985: 24.4 g) in THF (300 mL) was added benzoyl isothiocyanate (22.7 g), and the mixture was mixed for 2 hours. The reaction solution was concentrated, and the residue was dissolved in methanol (150 mL). To the resulting solution were added potassium carbonate (5.0 g) and water (50 mL), and the mixture was mixed for 2 hours. The insolubles were filtered off, and the filtrate was concentrated. The residue was dissolved in ethyl acetate, sequentially washed with 1 N hydrochloric acid, a saturated aqueous sodium bicarbonate solution and saturated brine, and then dried over anhydrous sodium sulfate. The solvent was distilled off to give the title compound (27.7 g) as a colorless oily matter.

NMR (CDCl$_3$) δ: 0.02 (6H, s), 0.83 (9H, s), 1.74 (1H, s), 3.28 (2H, br), 3.68-3.73 (2H, m), 6.05 (1H, br), 6.56 (1H, br), 6.98 (1H, br).

66b) tert-Butyl 4-(2-((2-hydroxyethyl)amino)-1,3-thiazol-5-yl)piperidine-1-carboxylate In the same manner as in Example 47a), the title compound (1.52 g) was obtained from the compound (2.34 g) obtained in Example 66a) and tert-butyl 4-(1-bromo-2-oxoethyl)piperi-dine-1-carboxylate (4.6 g).

NMR (CDCl$_3$) δ: 1.46 (9H, s), 1.46-1.60 (2H, m), 1.90 (2H, d, J=11.4), 2.74-2.83 (3H, m), 3.46 (2H, t, J=5.4), 3.81 (2H, t, J=5.4), 4.43 (1H, m), 6.75 (1H, s).

66c) 2-((5-(1-(3-((6-Chloro-2-naphthyl)sulfonyl) propanoyl)-1-piperidinyl)-1,3-thiazol-2-yl)amino) ethanol In the same manner as in Example 46b), the title compound (1.37 g) was obtained from the compound (1.26 g) obtained in Example 66b) and 3-((6-chloro-2-naphthyl)sulfonyl)pro-panoic acid (1.15 g).

NMR (CDCl$_3$) δ: 1.31-1.62 (2H, m), 1.88-2.03 (2H, m), 2.62 (1H, t, J=12.6), 2.80-2.93 (3H, m), 3.11 (1H, t, J=12.6), 3.45 (2H, t, J=5.4), 3.53-3.61 (2H, m), 3.81 (2H, t, J=5.4), 3.84 (1H, d, J=13.4), 4.51 (1H, d, J=13.4), 5.55 (1H, br), 6.74 (1H, s), 7.58 (1H, dd, J=2.0, 7.8), 7.88-7.96 (4H, m), 8.47 (1H, s).

66d) 2-(((2Z)-5-(1-(3-((6-Chloro-2-naphthyl)sulfo-nyl)propanoyl)-1-piperidinyl)-3-methyl-1,3-thiazol-2 (3H)-ylidene)amino)ethanol In the same manner as in Example 57b), the title compound (0.75 g) was obtained from the compound (1.0 g) obtained in Example 66c) and methyl iodide (0.25 mL).

NMR (CDCl$_3$) δ: 1.35-1.51 (2H, m), 1.82-1.98 (2H, m), 2.55-2.69 (2H, m), 2.88 (2H, dd, J=6.3, 9.7), 3.09 (1H, m), 3.15 (2H, t, J=5.3), 3.25 (3H, s), 3.51-3.64 (2H, m), 3.82 (2H, t, J=5.3), 3.86 (1H, d, J=13.8), 4.53 (1H, d, J=13.8), 6.18 (1H, s), 7.59 (1H, dd, J=2.0, 8.8), 7.89-7.98 (4H, m), 8.48 (1H, s).

EXAMPLE 67

(2Z)-5-(1-(3-((6-Chloro-2-naphthyl)sulfonyl)pro-panoyl)-1-piperidinyl)-3-methyl-2-(methylimino)-2,3-dihydro-1,3-thiazole-4-carbaldehyde

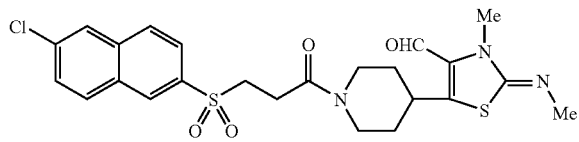

67a) tert-Butyl 4-((2Z)-4-formyl-3-methyl-2-(meth-ylimino)-2,3-dihydro-1,3-thiazol-5-yl)piperidine-1-carboxylate To a solution of tert-butyl 4-((2Z)-3-methyl-2-(meth-ylimino)-2,3-dihydro-1,3-thiazol-5-yl)piperidine-1-car-boxylate (5.0 g) obtained in Example 46a) in THF (75 mL) was added n-butyllithium (24 mL, a 1.6 M hexane solution) at −78° C. The reaction solution was mixed for 15 minutes, and then DMF (5 mL) was added thereto, and the mixture was further mixed for 30 minutes. To the reaction solution was added a saturated aqueous ammonium chloride solution, and then poured into a mixed solution of ethyl acetate and a saturated aqueous sodium bicarbonate solution. The organic layer was collected by separation, washed with saturated brine, and then dried over anhydrous sodium sulfate. The solvent was distilled off, and the residue was purified with a silica gel column to give the title compound (3.45 g) as a yellow solid.

NMR (CDCl$_3$) δ: 1.48 (9H, s), 1.55-1.76 (2H, m), 1.84 (2H, d, J=11.7), 2.78 (2H, m), 3.04 (3H, s), 3.43 (1H, m), 3.57 (3H, s), 4.25 (2H, br), 9.77 (1H, s).

67b) (2Z)-5-(1-(3-((6-Chloro-2-naphthyl)sulfonyl) propanoyl)-1-piperidinyl)-3-methyl-2-(meth-ylimino)-2,3-dihydro-1,3-thiazole-4-carbaldehyde In the same manner as in Example 46b), the title compound (1.89 g) as a pale yellow solid was obtained from the compound (1.07 g) obtained in Example 67a) and 3-((6-chloro-2-naphthyl)sulfonyl)propanoic acid.

NMR (CDCl$_3$) δ: 1.55-1.73 (2H, m), 1.86-1.97 (2H, m), 2.61 (1H, m), 2.88-2.96 (2H, m), 3.03 (3H, s), 3.16 (1H, m), 3.48-3.59 (3H, m), 3.55 (3H, s), 3.97 (1H, d, J=13.5), 4.67 (1H, d, J=13.5), 7.59 (1H, dd, J=1.8, 9.0), 7.89-7.96 (4H, m), 8.47 (1H, s), 9.76 (1H, s).

EXAMPLE 68

(2Z)-5-(1-(3-((6-Chloro-2-naphthyl)sulfonyl)pro-panoyl)-1-piperidinyl)-3-methyl-2-(methylimino)-2,3-dihydro-1,3-thiazole-4-carboxylic acid

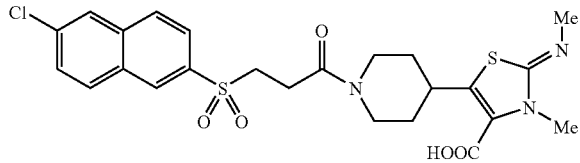

To a solution of (2Z)-5-(1-(3-((6-chloro-2-naphthyl)sulfo-nyl)propanoyl)-1-piperidinyl)-3-methyl-2-(methylimino)-2,3-dihydro-1,3-thiazole-4-carbaldehyde (0.20 g) obtained in Example 67b) in tert-butyl alcohol/water/2-methyl-2-butene (40 mL, 5:4:1) were added sodium chlorite (0.21 g) and sodium dihydrogen phosphate (0.28 g), and the mixture was mixed for 12 hours. The reaction solution was concentrated, and the residue was dissolved in chloroform and saturated brine. The chloroform layer was collected by separation, and dried over anhydrous sodium sulfate. The solvent was distilled off to give the title compound (0.19 g) as a colorless solid.

NMR (CDCl$_3$) δ: 1.38-1.69 (2H, m), 1.96-2.14 (2H, m), 2.60 (1H, m), 2.83-3.01 (3H, m), 3.19 (3H, s), 3.21 (1H, m), 3.53-3.61 (2H, m), 3.88 (3H, s), 3.96 (1H, s), 4.64 (1H, d, J=10.4), 7.60 (1H, dd, J=1.8, 9.2), 7.92-7.98 (4H, m), 8.48 (1H, s).

EXAMPLE 69

(2Z)-5-(1-(3-((6-Chloro-2-naphthyl)sulfonyl)pro-panoyl)-1-piperidinyl)-3-methyl-2-(methylimino)-2,3-dihydro-1,3-thiazole-4-carboxamide

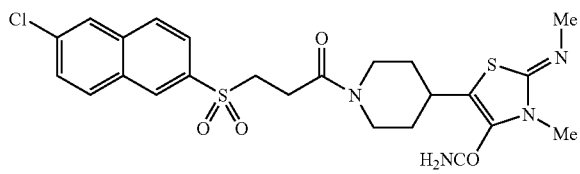

To a solution of (2Z)-5-(1-(3-((6-chloro-2-naphthyl)sulfo-nyl)propanoyl)-1-piperidinyl)-3-methyl-2-(methylimino)-2,3-dihydro-1,3-thiazole-4-carboxylic acid (0.21 g) obtained in Example 68) in dichloromethane (20 mL) was added WSC (0.11 g) and HOBt-NH$_3$ complex (0.09 g), and mixed for 12 hours. The reaction solution was diluted with chloroform, washed with a saturated aqueous sodium bicarbonate solution, and dried over anhydrous sodium sulfate. The solvent was distilled off, and the residue was purified with a silica gel column to give the title compound (0.07 g) as a colorless solid.

NMR (CDCl$_3$) δ: 1.46-1.59 (2H, m), 1.77-1.91 (2H, m), 2.55 (1H, m), 2.86-2.91 (2H, m), 2.99 (3H, s), 3.08 (1H, m), 3.18 (1H, m), 3.29 (3H, s), 3.53-3.58 (2H, m), 3.89 (1H, d,

J=14.1), 4.59 (1H, d, J=14.1), 5.78 (2H, br), 7.58 (1H, dd, J=1.8, 8.7), 7.88-7.96 (4H, m), 8.47 (1H, s).

EXAMPLE 70

(2Z)-5-(1-(3-((6-Chloro-2-naphthyl)sulfonyl)propanoyl)-1-piperidinyl)-N-(2-hydroxyethyl)-3-methyl-2-(methylimino)-2,3-dihydro-1,3-thiazole-4-carboxamide

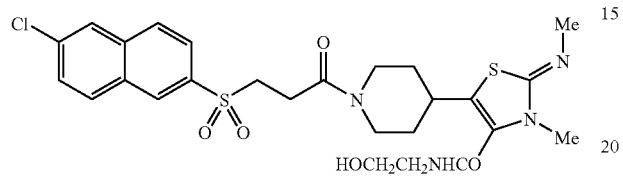

In the same manner as in Example 69), the title compound (0.08 g) was obtained from (2Z)-5-(1-(3-((6-chloro-2-naphthyl)sulfonyl)propanoyl)-1-piperidinyl)-3-methyl-2-(methylimino)-2,3-dihydro-1,3-thiazole-4-carboxylic acid (0.20 g) obtained in Example 68), WSC (0.11 g), HOBt (0.09 g) and 2-aminoethanol (0.05 mL).

NMR (CDCl$_3$) δ: 1.47-1.90 (4H, m), 2.53 (1H, m), 2.85-2.90 (2H, m), 2.98 (3H, s), 3.02-3.18 (2H, m), 3.25 (3H, s), 3.53-3.62 (4H, m), 3.81 (2H, t, J=5.1), 3.87 (1H, d, J=14.1), 4.59 (1H, d, J=14.1), 6.27 (1H, br), 7.59 (1H, dd, J=1.8, 8.7), 7.89-7.97 (4H, m), 8.48 (1H, s).

EXAMPLE 71

(2Z)-5-(1-(3-((6-Chloro-2-naphthyl)sulfonyl)propanoyl)-1-piperidinyl)-3-methyl-2-(methylimino)-N-propyl-2,3-dihydro-1,3-thiazole-4-carboxamide

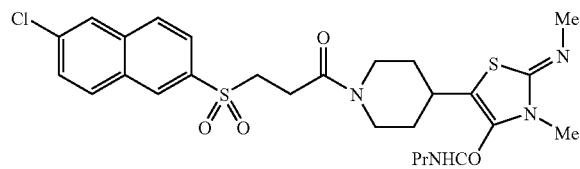

In the same manner as in Example 69), the title compound (0.05 g) was obtained from (2Z)-5-(1-(3-((6-chloro-2-naphthyl)sulfonyl)propanoyl)-1-piperidinyl)-3-methyl-2-(methylimino)-2,3-dihydro-1,3-thiazole-4-carboxylic acid (0.20 g) obtained in Example 68), WSC (0.11 g), HOBt (0.09 g) and propylamine (0.05 mL).

NMR (CDCl$_3$) δ: 0.99 (3H, t, J=6.9), 1.40-1.86 (4H, m), 2.52 (1H, m), 2.85-2.90 (2H, m), 2.98 (3H, s), 2.98-3.20 (3H, m), 3.23 (3H, s), 3.36 (2H, q, J=6.9), 3.55-3.60 (2H, m), 3.87 (1H, d, J=14.1), 4.60 (1H, d, J=14.1), 5.78 (1H, br), 7.60 (1H, dd, J=1.8, 7.8), 7.80-7.97 (4H, m), 8.48 (1H, s).

EXAMPLE 72

1-((2Z)-5-(1-(3-((6-Chloro-2-naphthyl)sulfonyl)propanoyl)-1-piperidinyl)-3-methyl-2-(methylimino)-2,3-dihydro-1,3-thiazol-4-yl)ethanol

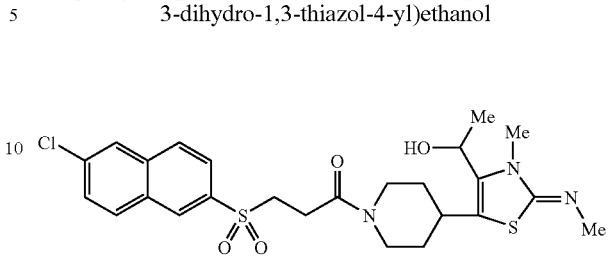

72a) tert-Butyl 4-((2Z)-4-(1-hydroxyethyl)-3-methyl-2-(methylimino)-2,3-dihydro-1,3-thiazol-5-yl)piperidine-1-carboxylate In the same manner as in Example 67a), the title compound (0.38 g) was obtained from tert-butyl 4-((2Z)-3-methyl-2-(methylimino)-2,3-dihydro-1,3-thiazol-5-yl)piperidine-1-carboxylate (1.0 g) obtained in Example 46a) and acetaldehyde (0.36 mL).

NMR (CDCl$_3$) δ: 1.39-1.83 (4H, m), 1.47 (9H, s), 1.51 (2H, d, J=6.6), 2.73 (2H, m), 2.95 (1H, m), 2.97 (3H, s), 3.41 (3H, s), 4.17 (2H, m), 5.03 (1H, q, J=6.6).

72b) 1-((2Z)-5-(1-(3-((6-Chloro-2-naphthyl)sulfonyl)propanoyl)-1-piperidinyl)-3-methyl-2-(methylimino)-2,3-dihydro-1,3-thiazol-4-yl)ethanol In the same manner as in Example 46b), the title compound (0.37 g) was obtained from the compound (0.38 g) obtained in Example 72a) and 3-((6-chloro-2-naphthyl)sulfonyl)propanoic acid (0.32 g).

NMR (CDCl$_3$) δ: 1.38-1.69 (2H, m), 1.96-2.14 (2H, m), 2.60 (1H, m), 2.83-3.01 (3H, m), 3.19 (3H, s), 3.21 (1H, m), 3.39 (3H, s), 3.53-3.61 (2H, m), 3.88 (3H, s), 3.96 (1H, s), 4.64 (1H, d, J=10.4), 7.60 (1H, dd, J=1.8, 9.2), 7.92-7.98 (4H, m), 8.48 (1H, s).

EXAMPLE 73

1-((2Z)-5-(1-(3-((6-Chloro-2-naphthyl)sulfonyl)propanoyl)-1-piperidinyl)-3-methyl-2-(methylimino)-2,3-dihydro-1,3-thiazol-4-yl)ethanone

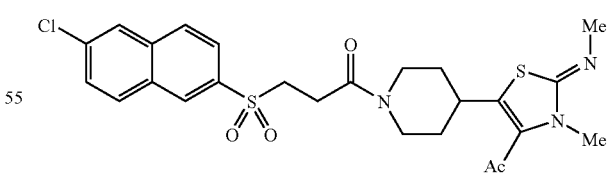

To a solution of 1-((2Z)-5-(1-(3-((6-chloro-2-naphthyl)sulfonyl)propanoyl)-1-piperidinyl)-3-methyl-2-(methylimino)-2,3-dihydro-1,3-thiazol-4-yl)ethanol (0.20 g) obtained in Example 72b) in dichloromethane (4 mL) was added Dess-Martin reagent (0.19 g) and mixed for 2 hours. The reaction solution was diluted with chloroform, washed with a saturated aqueous sodium bicarbonate solution, and then dried over anhydrous sodium sulfate. The solvent was distilled off, and the residue was purified with a silica gel column to give the title compound (0.10 g) as a colorless solid.

NMR (CDCl$_3$) δ: 1.39-1.52 (2H, m), 1.83-1.96 (2H, m), 2.45 (3H, s), 2.56 (1H, m), 2.81-2.95 (2H, m), 3.02 (3H, s), 3.09-3.21 (2H, m), 3.33 (3H, s), 3.50-3.65 (2H, m), 3.90 (1H, d, J=12.8), 4.59 (1H, d, J=12.8), 7.60 (1H, dd, J=2.0, 8.8), 7.89-7.98 (4H, m), 8.48 (1H, s).

EXAMPLE 74

(2E)-((2Z)-5-(1-(3-((6-Chloro-2-naphthyl)sulfonyl) propanoyl)-1-piperidinyl)-3-methyl-2-(methylimino)-1,3-thiazolidin-4-ylidene)acetonitrile

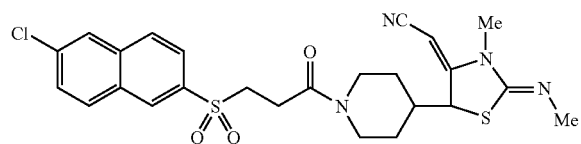

74a) tert-Butyl 4-((2Z,4E)-4-(cyanomethylene)-3-methyl-2-(methylimino)-1,3-thiazolidin-5-yl)piperidine-1-carboxylate To a solution of potassium tert-butoxide (1.4 g) in DME (40 mL) was added (p-tolylsulfonyl)methyl isocyanate (1.3 g) at −78° C. and mixed for 15 minutes. To the reaction solution was added a solution of the compound (2.0 g) obtained in Example 20a) in DME (20 mL). The reaction mixture was heated until the temperature reached room temperature and mixed for 1 hour. To the reaction solution was added methanol (15 mL) and further mixed at 80° C. for 1 hour. The reaction solution was concentrated, and the residue was dissolved in chloroform. The chloroform solution was washed with saturated brine, and dried over anhydrous sodium sulfate. The solvent was distilled off, and the residue was purified with a silica gel column to give the title compound (0.85 g) as a pale yellow solid.

NMR (CDCl$_3$) δ: 1.18-1.69 (4H, m), 1.45 (9H, s), 2.48 (1H, m), 2.63-2.79 (2H, m), 3.11 (3H, s), 3.14 (3H, s), 4.08-4.20 (2H, m), 4.39 (1H, d, J=0.9), 4.56 (1H, d, J=3.6).

74b) (2E)-((2Z)-5-(1-(3-((6-Chloro-2-naphthyl)sulfonyl)propanoyl)-1-piperidinyl)-3-methyl-2-(methylimino)-1,3-thiazolidin-4-ylidene)acetonitrile In the same manner as in Example 46b), the title compound (0.74 g) was obtained from the compound (0.55 g) obtained in Example 74a) and 3-((6-chloro-2-naphthyl)sulfonyl)propanoic acid.

NMR (CDCl$_3$) δ: 1.26-1.43 (3H, m), 1.76 (1H, m), 2.47-2.62 (2H, m), 2.83-2.90 (2H, m), 3.04-3.15 (7H, m), 3.51-3.56 (2H, m), 3.87 (1H, m), 4.41 (1H, d, J=2.1), 4.60 (1H, m), 4.67 (1H, d, J=3.3), 7.59 (1H, dd, J=1.8, 8.8), 7.88-7.96 (4H, m), 8.46 (1H, s).

EXAMPLE 75

2-((2Z)-5-(1-(3-((6-Chloro-2-naphthyl)sulfonyl)propanoyl)-1-piperidinyl)-3-methyl-2-(methylimino)-2,3-dihydro-1,3-thiazol-4-yl)acetamide

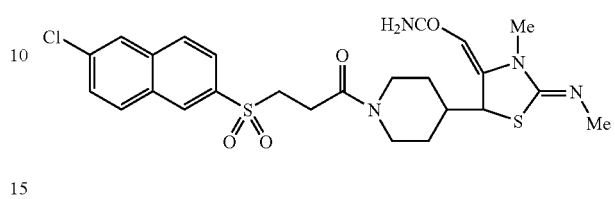

75a) tert-Butyl 4-((2Z)-4-carbamoylmethyl-3-methyl-2-(methylimino)-2,3-dihydro-1,3-thiazol-5-yl)piperidine-1-carboxylate To a solution of tert-butyl 4-((2Z,4E)-4-(cyanomethylene)-3-methyl-2-(methylimino)-1,3-thiazolidin-5-yl)piperidine-1-carboxylate (0.30 g) obtained in Example 74a) in DMSO (6.0 mL) were added potassium carbonate (0.1 g) and a 30% aqueous hydrogen peroxide solution (1 mL) at 0° C. and mixed for 30 minutes. The reaction solution was diluted with ethyl acetate, washed with saturated brine, and then dried over anhydrous sodium sulfate. The solvent was distilled off, and the residue was crystallized from hexane to give the title compound (0.32 g) as a colorless solid.

NMR (CDCl$_3$) δ: 1.47 (9H, s), 1.56-1.71 (4H, m), 2.70-2.79 (3H, m), 2.99 (3H, s), 3.23 (3H, s), 3.44 (2H, s), 4.19 (2H, br), 5.67 (2H, d, J=19.5).

75b) 2-((2Z)-5-(1-(3-((6-Chloro-2-naphthyl)sulfonyl)propanoyl)-1-piperidinyl)-3-methyl-2-(methylimino)-2,3-dihydro-1,3-thiazol-4-yl)acetamide In the same manner as in Example 46b), the title compound (0.43 g) as a colorless solid was obtained from the compound (0.32 g) obtained in Example 75a) and 3-((6-chloro-2-naphthyl)sulfonyl)propanoic acid.

NMR (DMSO-d$_6$) δ: 1.06-1.19 (1H, m), 1.32-1.46 (1H, m), 1.57-1.72 (2H, m), 2.44-2.54 (3H, m), 2.63-2.77 (2H, m), 2.82 (3H, s), 2.99 (2H, t, J=11.7), 3.10 (3H, s), 3.60-3.66 (2H, m), 3.82 (1H, d, J=12.6), 4.27 (1H, d, J=12.), 7.09 (1H, s), 7.54 (1H, s), 7.72 (1H, dd, J=2.1, 8.7), 7.98 (1H, dd, J=2.1, 8.7), 8.17 (1H, d, J=9.0), 8.24-8.31 (2H, m), 8.63 (1H, s).

EXAMPLE 76

N-((2Z)-5-(1-(3-((6-Chloro-2-naphthyl)sulfonyl) propanoyl)-1-piperidinyl)-3-methyl-4-(1H-tetrazol-5-ylmethyl)-1,3-thiazol-2(3H)-ylidene)-N-methylamine

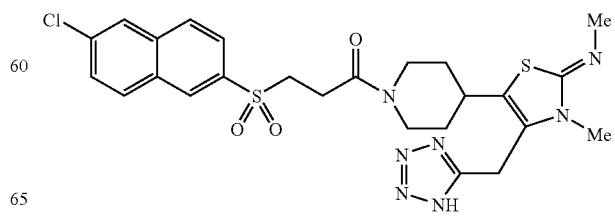

To a solution of the compound (0.3 g) obtained in Example 74b) in toluene (10 mL), trimethyltin azide (0.35 g) was added, and the mixture was overheated under reflux for 24 hours. To the reaction solution, methanol (2 mL) was added, and the mixture was mixed for 1 hour. The reaction solution was concentrated, and the residue was purified with a silica gel column to give the title compound (0.1-4 g) as a colorless solid.

NMR (CDCl$_3$) δ: 1.45-1.54 (2H, m), 1.97-2.12 (2H, m), 2.64 (1H, m), 2.84-2.93 (3H, m), 3.17 (3H, s), 3.31 (1H, m), 3.55-3.60 (3H, m), 3.67 (3H, s), 3.94 (1H, d, J=12.3), 4.21 (1H, d, J=4.5), 4.68 (1H, d, J=12.3), 7.60 (1H, dd, J=1.8, 8.7), 7.89-7.98 (4H, m), 8.45 (1H, s).

EXAMPLE 77

Methyl (2Z)-5-(1-(3-((6-chloro-2-naphthyl)sulfonyl)propanoyl)-1-piperidinyl)-3-methyl-2-(methylimino)-2,3-dihydro-1,3-thiazol-4-carboxylate

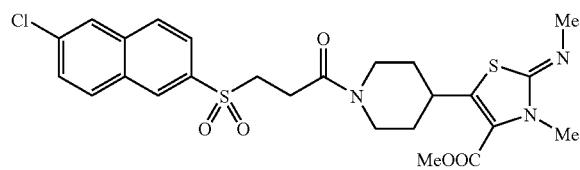

77a) tert-Butyl 4-((2Z)-4-(methoxycarbonyl)-3-methyl-2-(methylimino)-2,3-dihydro-1,3-thiazol-5-yl)piperidine-1-carboxylate In the same manner as in Example 67a), the title compound (0.24 g) as a pale yellow viscous oily matter was obtained from tert-butyl 4-((2Z)-3-methyl-2-(methylimino)-2,3-dihydro-1,3-thiazol-5-yl)piperidine-1-carboxylate (0.50 g) obtained in Example 46a) and methyl chlorocarbonate (0.25 mL).

NMR (CDCl$_3$) δ: 1.40-1.84 (4H, m), 1.47 (9H, s), 2.75 (2H, t, J=12.2), 3.00 (3H, s), 3.39 (3H, s), 3.39 (1H, m), 3.89 (3H, s), 4.17 (2H, m).

77b) Methyl (2Z)-5-(1-(3-((6-chloro-2-naphthyl)sulfonyl)propanoyl)-1-piperidinyl)-3-methyl-2-(methylimino)-2,3-dihydro-1,3-thiazole-4-carboxylate In the same manner as in Example 46b), the title compound (0.26 g) as a colorless solid was obtained from the compound (0.24 g) obtained in Example 77a) and 3-((6-chloro-2-naphthyl)sulfonyl)propanoic acid.

NMR (CDCl$_3$) δ: 1.43-1.56 (2H, m), 1.82-1.94 (2H, m), 2.51-2.59 (1H, m), 2.87-2.92 (2H, m), 3.00 (3H, s), 3.10 (1H, m), 3.39 (3H, s), 3.47 (1H, m), 3.53-3.59 (2H, m), 3.90 (3H, s), 3.91 (1H, d, J=13.5), 4.62 (1H, d, J=13.5), 7.60 (1H, dd, J=2.1, 8.7), 7.90-7.97 (4H, m), 8.49 (1H, s).

EXAMPLE 78

Butyl (2Z)-5-(1-(3-((6-chloro-2-naphthyl)sulfonyl)propanoyl)-1-piperidinyl)-3-methyl-2-(methylimino)-2,3-dihydro-1,3-thiazole-4-carboxylate

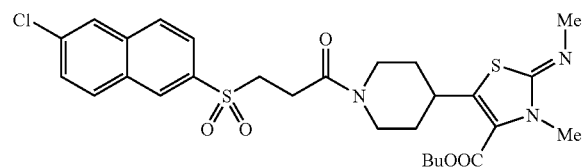

78a) tert-Butyl 4-((2Z)-4-(butoxycarbonyl)-3-methyl-2-(methylimino)-2,3-dihydro-1,3-thiazol-5-yl)piperidine-1-carboxylate In the same manner as in Example 67a), the title compound (0.91 g) as a pale yellow solid was obtained from tert-butyl 4-((2Z)-3-methyl-2-(methylimino)-2,3-dihydro-1,3-thiazol-5-yl)piperidine-1-carboxylate (0.80 g) obtained in Example 46a) and butyl chlorocarbonate (0.67 mL).

NMR (CDCl$_3$) δ: 0.96 (3H, t, J=7.5), 1.26 (2H, t, J=7.5), 1.47 (9H, s), 1.44-1.83 (6H, m), 2.73 (2H, t, J=12.3), 3.00 (3H, s), 3.39 (3H, s), 3.37-3.41 (1H, m), 4.25-4.34 (2H, m), 4.29 (2H, t, J=7.5).

78b) Butyl (2Z)-5-(1-(3-((6-chloro-2-naphthyl)sulfonyl)propanoyl)-1-piperidinyl)-3-methyl-2-(methylimino)-2,3-dihydro-1,3-thiazole-4-carboxylate In the same manner as in Example 46b), the title compound (0.49 g) as a pale yellow solid was obtained from the compound (0.50 g) obtained in Example 78a) and 3-((6-chloro-2-naphthyl)sulfonyl)propanoic acid.

NMR (CDCl$_3$) δ: 0.98 (3H, t, J=7.4), 1.38-1.70 (3H, m), 1.67-1.90 (4H, m), 2.53 (1H, m), 2.87-2.99 (2H, m), 3.00 (3H, s), 3.08 (1H, m), 3.39 (3H, s), 3.53-3.58 (3H, m), 3.92 (2H, d, J=13.8), 4.27 (2H, t, J=6.7), 4.63 (1H, d, J=13.8), 7.60 (1H, dd, J=2.1, 8.8), 7.89-7.98 (4H, m), 8.48 (1H, s).

EXAMPLE 79

((2Z)-5-(1-(3-((6-Chloro-2-naphthyl)sulfonyl)propanoyl)-1-piperidinyl)-3-methyl-2-(methylimino)-2,3-dihydro-1,3-thiazol-4-yl)(1,3-thiazol-2-yl)methanol

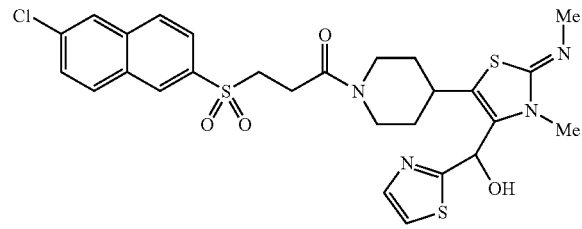

79a) tert-Butyl 4-((2Z)-4-(hydroxy(1,3-thiazol-2-yl)methyl)-3-methyl-2-(methylimino)-2,3-dihydro-1,3-thiazol-5-yl)piperidine-1-carboxylate In the same manner as in Example 67a), the title compound (0.10 g) as a pale yellow solid was obtained from tert-butyl 4-((2Z)-3-methyl-2-(methylimino)-2,3-dihydro-1,3-thiazol-5-yl)piperidine-1-carboxylate (0.47 g) obtained in Example 46a) and thiazole-2-carbaldehyde (0.26 g).

NMR (CDCl$_3$) δ: 1.47 (9H, s), 1.52-1.87 (4H, m), 2.70 (2H, br), 2.91 (1H, m), 2.96 (3H, s), 3.06 (3H, s), 4.21 (2H, s), 6.09 (1H, s), 7.38 (1H, d, J=1.2), 7.78 (1H, d, J=1.2).

79b) ((2Z)-5-(1-(3-((6-Chloro-2-naphthyl)sulfonyl)propanoyl)-1-piperidinyl)-3 methyl-2-(methylimino)-2,3-dihydro-1,3-thiazol-4-yl)(1,3-thiazol-2-yl)methanol In the same manner as in Example 46b), the title compound (0.11 g) as a pale yellow solid was obtained from the compound (0.10 g) obtained in Example 79a) and 3-((6-chloro-2-naphthyl)sulfonyl)propanoic acid.

NMR (CDCl$_3$) δ: 1.51-1.91 (5H, m), 2.51 (1H, m), 2.83-2.96 (5H, m), 2.99-3.12 (5H, m), 3.50-3.60 (2H, m), 3.88 (1H, d, J=13.5), 6.07 (1H, s), 7.39 (1H, d, J=3.2), 7.59 (1H, dd, J=1.9, 8.7), 7.75 (1H, d, J=7.2), 7.88-7.98 (4H, m), 8.48 (1H, s).

EXAMPLE 80

((2Z)-5-(1-(3-((6-Chloro-2-naphthyl)sulfonyl)propanoyl)-1-piperidinyl)-3-methyl-2-(methylimino)-2,3-dihydro-1,3-thiazol-4-yl)(3-methyl-1H-pyrazol-5-yl)methanol

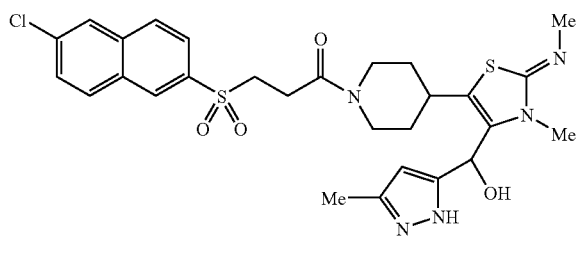

80a) 5-Methyl-1-trityl-1H-pyrazole-3-carbaldehyde

To a solution of 5-methyl-1H-pyrazole-3-carbaldehyde (Werner A. et al., Tetrahedron, 51, 4779 (1995): 1.1 g) in acetonitrile (20 mL), triethylamine (1.5 mL) and chlorotriphenylmethane (3.1 g) were added and mixed for 12 hours. The reaction solution was concentrated, and the residue was dissolved in chloroform. This solution was washed with a saturated aqueous sodium bicarbonate solution and dried over anhydrous sodium sulfate. The solvent was distilled off, and the residue was purified with a silica gel column to give the title compound (1.9 g) as a colorless solid.

NMR (CDCl$_3$) δ: 1.54 (3H, s), 6.66 (1H, s), 7.09-7.17 (6H, m), 7.25-7.34 (9H, m), 9.83 (1H, s).

80b) tert-Butyl 4-((2Z)-4-(hydroxy(5-methyl-1-trityl-1H-pyrazol-3-yl)methyl)-3-methyl-2-(methylimino)-2,3-dihydro-1,3-thiazol-5-yl)piperidine-1-carboxylate In the same manner as in Example 67a), the title compound (0.36 g) as a colorless solid was obtained from the compound (0.53 g) obtained in Example 80a) and tert-butyl 4-((2Z)-3-methyl-2-(methylimino)-2,3-dihydro-1,3-thiazol-5-yl)piperidine-1-carboxylate (0.47 g) obtained in Example 46a).

NMR (CDCl$_3$) δ: 1.47 (9H, s), 1.57-1.80 (4H, m), 2.65-2.78 (2H, m), 2.98 (1H, m), 2.99 (3H, s), 3.28 (3H, s), 4.17 (2H, m), 5.80 (1H, s), 5.88 (1H, s), 7.01-7.14 (6H, m), 7.26-7.30 (9H, m).

80c) ((2Z)-5-(1-(3-((6-Chloro-2-naphthyl)sulfonyl)propanoyl)-1-piperidinyl)-3-methyl-2-(methylimino)-2,3-dihydro-1,3-thiazol-4-yl)(3-methyl-1H-pyrazol-5-yl)methanol In the same manner as in Example 46b), the title compound (0.07 g) as a pale yellow solid was obtained from the compound (0.36 g) obtained in Example 80a) and 3-((6-chloro-2-naphthyl)sulfonyl)propanoic acid.

NMR (CDCl$_3$) δ: 1.49-1.89 (4H, m), 2.29 (3H, d, J=3.8), 2.51 (1H, m), 2.81-2.95 (2H, m), 2.96 (3H, s), 3.00-3.13 (5H, m), 3.49-3.62 (2H, m), 3.89 (1H, m), 4.56 (1H, m), 5.79 (1H, J=7.4), 5.94 (1H, s), 7.60 (1H, dd, J=2.0, 8.8), 7.88-7.98 (4H, m), 8.48 (1H, s).

EXAMPLE 81

((2Z)-5-(1-(3-((6-Chloro-2-naphthyl)sulfonyl)propanoyl)-1-piperidinyl)-3-methyl-2-(methylimino)-2,3-dihydro-1,3-thiazol-4-yl)(2-thienyl)methanol

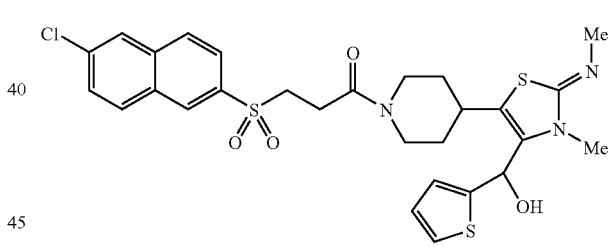

81a) tert-Butyl 4-((2Z)-4-(hydroxy(2-thienyl)methyl)-3-methyl-2-(methylimino)-2,3-dihydro-1,3-thiazol-5-yl)piperidine-1-carboxylate In the same manner as in Example 67a), the title compound (0.26 g) as a colorless solid was obtained from tert-butyl 4-((2Z)-3-methyl-2-(methylimino)-2,3-dihydro-1,3-thiazol-5-yl)piperidine-1-carboxylate (0.62 g) obtained in Example 46a) and thiophene-2-carbaldehyde (0.28 mL).

NMR (CDCl$_3$) δ: 1.47 (9H, s), 1.50-1.85 (4H, m), 2.69 (2H, br), 2.93 (1H, m), 2.95 (3H, s), 3.11 (3H, s), 4.18 (2H, br), 6.12 (1H, s), 6.78 (1H, s), 6.95 (1H, m), 7.28 (1H, br).

81b) ((2Z)-5-(1-(3-((6-Chloro-2-naphthyl)sulfonyl)propanoyl)-1-piperidinyl)-3-methyl-2-(methylimino)-2,3-dihydro-1,3-thiazol-4-yl)(2-thienyl)methanol In the same manner as in Example 46b), the title compound (0.03 g) as a pale yellow solid was obtained from the compound (0.25 g) obtained in Example 81a) and 3-((6-chloro-2-naphthyl)sulfonyl)propanoic acid.

NMR (CDCl$_3$) δ: 1.59-1.80 (4H, m), 2.51 (1H, m), 2.81-2.94 (2H, m), 2.97 (3H, s), 3.00-3.15 (5H, m), 3.50-3.65 (2H, m), 3.90 (1H, m), 4.57 (1H, m), 6.14 (1H, s), 6.82 (1H, s), 6.98 (1H, m), 7.31 (1H, s), 7.60 (1H, dd, J=1.8, 8.8), 7.89-7.98 (4H, m), 8.48 (1H, s).

EXAMPLE 82

((2Z)-5-(1-(3-((6-Chloro-2-naphthyl)sulfonyl)propanoyl)-1-piperidinyl)-3-methyl-2-(methylimino)-2,3-dihydro-1,3-thiazol-4-yl)(3-thienyl)methanol

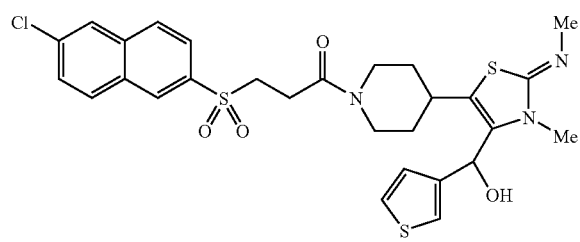

82a) tert-Butyl 4-((2Z)-4-(hydroxy(3-thienyl)methyl)-3-methyl-2-(methylimino)-2,3-dihydro-1,3-thiazol-5-yl)piperidine-1-carboxylate In the same manner as in Example 67a), the title compound (0.21 g) as a colorless solid was obtained from tert-butyl 4-((2Z)-3-methyl-2-(methylimino)-2,3-dihydro-1,3-thiazol-5-yl)piperidine-1-carboxylate (0.62 g) obtained in Example 46a) and thiophene-3-carbaldehyde (0.26 mL).

NMR (CDCl$_3$) δ: 1.47 (9H, s), 1.57-1.78 (4H, m), 2.70 (2H, m), 2.95 (1H, m), 2.96 (3H, s), 3.06 (3H, s), 4.18 (2H, br), 5.97 (1H, s), 6.90 (1H, m), 7.20 (1H, m), 7.31 (1H, m).

82b) ((2Z)-5-(1-(3-((6-Chloro-2-naphthyl)sulfonyl)propanoyl)-1-piperidinyl)-3-methyl-2-(methylimino)-2,3-dihydro-1,3-thiazol-4-yl)(3-thienyl)methanol In the same manner as in Example 46b), the title compound (0.02 g) as a pale yellow solid was obtained from the compound (0.20 g) obtained in Example 82a) and 3-((6-chloro-2-naphthyl)sulfonyl)propanoic acid.

NMR (CDCl$_3$) δ: 1.59-1.72 (4H, m), 2.50 (1H, m), 2.85-2.94 (2H, m), 2.98 (3H, s), 2.96-3.13 (5H, m), 3.50-3.62 (2H, m), 3.90 (1H, m), 4.62 (1H, m), 5.98 (1H, s), 6.92 (1H, br), 7.20 (1H, s), 7.33 (1H, m), 7.60 (1H, dd, J=1.8, 8.8), 7.89-7.98 (4H, m), 8.48 (1H, s).

EXAMPLE 83

N-((2Z)-3-(2-(1-(3-((6-Chloro-2-naphthyl)sulfonyl)propanoyl)-1-piperidinyl)ethyl)-1,3-thiazol-2(3H)-ylidene)-N-methylamine

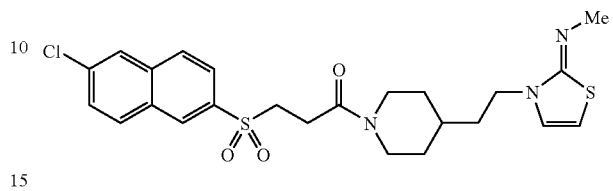

In the same manner as in Example 57b), the title compound (0.27 g) was obtained from 1-(3-((6-chloro-2-naphthyl)sulfonyl)propanoyl)-4-(2-iodoethyl)piperidine (0.52 g) obtained in Example 18c) and N-methyl-1,3-thiazol-2-amine (0.27 g).

NMR (CDCl$_3$) δ: 1.00-1.18 (2H, m), 1.58-1.84 (5H, m), 2.48 (1H, t, J=12.9), 2.81-2.88 (2H, m), 2.98 (3H, s), 2.98 (1H, t, J=12.9), 3.52-3.58 (2H, m), 3.79 (3H, m), 4.44 (1H, d, J=13.5), 5.96 (1H, d, J=5.1), 6.52 (1H, d, J=5.1), 7.57 (1H, dd, J=2.1, 7.8), 7.88-7.95 (4H, m), 8.46 (1H, s)

EXAMPLE 84

N-((2Z)-3-(2-(1-(3-((6-Chloro-2-naphthyl)sulfonyl)propanoyl)-1-piperidinyl)ethyl)-5-methyl-1,3-thiazol-2(3H)-ylidene)-N-methylamine

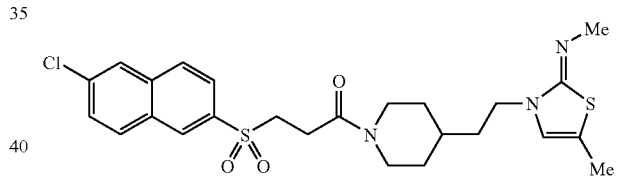

84a) N,5-Dimethyl-1,3-thiazol-2-amine

In the same manner as in Example 46a), the title compound (1.48 g) was obtained from 2-bromopropionaldehyde (Pews R. et al., Synthetic Commun., 15, 977-84 (1985): 8.7 g) and N-methylthiourea (5.7 g).

NMR (CDCl$_3$) δ: 2.29 (3H, s), 2.95 (3H, s), 5.02 (1H, br), 6.75 (1H, s).

84b) N-((2Z)-3-(2-(1-(3-((6-Chloro-2-naphthyl)sulfonyl)propanoyl)-1-piperidinyl)ethyl)-5-methyl-1,3-thiazol-2(3H)-ylidene)-N-methylamine In the same manner as in Example 57b), the title compound (0.24 g) was obtained from the compound (0.26 g) obtained in Example 84a) and 1-(3-((6-chloro-2-naphthyl)sulfonyl)propanoyl)-4-(2-iodoethyl)piperidine (0.52 g) obtained in Example 18c.

NMR (CDCl$_3$) δ: 1.00-1.16 (2H, m), 1.56-1.60 (3H, m), 1.70-1.84 (2H, m), 2.13 (3H, s), 2.49 (1H, m), 2.81-2.89 (2H, m), 2.95 (3H, s), 2.96 (1H, m), 3.52-3.58 (2H, m), 3.68-3.80 (3H, m), 4.43 (1H, d, J=13.5), 6.18 (1H, s), 7.59 (1H, dd, J=1.8, 8.3), 7.88-7.95 (4H, m), 8.45 (1H, s).

EXAMPLE 85

N-((2Z)-3-(2-(1-(3-((6-Chloro-2-naphthyl)sulfonyl)propanoyl)-1-piperidinyl)ethyl)-4-methyl-1,3-thiazol-2(3H)-ylidene)-N-methylamine

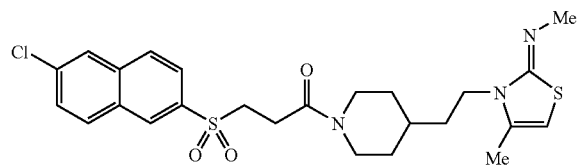

85a) N,4-Dimethyl-1,3-thiazol-2-amine

In the same manner as in Example 46a), the title compound (9.4 g) was obtained from bromoacetone (25 g) and N-methylthiourea (20 g).

NMR (CDCl$_3$) δ: 2.23 (3H, s), 2.94 (3H, s), 6.04 (1H, s), 6.28 (1H, br).

85b) N-((2Z)-3-(2-(1-(3-((6-Chloro-2-naphthyl)sulfonyl)propanoyl)-1-piperidinyl)ethyl)-4-methyl-1,3-thiazol-2(3H)-ylidene)-N-methylamine In the same manner as in Example 57b), the title compound (0.06 g) was obtained from the compound (0.26 g) obtained in Example 85a) and 1-(3-((6-chloro-2-naphthyl)sulfonyl)propanoyl)-4-(2-iodoethyl)piperidine (0.52 g) obtained in Example 18c).

NMR (CDCl$_3$) δ: 1.06-1.14 (2H, m), 1.60-1.86 (5H, m), 2.08 (3H, s), 2.49 (1H, t, J=12.3), 2.84-2.87 (2H, m), 2.95 (3H, s), 2.97 (1H, m), 3.53-3.56 (2H, m), 3.70-3.81 (3H, m), 4.44 (1H, d, J=13.2), 5.51 (1H, s), 7.58 (1H, dd, J=1.8, 7.8), 7.88-7.95 (4H, m), 8.46 (1H, s).

EXAMPLE 86

N-((2Z)-3-((1-(3-((6-Chloro-2-naphthyl)sulfonyl)propanoyl)-1-piperidinyl)methyl)-1,3-thiazol-2(3H)-ylidene)-N-methylamine

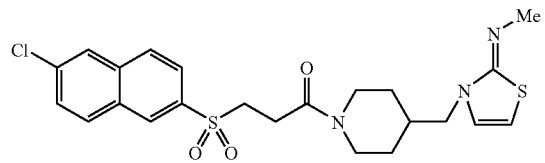

86a) 1-(3-((6-Chloro-2-naphthyl)sulfonyl)propanoyl)-4-(iodomethyl)piperidine In the same manner as in Example 46b), the title compound (4.0 g) was obtained from tert-butyl 4-(iodomethyl)piperidine-1-carboxylate (Villalobos A. et al., J. Med. Chem., 37, 2721 (1994): 3.3 g) and 3-((6-chloro-2-naphthyl)sulfonyl)propanoic acid (3. 0 g).

NMR (DMSO-d$_6$) δ: 0.65-0.89 (2H, m), 1.62-1.78 (3H, m), 2.40 (1H, m), 2.67 (2H, t, J=7.8), 2.90 (1H, m), 3.15 (2H, d, J=6.2), 3.59 (2H, t, J=7.8), 3.76 (1H, d, J=14.0), 4.17 (1H, d, J=14.0), 7.72 (1H, dd, J=2.2, 9.0), 7.97 (1H, dd, J=2.2, 8.8), 8.17 (1H, d, J=8.8), 8.19-8.25 (2H, m), 8.63 (1H, s).

86b) N-((2Z)-3-((1-(3-((6-Chloro-2-naphthyl)sulfonyl)propanoyl)-1-piperidinyl)methyl)-1,3-thiazol-2(3H)-ylidene)-N-methylamine In the same manner as in Example 57b), the title compound (0.06 g) was obtained from the compound (0.50 g) obtained in Example 86a) and N-methyl-1,3-thiazol-2-amine (0.23 g).

NMR (CDCl$_3$) δ: 0.94-1.16 (2H, m), 1.63-1.77 (2H, m), 2.10 (1H, m), 2.49 (1H, t, J=11.0), 2.84 (2H, dd, J=6.6, 10.4), 2.95 (3H, s), 2.99 (1H, t, J=11.0), 3.51-3.65 (4H, m), 3.81 (1H, d, J=13.4), 4.48 (1H, d, J=13.4), 5.87 (1H, d, J=4.8), 6.41 (1H, d, J=4.8), 7.59 (1H, dd, J=1.8, 8.8), 7.92-7.97 (4H, m), 8.47 (1H, s).

EXAMPLE 87

3-((1-(3-((6-Chloro-2-naphthyl)sulfonyl)propanoyl)-1-piperidinyl)methyl)-1,3-thiazol-2(3H)-imine

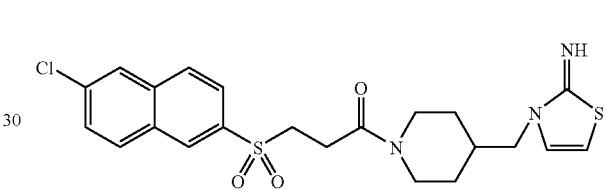

In the same manner as in Example 57 b), the title compound (0.08 g) was obtained from 1-(3-((6-chloro-2-naphthyl)sulfonyl)propanoyl)-4-(iodomethyl)piperidine (0.50 g) obtained in Example 86a) and 1,3-thiazol-2-amine (0.20 g).

NMR (CDCl$_3$) δ: 0.98-1.28 (2H, m), 1.65-1.79 (2H, m), 2.10 (1H, m), 2.51 (1H, t, J=13.2), 2.82-2.87 (2H, m), 3.00 (1H, t, J=13.2), 3.45-3.62 (4H, m), 3.83 (1H, d, J=13.8), 4.49 (1H, d, J=13.8), 5.74 (1H, d, J=4.8), 6.29 (1H, d, J=4.8), 7.58 (1H, dd, J=1.8, 7.8), 7.88-7.95 (4H, m), 8.46 (1H, s)

EXAMPLE 88

1-(3-((6-Chloro-2-naphthyl)sulfonyl)propanoyl)-N-((2Z)-3-methyl-1,3-thiazol-2(3H)-ylidene)-4-piperidinamine

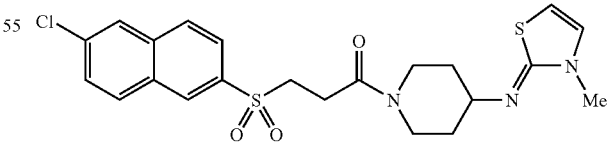

88a) tert-Butyl 4-thioureidopiperidine-1-carboxylate

In the same manner as in Example 66a), the title compound (2.8 g) as a pale yellow solid was obtained from tert-butyl 4-aminopiperidine-1-carboxylate (2.7 g).

NMR (CDCl$_3$) δ: 1.26-1.45 (2H, m), 1.45 (9H, s), 1.98-2.08 (2H, m), 2.90 (2H, t, J=9.8), 3.98-4.10 (3H, m), 6.10 (2H, s), 6.74 (1H, d, J=7.2).

88b) tert-Butyl 4-(1,3-thiazol-2-yl)aminopiperidine-1-carboxylate

In the same manner as in Example 46a), the title compound (0.88 g) as a pale yellow solid was obtained from the compound (1.0 g) obtained in Example 88a) and chloroacetaldehyde (1.13 mL, a 40% aqueous solution).
NMR (CDCl$_3$) δ: 1.33-1.49 (2H, m), 1.46 (9H, s), 2.06 (2H, m), 2.92 (2H, m), 3.56 (1H, m), 4.02 (2H, bd, J=10.5), 4.95 (1H, br), 5.71 (1H, d, J=4.8), 6.72 (1H, d, J=4.8).

88c) 1-(3-((6-Chloro-2-naphthyl)sulfonyl)propanoyl)-N-(1,3-thiazol-2-yl)-4-piperidinamine In the same manner as in Example 46b), the title compound (1.19 g) as a pale yellow solid was obtained from the compound (0.88 g) obtained in Example 88b) and 3-((6-chloro-2-naphthyl)sulfonyl)propanoic acid (0.86 g).
NMR (DMSO-d$_6$) δ: 1.12-1.40 (2H, m), 1.82-1.94 (2H, m), 2.56 (1H, m), 2.72-2.78 (3H, m), 3.10 (1H, m), 3.59-3.75 (2H, m), 3.99 (1H, d, J=14.1), 6.58 (1H, d, J=3.6), 6.98 (1H, d, J=3.6), 7.50 (1H, d, J=7.5), 7.72 (1H, d, J=1.8, 8.1), 7.97 (1H, dd, J=1.8, 8.1), 8.17 (1H, d, J=8.1), 8.24-8.28 (2H, m), 8.63 (1H, s).

88d) 1-(3-((6-Chloro-2-naphthyl)sulfonyl)propanoyl)-N-((2Z)-3-methyl-1,3-thiazol-2(3H)-ylidene)-4-piperidinamine In the same manner as in Example 57b), the title compound (0.15 g) as a colorless solid was obtained from the compound (0.50 g) obtained in Example 88c) and methyl iodide (0.13 mL).
NMR (CDCl$_3$) δ: 1.58 (2H, m), 1.82 (2H, m), 2.88 (2H, t, J=6.6), 2.93 (1H, m), 3.10-3.25 (5H, m), 3.56 (2H, t, J=6.6), 3.76 (1H, m), 4.05 (1H, m), 5.84 (1H, d, J=4.2), 6.44 (1H, d, J=4.2), 7.58 (1H, dd, J=1.8, 7.8), 7.88-7.96 (4H, m), 8.47 (1H, s).

EXAMPLE 89

1-(3-((6-Chloro-2-naphthyl)sulfonyl)propanoyl)-N-((2Z)-3,4-dimethyl-1,3-thiazol-2(3H)-ylidene)-4-piperidinamine

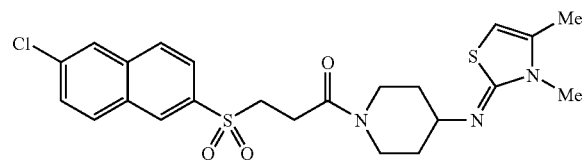

89a) tert-Butyl 4-((4-methyl-1,3-thiazol-2-yl)amino)piperidine-1-carboxylate

In the same manner as in Example 46a), the title compound (0.79 g) as a pale yellow solid was obtained from tert-butyl 4-thioureidopiperidine-1-carboxylate (0.69 g) obtained in Example 88a) and bromoacetone (0.34 mL).
NMR (CDCl$_3$) δ: 1.33-1.49 (2H, m), 1.46 (9H, s), 2.06 (2H, m), 2.22 (3H, s), 2.92 (2H, m), 3.56 (1H, m), 4.02 (2H, d, J=10.5), 4.95 (1H, br), 6.07 (1H, s).

89b) 1-(3-((6-Chloro-2-naphthyl)sulfonyl)propanoyl)-N-(4-methyl-1,3-thiazol-2-yl)-4-piperidinamine In the same manner as in Example 47b), the title compound (0.76 g) as a pale yellow solid was obtained from the compound (0.79 g) obtained in Example 89a) and 3-((6-chloro-2-naphthyl)sulfonyl)propanoic acid (0.80 g).
NMR (CDCl$_3$) δ: 1.25-1.46 (2H, m), 2.06-2.21 (2H, m), 2.22 (3H, s), 2.80-2.91 (3H, m), 3.20 (1H, m), 3.53-3.68 (3H, m), 3.79 (1H, d, J=9.4), 4.32 (1H, d, J=9.4), 4.87 (1H, d, J=4.8), 6.05 (1H, s), 7.58 (1H, dd, J=1.4, 9.0), 7.88-7.95 (4H, m), 8.46 (1H, s).

89c) 1-(3-((6-Chloro-2-naphthyl)sulfonyl)propanoyl)-N-((2Z)-3,4-dimethyl-1,3-thiazol-2(3H)-ylidene)-4-piperidinamine In the same manner as in Example 57b), the title compound (0.42 g) as a pale yellow solid was obtained from the compound (0.65 g) obtained in Example 89b) and methyl iodide (0.17 mL).
NMR (CDCl$_3$) δ: 1.38-1.64 (2H, m), 1.88-2.01 (2H, m), 2.36 (3H, s), 2.66 (2H, t, J=8.1), 2.92 (2H, m), 3.15 (1H, m), 3.46 (3H, s), 3.57 (2H, m), 3.93 (1H, brd, J=14.4), 4.57 (1H, brd, J=14.4), 6.61 (1H, s), 7.60 (1H, dd, J=1.8, 7.8), 7.90-7.97 (4H, m), 8.48 (1H, s).

EXAMPLE 90

1-(3-((6-Chloro-2-naphthyl)sulfonyl)propanoyl)-N-((2Z)-3,5-dimethyl-1,3-thiazol-2(3H)-ylidene)-4-piperidinamine

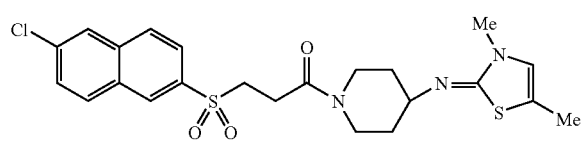

90a) tert-Butyl 4-((5-methyl-1,3-thiazol-2-yl)amino)piperidine-1-carboxylate

In the same manner as in Example 46a), the title compound (2.0 g) as a pale yellow solid was obtained from tert-butyl 4-thioureidopiperidine-1-carboxylate (5.2 g) obtained in Example 88a) and 2-bromopropionaldehyde (2.8 g).
NMR (CDCl$_3$) δ: 1.33-1.49 (2H, m), 1.46 (9H, s), 2.06 (2H, m), 2.28 (3H, s), 2.92 (2H, m), 3.56 (1H, m), 4.02 (2H, brd, J=10.5), 4.95 (1H, br), 5.71 (1H, s).

90b) 1-(3-((6-Chloro-2-naphthyl)sulfonyl)propanoyl)-N-(5-methyl-1,3-thiazol-2-yl)-4-piperidinamine In the same manner as in Example 46b), the title compound (2.84 g) as a pale yellow solid was obtained from the compound (1.8 g) obtained in Example 90a) and 3-((6-chloro-2-naphthyl)sulfonyl)propanoic acid (1.77 g).

NMR (CDCl₃) δ: 1.25-1.47 (2H, m), 2.03-2.21 (2H, m), 2.28 (3H, s), 2.77-2.91 (3H, m), 3.19 (1H, m), 3.54 (2H, m), 3.69 (1H, br), 3.80 (1H, d, J=13.2), 4.34 (1H, d, J=13.2), 4.87 (1H, br), 6.71 (1H, s), 7.60 (1H, dd, J=1.8, 8.7), 7.88-7.95 (4H, m), 8.46 (1H, s).

90c) 1-(3-((6-Chloro-2-naphthyl)sulfonyl)propanoyl)-N-((2Z)-3,5-dimethyl-1,3-thiazol-2(3H)-ylidene)-4-piperidinamine In the same manner as in Example 57b), the title compound (0.43 g) as a pale yellow solid was obtained from the compound (0.80 g) obtained in Example 90b) and methyl iodide (0.42 mL).

NMR (CDCl₃) δ: 1.40-1.88 (4H, m), 2.10 (3H, s), 2.88 (2H, dd, J=6.8, 9.0), 2.96-3.12 (2H, m), 3.15-3.27 (4H, m), 3.51-3.65 (2H, m), 3.76 (1H, m), 4.10 (1H, m), 6.13 (1H, s), 7.59 (1H, dd, J=2.0, 8.8), 7.89-7.98 (4H, m), 8.48 (1H, s).

EXAMPLE 91

2-((2Z)-2-((1-(3-((6-Chloro-2-naphthyl)sulfonyl)propanoyl)-1-piperidinyl)imino)-1,3-thiazol-3(2H)-yl)acetamide

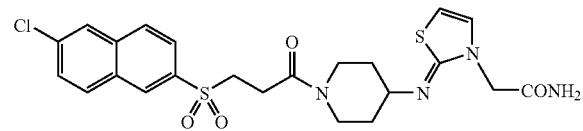

In the same manner as in Example 57b), the title compound (0.61 g) as a pale yellow solid was obtained from 1-(3-((6-chloro-2-naphthyl)sulfonyl)propanoyl)-N-(1,3-thiazol-2-yl)-4-piperidinamine (0.50 g) obtained in Example 88c) and iodoacetamide (0.40 g).

NMR (CDCl₃) δ: 1.39-1.62 (2H, m), 1.72-1.90 (2H, m), 2.89 (2H, t, J=7.2), 3.06 (1H, m), 3.15-3.33 (2H, m), 3.57 (2H, t, J=7.2), 3.71 (1H, m), 3.97 (1H, m), 4.31 (2H, s), 5.54 (1H, br), 5.98 (1H, d, J=4.6), 6.58 (1H, d, J=4.6), 7.08 (1H, br), 7.60 (1H, dd, J=2.2, 9.2), 7.88-7.98 (4H, m), 8.49 (1H, s).

EXAMPLE 92

2-((2Z)-2-((1-(3-((6-Chloro-2-naphthyl)sulfonyl)propanoyl)-4-piperidinyl)imino)-1,3-thiazol-3(2H)-yl)ethanol

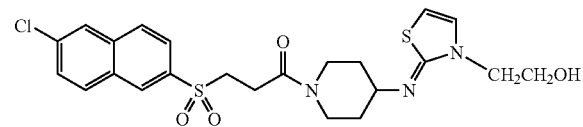

To a solution of the compound (0.60 g) obtained in Example 88c) in DMF (2.0 mL), 2-iodoethanol (0.2 mL) was added, and the mixture was mixed at 80° C. for 2 hours. The reaction solution was concentrated under reduced pressure. Chloroform and a saturated aqueous sodium hydrogen carbonate solution were added to the residue, and the mixture was mixed for 15 minutes. The organic layer was collected by separation, dried over anhydrous sodium sulfate, and the solvent was distilled off under reduced pressure. The residue was purified with a silica gel column to give the title compound (0.25 g) as a white solid.

NMR (CDCl₃) δ: 1.41-1.62 (2H, m), 1.72-1.87 (2H, m), 2.79-2.90 (2H, m), 3.03 (1H, m), 3.23-3.33 (2H, m), 3.53-3.59 (2H, m), 3.64-3.72 (1H, m), 3.85-3.91 (5H, m), 5.90 (1H, d, J=5.1), 6.59 (1H, d, J=5.1), 7.58 (1H, dd, J=1.8, 7.8), 7.89-7.95 (4H, m), 8.47 (1H, s).

EXAMPLE 93

1-(3-((6-Chloro-2-naphthyl)sulfonyl)propanoyl)-N-((2Z)-3-(2-methoxyethyl)-1,3-thiazol-2(3H)-ylidene)-4-piperidinamine

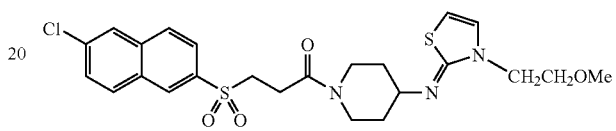

In the same manner as in Example 57b), the title compound (0.21 g) as a white solid was obtained from the compound (0.47 g) obtained in Example 88c), 1-bromo-2-methoxyethane (0.19 mL) and potassium iodide (0.33 g).

NMR (CDCl₃) δ: 1.53-1.85 (4H, m), 2.82-2.94 (2H, m), 3.01 (1H, m), 3.21-3.35 (2H, m), 3.34 (3H, s), 3.52-3.66 (4H, m), 3.73 (1H, m), 3.86 (2H, t, J=4.8), 3.95 (1H, m), 5.81 (1H, d, J=4.7), 6.58 (1H, d, J=4.7) 7.59 (1H, dd, J=2.0, 8.8), 7.89-7.98 (4H, m), 8.48 (1H, s).

EXAMPLE 94

((2Z)-2-((1-(3-((6-Chloro-2-naphthyl)sulfonyl)propanoyl)-1-piperidinyl)imino)-5-methyl-1,3-thiazol-3(2H)-yl)acetic acid hydrochloride

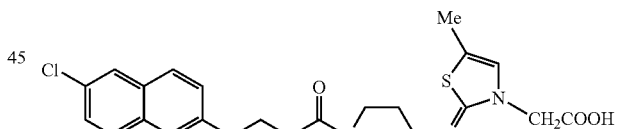

94a) tert-Butyl ((2Z)-2-((1-(3-((6-chloro-2-naphthyl)sulfonyl)propanoyl)-1-piperidinyl)imino)-5-methyl-1,3-thiazol-3(2H)-yl)acetate In the same manner as in Example 57b), the title compound (0.68 g) as a white solid was obtained from 1-(3-((6-chloro-2-naphthyl)sulfonyl)propanoyl)-N-(5-methyl-1,3-thiazol-2-yl)-4-piperidinamine (0.90 g) obtained in Example 90b), t-butyl bromoacetate (1.01 mL) and potassium iodide (0.63 g).

NMR (CDCl₃) δ: 1.44 (9H, s), 1.46-1.72 (4H, m), 2.09 (3H, s), 2.87 (2H, t, J=7.8), 3.01 (1H, m), 3.29 (2H, m), 3.54 (2H, t, J=7.8), 3.67 (1H, m), 3.84 (1H, m), 4.21 (2H, s), 6.13 (1H, s), 7.58 (1H, dd, J=1.8, 8.7), 7.89-8.00 (4H, m), 8.47 (1H, s).

94b) ((2Z)-2-((1-(3-((6-Chloro-2-naphthyl)sulfonyl)propanoyl)-1-piperidinyl)imino)-5-methyl-1,3-thiazol-3(2H)-yl)acetic acid hydrochloride To a solution of the compound (0.40 g) obtained in Example 94a) in THF (10 mL), concentrated hydrochloric acid (5 mL) was added, and the mixture was mixed for 12 hours. The reaction solution was concentrated, and the residue was washed with diethyl ether to give the title compound (0.38 g) as a colorless solid.

NMR (DMSO-$d_6$) δ: 1.45 (1H, m), 1.60 (1H, m), 1.83-1.98 (2H, m), 2.28 (3H, s), 2.64 (1H, m), 2.68-2.83 (2H, m), 3.14 (1H, m), 3.57-3.69 (3H, m), 3.88 (1H, d, J=14.5), 4.22 (1H, d, J=14.5), 5.01 (2H, s), 7.24 (1H, s), 7.74 (1H, dd, J=2.2, 8.8), 8.00 (1H, dd, J=1.9, 8.8), 8.17-8.31 (3H, m), 8.65 (1H, d, J=1.9), 10.00 (1H, br).

EXAMPLE 95

1-((2Z)-2-((1-(3-((6-Chloro-2-naphthyl)sulfonyl)propanoyl)-1-piperidinyl)imino)-3-methyl-2,3-dihydro-1,3-thiazol-5-yl)ethanol

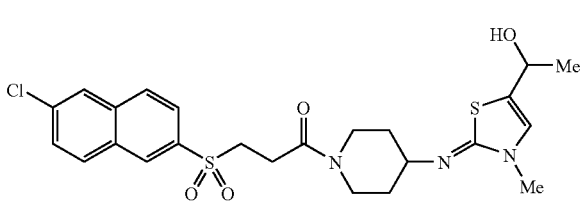

95a) tert-Butyl 4-(((2Z)-3-methyl-1,3-thiazol-2(3H)-ylidene)amino)piperidine-1-carboxylate In the same manner as in Example 57b), the title compound (4.2 g) as a pale yellow solid was obtained from tert-butyl 4-(1,3-thiazol-2-ylamino)piperidine-1-carboxylate (5.0 g) obtained in Example 88b) and methyl iodide (2.18 mL).

NMR (CDCl$_3$) δ: 1.46 (9H, s), 1.51-1.85 (4H, m), 2.82-3.08 (3H, m), 3.26 (3H, s), 3.96 (2H, br), 5.83 (1H, d, J=4.8), 6.45 (1H, d, J=4.8).

95b) tert-Butyl 4-((2Z)-5-(1-hydroxyethyl)-3-methyl-1,3-thiazol-2(3H)-ylidene)amino)piperidine-1-carboxylate In the same manner as in Example 67a), the title compound (0.18 g) was obtained from the compound (1.0 g) obtained in Example 95a) and acetaldehyde (0.5 mL).

NMR (CDCl$_3$) δ: 1.46 (9H, s), 1.47 (3H, d, J=6.3), 1.50-1.59 (2H, m), 1.67-1.78 (2H, m), 2.86-3.02 (2H, m), 3.21 (3H, s), 3.96 (2H, br), 4.75 (1H, q, J=6.3), 6.36 (1H, s).

95c) 1-((2Z)-2-((1-(3-((6-Chloro-2-naphthyl)sulfonyl)propanoyl)-1-piperidinyl)imino)-3-methyl-2,3-dihydro-1,3-thiazol-5-yl)ethanol To the compound (0.18 g) obtained in Example 95b), concentrated hydrochloric acid (2 mL) was added, and the mixture was mixed. After completion of expansion, ethanol was added thereto, and the mixture was concentrated. To the residue, DBU (0.16 mL), triethylamine (0.15 mL) and N-trimethylsilylacetamide (0.28 g) were added, and the mixture was dissolved in acetonitrile (5 mL). This solution was added to a suspension of 3-((6-chloro-2-naphthyl)sulfonyl)propanoic acid (0.16 g), WSC (0.15 g) and HOBt (0.12 g) in acetonitrile (5 mL) and mixed for 12 hours. The reaction solution was concentrated, and the residue was dissolved in chloroform and a saturated aqueous sodium bicarbonate solution. The organic layer was collected by separation, and dried over anhydrous sodium sulfate. The solvent was distilled off, and the residue was purified with a silica gel column to give the title compound (0.07 g) as a colorless solid.

NMR (CDCl$_3$) δ: 1.46 (3H, d, J=6.2), 1.48-1.80 (4H, m), 2.88 (2H, t, J=7.8), 2.92-3.29 (3H, m), 3.21 (3H, s), 3.56 (2H, t, J=7.8), 3.81 (1H, m), 4.10 (1H, m), 4.75 (1H, q, J=6.2), 6.38 (1H, s), 7.59 (1H, dd, J=1.8, 9.0), 7.88-7.97 (4H, m), 8.48 (1H, s).

EXAMPLE 96

((2Z)-2-((1-(3-((6-Chloro-2-naphthyl)sulfonyl)propanoyl)-1-piperidinyl)imino)-3-methyl-2,3-dihydro-1,3-thiazol-5-yl)methanol

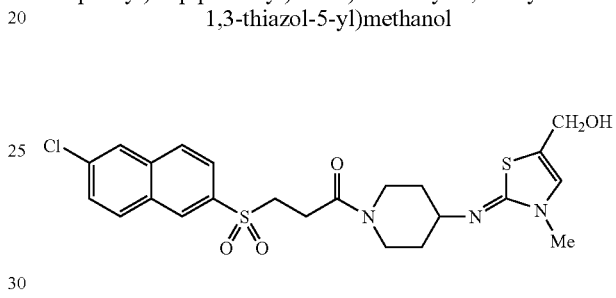

96a) tert-Butyl 4-(((2Z)-5-formyl-3-methyl-1,3-thiazol-2(3H)-ylidene)amino)piperidine-1-carboxylate In the same manner as in Example 67a), the title compound (4.6 g) as a pale yellow solid was obtained from the compound (5.0 g) obtained in Example 95a) and DMF (4 mL).

NMR (CDCl$_3$) δ: 1.47 (9H, s), 1.27-1.81 (4H, m), 2.97-3.14 (3H, m), 3.41 (3H, s), 3.91 (2H, br), 7.43 (1H, s), 9.46 (1H, s).

96b) tert-Butyl 4-(((2Z)-5-(hydroxymethyl)-3-methyl-1,3-thiazol-2(3H)-ylidene)amino)piperidine-1-carboxylate To a solution of the compound (1.0 g) obtained in Example 96a) in ethanol (10 mL), sodium borohydride (0.23 g) was added, and the mixture was mixed for 30 minutes. The reaction solution was concentrated, and the residue was purified with a silica gel column to give the title compound (0.98 g) as a colorless solid.

NMR (CDCl$_3$) δ: 1.46 (9H, s), 1.48-1.59 (2H, m), 1.69-1.80 (2H, m), 2.86-3.02 (3H, m), 3.22 (3H, s), 3.94 (2H, br), 4.45 (2H, s), 6.42 (1H, s).

96c) ((2Z)-2-((1-(3-((6-Chloro-2-naphthyl)sulfonyl)propanoyl)-1-piperidinyl)imino)-3-methyl-2,3-dihydro-1,3-thiazol-5-yl)methanol In the same manner as in Example 95c), the title compound (0.33 g) as a colorless solid was obtained from the compound (0.98 g) obtained in Example 96b) and 3-((6-chloro-2-naphthyl)sulfonyl)propanoic acid (0.91 g).

NMR (DMSO-$d_6$) δ: 1.18 (1H, m), 1.36 (1H, m), 1.56 (1H, m), 1.66 (1H, m), 2.65-2.79 (2H, m), 2.82-2.97 (2H, m), 3.11 (3H, s), 3.18 (1H, m), 3.59-3.72 (3H, m), 3.86 (1H, m), 4.23

(2H, d, J=5.3), 5.10 (1H, t, J=5.6), 6.77 (1H, s), 7.73 (1H, dd, J=2.2, 8.8), 7.99 (1H, dd, J=1.7, 8.8), 8.23-8.32 (2H, m), 8.65 (1H, s).

EXAMPLE 97

Ethyl (2Z)-2-((1-(3-((6-chloro-2-naphthyl)sulfonyl)propanoyl)-1-piperidinyl)imino)-3-methyl-2,3-dihydro-1,3-thiazol-4-carboxylate

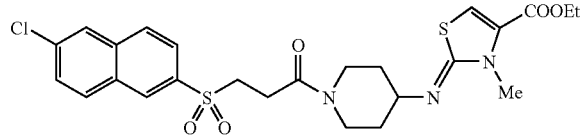

97a) tert-Butyl 4-((4-(ethoxycarbonyl)-1,3-thiazol-2-yl)amino)piperidine-1-carboxylate In the same manner as in Example 46a), the title compound (0.41 g) was obtained from tert-butyl 4-thioureidopiperidine-1-carboxylate (3.0 g) obtained in Example 88a) and ethyl bromopyruvate (2.18 mL).

NMR (CDCl$_3$) δ: 1.37 (3H, t, J=6.9), 1.46 (9H, s), 1.39-1.47 (2H, m), 2.04-2.09 (2H, m), 2.96 (2H, m), 3.53 (1H, m), 4.00 (2H, brd, J=12.0), 4.35 (2H, q, J=6.9), 5.22 (1H, d, J=8.4), 7.41 (1H, s).

97b) Ethyl 2-((1-(3-((6-chloro-2-naphthyl)sulfonyl)propanoyl)-1-piperidinyl)amino)-1,3-thiazol-4-carboxylate In the same manner as in Example 46b), the title compound (0.44 g) as a colorless solid was obtained from the compound (0.46 g) obtained in Example 97a) and 3-((6-chloro-2-naphthyl)sulfonyl)propanoic acid (0.39 g).

NMR (CDCl$_3$) δ: 1.29-1.50 (5H, m), 2.05-2.20 (2H, m), 2.81-2.91 (2H, m), 3.22 (1H, m), 3.53-3.58 (2H, m), 3.68 (1H, m), 3.81 (1H, d, J=14.4), 4.31-4.36 (3H, m), 5.17 (1H, d, J=8.1), 7.41 (1H, s), 7.59 (1H, dd, J=2.1, 8.7), 7.88-7.96 (4H, m), 8.46 (1H, s).

97c) Ethyl (2Z)-2-((1-(3-((6-chloro-2-naphthyl)sulfonyl)propanoyl)-1-piperidinyl)imino)-3-methyl-2,3-dihydro-1,3-thiazol-4-carboxylate In the same manner as in Example 57b), the title compound (0.21 g) was obtained from the compound (0.44 g) obtained in Example 97b) and methyl iodide (0.12 mL).

NMR (CDCl$_3$) δ: 1.35 (3H, t, J=7.2), 1.47-1.81 (4H, m), 2.84-2.96 (2H, m), 3.08 (1H, m), 3.19-3.33 (2H, m), 3.54 (3H, s), 3.51-3.60 (2H, m), 3.77 (1H, m), 3.97 (1H, m), 4.29 (2H, q, J=7.2), 6.91 (1H, s), 7.59 (1H, dd, J=1.8, 8.8), 7.90-8.01 (4H, m), 8.48 (1H, s).

EXAMPLE 98

(2Z)-2-((1-(3-((6-Chloro-2-naphthyl)sulfonyl)propanoyl)-1-piperidinyl)imino)-N,3,4-trimethyl-2,3-dihydro-1,3-thiazole-5-carboxamide

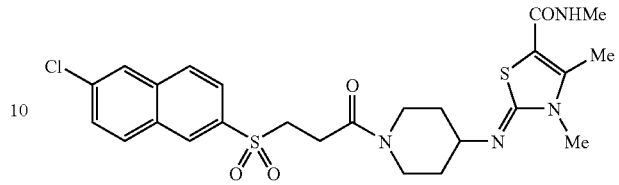

98a) tert-Butyl 4-((4-methyl-5-(methylcarbamoyl)-1,3-thiazol-2-yl)amino)piperidine-1-carboxylate In the same manner as in Example 46a), the title compound (1.4 g) was obtained from tert-butyl 4-thioureidopiperidine-1-carboxylate (1.5 g) obtained in Example 88a) and 2-chloro-N-methyl-3-oxobutanamide (1.0 g).

NMR (CDCl$_3$) δ: 1.39-1.49 (2H, m), 1.46 (9H, s), 2.03-2.10 (2H, m), 2.49 (3H, s), 2.81-2.95 (5H, m), 3.51 (1H, m), 4.03 (2H, brd, J=12.8), 5.32 (1H, d, J=6.6), 5.48 (1H, br).

98b) 2-((1-(3-((6-Chloro-2-naphthyl)sulfonyl)propanoyl)-1-piperidinyl)amino)-N,4-dimethyl-1,3-thiazole-5-carboxamide In the same manner as in Example 46b), the title compound (1.8 g) was obtained from the compound (1.4 g) obtained in Example 98a) and 3-((6-chloro-2-naphthyl)sulfonyl)propanoic acid (1.2 g).

NMR (CDCl$_3$) δ: 1.30-1.49 (2H, m), 2.01-2.19 (2H, m), 2.48 (3H, s), 2.77-2.94 (3H, m), 2.93 (3H, d, J=4.8), 3.19 (1H, t, J=14.1), 3.52-3.61 (2H, m), 3.69 (1H, m), 3.81 (1H, d, J=14.1), 4.37 (1H, d, J=14.1), 5.51 (1H, d, J=7.2), 5.55 (1H, d, J=4.8), 7.59 (1H, dd, J=1.8, 7.8), 7.88-7.97 (4H, m), 8.47 (1H, s).

98c) (2Z)-2-((1-(3-((6-Chloro-2-naphthyl)sulfonyl)propanoyl)-1-piperidinyl)imino)-N,3,4-trimethyl-2,3-dihydro-1,3-thiazole-5-carboxamide In the same manner as in Example 57b), the title compound (0.48 g) was obtained from the compound (0.8 g) obtained in Example 98b) and methyl iodide (0.25 mL).

NMR (DMSO-d$_6$) δ: 1.18 (1H, m), 1.41 (1H, m), 1.58 (1H, m), 1.70 (1H, m), 2.44 (3H, s), 2.63 (3H, d, J=4.5), 2.68-2.79 (2H, m), 2.86-3.00 (2H, m), 3.17 (1H, m), 3.21 (3H, s), 3.59-3.73 (3H, m), 3.86 (1H, s, J=13.0), 7.45 (1H, m), 7.73 (1H, dd, J=2.2, 8.8), 7.98 (1H, m), 8.17 (1H, d, J=8.8), 8.24-8.32 (2H, m), 8.65 (1H, d, J=1.5).

EXAMPLE 99

((2Z)-2-((1-(3-((6-Chloro-2-naphthyl)sulfonyl)propanoyl)-1-piperidinyl)imino)-3-methyl-2,3-dihydro-1,3-thiazol-4-yl)methanol

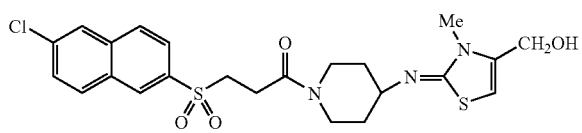

99a) tert-Butyl-4-((4-((acetyloxy)methyl)-1,3-thiazol-2-yl)amino)piperidine-1-carboxylate In the same manner as in Example 46a), the title compound (3.5 g) was obtained from tert-butyl 4-thioureidopiperidine-1-carboxylate (7.2 g) obtained in Example 88a) and 3-bromo-2-oxopropyl acetate (5.0 g).

NMR (CDCl$_3$) δ: 1.39-1.48 (2H, m), 1.46 (9H, s), 2.05-2.11 (2H, m), 2.95 (2H, t, J=7.8), 3.53 (1H, m), 4.02 (2H, br), 4.95 (2H, s), 5.04 (1H, d, J=5.2), 6.47 (1H, s).

99b) tert-Butyl 4-((4-(hydroxymethyl)-1,3-thiazol-2-yl)amino)piperidine-1-carboxylate In the same manner as in Example 57b), the title compound (0.92 g) was obtained from the compound (1.0 g) obtained in Example 99a) and methyl iodide (0.35 mL).

NMR (CDCl$_3$) δ: 1.46 (9H, s), 1.50-1.61 (2H, m), 1.73-1.83 (2H, m), 2.91-3.05 (3H, m), 3.32 (3H, s), 3.94 (2H, br), 4.39 (2H, d, J=5.7), 5.82 (1H, s).

99c) ((2Z)-2-((1-(3-((6-Chloro-2-naphthyl)sulfonyl)propanoyl)-1-piperidinyl)imino)-3-methyl-2,3-dihydro-1,3-thiazol-4-yl)methanol In the same manner as in Example 95c), the title compound (0.13 g) was obtained from the compound (0.33 g) obtained in Example 99b) and 3-((6-chloro-2-naphthyl)sulfonyl)propanoic acid (0.27 g).

NMR (CDCl$_3$) δ: 1.46-1.88 (4H, m), 2.88 (2H, t, J=6.9), 3.04 (1H, m), 3.10-3.30 (2H, m), 3.32 (3H, s), 3.55 (2H, t, J=6.9), 3.76 (1H, m), 4.05 (1H, m), 4.40 (2H, s), 5.83 (1H, s), 7.58 (1H, dd, J=1.8, 8.4), 7.89-7.96 (4H, m), 8.47 (1H, s).

EXAMPLE 100

N-((1-(3-((6-Chloro-2-naphthyl)sulfonyl)propanoyl)-1-piperidinyl)methyl)-N-((2Z)-3-methyl-1,3-thiazol-2(3H)-ylidene)amine

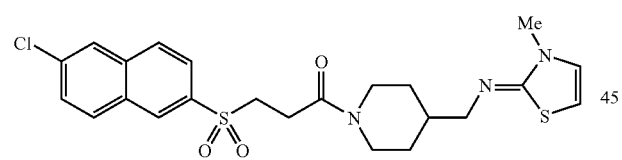

100a) tert-Butyl 4-((thioureido)methyl)piperidine-1-carboxylate

In the same manner as in Example 66a), the title compound (9.0 g) was obtained from tert-butyl 4-(aminomethyl)piperidine-1-carboxylate (10 g) and benzoyl isothiocyanate (6.3 mL).

NMR (CDCl$_3$) δ: 1.07-1.23 (2H, m), 1.45 (9H, s), 1.65-1.89 (3H, m), 2.62-2.77 (2H, m), 4.03-4.17 (2H, m), 6.03-6.18 (2H, br).

100b) tert-Butyl 4-((1,3-thiazol-2-yl)aminomethyl)piperidine-1-carboxylate

In the same manner as in Example 46a), the title compound (1.4 g) was obtained from the compound (3.0 g) obtained in Example 100a) and chloroacetaldehyde (3.3 mL, a 40% aqueous solution).

NMR (CDCl$_3$) δ: 1.12-1.27 (2H, m) 1.45 (9H, s), 1.73-1.86 (3H, m), 2.69 (2H, m), 3.18 (2H, d, J=6.6), 4.11 (2H, m), 5.73 (1H, br), 6.47 (1H, d, J=3.6), 7.09 (1H, d, J=3.6).

100c) N-((1-(3-((6-Chloro-2-naphthyl)sulfonyl)propanoyl)-1-piperidinyl)methyl)-1,3-thiazol-2-amine In the same manner as in Example 46b), the title compound (1.72 g) was obtained from the compound (1.26 g) obtained in Example 100b) and 3-((6-chloro-2-naphthyl)sulfonyl)propanoic acid (1.27 g).

NMR (CDCl$_3$) δ: 1.05-1.23 (2H, m), 1.76-1.95 (3H, m), 2.51 (1H, m), 2.85 (2H, m), 2.97 (1H, m), 3.19 (2H, d, J=3.9), 3.54 (2H, m), 3.85 (1H, d, J=13.8), 4.51 (1H, d, J=13.8), 5.44 (1H, br), 6.48 (1H, d, J=3.6), 7.09 (1H, d, J=3.6), 7.59 (1H, dd, J=1.8, 8.7), 7.88 (4H, m), 8.46 (1H, s).

100d) N-((1-(3-((6-Chloro-2-naphthyl)sulfonyl)propanoyl)-1-piperidinyl)methyl)-N-((2Z)-3-methyl-1,3-thiazol-2(3H)-ylidene)amine In the same manner as in Example 57b), the title compound (0.31 g) was obtained from the compound (0.80 g) obtained in Example 100c) and methyl iodide (0.42 mL).

NMR (CDCl$_3$) δ: 1.06-1.22 (4H, m), 1.73-1.82 (3H, m), 2.53 (1H, m), 2.82-2.96 (4H, m), 3.02 (1H, m), 3.27 (3H, s), 3.49-3.62 (2H, m), 3.87 (1H, d, J=13.5), 4.47 (1H, d, J=13.5), 5.85 (1H, d, J=4.9), 6.48 (1H, d, J=4.9), 7.59 (1H, dd, J=1.9, 8.6), 7.89-8.01 (4H, m), 8.47 (1H, s).

EXAMPLE 101

6-Chloro-N-(2-(4-(((2Z)-3-methyl-1,3-thiazol-2(3H)-ylidene)amino)-1-piperidinyl)-2-oxoethyl)-2-naphthalenesulfonamide

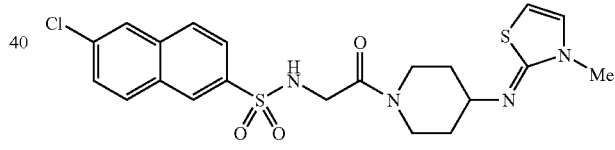

101a) 6-Chloro-N-(2-oxo-2-(4-(1,3-thiazol-2-ylamino)-1-piperidinyl)ethyl)-2-naphthalenesulfonamide In the same manner as in Example 46b), the title compound (0.7 g) was obtained from tert-butyl 4-(1,3-thiazol-2-yl)aminopiperidine-1-carboxylate (0.57 g) obtained in Example 88b) and N-((6-chloro-2-naphthyl)sulfonyl)glycine (0.6 g).

NMR (CDCl$_3$) δ: 1.14-1.42 (2H, m), 1.78-1.96 (2H, m), 2.75 (1H, t, J=11.0), 3.00-3.12 (2H, m), 3.62-4.01 (4H, m), 6.59 (1H, d, J=3.6), 6.98 (1H, d, J=3.6), 7.53 (1H, d, J=7.0), 7.68 (1H, dd, J=2.2, 7.0), 7.86-7.94 (2H, m), 8.10-8.23 (2H, m), 8.49 (1H, s).

101b) 6-Chloro-N-(2-(4-(((-2Z)-3-methyl-1,3-thiazol-2(3H)-ylidene)amino)-1-piperidinyl)-2-oxoethyl)-2-naphthalenesulfonamide In the same manner as in Example 57b), the title compound (0.29 g) was obtained from the compound (0.7 g) obtained in Example 101a) and methyl iodide (0.19 mL).

NMR (DMSO-d$_6$) δ: 1.20 (1H, m), 1.39 (1H, m), 1.55-1.72 (2H, m), 2.80-2.92 (2H, m), 3.13 (1H, m), 3.13 (3H, s), 3.61 (1H, m), 3.78-3.90 (3H, m), 6.18 (1H, br), 6.91 (1H, br), 7.68 (1H, dd, J=2.2, 8.8), 7.84 (1H, t, J=5.6), 7.92 (1H, dd, J=1.9, 8.8), 8.10 (1H, d, J=8.0), 8.17-8.24 (2H, m), 8.49 (1H, s).

EXAMPLE 102

2-(((6-Chloro-2-naphthyl)sulfonyl)(2-(4-(((2Z)-3-methyl-1,3-thiazol-2(3H)-ylidene)amino)-1-piperidinyl)-2-oxoethyl)amino)acetamide

102a) 2-(((6-Chloro-2-naphthyl)sulfonyl)(2-oxo-2-(4-(1,3-thiazol-2-ylamino)-1-piperidinyl)ethyl)amino)acetamide In the same manner as in Example 46b), the title compound (0.62 g) was obtained from tert-butyl 4-(1,3-thiazol-2-yl)aminopiperidine-1-carboxylate (0.57 g) obtained in Example 88b) and N-(2-amino-2-oxoethyl)-N-((6-chloro-2-naphthyl)sulfonyl)glycine (0.71 g).

NMR (CDCl$_3$) δ: 1.21-1.42 (2H, m), 1.89-2.05 (2H, m), 2.86 (1H, m), 3.16 (1H, m), 3.72-3.82 (4H, m), 4.10 (1H, m), 4.36 (1H, d, J=2.8), 6.61 (1H, d, J=3.6), 7.00 (1H, d, J=3.6), 7.16 (1H, br), 7.58 (1H, s, J=6.8), 7.70 (1H, dd, J=1.8, 8.8), 7.93 (1H, dd, J=1.8, 8.8), 8.02 (1H, br), 8.10 (1H, d, J=8.8), 8.20-8.25 (2H, m), 8.55 (1H, s)

102b) 2-(((6-Chloro-2-naphthyl)sulfonyl)(2-(4-(((2Z)-3-methyl-1,3-thiazol-2(3H)-ylidene)amino)-1-piperidinyl)-2-oxoethyl)amino)acetamide In the same manner as in Example 57b), the title compound (0.27 g) was obtained from the compound (0.62 g) obtained in Example 102a) and methyl iodide (0.15 mL).

NMR (DMSO-d$_6$) δ: 1.28-1.58 (2H, m), 1.68-1.84 (2H, m), 2.93-3.08 (2H, m), 3.15-3.30 (4H, m), 3.30 (3H, s), 3.75 (1H, m), 3.83 (2H, s), 4.03 (1H, m), 4.36 (2H, s), 7.14 (1H, s), 7.70 (1H, dd, J=2.0, 9.0), 7.94 (1H, dd, J=1.9, 8.8), 8.11 (1H, d, J=8.8), 8.19-8.27 (2H, m), 8.56 (1H, s).

EXAMPLE 103

1-(3-((5-Chloro-1H-indol-2-yl)sulfonyl)propanoyl)-N-((2Z)-3-methyl-1,3-thiazol-2(3H)-ylidene)-4-piperidinamine dihydrochloride

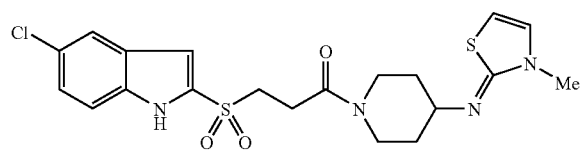

103a) tert-Butyl 5-chloro-2-((3-oxo-3-(4-(1,3-thiazol-2-ylamino)-1-piperidinyl)propyl)sulfonyl)-1H-indole-1-carboxylate In the same manner as in Example 46b), the title compound (0.64 g) was obtained from tert-butyl 4-(1,3-thiazol-2-ylamino)piperidine-1-carboxylate (0.57 g) obtained in Example 88b) and 3-((1-tert-butoxycarbonyl)-5-chloro-1H-indol-2-yl)sulfonylpropanoic acid (0.77 g).

NMR (CDCl$_3$) δ: 1.39-1.64 (2H, m), 1.74 (9H, s), 2.03-2.20 (2H, m), 2.90-3.03 (3H, m), 3.25 (1H, m), 3.62 (1H, m), 3.84 (1H, d, J=14.2), 3.95-4.10 (2H, m), 4.29 (1H, d, J=14.2), 6.49 (1H, d, J=3.6), 7.08 (1H, d, J=3.6), 7.37-7.52 (2H, m), 7.66 (1H, m), 8.00 (1H, d, J=8.8).

103b) tert-Butyl 5-chloro-2-((3-(4-(((2Z)-3-methyl-1,3-thiazol-2(3H)-ylidene)amino)-1-piperidinyl)-3-oxopropyl)sulfonyl)-1H-indole-1-carboxylate In the same manner as in Example 57b), the title compound (0.32 g) was obtained from the compound (0.64 g) obtained in Example 103a) and methyl iodide (0.14 mL).

NMR (CDCl$_3$) δ: 1.45-1.64 (2H, m), 1.64 (9H, s), 1.75-1.87 (2H, m), 2.90 (2H, t, J=6.6), 2.99 (1H, m), 3.04-3.31 (2H, m), 3.25 (3H, s), 3.68 (2H, t, J=6.6), 3.78 (1H, m), 4.08 (1H, m), 5.84 (1H, d, J=4.8), 6.45 (1H, d, J=4.8), 7.13 (1H, s), 7.31 (1H, dd, J=1.8, 8.7), 7.40 (1H, d, J=8.7), 7.68 (1H, d, J=1.8).

103c) 1-(3-((5-Chloro-1H-indol-2-yl)sulfonyl)propanoyl)-N-((2Z)-3-methyl-1,3-thiazol-2(3H)-ylidene)-4-piperidinamine dihydrochloride In the same manner as in Example 52b), the title compound (0.30 g) was obtained from the compound (0.32 g) obtained in Example 103b).

NMR (DMSO-d$_6$) δ: 1.48 (1H, m), 1.69 (1H, m), 1.86-2.01 (2H, m), 2.63 (1H, m), 2.68-2.82 (2H, m), 3.12 (1H, m), 3.40-3.50 (1H, m), 3.67 (5H, s), 3.87 (1H, d, J=13.5), 4.25 (1H, d, J=13.5), 7.10-7.18 (2H, m), 7.34 (1H, dd, J=2.1, 8.6), 7.48-7.61 (2H, m), 7.80-7.91 (1H, m), 9.70 (1H, d, J=7.7), 12.63 (1H, s).

EXAMPLE 104

N-((2Z)-5-((4-(3-((6-Chloro-2-naphthyl)sulfonyl)propanoyl)-1-piperazinyl)methyl)-3,4-dimethyl-1,3-thiazol-2(3H)-ylidene)-N-methylamine

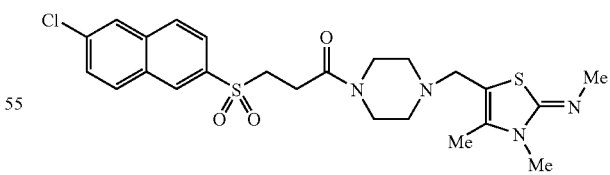

104a) N-((2Z)-3,4-Dimethyl-1,3-thiazol-2(3H)-ylidene)-N-methylamine

In the same manner as in Example 57b), the title compound (2.8 g) as a brownish-red viscous oily matter was obtained from methyl(4-methyl-1,3-thiazol-2-yl)amine (8.0 g) obtained in Example 85a) and methyl iodide (7.8 mL).

NMR (CDCl$_3$) δ: 2.08 (3H, s), 2.99 (3H, s), 3.23 (3H, s), 5.53 (1H, s).

104b) (2Z)-3,4-Dimethyl-2-(methylimino)-2,3-dihydro-1,3-thiazole-5-carbaldehyde

In the same manner as in Example 67a), the title compound (0.76 g) was obtained from the compound (1.0 g) obtained in Example 104a) and DMF (1.0 mL).

NMR (CDCl$_3$) δ: 2.49 (3H, s), 3.06 (3H, s), 3.38 (3H, s), 9.71 (1H, s).

104c) N-((2Z)-5-((4-(3-((6-Chloro-2-naphthyl)sulfonyl)propanoyl)-1-piperazinyl)methyl)-3,4-dimethyl-1,3-thiazol-2(3H)-ylidene)-N-methylamine To a solution of the compound (0.34 g) obtained in Example 104b) and 1-(3-((6-chloro-2-naphthyl)sulfonyl)propanoyl)piperazine (0.73 g) obtained in Example 3a) in 1,2-dichloroethane (10 mL), acetic acid (0.14 mL) and sodium triacetoxyborohydride (0.64 g) were added and mixed for 12 hours. The reaction solution was diluted with chloroform, washed with a saturated aqueous sodium bicarbonate solution, and dried over anhydrous sodium sulfate. The solvent was distilled off, and the residue was purified with a silica gel column to give the title compound (0.76 g).

NMR (CDCl$_3$) δ: 2.04 (3H, s), 2.36 (2H, t, J=5.0), 2.44 (2H, t, J=5.0), 2.87 (2H, dd, J=7.0, 8.0), 3.00 (3H, s), 3.25 (3H, s), 3.35 (2H, s), 3.46 (2H, t, J=5.0), 3.50-3.60 (4H, m), 7.60 (1H, dd, J=1.8, 8.8), 7.92-7.98 (4H, m), 8.48 (1H, s).

EXAMPLE 105

2-((4-(3-((6-Chloro-2-naphthyl)sulfonyl)propanoyl)-1-piperazinyl)methyl)-3-methyl-5,6-dihydroimidazo[2,1-b][1,3]thiazole

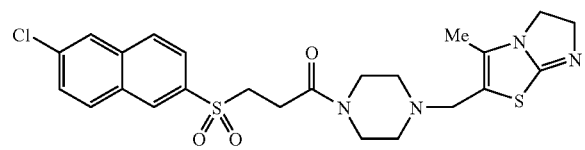

105a) 3-Methyl-5,6-dihydroimidazo[2,1-b][1,3]thiazole

In the same manner as in Example 46a), the title compound (15.0 g) was obtained from bromoacetone (25.0 g) and ethylene thiourea (12.4 g).

NMR (CDCl$_3$) δ: 2.11 (3H, s), 4.27-4.38 (4H, m), 6.55 (1H, s).

105b) 3-Methyl-5,6-dihydroimidazo[2,1-b][1,3]thiazole-2-carbaldehyde

In the same manner as in Example 67a), the title compound (1.17 g) was obtained from the compound (1.0 g) obtained in Example 105a) and DMF (1.0 mL).

NMR (CDCl$_3$) δ: 2.40 (3H, s), 3.90 (2H, dd, J=8.0, 9.6), 4.35 (2H, dd, J=8.0, 9.6), 9.57 (1H, s).

105c) 2-((4-(3-((6-Chloro-2-naphthyl)sulfonyl)propanoyl)-1-piperazinyl)methyl)-3-methyl-5,6-dihydroimidazo[2,1-b][1,3]thiazole In the same manner as in Example 104c), the title compound (0.34 g) was obtained from the compound (0.34 g) obtained in Example 105b).

NMR (CDCl$_3$) δ: 2.07 (3H, s), 2.33-2.49 (4H, m), 2.80-2.94 (2H, m), 3.33 (2H, s), 3.43-3.59 (6H, m), 4.04 (2H, t, J=9.4), 4.30 (2H, t, J=9.4), 7.60 (1H, dd, J=1.8, 8.8), 7.88-7.98 (4H, m), 8.47 (1H, s).

EXAMPLE 106

2-((4-(3-((6-Chloro-2-naphthyl)sulfonyl)propanoyl)-1-piperazinyl)methyl)-3-methyl-6,7-dihydro-5H-[1,3]thiazolo[3,2-a]pyrimidine

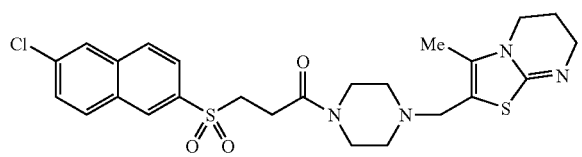

106a) 3-Methyl-6,7-dihydro-5H-[1,3]thiazolo[3,2-a]pyrimidine

In the same manner as in Example 46a), the title compound (17.9 g) was obtained from bromoacetone (25.0 g) and propylene thiourea (15.0 g).

NMR (CDCl$_3$) δ: 1.84-1.96 (2H, m), 1.99 (3H, s), 3.45 (2H, t, J=5.8), 3.66 (2H, t, J=5.8), 5.33 (1H, m).

106b) 3-Methyl-6,7-dihydro-5H-[1,3]thiazolo[3,2-a]pyrimidine-2-carbaldehyde

In the same manner as in Example 67a), the title compound (5.84 g) was obtained from the compound (7.0 g) obtained in Example 106a) and DMF (7.0 mL).

NMR (CDCl$_3$) δ: 1.98 (2H, dt, J=5.6, 6.0), 2.37 (3H, s), 3.53 (2H, t, J=5.6), 3.78 (2H, t, J=6.0), 9.71 (1H, s).

106c) 2-((4-(3-((6-Chloro-2-naphthyl)sulfonyl)propanoyl)-1-piperazinyl)methyl)-3-methyl-6,7-dihydro-5H-[1,3]thiazolo[3,2-a]pyrimidine In the same manner as in Example 104c), the title compound (0.51 g) was obtained from the compound (0.55 g) obtained in Example 106b).

NMR (CDCl$_3$) δ: 2.05 (3H, s), 2.35 (2H, t, J=5.1), 2.44 (2H, t, J=5.1), 2.85 (2H, t, J=8.1), 3.34 (2H, s), 3.44 (2H, t, J=5.1), 3.49-3.58 (8H, m), 3.77 (2H, t, J=5.1), 7.59 (1H, dd, J=2.1, 8.7), 7.88-7.96 (4H, m), 8.46 (1H, s).

EXAMPLE 107

N-((2Z)-5-((4-(3-((5-Chloro-1H-indol-2-yl)sulfonyl)propanoyl)-1-piperazinyl)methyl)-3,4-dimethyl-1,3-thiazol-2(3H)-ylidene)-N-methylamine dihydrochloride

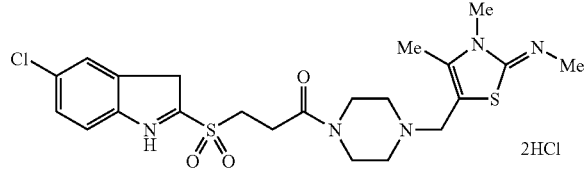

107a) tert-Butyl 4-(((2Z)-3,4-dimethyl-2-(methylimino)-2,3-dihydro-1,3-thiazol-5-yl)methyl)-1-piperazine carboxylate In the same manner as in Example 104c), the title compound (0.64 g) as a colorless solid was obtained from (2Z)-3,4-dimethyl-2-(methylimino)-2,3-dihydro-1,3-thiazol-5-carbaldehyde (0.41 g) obtained in Example 104b) and tert-butyl piperazine-1-carboxylate (0.45 g).

NMR (CDCl$_3$) δ: 1.46 (9H, s), 2.04 (3H, s), 2.39 (4H, t, J=5.1), 2.99 (3H, s), 3.24 (3H, s), 3.35 (2H, s), 3.43 (4H, t, J=5.1).

107b) tert-Butyl 5-chloro-2-((3-(4-(((2Z)-3,4-dimethyl-2-(methylimino)-2,3-dihydro-1,3-thiazol-5-yl)methyl)-1-piperazinyl)-3-oxopropyl)sulfonyl)-1H-indole-1-carboxylate In the same manner as in Example 46b), the title compound (0.40 g) was obtained from the compound (0.34 g) obtained in Example 107c) and 3-((1-tert-butoxycarbonyl)-5-chloro-1H-indol-2-yl)sulfonylpropanoic acid (0.39 g).

NMR (CDCl$_3$) δ: 1.73 (9H, s), 2.05 (3H, s), 2.32-2.46 (4H, m), 2.91 (2H, t, J=7.6), 3.00 (3H, s), 3.24 (3H, s), 3.35 (2H, s), 3.44-3.58 (4H, m), 4.04 (2H, t, J=7.6), 7.44 (1H, dd, J=2.2, 9.0), 7.51 (1H, s), 7.65 (1H, d, J=2.2), 8.00 (1H, d, J=9.0).

107c) N-((2Z)-5-((4-(3-((5-Chloro-1H-indol-2-yl)sulfonyl)propanoyl)-1-piperazinyl)methyl)-3,4-dimethyl-1,3-thiazol-2(3H)-ylidene)-N-methylamine dihydrochloride In the same manner as in Example 7b), the title compound (0.38 g) was obtained from the compound (0.40 g) obtained in Example 107a).

NMR (DMSO-d$_6$) δ: 2.34 (3H, s), 2.77-2.92 (4H, m), 2.97-3.13 (5H, m), 3.32-3.69 (6H, m), 4.04 (1H, m), 4.30 (1H, m), 4.47 (2H, s), 7.16 (1H, s), 7.35 (1H, dd, J=2.1, 8.6), 7.51-7.66 (2H, m), 7.81 (1H, s), 10.57 (1H, br), 12.67 (1H, br).

EXAMPLE 108

4-(3-((6-Chloro-2-naphthyl)sulfonyl)propanoyl)-N-((2Z)-3-methyl-1,3-thiazol-2(3H)-ylidene)-1-piperazinamine

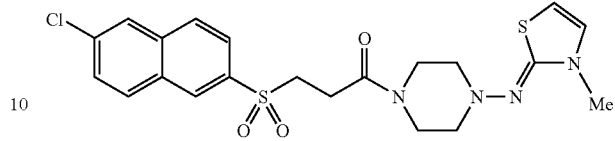

108a) tert-Butyl 4-thioureidopiperazine-1-carboxylate

In the same manner as in Example 66a), the title compound (2.34 g) was obtained from tert-butyl 4-aminopiperazine-1-carboxylate (WO 0214271: 2.0 g) and benzoyl isothiocyanate (1.34 mL).

NMR (CDCl$_3$) δ: 1.46 (9H, s), 2.56 (2H, m), 2.99 (4H, m), 4.08 (2H, br), 6.41 (1H, br), 7.03 (1H, Br), 7.32 (1H, s).

108b) tert-Butyl 4-(1,3-thiazol-2-yl)aminopiperazine-1-carboxylate

In the same manner as in Example 46a), the title compound (1.83 g) was obtained from the compound (2.3 g) obtained in Example 108a) and chloroacetaldehyde (2.2 mL, a 40% aqueous solution).

NMR (CDCl$_3$) δ: 1.47 (9H, s), 2.83 (4H, br), 3.55 (4H, br), 6.61 (1H, d, J=3.6), 7.15 (1H, d, J=3.6).

108c) 4-(3-((6-Chloro-2-naphthyl)sulfonyl)propanoyl)-N-(1,3-thiazol-2-yl)piperazin-1-amine In the same manner as in Example 46b), the title compound (2.42 g) was obtained from the compound (1.83 g) obtained in Example 108b) and 3-((6-chloro-2-naphthyl)sulfonyl)propanoic acid (1.92 g).

NMR (CDCl$_3$) δ: 2.80-2.92 (6H, m), 3.53-3.67 (6H, m), 6.18 (1H, br), 6.63 (1H, d, J=3.6), 7.16 (1H, d, J=3.6), 7.59 (1H, dd, J=2.1, 9.0), 7.88-7.96 (4H, m), 8.47 (1H, s).

108d) 4-(3-((6-Chloro-2-naphthyl)sulfonyl)propanoyl)-N-((2Z)-3-methyl-1,3-thiazol-2(3H)-ylidene)-1-piperazinamine In the same manner as in Example 57b), the title compound (0.42 g) was obtained from the compound (0.50 g) obtained in Example 108c) and methyl iodide (0.10 mL).

NMR (CDCl$_3$) δ: 2.68-2.74 (4H, m), 2.86-2.91 (2H, m), 3.28 (3H, s), 3.50-3.59 (6H, m), 5.88 (1H, d, J=4.5), 6.41 (1H, d, J=4.5), 7.59 (1H, dd, J=1.5, 7.8), 7.90-7.97 (4H, m), 8.48 (1H, s)

EXAMPLE 109

2-((2Z)-2-((4-(3-((6-Chloro-2-naphthyl)sulfonyl)propanoyl)-1-piperazinyl)imino)-1,3-thiazol-3(2H)-yl)ethanol

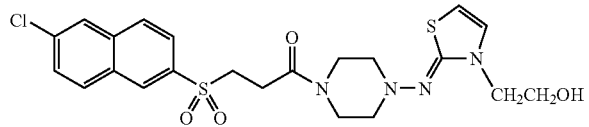

In the same manner as in Example 57b), the title compound (0.28 g) was obtained from 4-(3-((6-chloro-2-naphthyl)sulfonyl)propanoyl)-N-(1,3-thiazol-2-yl)piperazin-1-amine (0.50 g) obtained in Example 108c) and 2-iodoethanol (0.28 mL).

NMR (CDCl₃) δ: 2.70 (4H, m), 2.87 (2H, t, J=8.2), 3.52-3.60 (6H, m), 3.88 (4H, s), 5.92 (1H, d, J=4.4), 6.43 (1H, d, J=4.4), 7.59 (1H, dd, J=1.8, 8.8), 7.93-7.97 (4H, m), 8.48 (1H, s).

EXAMPLE 110

2-((2Z)-2-((4-(3-((6-Chloro-2-naphthyl)sulfonyl)propanoyl)-1-piperazinyl)imino)-1,3-thiazol-3(2H)-yl)acetamide

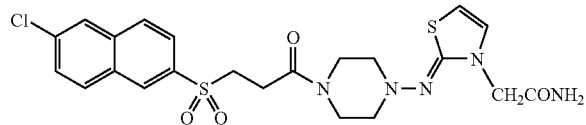

In the same manner as in Example 57b), the title compound (0.25 g) was obtained from 4-(3-((6-chloro-2naphthyl)sulfonyl)propanoyl)-N-(1,3-thiazol-2-yl)piperazine-1-amine (0.50 g) obtained in Example 108c) and 2-iodoacetamide (0.30 g).

NMR (CDCl₃) δ: 2.66-2.76 (4H, m), 2.87 (2H, t, J=7.8), 3.53-3.58 (6H, m), 4.30 (2H, s), 5.36 (1H, br), 5.98 (1H, d, J=5.1), 6.52 (1H, d, J=5.1), 6.95 (1H, br), 7.58 (1H, dd, J=2.1, 7.8), 7.89-7.96 (4H, m), 8.46 (1H, s).

EXAMPLE 111

(3Z)-7-(1-(3-((6-Chloro-2-naphthyl)sulfonyl)propanoyl)-1-piperidinyl)-3-(methylimino)-6,7-dihydro[1,3]thiazolo[3,4-a]pyrazin-8(5H)-one

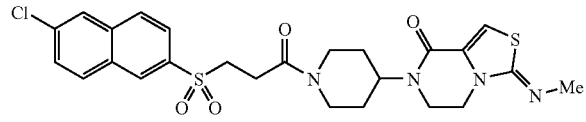

111a) Ethyl 2-(methylamino)-1,3-thiazol-4-carboxylate

In the same manner as in Example 46a), the title compound (6.42 g) as a pale yellow solid was obtained from ethyl bromopyruvate (10 g) and N-methylthiourea.

NMR (CDCl₃) δ: 1.37 (3H, t, J=7.1), 3.01 (3H, d, J=4.9), 4.35 (2H, q, J=7.1), 6.48 (1H, br), 7.40 (1H, s).

111b) tert-Butyl 4-((2-hydroxyethyl)((2-(methylamino)-1,3-thiazol-4-yl)carbonyl)amino)piperidine-1-carboxylate To a solution of the compound (2.00 g) obtained in Example 111a) in ethanol (10 mL), a 1 N aqueous sodium hydroxide solution (10 mL) was added, and the mixture was mixed for 24 hours. The reaction solution was neutralized with hydrochloric acid, and the mixture was concentrated. The residue was suspended in acetonitrile (10 mL), and WSC (1.45 g) and HOBt (1.16 g) were added thereto. To the reaction solution, a solution of tert-butyl 4-((2-hydroxyethyl)amino)piperidine-1-carboxylate (1.24 g), N-trimethylsilylacetamide (2.65 g) and triethylamine (1.40 mL) in acetonitrile (10 mL) was added, and the mixture was mixed for 24 hours. The reaction solution was concentrated, and the residue was dissolved in chloroform and a saturated aqueous sodium bicarbonate solution. The organic layer was collected by separation, and dried over anhydrous sodium sulfate. The solvent was distilled off, and the residue was purified with a silica gel column to give the title compound (0.66 g) as a pale yellow solid.

NMR (CDCl₃) δ: 1.46 (9H, s), 1.72-1.90 (4H, m), 2.74 (2H, br), 3.99 (3H, d, J=5.2), 3.60 (2H, m), 3.78 (2H, m), 4.18-4.24 (3H, m).

111c) tert-Butyl 4-((3Z)-3-(methylimino)-8-oxo-5,6-dihydro[1,3]thiazolo[3,4-a]pyridin-7(8H)-yl)piperidine-1-carboxylate To a solution of the compound (0.80 g) obtained in Example 111b) and 2,6-lutidine (0.54 mL) in dichloromethane (20 mL), trifluoromethane sulfonic acid anhydride (0.38 mL) was added at −40° C. The reaction solution was heated for 1 hour until the temperature reached room temperature, and the reaction solution was poured into chloroform and a saturated aqueous sodium bicarbonate solution. The chloroform layer was collected by separation, and dried over anhydrous sodium sulfate. The solvent was distilled off, and the residue was purified with a silica gel column to give the title compound (0.34 g) as a pale yellow solid.

NMR (CDCl₃) δ: 1.47 (9H, s), 1.55-1.70 (4H, m), 2.76-2.89 (2H, m), 3.01 (3H, s), 3.49 (2H, t, J=5.2), 3.84 (2H, t, J=5.2), 4.24 (1H, d, J=12.2), 4.71 (1H, m), 6.91 (1H, s).

111d) (3Z)-7-(1-(3-((6-Chloro-2-naphthyl)sulfonyl)propanoyl)-1-piperidinyl)-3-(methylimino)-6,7-dihydro[1,3]thiazolo[3,4-a]pyrazin-8(5H)-one In the same manner as in Example 46b), the title compound (0.34 g) as a colorless solid was obtained from the compound (0.34 g) obtained in Example 111c) and 3-((6-chloro-2-naphthyl)sulfonyl)propanoic acid.

NMR (CDCl₃) δ: 1.51-1.83 (4H, m), 2.62 (1H, t, J=11.7), 2.80-2.95 (2H, m), 3.00 (3H, s), 3.18 (1H, t, J=11.7), 3.43-3.48 (2H, m), 3.50-3.63 (2H, m), 3.81-3.83 (2H, m), 3.96 (1H, d, J=14.1), 4.68 (1H, d, J=14.1), 4.80 (1H, m), 6.91 (1H, s), 7.60 (1H, dd, J=1.8, 8.7), 7.88-7.95 (4H, m), 8.47 (1H, s).

EXAMPLE 112

(2S)-3-((6-Chloro-2-naphthyl)sulfonyl)-1-(4-(((2Z)-3-methyl-2-(methylimino)-2,3-dihydro-1,3-thiazol-4-yl)methyl)-1-piperazinyl)-1-oxopropan-2-ol

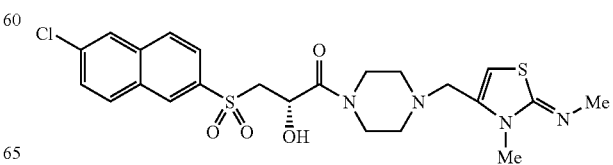

112a) Methyl (2S)-3-[(6-chloronaphthalen-2-yl)thio]-2-hydroxypropionate

Under argon atmosphere, a 3 M solution of ethylmagnesium bromide in diethyl ether was added dropwise to THF (25 mL) with ice cooling. To this solution, a solution of 6-chloronaphthalene-2-thiol (5.0 g) in THF (50 mL) was added dropwise at 0C, and the mixture was mixed at room temperature for 30 minutes. To this solution, a solution of methyl (2R)-oxirane-2-carboxylate (2.3 mL) in THF (15 mL) was added dropwise, and the reaction solution was mixed at room temperature for 3 hours. To the reaction solution, an aqueous ammonium chloride solution (50 mL) was added, and the mixture was extracted with ethyl acetate (100 mL). The extract was washed with saturated brine, dried over anhydrous magnesium sulfate, and concentrated under reduced pressure. The residue was recrystallized from hexane/ethyl acetate (3:1) to give the title compound (5.9 g, 77%) as colorless needle-shaped crystals.

NMR (CDCl$_3$) δ: 3.12 (1H, d, J=6.0), 3.35 (1H, dd, J=14.1, 5.7), 3.48 (1H, dd, J=14.1, 4.2), 3.58 (3H, s), 4.43-4.48 (1H, m), 7.39-7.43 (1H, m), 7.49-7.52 (1H, m), 7.66-7.69 (2H, m), 7.76-7.77 (1H, m), 7.83-7.84 (1H, m).

112b) (2S)-3-[(6-Chloronaphthalen-2-yl)thio]-2-hydroxypropionic acid

To a suspension of methyl (2S)-3-[(6-chloronaphthalen-2-yl)thio]-2-hydroxypropionate (5.4 g) obtained in Example 112a) in ethanol (150 mL), a 8 N aqueous sodium hydroxide solution (6.8 mL) was added, and the mixture was mixed at room temperature for 3 hours. Ethanol was distilled off under reduced pressure, and then the precipitates were collected by filtration. The solid was suspended in water (100 mL), pH was adjusted to about 3 with 1 N hydrochloric acid, and the precipitates were then collected by filtration to give the title compound (5.0 g, 97%) as a white solid.

NMR (CD$_3$OD) δ: 3.27 (1H, dd, J=14.1, 6.9), 3.51 (1H, dd, J=14.1, 4.2), 4.33 (1H, dd, J=6.9, 4.2), 7.40-7.43 (1H, m), 7.51-7.54 (1H, m), 7.71-7.77 (2H, m), 7.82 (1H, s), 7.86 (1H, s).

112c) (2S)-3-((6-Chloro-2-naphthyl)sulfonyl)-1-(4-(((2Z)-3-methyl-2-(methylimino)-2,3-dihydro-1,3-thiazol-4-yl)methyl)-1-piperazinyl)-1-oxopropan-2-ol To a suspension of (2S)-3-((6-chloronaphthalen-2-yl)sulfonyl)-2-hydroxypropanoic acid (0.32 g), N-((2Z)-3-methyl-4-(-1-piperazinylmethyl)-1,3-thiazol-2(3H)-ylidene)methanamine trihydrochloride (0.51 g), HOBt (0.20 g) and triethylamine (0.63 mL) in DMF (5 mL), WSC (0.21 g) was added, and the mixture was mixed at room temperature for 22 hours. The reaction solution was concentrated under reduced pressure. The residue was basified with an aqueous potassium carbonate solution, and then the mixture was extracted with ethyl acetate/THF. The extract was dried over anhydrous magnesium sulfate, the solvent was then distilled off, and the residue was purified with a basic silica gel column to give the title compound (0.12 g, 23%) as a colorless powder.

NMR (CDCl$_3$) δ: 2.42-2.55 (4H, m), 3.01 (3H, s), 3.28 (2H, s), 3.31-3.43 (5H, m), 3.47-3.76 (4H, m), 4.97-5.03 (1H, m), 5.77 (1H, s), 7.59 (1H, dd, J=2.0, 9.0), 7.93-7.97 (4H, m), 8.50 (1H, s).

PREPARATION EXAMPLE 1

FXa inhibitors (e.g., therapeutic agent for deep-vein thrombosis, therapeutic agent for cardiogenic cerebral infarction, etc.) comprising the compound represented by Formula (1) in the invention or a salt thereof as an active ingredient can be prepared by, for example, the following formulation.

In addition, as ingredients (additives) in addition to the active ingredients in the following formulation, the list of ingredients according to Japanese Pharmacopoeia, Japanese Standards for Pharmaceutical Ingredients or Standards for Pharmaceutical additives can be used.

| 1. Capsule | |
|---|---|
| (1) Compound obtained in Example 12 | 120 mg |
| (2) Lactose | 210 mg |
| (3) Microcrystalline cellulose | 27 mg |
| (4) Magnesium stearate | 3 mg |
| 1 Capsule | 360 mg |

(1), (2), (3) and ½ of (4) were mixed and then granulated. The remaining (4) was added thereto, and the whole mixture was encapsulated in a gelatin capsule.

| 2. Capsule | |
|---|---|
| (1) Compound obtained in Example 83 | 120 mg |
| (2) Lactose | 210 mg |
| (3) Microcrystalline cellulose | 27 mg |
| (4) Magnesium stearate | 3 mg |
| 1 Capsule | 360 mg |

(1), (2), (3) and ½ of (4) were mixed and then granulated. The remaining (4) was added thereto, and the whole mixture was encapsulated in a gelatin capsule.

| 3. Tablet | |
|---|---|
| (1) Compound obtained in Example 12 | 120 mg |
| (2) Lactose | 174 mg |
| (3) Corn starch | 54 mg |
| (4) Microcrystalline cellulose | 10.5 mg |
| (5) Magnesium stearate | 1.5 mg |
| 1 Tablet | 360 mg |

(1), (2), (3), ⅔ of (4) and ½ of (5) were mixed and then granulated. The remaining (4) and (5) were added to the granules, and the mixture was compressed to give tablets.

| 4. Tablet | |
|---|---|
| (1) Compound obtained in Example 83 | 120 mg |
| (2) Lactose | 174 mg |
| (3) Corn starch | 54 mg |

-continued

| 4. Tablet | |
|---|---|
| (4) Microcrystalline cellulose | 10.5 mg |
| (5) Magnesium stearate | 1.5 mg |
| 1 Tablet | 360 mg |

(1), (2), (3), ⅔ of (4) and ½ of (5) were mixed and then granulated. The remaining (4) and (5) were added to the granules, and the mixture was compressed to give tablets.

PREPARATION EXAMPLE 2

50 mg of the compound obtained in Example 12 was dissolved in 50 mL of the distilled water for injection according to Japanese Pharmacopoeia, and then the distilled water for injection according to Japanese Pharmacopoeia was added to a volume of 100 mL. The solution was filtered under the sterilized condition, and then taken out in 1 mL-portions, and under sterilized condition, charged into a vial for injection. The vials were freeze-dried for sealing.

EXPERIMENTAL EXAMPLE (1) Inhibitory Action of Human Activated Blood Coagulation Factor X (FXa):

Test method: A solution (225 µL) of 0.05M tris-hydrochloric acid buffers (pH=8.3) containing 0.145 M of sodium chloride and 2 mM of calcium chloride, a test compound dissolved in dimethyl sulfoxide (5 µL) and human FXa (10 µL, 0.3 unit/ml) were added to a 96-well microplate and reacted at 37° C. for about 10 minutes, and then a substrate (10 µL, 3 mM, S-2765) was added to be reacted at 37° C. for 10 minutes. Then, after aqueous 50% acetic acid (25 µL) was added there to stop the reaction, the change of absorbance at 405 nm was measured by a microplatereader, and a concentration inhibiting FXa activity by 50% ($IC_{50}$) was calculated.

(2) Measurement of In Vitro Coagulation Time (2-1) Measurement of Extrinsic Coagulation Time (PT):

The extrinsic coagulation time was measured with an automatic blood coagulation time measuring apparatus (STA compact, DIAGNOSTICA STAGO) using a PT reagent (DIAGNOSTICA STAGO). 3 µl of the drug was added to 97 µl of human normal plasma (fresh human plasma (FFP), SEKISUI CHEMICAL Co., Ltd.) and preliminarily warmed to 37° C. for 4 minutes. To 50 µl of the aforementioned plasma, 100 µl of a rabbit-brain-derived tissue thromboplastin solution was added, and then the time taken to coagulation was measured. The drug was used after dissolving in dimethyl sulfoxide (DMSO). The concentration for doubling the coagulation time was calculated based on the coagulation time obtained when DMSO was added instead of the drug.

(2-2) Measurement of Intrinsic Coagulation Time (APTT):

The intrinsic coagulation time was measured with an automatic blood coagulation time measuring apparatus using an STA-APTT-LT (DIAGNOSTICA STAGO). 3 µl of the drug was added to 97 µl of human normal plasma. To 50 µl of the plasma, 50 µl of an active partial thromboplastin solution was added, and preliminarily warmed to 37° C. for 4 minutes. 50 µl of a 25 mmol/l $CaCl_2$ solution was added, and the time taken to coagulation was measured. The drug was used after dissolving in DMSO. The concentration for doubling the coagulation time was calculated in the same manner as in (2-1).

(2-3) Measurement of Thrombin Coagulation Time (TT).

The thrombin coagulation time was measured with an automatic blood coagulation time measuring apparatus using a fibrinogen reagent (DIAGNOSTICA STAGO). The fibrinogen reagent (containing thrombin) was dissolved in 5 mL of distilled water, and then was conditioned by diluting to 20-folds with 0.5% bovine serum albumin-added physiological saline. 3 µl of the drug was added to 97 µl of human normal plasma (fresh human plasma (FFP), SEKISUI CHEMICAL Co., Ltd.), and was preliminarily warmed to 37° C. for 3 minutes. To 50 µl of the above-described plasma, 100 µl of the thrombin solution was added, and the time taken to coagulation was measured. The drug was used after dissolving in DMSO. The concentration for doubling the coagulation time was calculated in the same manner as in (2-1).

(3) Measurement of Ex Vivo Coagulation Time (Mouse)

(3-1) Intravenous Administration:

Male ICR mice (25 to 35 g, CREA Japan, Inc.) were used. Under pentobarbital (50 mg/kg, i.p.) anesthesia, the drug was administered once in a dose of 5 mL/kg from the tail vein of each mouse. After 5 minutes of administration, 0.8 mL of blood was collected from the abdominal aorta or heart using ¹⁄₁₀ of 3.8% sodium citrate (Citral, YAMANOUCHI PHARMACEUTICAL Co., Ltd.), and was centrifuged at 3000 rpm for 15 minutes to obtain the plasma. To 50 µl of the plasma, 100 µl of a rabbit brain-derived tissue thromboplastin solution was added, and then the time taken to coagulation was measured. The coagulation time was measured with an automatic blood coagulation time measuring apparatus (STA compact) using a PT reagent (DIAGNOSTICA STAGO). The drug was used after dissolving in a mixed solution containing dimethylacetamide, ¹⁄₁₀ N hydrochloric acid and physiological saline solution, and for the control, a mixed solution containing dimethylacetamide, ¹⁄₁₀ N hydrochloric acid and physiological saline solution was administered instead of the drug. The drug activity was indicated as a ratio (%) of the coagulation time for the drug administered group to the coagulation time for the control.

(3-2) Oral Administration:

Male ICR mice (25 to 35 g, CREA Japan, Inc.) were used. Each mouse which had fasted for over 12 hours was forcibly subjected to oral administration of the drug in a dose of 5 mL/kg. After 1 hour of administration, blood was collected from the abdominal aorta under pentobarbital (50 mg/kg, i.p.) anesthesia. The drug was used after suspending in a 0.5% methylcellulose solution, and for the control, a 0.5% methylcellulose solution was administered instead of the drug. The other conditions were provided in the same manner as in (3-1).

(4) Measurement of In Vivo Antithrombotic Effect (4-1) Rat Arteriovenous Shunt Method:

The rat arteriovenous shunt method was carried out according to the method of Umetsu, et al., Thromb. Haemostas., 39, 74-73 (1978). Male SD rats (200 to 350 g, CREA Japan, Inc.) were used, and under pentobarbital (50 mg/kg, i.p.) anesthesia, an extracorporeal circuit was established using a polyethylene tube having a silk thread attached, between the left jugular vein and the right jugular vein of each rat. In order to prevent blood coagulation, the tube was filled in advance with physiological saline containing heparin (50 U/mL). The blood was circulated for 15 minutes, and the wet weight of thrombi adhered to the silk thread during the circulation was measured. The drug was administered via oral or intravenous administration. In the case of oral administration, the drug was administered (2 mL/kg) after suspending in a 0.5% methylcellulose solution, with the rat having fasted, and for the control, a 0.5% methylcellulose solution was administered instead of the drug. In the case of intravenous administration, the drug was dissolved in physiological saline and was administered in a dose of 1 mL/kg from the tail vein, and for the control, physiological saline was administered instead of the drug. The drug activity was calculated as a ratio (%) of the wet weight of thrombi in the drug administered group to the wet weight of thrombi in the control group.

(4-2) Model of Rat Abdominal Vena Cava Partial Ligation

Male SD rats (200 to 400 g, CREA Japan, Inc.) were used. Under pentobarbital (50 mg/kg, i.p.) anesthesia, the abdominal vena cava of each rat was carefully removed, and then threads were placed at the renal vein bifurcation of the abdominal vena cava and at a position 1 cm distal to the bifurcation, thus to ligate all of the rami present in between. A balloon catheter (Fogarty 2F, BAXTER HEALTHCARE Corp.) was introduced from the left femoral vein, and the area in between the two threads was injured three times using the balloon expanded with 200 to 300 mL of air. The balloon catheter was removed, the thread placed at the renal vein bifurcation was tied together with a 26 G needle, and then the needle was removed to provide a partial ligation. After 30 minutes, another thread was tied, the thrombi obtained from between the two threads were carefully isolated, and the wet weight of thrombi was measured with an analytical balance equipped with windshield (BP110S, SATORIUS AG). The drug was administered via oral or intravenous administration, in the same manner as in (4-1). The drug activity was calculated in the same manner as in (4-1).

(4-3) Model of Rat Deep Vein Thrombosis (DVT)

Male SD rats (200 to 350 g, CREA Japan, Inc.) were used. Under pentobarbital (50 mg/kg, i.p.) anesthesia, a polyethylene tube was inserted into the left femoral vein of each rat. A silk thread (length 5 cm) preliminarily connected to a guide wire was inserted into the polyethylene tube, and the tube was filled with physiological saline containing heparin (50 U/mL) in order to prevent blood coagulation. After inserting the polyethylene tube until the tube reached the abdominal vena cava, the silk thread was fixed in the abdominal vena cava using the guide wire. After 30 minutes of the fixing, heparin (200 U/kg) was intravenously administered from the tail vein. The rat was exsanguinated by cutting the brachial artery, and then was subjected to abdominal celiotomy to take out the silk thread, and the wet weight of adhered thrombi (including the weight of the silk thread) was measured. The drug was administered via oral or intravenous administration, in the same manner as in (4-1). The wet weight of thrombi only was determined from the calculation formula: (wet weight of thrombi adhered to the silk thread)−(wet weight measured by immersing a silk thread in the heparin-collected venous blood). The drug activity was calculated in the same manner as in (4-1).

Experimental Results

The $IC_{50}$ values determined in Experimental Example (1) are presented in Table 1. It is obvious from the results that the compound of the invention has an excellent FXa inhibiting effect.

TABLE 1

| Example No. | $IC_{50}$ (nM) | Example No. | $IC_{50}$ (nM) |
|---|---|---|---|
| 5 | 57 | 12 | 22 |
| 38 | 11 | 44 | 14 |
| 46 | 30 | 58 | 60 |
| 68 | 8.3 | 77 | 9.4 |
| 83 | 6.7 | 92 | 47 |

INDUSTRIAL APPLICABILITY

Compound (I) of the present invention has excellent FXa inhibiting effect, and is useful as an anti-coagulant capable of oral uptake and having less side effect of hemorrhage. Compound (I) of the invention is advantageously used for the prevention and/or treatment of various diseases caused by thrombus and infarction.

The invention claimed is:

1. A compound represented by Formula (I):

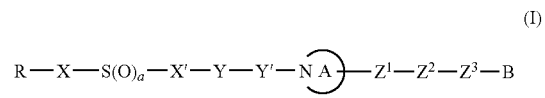

(I)

wherein R is naphthyl which may be substituted; X is a bond; X' is a bond; Y is a $C_{1-3}$ alkylene which may be substituted; Y' is —C(=O)—; ring A is a piperazine ring which may be substituted; $Z^1$ and $-Z^2$ are each a bond; $-Z^3$ is $C_{1-3}$ alkylene which may be substituted; B is a group represented by the formula:

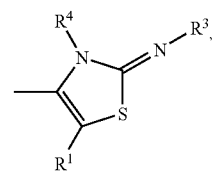

(wherein $R^1$, $R^3$ and $R^4$ are each a hydrogen atom or a $C_{1-6}$ alkyl which may be substituted, and $R^3$ and $R^4$ may be bonded to each other to form tetrahydroimidazole which may be substituted); and a is 0, 1 or 2, or a salt thereof.

2. The compound according to claim 1, wherein R is naphthyl which may be substituted with a substituent selected from a halogen atom, $C_{1-6}$ alkyl, $C_{2-6}$ alkenyl, $C_{2-6}$ alkynyl, amino which may be substituted, nitro, cyano, amidino which may be substituted, and carboxyl which may be esterified or amidated.

3. The compound according to claim 1, wherein R is naphthyl which may be substituted with a halogen atom.

4. The compound according to claim 1, wherein Y is $C_{1-3}$ alkylene substituted with a hydroxyl group.

5. The compound according to claim 1, wherein ring A is a ring represented by the formula:

wherein ring A' may be further substituted.

6. The compound according to claim 1, wherein a is 2.

7. A compound selected from the group consisting of N-(4-((4-( 3-((6-chloro-2-naphthyl)sulfonyl)propanoyl)-1-piperazinyl)methyl)-3-methyl-1,3-thiazol-2(3H)-ylidene)-N-methylamine and 4-((4-(3-((6-chloro-2-naphthyl) sulfonyl) propanoyl)-1-piperazinyl)methyl)-3-methyl-1,3-thiazol-2 (3H)-imine, or a salt thereof.

8. A pharmaceutical composition comprising the compound according to claim 1.

9. The pharmaceutical composition according to claim 8, which is an anticoagulant.

10. The pharmaceutical composition according to claim 8, which is an activated blood coagulation factor X inhibitor.

11. The pharmaceutical composition according to claim 8, which is a medicament for treating deep vein thrombosis.

* * * * *